(12) United States Patent
Bautista et al.

(10) Patent No.: US 12,157,904 B2
(45) Date of Patent: Dec. 3, 2024

(54) THIOESTERASE VARIANTS HAVING IMPROVED ACTIVITY FOR THE PRODUCTION OF MEDIUM-CHAIN FATTY ACID DERIVATIVES

(71) Applicant: Genomatica, Inc., San Diego, CA (US)

(72) Inventors: Angelica Zabala Bautista, San Diego, CA (US); Min Sun Park, San Diego, CA (US); Alma Itzel Ramos-Solis, San Diego, CA (US); Bernardo Moura Torres Da Costa, San Diego, CA (US); Behnaz Behrouzian, San Diego, CA (US); Donald E. Trimbur, San Diego, CA (US); Emanuela Popova, San Diego, CA (US); Qijun Hu, San Diego, CA (US); Stephen Bralley Del Cardayre, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 26 days.

(21) Appl. No.: 17/715,587

(22) Filed: Apr. 7, 2022

(65) Prior Publication Data

US 2022/0243185 A1    Aug. 4, 2022

Related U.S. Application Data

(62) Division of application No. 16/500,188, filed as application No. PCT/US2018/025970 on Apr. 3, 2018, now Pat. No. 11,339,384.

(60) Provisional application No. 62/481,078, filed on Apr. 3, 2017.

(51) Int. Cl.
*C12N 9/16* (2006.01)
*C12P 7/6409* (2022.01)
*C12P 7/6436* (2022.01)

(52) U.S. Cl.
CPC .............. *C12N 9/16* (2013.01); *C12P 7/6409* (2013.01); *C12P 7/6436* (2013.01); *C12Y 301/02014* (2013.01)

(58) Field of Classification Search
CPC combination set(s) only.
See application file for complete search history.

(56) References Cited

U.S. PATENT DOCUMENTS

| | | |
|---|---|---|
| 2011/0020883 A1 | 1/2011 | Roessler et al. |
| 2016/0032332 A1 | 2/2016 | Davis et al. |
| 2021/0207111 A1 | 7/2021 | Bautista et al. |

FOREIGN PATENT DOCUMENTS

| | | |
|---|---|---|
| CN | 102712858 A | 10/2012 |
| JP | 2015091228 A | 5/2015 |
| JP | 2015123062 A | 7/2015 |
| JP | 2016518112 A | 6/2016 |
| KR | 20150113973 A | 10/2015 |
| WO | 2011038134 A1 | 3/2011 |
| WO | WO-2012087982 A2 | 6/2012 |
| WO | WO-2014120829 A1 | 8/2014 |
| WO | WO2014151904 A | 9/2014 |
| WO | 2016014968 A1 | 1/2016 |
| WO | 2016044336 A1 | 3/2016 |

OTHER PUBLICATIONS

Youngquist, J.T., et al., "Production of medium chain length fatty alcohols from glucose in *Escherichia coli*," Metab Eng., 20: 1-22 (2013).
Examination Report from corresponding European Application No. 18720824.4 dated Oct. 4, 2021.
International Preliminary Report on Patentability in International Application PCT/US2018/025970 dated Oct. 17, 2019.
International Search Report and Written Opinion in International Application No. PCT/US2018/025970 mailed on Dec. 19, 2018 (16 pages).
Liu, et al., "Fatty alcohol production in engineered *E. coli* expressing Marinobacter fatty acyl-CoA reductases," Applied Microbiology and Biotechnology, Aug. 2013, 97(15): 7061-7071.
Nawabi, et al., "Engineering *Escherichia coli* for Biodiesel Production Utilizing a Bacterial Fatty Acid Methyltransferase," Applied and Environmental Microbiology, Nov. 2011, 77(22): 8052-8061.
Office Action from corresponding U.S. Appl. No. 16/500,188 dated Sep. 23, 2021.
Zoller, M.J., and Smith, M., "Oligonucleotide-directed mutagenesis using M13-derived vectors: an efficient and general procedure for the production of point mutations in any fragment of DNA," Nucleic Acids Research, 10(20): 6487-6500 (1982).
Office Action from corresponding Japanese Application No. 2020-502555 dated Mar. 9, 2022.
Office Action from corresponding Korean Application No. 1020197032078 dated Nov. 15, 2022.
Office Action from corresponding Japanese Application No. 2020-502555 dated May 2, 2024.
Office Action from corresponding Chinese Application No. 201880035676.0 dated Apr. 11, 2024.

*Primary Examiner* — Tekchand Saidha
(74) *Attorney, Agent, or Firm* — Harness Dickey & Pierce P.L.C.

(57) ABSTRACT

The disclosure relates to engineered plant acyl-ACP thioesterases having improved activity for the production of medium-chain fatty acid derivatives including e.g., eight carbon and ten carbon fatty acids and fatty acid derivatives. The disclosure further relates to recombinant host cells comprising the engineered plant acyl-ACP thioesterases having improved activity for the production of medium-chain fatty acid derivatives. The disclosure also relates to methods of decreasing toxicity and improving production of medium-chain fatty acids and derivatives.

14 Claims, 17 Drawing Sheets
Specification includes a Sequence Listing.

FIG. 9

Structure-Based Sequence Alignment

```
                36 a.a
        ◄━━━━━━━━━━━━━━━━━━━━━━━━━━━━━━━━━━━►
2ess    ~~~~~~~~~~~~~~~~~~~~~~~~~~~~~~....MSEEN...KIGTYQFVAEPF
2own    ~~~~~~~~~~~~~~~~~~~~~~~~~~~~~~TLGA..N....ASLYSEQHRITYY
4gak    ~~~~~~~~~~~~~~~~~~~~~~~~~~~~~~........MA.FIQTDTFTLRGY
ChfatB2 MLPOWSRLLTAITTYFVKSKRPDMHDRKSKRPDMLVDSFGLESTVQDGLVPRQSFSIRSY 2ess    HVDFNQRLTMGVLGNHLLNCAGFHASDR.~~~~GFG.IATLNEDNYTWVLSRLAIELDRM
2own    ECDRTGRATLTTLIDIAVLAGEDOSDALG~~~~L.Y.TEMVQSHGVGWVYQYAIDITRM
4gak    ECDAFGPMSIPALNNLMQESANRNAIDY.~~~~GIG.IADLAGKGYGWNLMRFCLRIMQY
ChfatB2 EIGTDRTASIETLMNHLGETSLNHCKSTGILLDGFGRTLEMCKRDLIWVVIKMQIKVMRY 2ess    PYQYEKFSVQTWVGNVYRLFTDRNFAVIDKD.GKKIGYARSVWAMINLNTRKPA..L.HG
2own    PRQDEVVTIAVRGSAYNPYFAYREFWIRDAQ.GQQLAYITSIWVMMSQTTRRIVKIL.P.
4gak    PRYGDTIQLMTYPTTVDKYFIHRDFRVLAYD.GTLLADARSTWLVFSMEKRSMVPLP.Q.
ChfatB2 PAMGDTVEINTRFSRLGKIGMGRDWLISDCNTGEILVRATSAVAMMNQKTRRLSKLPYEV 2ess    GS.I..VD..YIC..DEP.CP.........IEKP..SRI...KVTSN....QPVATLTAKY
2own    E.LV..A.PYQS.........EVVKRIPR..LP..R.P.I.SFEA..TDTTITKPYHVRF
4gak    F..IRQL...SPPAN.VDPLP........A...LPLKP..DFQTASFAT...AAGSKSVQYGW
ChfatB2 HQEIVPLFVDGPVIEDSG~~~~~~~~~~~~~~~~~LKVHKFKVKTGG.SIQKGLTPGW 2ess    SDID..INGHVNSIRYIEHILQLF.PIELYQTKRIBRFEMAYVAESYFGQELSFFCDEVS
2own    FDIDPNRN..VNNAHYFDWLVDTL..PATFLLQNQLVHVDVRYENEVAYGQTVTAHANILP
4gak    LNIDQNQH..VNNVAYVQWLLEGVQS.EIVQTRNEIAEIDLVYRTESMMHQWLSVQSYTEY
ChfatB2 NDLDVNQH~~VSNVKYIGWILESM.PTEVLETQELCSLALEYRRECGRDSVLESVTAMDP 2ess    E....NEFHVEVKKNG.SEVVCRSKVIFE~~~~~~~~~~~~~~~~~~~~~~
2own    SEVADQVTTSHLIEVD..DEKCCEVTIQWRTLPE~~~~~~~~~~~~~~~~~~
4gak    D....NSVLHRTSQTESGKDVLLARSRWR~~~~~~~~~~~~~~~~~~~~~~
ChfatB2 SKVGVRSQYQHLLRL.EDGTAIVNGATEWRPKNAGANGAISTGKTSNGNSVS
                                         ◄━━━━━━━━━━━━━━━━━►
                                              18 a.a
```

THIOESTERASE VARIANTS HAVING IMPROVED ACTIVITY FOR THE PRODUCTION OF MEDIUM-CHAIN FATTY ACID DERIVATIVES

CROSS-REFERENCE TO RELATED APPLICATIONS

This application is a divisional of U.S. patent application Ser. No. 16/500,188, filed Oct. 2, 2019, now pending, which is a U.S. 371 National Stage Entry of PCT/US2018/025970 filed on Apr. 3, 2018, which claims the benefit of U.S. Provisional Patent Application No. 62/481,078, filed Apr. 3, 2017. Each application referenced above is incorporated herein by reference in its entirety.

REFERENCE TO A SEQUENCE LISTING

This application contains references to amino acid sequences and/or nucleic acid sequences as an ASC II text file. The name of the ASC II text file is "62746532_1.TXT". It was created on 18 Nov. 2020 and is 165 KB. The aforementioned sequence listing is hereby incorporated by reference in its entirety pursuant to 37 C.F.R. § 1.52(e).

FIELD

The disclosure relates to molecular tools useful for the production of medium-chain length fatty acids and fatty acid derivatives. Thus, the disclosure relates to genes that confer tolerance to microorganisms to medium-chain length fatty acids and fatty acid derivatives. The disclosure further relates to novel engineered thioesterase variants and the polynucleotides that encode them which have improved activity and/or selectivity for the production of medium-chain fatty acid derivatives including e.g., eight carbon and ten carbon fatty acids and fatty acid derivatives. Thus, the disclosure also relates to host cells that comprise the engineered thioesterase variants, their encoding polynucleotides, and the related cell cultures. Further encompassed are methods of producing medium-chain fatty acid derivatives by employing the host cells expressing the engineered thioesterase variants and compositions of biologically produced medium-chain fatty acid derivatives.

BACKGROUND

There is immense interest in producing medium-chain fatty acid (MCFA)-derived products. Medium-chain fatty acids and medium-chain fatty acid derivatives find numerous industrial applications e.g., as biofuel, lubricants and greases, metalworking fluids, coatings and adhesives, cosmetics and personal care, perfumery, food and nutrition, pharmaceutical, plastics and rubber and other feedstocks for the chemical industry.

In addition to their value in industry, medium-chain fatty acids find valuable applications as dietary supplements and nutraceuticals (see e.g., Stig Bengmark (2013) Nutrients 5(1): 162-207). Indeed, medium-chain fatty acids and their derivatives exhibit antimicrobial properties (see e.g., Nobmann et al. International Journal of Food Microbiology. 2009; 128(3):440-445; B W Petschow, et al., (1996) Antimicrob. Agents Chemother. 40(2):302-306) suppress body fat accumulation and prevent metabolic syndrome (see e.g., Takeuchi H., et al. (2008) Asia Pac J Clin Nutr. 17 Suppl 1:320-3; Koji Nagao (2010) Pharmacological Research 61:208-212). Omura Y., et al. (2011) Acupunct Electrother Res. 36(1-2):19-64) and have antiseizure effects at clinically relevant concentrations (see e.g., Chang et al., (2013) Neuropharmacology 2013; 69: 105-14; Wlaz et al., (2015) Prog Neuropsychopharmacol Biol Psychiatry 2015; 57: 110-16).

Given the many useful applications it is not surprising that the demand for medium-chain fatty acids has trended upwards over the past few years. Unfortunately, the supply of medium-chain fatty acids has always been tied to production of longer-chain free fatty acid (FFA) products from plants (palm oil) or from chemical synthesis, where medium length chains are produced as shoulders representing less than 20% of the total fatty acyl species (see e.g., Kostik, V. et al. (2013) J. Hyg. Eng. Des. 4:112-116). This makes the supply of medium-chain fatty acids quite volatile and unstable. Thus, there is a need in the art for methods that can deliver a reliable, stable and renewable supply of these compounds.

An alternative to the present sources of medium-chain fatty acids is their production using biological systems, such as microbial fermentations. However, production of free fatty acids by biological systems represents two major challenges. First, it often depends on thioesterases, which act over alkyl thioester molecules produced by the host organism. The available thioesterases active over medium-chain alkyl thioesters have either suboptimal catalytic activity, or their specificity is too wide, acting over a range of alkyl thioester chain lengths. Second, medium-chain aliphatic compounds are often highly toxic to microbial cells, hampering their production at high levels. Additionally, the toxicity of medium-chain acyl compounds can handicap the selection and engineering of highly active thioesterases. Thus, for biological systems to provide an alternative supply of medium-chain fatty acids, there is a need for biological systems that have improved thioesterases of higher activity and selectivity for medium chain alkyl thioesterases and that show improved tolerance to medium-chain aliphatic compounds.

Fortunately, as will be clear from the disclosure that follows, the present invention provides for these and other needs.

SUMMARY

One aspect of the disclosure provides an engineered thioesterase variant having improved activity for production of medium-chain fatty acid derivatives. Thus, in one embodiment, the disclosure provides an engineered thioesterase variant having improved activity for production of medium-chain fatty acid derivatives. In one embodiment, the engineered thioesterase variant of claim 1, wherein the engineered thioesterase variant has improved activity for production of C8 fatty acid derivatives. In one embodiment, the engineered thioesterase variant has an amino acid sequence that has at least 90% sequence identity to SEQ ID NO:1 and at least one substitution mutation at an amino acid position selected from the group consisting of: 3, 4, 6, 14, 15, 17, 22, 37, 44, 45, 50, 54, 56, 64, 67, 73, 76, 91, 99, 102, 110, 111, 114, 129, 132, 137, 158, 162, 165, 176, 178, 185, 186, 196, 197, 198, 203, 213, 217, 225, 227, 236, 244, 254, 256, 258, 278, 282, 292, 297, 298, 299, 300, 301, 302, 316, 321, and 322. In one embodiment, the engineered thioesterase the at least one substitution mutation is a member selected from the group consisting of: (a) a lysine at amino acid position 3; (b) a methionine at amino acid position 4; (c) an arginine at amino acid position 6; (d) a glycine or an arginine at amino acid position 14; (e) a leucine or a tryptophan at amino acid position 15; (0 an alanine or a cysteine at amino acid position 17; (g) an arginine at amino acid position 22; (h) a proline at amino acid position 37; (i) a glycine or isoleucine at amino acid position 44; (j) a serine at position 45; (k) a tryptophan at amino acid position 50; (l) an arginine at amino acid position 54; (m) a lysine or a cysteine at amino acid position 56; (n) an arginine or a proline at amino acid position 64; (o) a leucine at amino acid position 67; (p) a valine at position 73; (q) a phenylalanine or a leucine or a tyrosine at amino acid position 76; (r) a methionine at amino acid position 91; (s) a lysine or a proline at amino acid position 99; (t) an isoleucine at amino acid position 102; (u) a leucine at amino acid position 110; (v) a threonine at position 111; (w) a lysine at position 114; (x) a valine at amino acid position 129; (y) a tryptophan at amino acid position 132; (z) a cysteine at amino acid position 137; (aa) a glutamine at amino acid position 158; (bb) a glutamic acid at amino acid position 162; (cc) a valine at amino acid position 176; (dd) a proline at amino acid position 178; (ee) an alanine at amino acid position 185; (ff) a glycine at amino acid position 186; (gg) a valine at amino acid position 196; (hh) an asparagine at amino acid position 197; (ii) a tryptophan at amino acid position 198; (jj) an arginine at amino acid position 203; (kk) a histadine or an arginine at amino acid position 213; (ll) an arginine at amino acid position 217; (mm) a leucine at amino acid position 225; (nn) a glycine at amino acid position 227; (oo) a threonine at amino acid position 236; (pp) a methionine or an arginine at amino acid position 244; (qq) a glycine at amino acid position 254; (rr) a cysteine or an arginine at amino acid position 256; (ss) a threonine or a valine at amino acid position 258; (tt) a lysine or a valine at amino acid position 278; (uu) a serine or a valine at amino acid position 282; (vv) a phenylalanine at amino acid position 292; (ww) a threonine or an aspartic acid or a valine at amino acid position 297; (xx) a valine or a cysteine at amino acid position 298; (yy) a leucine at amino acid position 299; (zz) a lysine or a tryptophan or a leucine at amino acid position 300; (aaa) a cysteine at amino acid position 301; (bbb) a threonine at amino acid position 302; (ccc) an arginine at amino acid position 316; (ddd) an arginine at amino acid position 321; and (eee) a lysine at amino acid position 322.

In one embodiment, the engineered thioesterase variant of is a member selected from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58 and SEQ ID NO:59.

In one embodiment, the engineered thioesterase variant has an overall increased net positive charge as compared to a thioesterase having SEQ ID NO:1. In one embodiment, the engineered thioesterase variant has an overall increased net positive charge as compared to a variant thioesterase having SEQ ID NO:4.

In one embodiment, the engineered thioesterase variant is selected from SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, and SEQ ID NO:46.

In one embodiment, the engineered thioesterase variant has an increased positive surface charge by comparison to SEQ ID NO:15. In one embodiment, the engineered thioesterase variant is a member selected from the group consisting of: SEQ ID NO:47, SEQ ID NO:48, SEQ ID NO:49, SEQ ID NO:50 and SEQ ID NO:51.

In one embodiment, the engineered thioesterase variant has improved solubility. In one embodiment, the engineered thioesterase variant has improved solubility by comparison to SEQ ID NO:49.

In one embodiment, the engineered thioesterase variant has a truncation mutation between amino acids 2 and 40 of SEQ ID NO:49. In one embodiment, the engineered thioesterase variant is a member selected from the group consisting of: SEQ ID NO:52, SEQ ID NO:53, SEQ ID NO:54, SEQ ID NO:55, SEQ ID NO:56, SEQ ID NO:57, SEQ ID NO:58 and SEQ ID NO:59.

In one embodiment, the variant thioesterase has improved activity for production of C10 fatty acid derivatives. In one embodiment, the variant thioesterase has improved activity for production of C8 fatty acid derivatives.

In one aspect, the disclosure provides a recombinant host cell comprising one or more heterologous genes that encode a biochemical pathway that converts a first fatty acid derivative to a second fatty acid derivative, wherein the second fatty acid derivative has a higher minimum inhibitory concentration (MIC) than the first fatty acid derivative, and wherein the presence of the second fatty acid derivative increases the MIC of the first fatty acid derivative.

In one embodiment, the biochemical pathway comprises one of: a carboxylic acid reductase, a carboxylic acid reductase and an alcohol dehydrogenase, a carboxylic acid reductase and an alcohol-O-acetyl transferase, a carboxylic acid reductase, and alcohol dehydrogenase, and an alcohol O-acetyl transferase, an ester synthase, an ester synthase and fatty acyl CoA synthetase, an acyl CoA reductase, an acyl CoA reductase and an acyl CoA synthetase, an acyl CoA reductase and an alcohol O-acetyl transferase, an acyl CoA reductase, an alcohol O-acetyl transferase, and an acyl CoA synthetase, an O-methyl transferase, an acyl ACP reductase, an acyl ACP reductase and aldehyde decarbonylase, an Acyl ACP reductase and aldehyde oxidative deformylase, an Acyl ACP reductase and alcohol O-acetyl transferase, an acyl ACP reductase, an alcohol —O-acetyl transferase, and an alcohol dehydrogenase, an OleA protein, an OleA, C, and D protein, an OleA protein and a fatty acyl CoA synthetase, or an OleA, C, and D protein and a fatty acyl CoA synthetase.

In an embodiment, the first fatty acid derivative is a fatty acid and the second fatty acid derivative is a fatty acid alkyl ester, and the biochemical pathway comprises an ester synthase and fatty acyl-CoA synthetase.

In one embodiment, the fatty acid alkyl ester is a fatty acid methyl ester or a fatty acid ethyl ester.

In one embodiment, the first fatty acid derivative is a fatty alcohol and the second fatty acid derivative is a fatty alcohol acetate, and the biochemical pathway comprises a carboxylic acid reductase and an alcohol-O-acetyl transferase.

In one embodiment, the first fatty acid derivative and the second fatty acid derivative are medium-chain fatty acid derivatives.

In one embodiment, the recombinant host cell further comprises a engineered thioesterase variant.

In one embodiment, the engineered thioesterase variant is a member selected from the group consisting of: a variant thioesterase having an amino acid sequence that has at least 90% sequence identity to SEQ ID NO:1 and at least one substitution mutation at an amino acid position selected from the group consisting of: 3, 4, 6, 14, 15, 17, 22, 37, 44, 45, 50, 54, 56, 64, 67, 73, 76, 91, 99, 102, 110, 111, 114, 129, 132, 137, 158, 162, 165, 176, 178, 185, 186, 196, 197, 198, 203, 213, 217, 225, 227, 236, 244, 254, 256, 258, 278, 282, 292, 297, 298, 299, 300, 301, 302, 316, 321, and 322.

In one embodiment, the at least one substitution mutation is a member selected from the group consisting of: (a) a lysine at amino acid position 3; (b) a methionine at amino acid position 4; (c) an arginine at amino acid position 6; (d) a glycine or an arginine at amino acid position 14; (e) a leucine or a tryptophan at amino acid position 15; (0 an alanine or a cysteine at amino acid position 17; (g) an arginine at amino acid position 22; (h) a proline at amino acid position 37; (i) a glycine or isoleucine at amino acid position 44; (j) a serine at position 45; (k) a tryptophan at amino acid position 50; (l) an arginine at amino acid position 54; (m) a lysine or a cysteine at amino acid position 56; (n) an arginine or a proline at amino acid position 64; (o) a leucine at amino acid position 67; (p) a valine at position 73; (q) a phenylalanine or a leucine or a tyrosine at amino acid position 76; (r) a methionine at amino acid position 91; (s) a lysine or a proline at amino acid position 99; (t) an isoleucine at amino acid position 102; (u) a leucine at amino acid position 110; (v) a threonine at position 111; (w) a lysine at position 114; (x) a valine at amino acid position 129; (y) a tryptophan at amino acid position 132; (z) a cysteine at amino acid position 137; (aa) a glutamine at amino acid position 158; (bb) a glutamic acid at amino acid position 162; (cc) a valine at amino acid position 176(dd) a proline at amino acid position 178; (ee) an alanine at amino acid position 185; (ff) a glycine at amino acid position 186; (gg) a valine at amino acid position 196; (hh) an asparagine at amino acid position 197; (ii) a tryptophan at amino acid position 198; (jj) an arginine at amino acid position 203; (kk) a histadine or an arginine at amino acid position 213; (ll) an arginine at amino acid position 217; (mm) a leucine at amino acid position 225; (nn) a glycine at amino acid position 227; (oo) a threonine at amino acid position 236; (pp) a methionine or an arginine at amino acid position 244; (qq) a glycine at amino acid position 254; (rr) a cysteine or an arginine at amino acid position 256; (ss) a threonine or a valine at amino acid position 258; (tt) a lysine or a valine at amino acid position 278; (uu) a serine or a valine at amino acid position 282; (vv) a phenylalanine at amino acid position 292; (ww) a threonine or an aspartic acid or a valine at amino acid position 297; (xx) a valine or a cysteine at amino acid position 298; (yy) a leucine at amino acid position 299; (zz) a lysine or a tryptophan or a leucine at amino acid position 300; (aaa) a cysteine at amino acid position 301; (bbb) a threonine at amino acid position 302; (ccc) an arginine at amino acid position 316; (ddd) an arginine at amino acid position 321; and (eee) a lysine at amino acid position 322.

In one embodiment, the engineered thioesterase variant is a member selected from the group consisting of: SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58 and SEQ ID NO:59.

In one embodiment, the engineered thioesterase variant has an increased positive surface charge by comparison to SEQ ID NO:1. In one embodiment, the engineered thioesterase variant has an increased positive surface charge by comparison to SEQ ID NO:4. In one embodiment, the engineered thioesterase variant is a member selected from the group consisting of: SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, and SEQ ID NO:46.

In one embodiment, the engineered thioesterase variant has an increased positive surface charge by comparison to SEQ ID NO:15. In one embodiment, the engineered thioesterase variant is a member selected from the group consisting of: SEQ ID NO:47, SEQ ID NO:48, SEQ ID NO:49, SEQ ID NO:50 and SEQ ID NO:51.

In one embodiment, wherein the engineered thioesterase variant has improved solubility. In one embodiment, the engineered thioesterase variant has improved solubility by comparison to SEQ ID NO:49. In one embodiment, the engineered thioesterase variant has a truncation mutation between amino acids 2 and 40 of SEQ ID NO:49. In one embodiment, the engineered thioesterase variant is a member selected from the group consisting of: SEQ ID NO:52, SEQ ID NO:53, SEQ ID NO:54, SEQ ID NO:55, SEQ ID NO:56, SEQ ID NO:57, SEQ ID NO:58 and SEQ ID NO:59.

In another aspect the disclosure provides a method for producing a medium-chain fatty acid derivative at commercial titers, the method comprising: culturing a recombinant host cell that comprises an engineered thioesterase variant in the presence of a carbon source under conditions suitable for the production of the medium-chain fatty acid derivative, wherein the recombinant host cell comprises one or more heterologous genes that encode a biochemical pathway that converts a first fatty acid derivative to a second fatty acid derivative, and wherein the second fatty acid derivative has a higher minimum inhibitory concentration (MIC) than the first fatty acid derivative, and wherein the presence of the second fatty acid derivative increases the MIC of the first fatty acid derivative.

In one embodiment, the first fatty acid derivative is a medium-chain fatty acid and the second fatty acid derivative is a medium-chain fatty acid alkyl ester, and the biochemical pathway comprises an ester synthase and fatty acyl-CoA synthetase.

In one embodiment, the fatty acid alkyl ester is a medium-chain fatty acid methyl ester or a medium-chain fatty acid ethyl ester.

In one embodiment, the first fatty acid derivative is a medium-chain fatty alcohol and the second fatty acid derivative is a medium-chain fatty alcohol acetate, and the biochemical pathway comprises a carboxylic acid reductase and an alcohol-O-acetyl transferase.

In one embodiment, the engineered thioesterase variant has an amino acid sequence that has at least 90% sequence identity to SEQ ID NO:1 and at least one substitution mutation at an amino acid position selected from the group consisting of: 3, 4, 6, 14, 15, 17, 22, 37, 44, 45, 50, 54, 56, 64, 67, 73, 76, 91, 99, 102, 110, 111, 114, 129, 132, 137, 158, 162, 165, 176, 178, 185, 186, 196, 197, 198, 203, 213, 217, 225, 227, 236, 244, 254, 256, 258, 278, 282, 292, 297, 298, 299, 300, 301, 302, 316, 321, and 322. In one embodiment, the at least one substitution mutation is a member selected from the group consisting of: (a) a lysine at amino acid position 3; (b) a methionine at amino acid position 4; (c) an arginine at amino acid position 6; (d) a glycine or an arginine at amino acid position 14; (e) a leucine or a tryptophan at amino acid position 15; (f) an alanine or a cysteine at amino acid position 17; (g) an arginine at amino acid position 22; (h) a proline at amino acid position 37; (i) a glycine or isoleucine at amino acid position 44; (j) a serine at position 45; (k) a tryptophan at amino acid position 50; (l) an arginine at amino acid position 54; (m) a lysine or a cysteine at amino acid position 56; (n) an arginine or a proline at amino acid position 64; (o) a leucine at amino acid position 67; (p) a valine at position 73; (q) a phenylalanine or a leucine or a tyrosine at amino acid position 76; (r) a methionine at amino acid position 91; (s) a lysine or a proline at amino acid position 99; (t) an isoleucine at amino acid position 102; (u) a leucine at amino acid position 110; (v) a threonine at position 111; (w) a lysine at position 114; (x) a valine at amino acid position 129; (y) a tryptophan at amino acid position 132; (z) a cysteine at amino acid position 137; (aa) a glutamine at amino acid position 158; (bb) a glutamic acid at amino acid position 162; (cc) a valine at amino acid position 176(dd) a proline at amino acid position 178; (ee) an alanine at amino acid position 185; (ff) a glycine at amino acid position 186; (gg) a valine at amino acid position 196; (hh) an asparagine at amino acid position 197; (ii) a tryptophan at amino acid position 198; (jj) an arginine at amino acid position 203; (kk) a histadine or an arginine at amino acid position 213; (ll) an arginine at amino acid position 217; (mm) a leucine at amino acid position 225; (nn) a glycine at amino acid position 227; (oo) a threonine at amino acid position 236; (pp) a methionine or an arginine at amino acid position 244; (qq) a glycine at amino acid position 254; (rr) a cysteine or an arginine at amino acid position 256; (ss) a threonine or a valine at amino acid position 258; (tt) a lysine or a valine at amino acid position 278; (uu) a serine or a valine at amino acid position 282; (vv) a phenylalanine at amino acid position 292; (ww) a threonine or an aspartic acid or a valine at amino acid position 297; (xx) a valine or a cysteine at amino acid position 298; (yy) a leucine at amino acid position 299; (zz) a lysine or a tryptophan or a leucine at amino acid position 300; (aaa) a cysteine at amino acid position 301; (bbb) a threonine at amino acid position 302; (ccc) an arginine at amino acid position 316; (ddd) an arginine at amino acid position 321; and (eee) a lysine at amino acid position 322.

In one embodiment, the engineered thioesterase variant is a member selected from the group consisting of: SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58 and SEQ ID NO:59.

In one embodiment, the engineered thioesterase variant has an increased positive surface charge by comparison to SEQ ID NO:1.

In one embodiment, the engineered thioesterase variant has an increased positive surface charge by comparison to SEQ ID NO:4. In one embodiment, the engineered thioesterase variant is a member selected from the group consisting of: SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, and SEQ ID NO:46.

In one embodiment, the engineered thioesterase variant has an increased positive surface charge by comparison to SEQ ID NO:15. In one embodiment, the engineered thioesterase variant is a member selected from the group consisting of: SEQ ID NO:47, SEQ ID NO:48, SEQ ID NO:49, SEQ ID NO:50 and SEQ ID NO:51.

In one embodiment, the engineered thioesterase variant has improved solubility. In one embodiment, the engineered thioesterase variant has improved solubility by comparison to SEQ ID NO:49. In one embodiment, the engineered thioesterase variant has a truncation mutation between amino acids 2 and 40 of SEQ ID NO:49. In one embodiment, the engineered thioesterase variant is a member selected from the group consisting of: SEQ ID NO:52, SEQ ID NO:53, SEQ ID NO:54, SEQ ID NO:55, SEQ ID NO:56, SEQ ID NO:57, SEQ ID NO:58 and SEQ ID NO:59.

In another aspect, the disclosure provides a composition of medium-chain fatty acid derivatives having a ratio of C8 fatty acid derivatives to C10 fatty acid derivatives (C8/C10) of at least 3.6. In one embodiment, the ratio of C8 fatty acid derivatives to C10 fatty acid derivatives is 7.7.

BRIEF DESCRIPTION OF THE FIGURES

FIG. 5A Illustrates that the FALC-producing strain (sRG.674) was unable to grow on minimal salt medium with glucose as the carbon source. In contrast, on the same media with the expression of the o-alcohol acetyl transferase (AAT) in strain sJN.209, there was no growth inhibition. FIG. 5B Illustrates the level of total fatty species (FAS) produced by the FALC-producing strain (sRG.674) and the AAT expressing strain, sJN.209. FIG. 5C Illustrates a comparison of the level and composition of the fatty species produced by the FALC-producing strain (sRG.674) and the AAT expressing strain, sJN.209.

Strains sRS.786 and Stpay.179 were grown in minimal salt medium with glucose as the carbon source. Additionally, ethanol was fed during the course of the fermentation run to maintain a concentration around 2 g/L of the alcohol. FIG. 7A The strain producing solely FFAs (sRS.786) stopped growth and glucose consumption approximately 10 hours after IPTG was added to induce the expression of the medium-chain length acyl-ACP thioesterase. In contrast, strain Stpay.179, which expressed the esterification pathway, was able to continue growth following IPTG induction. FIG. 7B Strain sRS.786 ceased production of medium-chain fatty acid species (FAS) approximately 10 hours after IPTG was added to induce the expression of the medium-chain length acyl-ACP thioesterase, ultimately producing only about 5 g of C8+C10. In contrast, strain Stpay.179 continued to grow and produce FAS throughout the entire fermentation run ultimately producing over 84 g/kg of total fatty acid species. FIG. 7C. Strain Stpay.179, which expressed the esterification pathway, was able to grow and produce a titer of over 84 g/kg of total fatty acid species, 93% of which were C8-C10 FFAs.

FIG. 9 Illustrates the structure based sequence alignment used for building the model of SEQ ID NO:1 disclosed in Example 6.

DETAILED DESCRIPTION

Definitions

Figure 1:
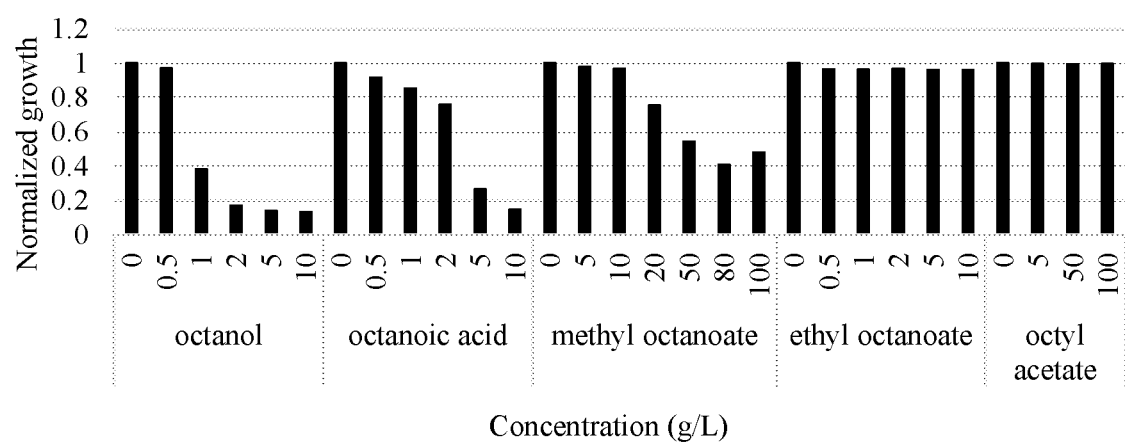
FIG. 1 Illustrates Minimum Inhibitory Concentration (MIC) curves for different C8 aliphatic compounds.

As used herein and in the appended claims, singular articles such as "a" and "an" and "the" and similar referents in the context of describing the elements are to be construed to cover both the singular and the plural, unless otherwise indicated herein or clearly contradicted by context. Thus, for example, reference to "a host cell" includes two or more such host cells, reference to "a nucleic acid sequence" includes one or more nucleic acid sequences, reference to "an enzyme" includes one or more enzymes, and the like.

As used herein, "about" is understood by persons of ordinary skill in the art and may vary to some extent depending upon the context in which it is used. If there are uses of the term which are not clear to persons of ordinary skill in the art given the context in which the term "about" is used, "about" will mean up to plus or minus 10% of the particular term.

As will be understood by one skilled in the art, for any and all purposes, all ranges disclosed herein also encompass any and all possible subranges and combinations of subranges thereof. Furthermore, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Unless defined otherwise, technical and scientific terms used herein have the same meaning as commonly understood by a person of ordinary skill in the art. In particular, this disclosure utilizes routine techniques in the field of recombinant genetics, organic chemistry, fermentation and biochemistry. Basic texts disclosing the general terms in molecular biology and genetics include e.g., Lackie, *Dictionary of Cell and Molecular Biology*, Elsevier (5th ed. 2013). Basic texts disclosing the general methods and terms in biochemistry include e.g., Lehninger *Principles of Biochemistry* Sixth edition, David L. Nelson and Michael M. Cox eds. W.H. Freeman (2012). Basic texts disclosing the general methods and terminology of fermentation include e.g., *Principles of Fermentation Technology*, 3rd Edition by Peter F Stanbury, Allan Whitaker and Stephen J Hall. Butterworth-Heinemann (2016). Basic texts disclosing the general methods and terms organic chemistry include e.g., Favre, Henri A. and Powell, Warren H. *Nomenclature of Organic Chemistry. IUPAC Recommendations and Preferred Name* 2013. Cambridge, UK: The Royal Society of Chemistry, 2013; *Practical Synthetic Organic Chemistry: Reactions, Principles, and Techniques*, Stephane Caron ed., John Wiley and Sons Inc. (2011); *Organic Chemistry*, 9th Edition—Francis Carey and Robert Giuliano, McGraw Hill (2013).

Sequence Accession numbers throughout this description were obtained from databases provided by the NCBI (National Center for Biotechnology Information) maintained by the National Institutes of Health, U.S.A. (which are identified herein as "NCBI Accession Numbers" or alternatively as "GenBank Accession Numbers" or alternatively a simply "Accession Numbers"), and from the UniProt Knowledgebase (UniProtKB) and Swiss-Prot databases provided by the Swiss Institute of Bioinformatics (which are identified herein as "UniProtKB Accession Numbers").

Enzyme Classification (EC) numbers are established by the Nomenclature Committee of the International Union of Biochemistry and Molecular Biology (IUBMB), description of which is available on the IUBMB Enzyme Nomenclature website on the World Wide Web. EC numbers classify enzymes according to the reaction they catalyze. For example, thioesterase enzymatic activity is classified under E.C. 3.1.2.1-3.1.2.27 and 3.1.2.-. A particular classification is based on the activities of different thioesterases on different substrates.

For example, in some exemplary embodiments, thioestrases which catalyze the hydrolysis of the thioester bond of C6-C18 alkyl thioesters, such as acyl-acyl carrier protein thioesters (Acyl-ACP) and acyl-CoenzymeA thioesters (Acyl-CoA) are classified under E.C. 3.1.2.- to 3.1.2.14. Thioesterases are present in most prokaryotes and in the chloroplasts of most plants and algae. The functionality of thioesterases is conserved in most prokaryotes from one species to the next. Thus, different microbial species can carry out the same thioesterase enzymatic activity that is classified under E.C. 3.1.2.1-3.1.2.27 and 3.1.2.-.

The term "fatty acid" as used herein, refers to an aliphatic carboxylic acid having the formula RCOOH wherein R is an aliphatic group having at least 4 carbons, typically between about 4 and about 28 carbon atoms. The aliphatic R group can be saturated or unsaturated, branched or unbranched. Unsaturated "fatty acids" may be monounsaturated or polyunsaturated.

A "fatty acid" or "fatty acids", as used herein, are produced within a cell through the process of fatty acid biosynthesis, through the reverse of fatty acid beta-oxidation, or they can be fed to a cell. As is well known in the art, fatty acid biosynthesis is generally a malonyl-CoA dependent synthesis of acyl-ACPs, while the reverse of beta-oxidation results in acyl-CoAs. Fatty acids fed to cell are converted to acyl-CoAs.

Fatty acid biosynthesis and degradation occur in all life forms, including prokaryotes, single cell eukaryotes, higher eukaryotes, and Archaea. The tools and methods disclosed herein are useful in the production of medium-chain fatty acid derivatives that are derived through any one or more of fatty acid synthesis, degradation, or feeding in any organism that naturally produces alkyl thioesters.

The term "medium-chain fatty acid" or equivalently "medium-chain length fatty acid" as used herein, refers to a fatty acid having a carbon chain length of between 6 to 10 carbons. Thus, in some exemplary embodiments, a "medium-chain fatty acid" is a fatty acid having a carbon chain length of six carbons, a carbon chain length of seven carbons, a carbon chain length of eight carbons, a carbon chain length of nine carbons, or a carbon chain length of ten carbons.

The term "fatty acid derivative" as used herein, refers to a product made derived from a fatty acid. Thus, a "fatty acid derivative" includes "fatty acids" and "medium-chain fatty acids" as defined above. In general, "fatty acid derivatives" include malonyl-CoA derived compounds including acyl-ACP or acyl-ACP derivatives. "Fatty acid derivatives" also include malonyl-CoA derived compounds such as acyl-CoA or acyl-CoA derivatives. Thus, a "fatty acid derivative" includes a molecule/compound that is derived from a metabolic pathway that includes a thioesterase reaction. Exemplary fatty acid derivatives include fatty acids, fatty acid esters (e.g., waxes, fatty acid esters, fatty acid methyl esters (FAME), fatty acid ethyl esters (FAEE)), fatty alcohol acetate esters (FACE), fatty amines, fatty aldehydes, fatty alcohols, hydrocarbons e.g., alkanes, alkenes, etc, ketones, terminal olefins, internal olefins, 3-hydroxy fatty acid derivatives, bifunctional fatty acid derivatives (e.g., ω-hydroxy fatty acids, 1,3 fatty-diols, α,ω-diols, α,ω-3-hydroxy triols, ω-hydroxy FAME, ω-OH FAEE, etc), and unsaturated fatty acid derivatives, including unsaturated compounds of each of the above mentioned fatty acid derivatives.

The expression "fatty acid derivative composition" as used herein, refers to a composition of fatty acid derivatives, for example a fatty acid composition produced by an organism. A "fatty acid derivative composition" may comprise a single fatty acid derivative species or may comprise a mixture of fatty acid derivative species. In some exemplary embodiments, the mixture of fatty acid derivatives includes more than one type of fatty acid derivative product (e.g., fatty acids, fatty acid esters, fatty alcohols, fatty alcohol acetates, fatty aldehydes, fatty amine, bifunctional fatty acid derivatives, etc.). In other exemplary embodiments, the mixture of fatty acid derivatives includes a mixture of fatty acid esters (or another fatty acid derivative) with different chain lengths, saturation and/or branching characteristics. In other exemplary embodiments, the mixture of fatty acid derivatives comprises predominantly one type of fatty acid derivative e.g., a medium-chain fatty acid derivative composition. In still other exemplary embodiments, the mixture of fatty acid derivatives comprises a mixture of more than one type of fatty acid derivative product e.g., fatty acid derivatives with different chain lengths, saturation and/or branching characteristics. In still other exemplary embodiments, the mixture of fatty acid derivatives comprises a mixture of fatty esters and beta-hydroxy esters. In still other exemplary embodiments, a fatty acid derivative composition comprises a mixture of fatty alcohols and fatty aldehydes. In still other exemplary embodiments, a fatty acid derivative composition comprises a mixture of FAME and/or FAEE, in particular a mixture of medium-chain FAME and/or FAEE. In still other exemplary embodiments, a fatty acid derivative composition comprises a mixture of fatty alcohol acetate esters (FACE), in particular a mixture of medium-chain fatty alcohol acetate esters (FACE).

As used herein, the term "nucleotide" takes its customary meaning as known in the art. In addition to referring to the naturally occurring ribonucleotide or deoxyribonucleotide monomers, the term "nucleotide" encompasses nucleotide analogs, and modified nucleotides such as amino modified nucleotides. In addition, "nucleotide" includes non-naturally occurring analog structures. Thus, for example, the individual units of a peptide nucleic acid, each containing a base, may be referred to herein as a nucleotide.

The term "polynucleotide" refers to a polymer of ribonucleotides (RNA) or deoxyribonucleotides (DNA) typically in phosphodiester linkage which can be single-stranded or double-stranded and which may contain natural and/or non-natural and/or altered nucleotides. The terms "polynucleotide," "nucleic acid sequence," and "nucleotide sequence" are used interchangeably herein to refer to a polymeric form of nucleotides of any length, either RNA or DNA. These terms refer to the primary structure of the molecule, and thus include polynucleotides that are single-stranded, double-stranded, triple-stranded, quadruplexed, partially double-stranded, branched, hairpinned, circular, in a padlocked conformation, etc. The terms include, as equivalents, analogs of either RNA or DNA made from nucleotide analogs and modified polynucleotides such as, though not limited to methylated and/or capped polynucleotides. A polynucleotide can be in any form, including but not limited to, plasmid, viral, chromosomal, EST, cDNA, mRNA, and rRNA and may be prepared by any known method, including synthetic, recombinant, ex vivo generation, or a combination thereof, as well as utilizing any purification methods known in the art As used herein, the terms "polypeptide" and "protein" are used interchangeably to refer to a polymer of amino acid residues that is typically 12 or more amino acids in length. Polypeptides less than 12 amino acids in length are referred to herein as "peptides". The terms apply to amino acid polymers in which one or more amino acid residue is an artificial chemical mimetic of a corresponding naturally occurring amino acid, as well as to naturally occurring amino acid polymers and non-naturally occurring amino acid polymers. The term "recombinant polypeptide" refers to a polypeptide that is produced by recombinant techniques, wherein generally DNA or RNA encoding the expressed protein is inserted into a suitable expression vector that is in turn used to transform a host cell to produce the polypeptide. In some exemplary embodiments, DNA or RNA encoding an expressed peptide, polypeptide or protein is inserted into the host chromosome via homologous recombination or other means well known in the art, and is so used to transform a host cell to produce the peptide or polypeptide. Similarly, the terms "recombinant polynucleotide" or "recombinant nucleic acid" or "recombinant DNA" are produced by recombinant techniques that are known to those of skill in the art (see e.g., methods described in Sambrook et al., Molecular Cloning—A Laboratory Manual, Cold Spring Harbor Press 4$^{th}$ Edition (Cold Spring Harbor, N.Y. 2012) or Current Protocols in Molecular Biology Volumes 1-3, John Wiley & Sons, Inc. (1994-1998) and Supplements 1-115 (1987-2016)).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. In some exemplary embodiments, the single letter code set forth in the Table below is used to refer to a particular member of the 20 common naturally occurring amino acids. The single letter amino acid code is well known in the art (see e.g., Lehninger, supra).

| Amino Acid | Single Letter Code | Amino Acid | Single Letter Code |
| --- | --- | --- | --- |
| Glycine | G | Proline | P |
| Alanine | A | Valine | V |
| Leucine | L | Isoleucine | I |
| Methionine | M | Cysteine | C |
| Phenylalanine | F | Tyrosine | Y |
| Tryptophan | W | Histidine | H |
| Lysine | K | Arginine | R |
| Glutamine | Q | Asparagine | N |
| Glutamic acid | E | Aspartic Acid | D |
| Serine | S | Threonine | T |

When referring to two nucleotide or polypeptide sequences, the "percentage of sequence identity" between the two sequences is determined by comparing the two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The "percentage of sequence identity" is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Thus, the expression "percent identity," or equivalently "percent sequence identity" in the context of two or more nucleic acid sequences or peptides or polypeptides, refers to two or more sequences or subsequences that are the same or have a specified percentage of nucleotides or amino acids that are the same (e.g., about 50% identity, preferably 55%, 60%, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured e.g., using a BLAST or BLAST 2.0 sequence comparison algorithm with default parameters (see e.g., Altschul et al. (1990) J Mol. Biol. 215(3):403-410) and/or the NCBI web site at ncbi.nlm.nih.gov/BLAST/) or by manual alignment and visual inspection. Percent sequence identity between two nucleic acid or amino acid sequences also can be determined using e.g., the Needleman and Wunsch algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6 (Needleman and Wunsch (1970) J. Mol. Biol. 48:444-453). The percent sequence identity between two nucleotide sequences also can be determined using the GAP program in the GCG software package, using a NWSgapdna.CMP matrix and a gap weight of 40, 50, 60, 70, or 80 and a length weight of 1, 2, 3, 4, 5, or 6. One of ordinary skill in the art can perform initial sequence identity calculations and adjust the algorithm parameters accordingly. A set of parameters that may be used if a practitioner is uncertain about which parameters should be applied to determine if a molecule is within a homology limitation of the claims, are a Blossum 62 scoring matrix with a gap penalty of 12, a gap extend penalty of 4, and a frameshift gap penalty of 5. Additional methods of sequence alignment are known in the biotechnology arts (see, e.g., Rosenberg (2005) BMC Bioinformatics 6:278; Altschul et al. (2005) FEBS J. 272(20): 5101-5109).

Two or more nucleic acid or amino acid sequences are said to be "substantially identical," when they are aligned and analyzed as discussed above and are found to share about 50% identity, preferably 55%, 60%, 65%, 70%, 75%, 80%, 85%, 90%, 91%, 92%, 93%, 94%, 95%, 96%, 97%, 98%, 99%, or higher identity over a specified region. Two nucleic acid sequences or polypeptide sequences are said to be "identical" if the sequence of nucleotides or amino acid residues, respectively, in the two sequences are the same when aligned for maximum correspondence as described above. This definition also refers to, or may be applied to, the compliment of a test sequence. Identity is typically calculated over a region that is at least about 25 amino acids or nucleotides in length, or more preferably over a region that is 50-100 amino acids or nucleotides in length, or over the entire length of a given sequence.

The expressions "hybridizes under low stringency, medium stringency, high stringency, or very high stringency conditions" describes conditions for hybridization and washing. Guidance for performing hybridization reactions can be found e.g., in Current Protocols in Molecular Biology, John Wiley & Sons, N.Y. (1989), 6.3.1-6.3.6. Aqueous and non-aqueous methods are described in the cited reference and either method can be used. Specific hybridization conditions referred to herein are as follows: (1) low stringency hybridization conditions—6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions—6×SSC at about 45° C., followed by one or more washes in 0.2×SSC, 0.1% SDS at 60° C.; (3) high stringency hybridization conditions—6×SSC at about 45° C., followed by one or more washes in 0.2.×SSC, 0.1% SDS at 65° C.; and (4) very high stringency hybridization conditions—0.5M sodium phosphate, 7% SDS at 65° C., followed by one or more washes at 0.2×SSC, 1% SDS at 65° C. Very high stringency conditions (4) are the preferred conditions unless otherwise specified.

The term "endogenous" as used herein refers to a substance e.g., a nucleic acid, protein, etc. that is produced from within a cell. Thus, an "endogenous" polynucleotide or polypeptide refers to a polynucleotide or polypeptide produced by the cell. In some exemplary embodiments an "endogenous" polypeptide or polynucleotide is encoded by the genome of the parental cell (or host cell). In other exemplary embodiments, an "endogenous" polypeptide or polynucleotide is encoded by an autonomously replicating plasmid carried by the parental cell (or host cell). In some exemplary embodiments, an "endogenous" gene is a gene that was present in the cell when the cell was originally isolated from nature i.e., the gene is "native to the cell". In other exemplary embodiments, an "endogenous" gene has been altered through recombinant techniques e.g., by altering the relationship of control and coding sequences. Thus, a "heterologous" gene may, in some exemplary embodiments, be "endogenous" to a host cell.

In contrast, an "exogenous" polynucleotide or polypeptide, or other substance (e.g., fatty acid derivative, small molecule compound, etc.) refers to a polynucleotide or polypeptide or other substance that is not produced by the parental cell and which is therefore added to a cell, a cell culture or assay from outside of the cell.

As used herein the term "native" refers to the form of a nucleic acid, protein, polypeptide or a fragment thereof that is isolated from nature or a nucleic acid, protein, polypeptide or a fragment thereof that is without intentionally introduced mutations.

As used herein, the term "fragment" of a polypeptide refers to a shorter portion of a full-length polypeptide or protein ranging in size from two amino acid residues to the entire amino acid sequence minus one amino acid residue. In certain embodiments of the disclosure, a fragment refers to the entire amino acid sequence of a domain of a polypeptide or protein (e.g., a substrate binding domain or a catalytic domain).

The term "mutagenesis" refers to a process by which the genetic information of an organism is changed in a stable manner to produce a "mutant" or "variant". Mutagenesis of a protein coding nucleic acid sequence to produce a mutant nucleic acid sequence produces a mutant protein. Mutagenesis also refers to changes in non-coding nucleic acid sequences. In some exemplary embodiments, a mutation in a non-coding nucleic acid sequence results in modified protein activity.

Thus, a "mutation", as used herein, refers to a permanent change in a nucleic acid position of a gene or in an amino acid position (residue) of a polypeptide or protein. Indeed, the term "mutation" refers to, in the context of a polynucleotide, a modification to the polynucleotide sequence resulting in a change in the sequence of a polynucleotide with reference to a control or reference polynucleotide sequence. In some exemplary embodiments, a mutant polynucleotide sequence refers to an alteration that does not change the encoded amino acid sequence, for example, with regard to codon optimization for expression purposes. In other exemplary embodiments, a mutation in a polynucleotide sequence modifies a codon in such a way as to result in a modification of the encoded amino acid sequence. Thus a polynucleotide encoding an engineered thioesterase variant having improved ability to produce medium chain fatty acid derivatives will have at least one mutation in comparison to a polynucleotide encoding a control thioesterase.

Similarly in the context of a protein, the term "mutation" or "mutated" refers to a modification to the amino acid sequence resulting in a change in the sequence of a protein with reference to a control or reference protein sequence. A mutation can refer to a substitution of one amino acid with another amino acid, or an insertion or a deletion of one or more amino acid residues. In some exemplary embodiments, a "mutation" is the replacement of an amino acid with a non-natural amino acid, or with a chemically-modified amino acid residues. In other exemplary embodiments, a "mutation" is a truncation (e.g., a deletion or interruption) in a sequence or a subsequence relative to the precursor sequence or a shortening of a sequence by deletion from one or another end. In other exemplary embodiments, a mutation is an addition of an amino acid or of a subsequence (e.g., two or more amino acids in a stretch, which are inserted between two contiguous amino acids in a precursor protein sequence) within a protein, or at either terminal end of a protein, thereby increasing the length of (or elongating) the protein. Mutations can be introduced into a polynucleotide through any number of methods known to those of ordinary skill in the art, including e.g., random mutagenesis, site-specific mutagenesis, oligonucleotide directed mutagenesis, gene shuffling, directed evolution techniques, combinatorial mutagenesis, chemical synthesis, site saturation mutagenesis, etc.

The term "mutant" or equivalently, "variant" as used herein, refers to a polynucleotide sequence or polypeptide sequence which comprises at least one mutation. Thus, an engineered thioesterase variant having improved ability to produce medium chain fatty acid derivatives will have at least one mutation in its polypeptide sequence in comparison to a control thioesterase.

As used herein, the term "engineered thioesterase variant" refers to a mutant or variant thioesterase having at least one mutation as compared to SEQ ID NO:1 wherein the thioesterase variant has improved activity for the production of medium-chain fatty acid derivatives.

The term "gene" as used herein, refers to nucleic acid sequences e.g., DNA sequences, which encode either an RNA product or a protein product, as well as operably-linked nucleic acid sequences that affect expression of the RNA or protein product (e.g., expression control sequences such as e.g., promoters, enhancers, ribosome binding sites, translational control sequences, etc). The term "gene product" refers to either the RNA e.g., tRNA, mRNA and/or protein expressed from a particular gene.

The term "expression" or "expressed" as used herein in reference to a gene, refers to the production of one or more transcriptional and/or translational product(s) of a gene. In exemplary embodiments, the level of expression of a DNA molecule in a cell is determined on the basis of either the amount of corresponding mRNA that is present within the cell or the amount of protein encoded by that DNA produced by the cell. The term "expressed genes" refers to genes that are transcribed into messenger RNA (mRNA) and then translated into protein, as well as genes that are transcribed into other types of RNA, such as e.g., transfer RNA (tRNA), ribosomal RNA (rRNA), and regulatory RNA, which are not translated into protein.

The level of expression of a nucleic acid molecule in a cell or cell free system is influenced by "expression control sequences" or equivalently "regulatory sequences". "Expression control sequences" or "regulatory sequences" are known in the art and include, for example, promoters, enhancers, polyadenylation signals, transcription terminators, nucleotide sequences that affect RNA stability, internal ribosome entry sites (IRES), and the like, that provide for the expression of the polynucleotide sequence in a host cell. In exemplary embodiments, "expression control sequences" interact specifically with cellular proteins involved in transcription (see e.g., Maniatis et al., *Science,* 236: 1237-1245 (1987); Goeddel, Gene Expression Technology: Methods in Enzymology, Vol. 185, Academic Press, San Diego, Calif. (1990)). In exemplary methods, an expression control sequence is operably linked to a polynucleotide sequence. By "operably linked" is meant that a polynucleotide sequence and an expression control sequence(s) are functionally connected so as to permit expression of the polynucleotide sequence when the appropriate molecules (e.g., transcriptional activator proteins) contact the expression control sequence(s). In exemplary embodiments, operably linked promoters are located upstream of the selected polynucleotide sequence in terms of the direction of transcription and translation. In some exemplary embodiments, operably linked enhancers can be located upstream, within, or downstream of the selected polynucleotide.

In general, "minimum inhibitory concentration" (MIC) is the lowest concentration of an antimicrobial substance that will inhibit the visible growth of a microorganism after overnight incubation. MICs can be determined on plates of solid growth medium or broth dilution methods. For example, to identify the MIC via broth dilution, identical doses of bacteria are cultured in wells of liquid media containing progressively lower concentrations of the drug. The minimum inhibitory concentration of the antibiotic is between the concentrations of the last well in which no bacteria grew and the next lower dose, which allowed bacterial growth. As used herein, the expression "Minimum Inhibitory Concentration" or "MIC" refers to the concentration o of a compound that results in a 50% reduction in the growth of a microbial culture in a 24 hour incubation period relative to a control. In an embodiment, the "Minimum Inhibitory Concentration" of a potentially toxic compound e.g., octanol, is measured by growing a culture of cells e.g., *E. coli* cells, in varying concentrations of the potentially toxic compound, and then determining how much growth of the cultures has occurred over a 24 hour period in the presence of the potentially toxic compound. In exemplary embodiments, growth of the culture is measured by measuring the total protein from a lysed culture after 24 hours of growth as a measure of the total number of cells in the culture.

As used herein, "modified activity" or an "altered level of activity" of a protein/polypeptide e.g., of a engineered thioesterase variant, refers to a difference in one or more characteristics in the activity the protein/polypeptide as compared to the characteristics of an appropriate control protein e.g., the corresponding parent protein or corresponding wild type protein. Thus, in exemplary embodiments, a difference in activity of a protein having "modified activity" as compared to a corresponding control protein is determined by measuring the activity of the modified protein in a recombinant host cell and comparing that to a measure of the same activity of a corresponding control protein in an otherwise isogenic host cell. Modified activities can be the result of, for example, changes in the structure of the protein (e.g., changes to the primary structure, such as e.g., changes to the protein's nucleotide coding sequence that result in changes in substrate specificity, changes in observed kinetic parameters, changes in solubility, etc.); changes in protein stability (e.g., increased or decreased degradation of the protein) etc. In some exemplary embodiments, a polypeptide having "modified activity" is a mutant or an engineered TE variant disclosed herein.

In exemplary embodiments, a polypeptide disclosed herein has "modified activity" that is e.g., an "improved level of activity". The expression "improved level of activity" as used herein, refers to a polypeptide that has a higher level of biochemical or biological function (e.g., DNA binding or enzymatic activity) as compared to a level of biochemical and/or biological function of a corresponding control polypeptide under the same conditions. The degree of improved activity can be about 10% or more, about 20% or more, about 50% or more, about 75% or more, about 100% or more, about 200% or more, about 500% or more, about 1000% or more, or any range therein, Thus, "improved activity" may refer to improved catalytic activity or improved catalytic efficiency of a polypeptide, wherein catalytic efficiency refers to e.g. an increase in the reaction rate of the reaction catalyzed by such enzyme of polypeptide. Catalytic activity/catalytic efficiency can be improved e.g., by improving one or more kinetic parameters (measure or calculated) of the reaction such as Vmax (maximum rate the reaction can proceed at), Km (Michaelis constant), kcat (number of substrate molecules turned over per enzyme molecule per second), etc., or any ratio between such parameter, such as kcat/Km (a measure of enzyme efficiency. Thus, "improved catalytic activity" or "improved catalytic efficiency" of a polypeptide can be measured in any number of ways. For example, "improved activity" may be measured as an increase in titer (concentration: g/L, or mg/L, or g/Kg), a change in composition (amount of a specific fatty acid species/total fatty acid derivatives (FAS) produced), an improved ratio of molecular components (e.g. C8/C10 content or C10/C12 content, etc.) or an increase in FOC (fold over control, see below) of the products produced by a recombinant cell expressing an enzyme of improved activity.

Thus, the expression "having improved activity for production of medium-chain fatty acid derivatives" or "having improved activity for production of medium-chain length fatty acid derivative compounds" or "having improved activity for production of medium-chain aliphatic compounds" or "having improved ability to produce medium-chain length fatty acid derivatives" or "having improved ability to produce medium-chain fatty acid derivatives" as used herein refers to "improved activity" e.g., "improved catalytic activity" of a polypeptide/protein that leads to an increase in production of medium-chain fatty acid derivative species (fatty acids and fatty acid derivatives having alkyl chains of 6-10 carbons in length) when compared to an appropriate control polypeptide/protein under the same conditions.

In some exemplary embodiments, a polypeptide/protein "having improved activity for production of medium-chain fatty acid derivatives" or equivalently "having improved ability to produce medium-chain fatty acid derivatives" has improved activity for the production of a particular chain length medium-chain fatty acid derivative. Thus, for example the expression "having improved activity for production of C8 fatty acid derivatives" as used herein, refers to a polypeptide/protein that has "improved catalytic activity" or "improved activity" that leads to an increase in production of eight carbon fatty acid derivatives (measured e.g., as % C8 FAS, increased C8/C10 ratio, etc.)

Similarly, in some exemplary embodiments, a polypeptide/protein "having improved activity for production of medium-chain fatty acid derivatives" or equivalently "having improved ability to produce medium-chain fatty acid derivatives" has "improved activity for production of C10 fatty acid derivatives". Thus, such a polypeptide/protein has "improved activity" that leads to an increase in production of ten carbon fatty acid derivatives (measured e.g., as % C10 FAS, increased C10/C12 ratio, etc.)

The expression "fold over control" or equivalently "FOC" as used herein refers to the ratio of a particular metric measured of a cell comprising an engineered thioesterase variant to the same metric measured in an appropriate control cell e.g., an isogenic host cell which comprises a control thioesterase that does not have the engineered variation. Thus, generally, FOC is equivalent to Metric A of variant/Metric A of control (In some exemplary embodiments, FOC of % C8 means the % C8 produced by a cell comprising a engineered thioesterase variant compared to the % C8 of an appropriate control e.g., an isogenic control comprising a thioesterase that was not engineered to contain the specific variation. Thus, in an exemplary embodiment, a recombinant cell comprising a engineered thioesterase variant that has an FOC of 1.1 of % C8 indicates a 10% improvement (increase) in the percent of eight carbon fatty acid derivatives produced by the cell comprising a engineered thioesterase variant as compared to the % C8 of an isogenic control comprising a control thioesterase.

A "control" sample e.g., a "control" nucleotide sequence, a "control" polypeptide sequence, a "control" cell, etc., or value refers to a sample that serves as a reference, usually a known reference, for comparison to a test sample. For example, in an exemplary embodiment, a test sample comprises a fatty acid derivative composition made by a engineered thioesterase variant, while the control sample comprises a fatty acid derivative composition made by the corresponding or designated un-modified/non-variant thioesterase (e.g., SEQ ID NO:1). One of skill will recognize that controls can be designed for assessment of any number of parameters. Furthermore, one of skill in the art will understand which controls are valuable in a given situation and will be able to analyze data based on comparisons to control values.

The term "recombinant" as used herein, refers to a genetically modified polynucleotide, polypeptide, cell, tissue, or organism. The term "recombinant applies equally to the first generation of genetically modified polynucleotides, polypeptides, cells, tissues, or organisms as well as to the descendants of genetically modified polynucleotides, polypeptides, cells, tissues, or organisms that carry the genetic modification.

When used with reference to a cell, the term "recombinant" indicates that the cell has been modified by the introduction of a heterologous nucleic acid or protein or has been modified by alteration of a native nucleic acid or protein, or that the cell is derived from a cell so modified and that the derived cell comprises the modification. Thus, for example, "recombinant cells" or equivalently "recombinant host cells" may be modified to express genes that are not found within the native (non-recombinant) form of the cell or may be modified to abnormally express native genes e.g., native genes may be overexpressed, underexpressed or not expressed at all. In exemplary embodiments, a "recombinant cell" or "recombinant host cell" is engineered to express a heterologous thioesterase, such as an engineered thioesterase variant that has improved activity for the production of medium-chain fatty acid derivatives. A recombinant cell can be derived from a microorganism such as a bacterium, a virus or a fungus. In addition, a recombinant cell can be derived from a plant or an animal cell. In exemplary embodiments, a "recombinant host cell" or "recombinant cell" is used to produce one or more fatty acid derivatives including, but not limited to, fatty acids, fatty esters (e.g., waxes, fatty acid esters, fatty esters, fatty acid methyl esters (FAME), fatty acid ethyl esters (FAEE)), fatty alcohol acetate esters (FAce), fatty alcohols, fatty aldehydes, hydrocarbons, fatty amines, terminal olefins, internal olefins, ketones, bifunctional fatty acid derivatives (e.g., omega-hydroxy fatty acids, omega-hydroxy diols, omega-hydroxy FAME, omega-hydroxy FAEE) etc. Therefore, in some exemplary embodiments a "recombinant host cell" is a "production host" or equivalently, a "production host cell". In some exemplary embodiments, the recombinant cell includes one or more polynucleotides, each polynucleotide encoding a polypeptide having fatty acid biosynthetic enzyme activity, wherein the recombinant cell produces a fatty acid derivative composition when cultured in the presence of a carbon source under conditions effective to express the polynucleotides.

When used with reference to a polynucleotide, the term "recombinant" or equivalently "heterologous" indicates that the polynucleotide has been modified by comparison to the native or naturally occurring form of the polynucleotide or has been modified by comparison to a naturally occurring variant of the polynucleotide. In an exemplary embodiment, a recombinant polynucleotide (or a copy or complement of a recombinant polynucleotide) is one that has been manipulated by the hand of man to be different from its naturally occurring form. Thus, in an exemplary embodiment, a recombinant polynucleotide is a mutant form of a native gene or a mutant form of a naturally occurring variant of a native gene wherein the mutation is made by intentional human manipulation e.g., made by saturation mutagenesis using mutagenic oligonucleotides, through the use of UV radiation or mutagenic chemicals, etc. Such a recombinant polynucleotide might comprise one or more point mutations, deletions and/or insertions relative to the native or naturally occurring variant form of the gene. Similarly, a polynucleotide comprising a promoter operably linked to a second polynucleotide (e.g., a coding sequence) is a "recombinant" polynucleotide. Thus, a recombinant polynucleotide comprises polynucleotide combinations that are not found in nature. A recombinant protein (discussed supra) is typically one that is expressed from a recombinant polynucleotide, and recombinant cells, tissues, and organisms are those that comprise recombinant sequences (polynucleotide and/or polypeptide).

As used herein, the term "microorganism" refers generally to a microscopic organism. Microorganisms can be prokaryotic or eukaryotic. Exemplary prokaryotic microorganisms include e.g., bacteria, archaea, cyanobacteria, etc. An exemplary bacterium is *Escherichia coli*. Exemplary eukaryotic microorganisms include e.g., yeast, protozoa, algae, etc. In exemplary embodiments, a "recombinant microorganism" is a microorganism that has been genetically altered and thereby expresses or encompasses a heterologous nucleic acid sequence and/or a heterologous protein.

A "production host" or equivalently a "production host cell" is a cell used to produce products. As disclosed herein, a "production host" is typically modified to express or overexpress selected genes, or to have attenuated expression of selected genes. Thus, a "production host" or a "production host cell" is a "recombinant host" or equivalently a "recombinant host cell". Non-limiting examples of production hosts include plant, animal, human, bacteria, yeast, cyanobacteria, algae, and/or filamentous fungi cells. An exemplary "production host" is a recombinant *Escherichia coli* cell.

As used herein "acyl-ACP" refers to an acyl thioester formed between the carbonyl carbon of an acyl chain and the sulfhydryl group of the phosphopantetheinyl moiety of an acyl carrier protein (ACP). In some exemplary embodiments an acyl-ACP is an intermediate in the synthesis of fully saturated acyl-ACPs. In other exemplary embodiments an acyl-ACP is an intermediate in the synthesis of unsaturated acyl-ACPs. In some exemplary embodiments, the carbon chain of the acyl group of acyl-ACP has 5, 6, 7, 8, 9, 10, 11, 12, 13, 14, 15, 16, 17, 18, 19, 20, 21, 22, 23, 24, 25, 26, 27 or 28 carbons. In other exemplary embodiments, the carbon chain of the acyl group of acyl-ACP is a medium-chain and has 6, 7, 8, 9, 10, 11, or 12 carbons. In other exemplary embodiments the carbon chain of the acyl group of acyl-ACP is 8 carbons in length. In still other exemplary embodiments, the carbon chain of the acyl group of acyl-ACP is 10 carbons in length. Each of these acyl-ACPs are substrates for enzymes such as e.g., thioesterases e.g., engineered thioesterase variants that convert the acyl-ACP to fatty acid derivatives.

As used herein, the expression "fatty acid derivative biosynthetic pathway" refers to a biochemical pathway that produces fatty acid derivatives. The enzymes that comprise a "fatty acid derivative biosynthetic pathway" are thus referred to herein as "fatty acid derivative biosynthetic polypeptides" or equivalently "fatty acid derivative enzymes". As discussed supra, the term "fatty acid derivative," includes a molecule/compound derived from a biochemical pathway that includes a thioesterase reaction. Thus, a thioesterase enzyme (e.g., an enzyme having thioesterase activity EC 3.1.1.14) is a "fatty acid derivative biosynthetic peptide" or equivalently a "fatty acid derivative enzyme." In addition to a thioesterase, a fatty acid derivative biosynthetic pathway may include additional enzymes to produce fatty acid derivatives having desired characteristics. Thus the term "fatty acid derivative enzymes" or equivalently "fatty acid derivative biosynthetic polypeptides" refers to, collectively and individually, enzymes that may be expressed or overexpressed to produce fatty acid derivatives. Non-limiting examples of "fatty acid derivative enzymes" or equivalently "fatty acid derivative biosynthetic polypeptides" include e.g., fatty acid synthetases, thioesterases, acyl-CoA synthetases, acyl-CoA reductases, acyl ACP reductases, alcohol dehydrogenases, alcohol O-acyltransferases, fatty alcohol-forming acyl-CoA reductases, fatty acid decarboxylases, fatty aldehyde decarbonylases and/or oxidative deformylases, carboxylic acid reductases, fatty alcohol O-acetyl transferases, ester synthases, etc. "Fatty acid derivative enzymes" or equivalently "fatty acid derivative biosynthetic polypeptides" convert substrates into fatty acid derivatives. In exemplary embodiments, a suitable substrate for a fatty acid derivative enzyme may be a first fatty acid derivative, which is converted by the fatty acid derivative enzyme into a different, second fatty acid derivative.

As used herein, the term "culture" refers to a liquid media comprising viable cells. In one embodiment, a culture comprises cells growing in a predetermined culture media under controlled conditions, for example, a culture of recombinant host cells grown in liquid media comprising a selected carbon source and nitrogen. "Culturing" or "cultivation" refers to growing a population of host cells (e.g., recombinant host cells) under suitable conditions in a liquid or solid medium. In certain embodiments, culturing refers to the bioconversion of a substrate to an end-product. Culturing media are well known and individual components of such culture media are available from commercial sources, e.g., Difco™ media and BBL™ media. In one non-limiting example, the aqueous nutrient medium is a "rich medium" including complex sources of nitrogen, salts, and carbon, such as YP medium, comprising 10 g/L of peptone and 10 g/L yeast extract.

As used herein, the term "titer" refers to the quantity of a fatty acid derivative e.g., a medium-chain fatty acid derivative, produced per unit volume of host cell culture. The titer may refer to the quantity a particular fatty acid derivative e.g., a medium-chain fatty acid derivative, or a combination of a fatty acid derivatives of different chain length or different functionalities such as e.g., a mixture of saturated and unsaturated medium-chain fatty acid derivatives produced by a given recombinant host cell culture or a fatty acid derivative composition.

The expression "commercial titers" or "commercial titer" as used herein refers to the quantity of a fatty acid derivative e.g., a medium-chain fatty acid derivative, produced per unit volume of host cell culture that makes commercial production economically feasible. Typically, commercial titers are in a range that is between about 10 g/L (or equivalently 10 g/Kg) to about 200 g/L or more. Thus, commercial titers are 10 g/L or more, 20 g/L or more, 30 g/L or more, 40 g/L or more, 50 g/L or more, 60 g/L or more, 70 g/L or more, 80 g/L or more, 90 g/L or more, 100 g/L or more, 110 g/L or more, 120 g/L or more, 130 g/L or more, 140 g/L or more, 150 g/L or more, 160 g/L or more, 170 g/L or more, 180 g/L or more, 190 g/L or more, 200 g/L or more.

As used herein, the "yield of a fatty acid derivative" e.g., yield of a medium-chain fatty acid derivative or other compounds produced by a "host cell", refers to the efficiency by which an input carbon source is converted to product (i.e., a medium-chain fatty acid derivative) in a host cell. Thus, the expression "yield of a fatty acid derivative" refers to the amount of product produced from a given amount of carbon substrate. Percent yield is the percent of the theoretical yield (product synthesized in ideal conditions, with no loss of carbon or energy). Therefore, percent yield=(mass of product/mass of theoretical yield)×100. The yield may refer to a particular medium-chain fatty acid derivative or a combination of fatty acid derivatives.

As used herein, the term "productivity" refers to the quantity of medium-chain fatty acid derivative e.g., a 6-carbon fatty acid derivative, 8-carbon fatty acid derivative, 10-carbon fatty acid derivative, etc. produced per unit volume of host cell culture per unit time. The productivity may refer to a particular 8 and/or 10 carbon fatty acid derivative or a combination of fatty acid derivatives or other compound(s) produced by a given host cell culture. Thus, in exemplary embodiments, the expression of an engineered thioesterase variant in a recombinant host cell such as e.g., *E. coli* results in increased productivity of an 8 and/or 10 carbon fatty acid derivatives and/or other compounds as compared to a recombinant host cell expressing the corresponding control thioesterase or other appropriate control. As used herein, the term "total fatty species" and "total fatty acid product" and "total fatty acid derivatives" may be used interchangeably herein with reference to the amount (titer) of fatty acid derivatives that are produced by a host cell e.g., a host cell that expresses an engineered thioesterase variant. Total fatty species, etc. can be evaluated by Gas Chromatography with Flame Ionization Detector (GC-FID). The same terms may be used to mean, for example, total fatty esters, total fatty alcohols, total fatty aldehydes, total fatty amines, and total free fatty acids when referring to a total fatty acid derivative analysis. In particular, the same terms may be used to mean total fatty acid methyl esters, fatty acid ethyl esters, or fatty alcohol acetate esters.

As used herein, the term "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, and gases (e.g., CO and $CO_2$). Exemplary carbon sources include, but are not limited to, monosaccharides, such as glucose, fructose, mannose, galactose, xylose, and arabinose; oligosaccharides, such as fructo-oligosaccharide and galacto-oligosaccharide; polysaccharides such as starch, cellulose, pectin, and xylan; disaccharides, such as sucrose, maltose, cellobiose, and turanose; cellulosic material and variants such as hemicelluloses, methyl cellulose and sodium carboxymethyl cellulose; saturated or unsaturated fatty acids, succinate, lactate, and acetate; alcohols, such as ethanol, methanol, and glycerol, or mixtures thereof. The carbon source can also be a product of photosynthesis, such as glucose. In certain embodiments, the carbon source is biomass. In other embodiments, the carbon source is glucose. In other embodiments the carbon source is sucrose. In other embodiments the carbon source is glycerol. In other embodiments, the carbon source is a simple carbon source. In other embodiments, the carbon source is a renewable carbon source. In other examples, the carbon source is natural gas or a component of natural gas, such as methane, ethane, propane, etc.

As used herein, the term "biomass" refers to any biological material from which a carbon source is derived. In some embodiments, a biomass is processed into a carbon source, which is suitable for bioconversion. In other embodiments, the biomass does not require further processing into a carbon source. The carbon source can be converted into a composition comprising medium-chain fatty acid derivatives.

An exemplary source of biomass is plant matter or vegetation, such as that derived from corn, sugar cane, switchgrass, rice, wheat, hard wood, soft wood, palm, hemp, etc. Another exemplary source of biomass is metabolic waste products, such as animal matter (e.g., cow manure). Further exemplary sources of biomass include algae and other marine plants, such as macroalgae, and kelp. Biomass also includes waste products from industry, agriculture, forestry, and households, including, but not limited to, glycerol, fermentation waste, ensilage, straw, lumber, pulp, sewage, garbage, cellulosic urban waste, municipal solid waste, oleochemical waste, and food leftovers (e.g., soaps, oils and fatty acids). The term "biomass" also can refer to sources of carbon, such as carbohydrates (e.g., monosaccharides, disaccharides, or polysaccharides).

As used herein, the term "isolated," with respect to products (such as medium-chain fatty acid derivatives) refers to products that are separated from cellular components, cell culture media, or chemical or synthetic precursors. The medium-chain fatty acid derivatives produced by the methods disclosed herein can be relatively immiscible in the fermentation broth, as well as in the cytoplasm. Therefore, in exemplary embodiments, medium-chain fatty acid derivatives collect in an organic phase extracellularly and are thereby "isolated".

As used herein, the terms "purify," "purified," or "purification" mean the removal or isolation of a molecule from its environment by, for example, isolation or separation. "Substantially purified" molecules are at least about 60% free (e.g., at least about 65% free, at least about 70% free, at least about 75% free, at least about 80% free, at least about 85% free, at least about 90% free, at least about 95% free, at least about 96% free, at least about 97% free, at least about 98% free, at least about 99% free) from other components with which they are associated. As used herein, these terms also refer to the removal of contaminants from a sample. For example, the removal of contaminants can result in an increase in the percentage of medium-chain fatty acid derivatives or other compounds in a sample. For example, when a medium-chain fatty acid derivative or other compound is produced in a recombinant host cell, the medium-chain fatty acid derivative or other compound can be purified by the removal of the host cell biomass or its components, should they have lysed, such as proteins, nucleic acids, and other cellular components. After purification, the percentage of malonyl-CoA derived compounds including medium-chain fatty acid derivatives or other compounds in the sample is increased. The terms "purify," "purified," and "purification" are relative terms which do not require absolute purity. Thus, for example, when a medium-chain fatty acid derivative is produced in recombinant host cells, a medium-chain fatty acid derivative is substantially separated from other cellular components (e.g., nucleic acids, polypeptides, lipids, carbohydrates, or other hydrocarbons).

As used herein, the term "attenuate" means to weaken, reduce, or diminish. For example, the activity of a polypeptide can be attenuated, for example by modifying the polypeptide structure to reduce its activity (e.g., by modifying a nucleotide sequence that encodes the polypeptide).

I. Introduction

As discussed above, there is immense interest in medium-chain fatty acid (MCFA) derivatives and medium-chain fatty acid (MCFA)-derived products. MCFAs are valued for their many favorable properties. Indeed, MCFAs find use e.g., as renewable and biodegradable components of surfactants, adhesives, emulsifiers, edible oils, flavorants, fragances, monomer, polymers, natural product pesticides and antimicrobials, etc.

Because of their many uses, the demand for medium-chain fatty acid derivative compounds in industrial and nutraceutical applications has trended upwards over the past few years and continues to increase. Unfortunately, however, the supply of medium-chain fatty acid derivatives is largely tied to production of other longer-chain free fatty-acid products from plants or from chemical synthesis; hence, supply is quite volatile and unstable.

Thus, what is needed in the art are materials and methods that can provide a robust and stable supply chain for MCFAs and their derivatives. Fortunately, the instant disclosure provides needed tools and methods to support a robust, selective, and stable supply chain for medium-chain fatty acid derivatives and so provides for this and other needs.

II. Engineered Thioesterase Variants Having Improved Activity for Production of Medium-Chain Fatty Acid Derivatives A. General Methods This disclosure utilizes routine techniques in the field of recombinant genetics. Basic texts disclosing the general methods and terms in molecular biology and genetics include e.g., Sambrook et al., *Molecular Cloning, a Laboratory Manual*, Cold Spring Harbor Press 4th edition (Cold Spring Harbor, N.Y. 2012); *Current Protocols in Molecular Biology* Volumes 1-3, John Wiley & Sons, Inc. (1994-1998) and Supplements 1-115 (1987-2016). This disclosure also utilizes routine techniques in the field of biochemistry. Basic texts disclosing the general methods and terms in biochemistry include e.g., *Lehninger Principles of Biochemistry* sixth edition, David L. Nelson and Michael M. Cox eds. W.H. Freeman (2012). This disclosure also utilizes routine techniques in industrial fermentation. Basic texts disclosing the general methods and terms in fermentation include e.g., *Principles of Fermentation Technology,* 3rd Edition by Peter F. Stanbury, Allan Whitaker and Stephen J. Hall. Butterworth-Heinemann (2016); *Fermentation Microbiology and Biotechnology,* 2nd Edition, E. M. T. El-Mansi, C. F. A. Bryce, Arnold L. Demain and A. R. Allman eds. CRC Press (2007). This disclosure also utilizes routine techniques in the field of organic chemistry. Basic texts disclosing the general methods and terms in organic chemistry include e.g., *Practical Synthetic Organic Chemistry: Reactions, Principles, and Techniques*, Stephane Caron ed., John Wiley and Sons Inc. (2011); *The Synthetic Organic Chemist's Companion*, Michael C. Pirrung, John Wiley and Sons Inc. (2007); *Organic Chemistry,* 9th Edition—Francis Carey and Robert Giuliano, McGraw Hill (2013).

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized e.g., according to the solid phase phosphoramidite triester method first described by Beaucage & Caruthers, Tetrahedron Letts. 22:1859-1862 (1981), using an automated synthesizer, as described in Van Devanter et al., Nucleic Acids Res. 12:6159-6168 (1984). Purification of oligonucleotides is e.g., by either native acrylamide gel electrophoresis or by anion-exchange HPLC as described in Pearson & Reanier, J. Chrom. 255:137-149 (1983).

The sequence of the cloned genes and synthetic oligonucleotides can be verified after cloning using, e.g., the chain termination method for sequencing double-stranded templates of Wallace et al., Gene 16:21-26 (1981).

B. Thioesterases

1. General

Thioesterases or thiolester hydrolases catalyze the hydrolysis of a thioester into an acid and a thiol. Thioesterases (TEs) are classified into EC 3.1.2.1 through EC 3.1.2.27 based on their activities on different substrates, with many remaining unclassified (EC 3.1.2.-) (see e.g., Cantu, D. C., et al. (2010) Protein Science 19:1281-1295). TEs are obtainable from a variety of sources. Exemplary TEs include plant TEs (see e.g., Voelker and Davies, J. Bact., Vol., 176, No. 23, pp. 7320-27, 1994, U.S. Pat. Nos. 5,667,997, and 5,455,167) bacterial TEs (see e.g., U.S. Pat. No. 9,175,234); cyanobacterial TEs, as well as algal, mammalian, insect, and fungal sources.

In particular, acyl-acyl carrier protein (ACP) thioesterases (TE), which are classified under EC Number 3.1.2.14, selectively hydrolyze the thioester bonds of acyl-ACPs and release free fatty acids (FFA) and ACP. Thus, acyl-ACP thioesterases play an important role in determining the carbon chain-length of a fatty acid derivative that results from the product of their hydrolysis of a alky thioester The FatB2 thioesterase from *Cuphea hookeriana* (ChFatB2) is an exemplary acyl-ACP thioestrase. ChFatB2 has a naturally high selectivity for medium-chain length fatty acid derivatives. However, this plant enzyme has low activity when expressed in microorganisms, such as the industrial microorganism, *E. coli*. As is disclosed in detail herein, low ability to produce medium-chain length fatty acids in microbes is a result of its low activity, insufficient selectivity for C8 and C10, and poor solubility.

The polypeptide/protein sequence of the wild-type ChFatB2 from *Cuphea hookeriana* has GenBank accession number AAC49269 (see e.g., Dehesh, K., et al. (1996) The Plant Journal 9(2):167-72). The amino acid sequence of the ChFatB2 polypeptide disclosed herein is comprises the wild-type sequence wherein the first 88 amino acids, which comprise a plant translocation leader sequence at the N-terminus of the wild-type protein, are removed and replaced with a methionine (M) to facilitate production of the active form of the enzyme in the cytoplasm of a bacteria. Therefore, the amino acid sequence of the wild type ChFatB2 thioesterase disclosed herein as wild type (wt) ChFatB2 is shown below as SEQ ID NO:1:

(SEQ ID NO: 1)
MLPDWSRLLTAITTVFVKSKRPDMHDRKSKRPDMLVDSFGLESTVQDGLV

FRQSFSIRSYEIGTDRTASIETLMNHLQETSLNHCKSTGILLDGFGRTLE

MCKRDLIWVVIKMQIKVNRYPAWGDTVEINTRFSRLGKIGMGRDWLISDC

NTGEILVRATSAYAMMNQKTRRLSKLPYEVHQEIVPLFVDSPVIEDSDLK

VHKFKVKTGDSIQKGLTPGWNDLDVNQHVSNVKYIGWILESMPTEVLETQ

ELCSLALEYRRECGRDSVLESVTAMDPSKVGVRSQYQHLLRLEDGTAIVN

GATEWRPKNAGANGAISTGKTSNGNSVS

The activity of SEQ ID NO:1 is known to be specific for saturated 8-carbon (8:0) and saturated ten carbon (10:0) ACP substrates (see e.g., Dehesh, K., et al. (1996) supra). Unfortunately however, the ability to produce medium-chain length fatty acid derivatives possessed by SEQ ID NO:1 is insufficient for large scale production of medium-chain fatty acid derivatives. Therefore in response to the need for a stable and reliable supply of medium-chain fatty acid derivatives, in exemplary embodiments, SEQ ID NO:1 is altered to produce engineered TE variants having improved activity for production of medium-chain fatty acid derivatives.

Thus, in exemplary embodiments, the disclosure provides engineered TE variant polypeptides having improved activity for the production of medium-chain fatty acid derivatives e.g., medium-chain fatty esters such as e.g., medium-chain fatty acid methyl esters (FAME) and medium-chain fatty acid ethyl esters (FAEE), medium-chain fatty alcohol acetate esters (FACE), medium-chain fatty amines, medium-chain fatty aldehydes, medium-chain fatty alcohols, medium-chain hydrocarbons, medium-chain fatty ketones, medium-chain alkanes, medium-chain terminal olefins, medium-chain internal olefins, medium-chain-hydroxy fatty acid derivatives, medium-chain bifunctional fatty acid derivatives e.g., medium-chain fatty diacids, medium-chain fatty diols, unsaturated medium-chain fatty acid derivatives as compared to the an enzyme having SEQ ID NO:1.

In some exemplary embodiments, an engineered TE variant of SEQ ID NO:1 having improved activity for the production of medium-chain fatty acid derivatives (e.g., SEQ ID NO:16 through SEQ ID NO: 46) has an increased net positive surface charge as compared to a non-variant/non-engineered control thioesterase e.g., SEQ ID NO:1.

2. Assaying for Engineered Thioesterase Variants Having Improved Activity for the Production of Medium-Chain Fatty Acid Derivatives In exemplary embodiments, engineered TE variants having improved activity for the production of medium-chain fatty acid derivatives are identified by measuring the medium-chain fatty acid derivatives (e.g., free fatty acids (FFA), fatty acid ethyl esters, FAEE, fatty alcohols (FALC), fatty alcohol acetate esters (FACe), etc.) produced by a bacterial strain comprising an engineered TE variant (i.e., a test strain) and comparing these medium-chain fatty acid derivatives to the measured value of medium-chain fatty acid derivatives (e.g., FFA, FAEE, FALC, FACE, etc.) produced by an appropriate control test strain that is isogenic to the test strain except for the control TE that it comprises.

In some exemplary embodiments, the total titer of medium-chain fatty acid derivatives are measured and compared between the test and the control strain. In some exemplary embodiments, the percent of the total titer of medium-chain fatty acid derivatives comprising a specific medium-chain fatty acid derivative (e.g. C8 fatty acid derivatives) produced by a test strain is measured and compared to the percent of the total titer of medium-chain fatty acid derivatives comprising a specific medium-chain fatty acid derivative produced by an appropriate control strain that is isogenic to the test strain except for the control TE (e.g., SEQ ID NO:1) that it comprises.

In exemplary embodiments, Gas-Chromatography with Flame-Ionization Detection (GC-FID) is used to assay the medium-chain fatty acid derivative. GC-FID is known in the art (see e.g., Adlard, E. R.; Handley, Alan J. (2001). Gas chromatographic techniques and applications. London: Sheffield Academic). However, any appropriate method for quantitation and analysis may be used e.g., mass spectrometry (MS), Gas Chromatography-mass spectrometry (GC-MS), liquid chromatography-mass spectrometry (LC-MS), thin layer chromatography (TLC), etc.

C. Methods of Making Engineered Thioesterase Variants

Engineered TE variants can be prepared by any method known in the art (see e.g., Current Protocols in Molecular Biology, supra). Thus, in exemplary embodiments, mutagenesis is used to prepare polynucleotide sequences encoding engineered TE variants that can then be screened for improved activity for the production of medium-chain fatty acid derivatives. In other exemplary embodiments, polynucleotide sequences encoding engineered TE variants that can then be screened for improved activity for the production of medium-chain fatty acid derivatives are prepared by chemical synthesis of the polynucleotide sequence (see e.g., M. H. Caruthers et al. (1987) Methods in Enzymology Volume 154, Pages 287-313; Beaucage, S. L. and Iyer, R. P. (1992) Tetrahedron 48(12):2223-2311).

Mutagenesis methods are well known in the art. An exemplary mutagenesis technique for preparation of engineered TE variants having improved activity for the production of medium-chain fatty acid derivatives includes e.g., site saturation mutagenesis (see e.g., Chronopoulou EG1, Labrou N E. Curr. Protoc. Protein Sci. 2011 February; Chapter 26:Unit 26.6, John Wiley and Sons, Inc; Steffens, D. L. and Williams., J. G. K (2007) J Biomol Tech. 18(3): 147-149; Siloto, R. M. P and Weselake, R. J. (2012) Biocatalysis and Agricultural Biotechnology 1(3):181-189).

Another exemplary mutagenesis technique for preparation of engineered TE variants having improved activity for the production of medium-chain fatty acid derivatives includes transfer PCR (tPCR) see e.g., Erijman A., et al. (2011) J. Struct. Biol. 175(2):171-7.

Other exemplary mutagenesis techniques include e.g., error prone Polymerase Chain Reaction (PCR) (see e.g., Leung et al. (1989) Technique 1:11-15; and Caldwell et al. (1992) PCR Methods Applic. 2:28-33).

Another exemplary mutagenesis technique for preparation of engineered TE variants having improved activity for the production of medium-chain fatty acid derivatives includes using oligonucleotide directed mutagenesis (see e.g., Reidhaar-Olson et al. (1988) Science 241:53-57) to generate site-specific mutations in any cloned DNA of interest.

The mutagenized polynucleotides resulting from any method of synthesis or mutagenesis, such as those described above, are then cloned into an appropriate vector and the activities of the affected polypeptides encoded by the mutagenized polynucleotides are evaluated as disclosed above.

Those of ordinary skill in the art will recognize that the protocols and procedures disclosed herein can be modified and that such modifications are in accordance with the variations of the disclosure. For example, when method steps are described in a certain order, the ordering of steps can be modified and/or performed in parallel or sequentially.

III. Host Cells and Host Cell Cultures

In view of the present disclosure, the person having ordinary skill in the art will appreciate that any of the embodiments contemplated herein may be practiced with any host cell or microorganism that can be genetically modified via the introduction of one or more nucleic acid sequences that code for the disclosed engineered TE variants. Accordingly, the recombinant microorganisms disclosed herein function as host cells and comprise one or more polynucleotide sequences that include an open reading frame that encodes a engineered TE variant polypeptide having improved activity for production of medium-chain fatty acid derivatives together with operably-linked regulatory sequences that facilitate expression of the engineered TE variant polypeptide in the host cell.

Exemplary microorganisms that provide suitable host cells, include but are not limited to cells from the genus *Escherichia, Bacillus, Lactobacillus, Zymomonas, Rhodococcus, Pseudomonas, Aspergillus, Trichoderma, Neurospora, Fusarium, Humicola, Rhizomucor, Kluyveromyces, Pichia, Mucor, Myceliophtora, Marinobacter, Penicillium, Phanerochaete, Pleurotus, Trametes, Chrysosporium, Saccharomyces, Stenotrophomonas, Schizosaccharomyces, Yarrowia,* or *Streptomyces*. In some exemplary embodiments, the host cell is a Gram-positive bacterial cell. In other exemplary embodiments, the host cell is a Gram-negative bacterial cell. In some embodiments, the host cell is an *E. coli* cell. In other exemplary embodiments, the host cell is a *Bacillus lentus* cell, a *Bacillus brevis* cell, a *Bacillus stearothermophilus* cell, a *Bacillus licheniformis* cell, a *Bacillus alkalophilus* cell, a *Bacillus coagulans* cell, a *Bacillus circulars* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell.

In still other exemplary embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus* fumigates cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcus opacus* cell, a *Rhizomucor miehei* cell, or a *Mucor michei* cell. In still other exemplary other embodiments, the host cell is a *Streptomyces lividans* cell or a *Streptomyces murinus* cell. In yet other embodiments, the host cell is an Actinomycetes cell. In some exemplary embodiments, the host cell is a *Saccharomyces cerevisiae* cell.

In still other exemplary embodiments, the host cell is a cell from a eukaryotic plant, algae, cyanobacterium, green-sulfur bacterium, green non-sulfur bacterium, purple sulfur bacterium, purple non-sulfur bacterium, extremophile, yeast, fungus, engineered organisms thereof, or a synthetic organism. In some exemplary embodiments, the host cell is a cell from *Arabidopsis thaliana, Panicum virgatums, Miscanthus giganteus, Zea mays, botryococcuse braunii, Chalamydomonas reinhardtii, Dunaliela salina, Thermosynechococcus elongatus, Synechococcus elongatus, Synechococcus* sp., *Synechocystis* sp., *Chlorobium tepidum, Chlorojlexus auranticus, Chromatiumm vinosum, Rhodospirillum rubrum, Rhodobacter capsulatus, Rhodopseudomonas palusris, Clostridium ljungdahlii, Clostridiuthermocellum,* or *Pencillium chrysogenum*. In some other exemplary embodiments, the host cell is from *Pichia pastories, Saccharomyces cerevisiae, Yarrowia lipolytica, Schizosaccharomyces pombe, Pseudomonas fluorescens, Pseudomonas putida* or *Zymomonas mobilis*. In still further exemplary embodiments, the host cell is a cell from *Synechococcus* sp. PCC 7002, *Synechococcus* sp. PCC 7942, or *Synechocystis* sp. PCC6803. In some exemplary embodiments, the host cell is a CHO cell, a COS cell, a VERO cell, a BHK cell, a HeLa cell, a Cv1 cell, an MDCK cell, a 293 cell, a 3T3 cell, or a PC12 cell. In some exemplary embodiments, the host cell is an *E. coli* cell. In some exemplary embodiments, the *E. coli* cell is a strain B, a strain C, a strain K, or a strain W *E. coli* cell.

In some exemplary embodiments, host cells comprise optional genetic manipulations and alterations that can be used interchangeably from one host cell to another, depending on what other heterologous enzymes and what native enzymatic pathways are present in the host cell. In one exemplary embodiment, the host cell optionally comprises a fadE and/or an fhuA deletion. In other exemplary embodiments, the host cell is optionally manipulated to have the ability to produce over 200 mg/L of fatty acid derivatives, over 1000 mg/L of fatty acid derivatives, over 1200 mg/L of fatty acid derivatives, over 1700 mg/L of fatty acid derivatives, over 2000 mg/L of fatty acid derivatives, or over 3000 mg/L of fatty acid derivatives. The above mentioned optionally manipulated strains are useful for the identification and characterization of useful engineered TE variants having improved ability to produce medium-chain fatty acid derivatives as well as for the selective production of medium-chain fatty acid derivatives when expressing an engineered TE variant having an improved ability to produce medium-chain fatty acid derivatives.

As will be discussed in detail herein below, in some exemplary embodiments, the host cells or host microorganisms that are used to express the engineered TE variant polypeptides further express genes that have enzymatic activities that can increase the production of one or more particular fatty acid derivative(s) such as e.g., fatty esters, fatty alcohols, fatty alcohol acetate esters, fatty acid methyl esters, fatty acid ethyl esters, fatty amines, fatty aldehydes, bifunctional fatty acid derivatives, diacids, alkanes, alkenes or olefins, ketones, etc.

For example, the entD gene codes for a phosphopantetheinyl transferase. Overexpression of native *E. coli* entD, a phosphopantetheinyl transferase, is an optional genetic modification to cells expressing a carboxylic acid reductase, such as CarB, as it enables an improved activation of CarB from apo-CarB to holo-CarB, thereby allowing for an improved conversion by holo-CarB, of free fatty acids into fatty aldehydes, which can then be converted to fatty alcohols by a fatty aldehyde reductase see e.g., U.S. Pat. No. 9,340,801.

In exemplary embodiments, the host cells or host microorganisms that are used to express engineered TE variant polypeptides further express ester synthase activity (E.C. 2.3.1.75) for the production of fatty esters. In another exemplary embodiment, the host cell has acyl-ACP reductase (AAR) (E.C. 1.2.1.80) activity and/or alcohol dehydrogenase activity (E.C. 1.1.1.1.) and/or fatty alcohol acyl-CoA reductase (FAR) (E.C. 1.1.1.*) activity and/or carboxylic acid reductase (CAR) (EC 1.2.99.6) activity for the production of fatty alcohols. In another exemplary embodiment, the host cell has acyl-ACP reductase (AAR) (E.C. 1.2.1.80) activity for the production of fatty aldehydes. In another exemplary embodiment, the host cell has acyl-ACP reductase (AAR) (E.C. 1.2.1.80) activity and decarbonylase or fatty aldehyde oxidative deformylating activity for the production of alkanes and alkenes. In another exemplary embodiment, the host cell has acyl-CoA reductase (E.C. 1.2.1.50) activity, and acyl-CoA synthetase (FadD) (E.C. 2.3.1.86) activity, for the production of fatty alcohols. In another exemplary embodiment, the host cell has ester synthase activity (E.C. 2.3.1.75) and acyl-CoA synthetase (FadD) (E.C. 2.3.1.86) activity for the production of fatty esters. In another exemplary embodiment, the host cell has OleA activity for the production of ketones. In another exemplary embodiment, the host cell has OleBCD activity for the production of internal olefins. In another exemplary embodiment, the host cell has acyl-ACP reductase (AAR)

(E.C. 1.2.1.80) activity and alcohol dehydrogenase activity (E.C. 1.1.1.1.) for the production of fatty alcohols. In another exemplary embodiment, the host cell has decarboxylase activity for making terminal olefins. The expression of enzymatic activities in microorganisms and microbial cells is taught e.g., by the following U.S. Pat. Nos. 9,133,406; 9,340,801; 9,200,299; 9,068,201; 8,999,686; 8,658,404; 8,597,922; 8,535,916; 8,530,221; 8,372,610; 8,323,924; 8,313,934; 8,283,143; 8,268,599; 8,183,028; 8,110,670; 8,110,093; and 8,097,439.

In some exemplary embodiments, host cells or microorganisms that are used to express engineered TE variant polypeptides comprise certain native enzyme activities that are upregulated or overexpressed in order to produce one or more particular fatty acid derivative(s) such as e.g., fatty esters, fatty acid methyl esters, fatty acid ethyl esters, fatty alcohols, fatty alcohol acetate esters, fatty amines, fatty amides, fatty aldehydes, bifunctional fatty acid derivatives, diacids, etc.

In some exemplary embodiments, a recombinant host cell produces a medium-chain fatty ester, such as a medium-chain fatty acid methyl ester (FAME) or a medium-chain fatty acid ethyl ester (FAEE), medium-chain fatty alcohol acetate ester (FACE), a medium-chain fatty alcohol (FALC), a medium-chain fatty amine, a medium-chain fatty aldehyde, a medium-chain bifunctional fatty acid derivative, a medium-chain diacid, a medium-chain alkane, a medium-chain olefin, etc.

The medium-chain fatty acid derivatives are typically recovered from the culture medium and/or are isolated from the host cells. In one exemplary embodiment, the fatty acid derivatives are recovered from the culture medium (extracellular). In another exemplary embodiment, the fatty acid derivatives are isolated from the host cells (intracellular). In another exemplary embodiment, the fatty acid derivatives or non-fatty acid compounds are recovered from the culture medium and isolated from the host cells.

A fatty acid derivative composition produced by a host cell can be analyzed using methods known in the art, for example, Gas-Chromatography with Flame Ionization Detection (GC-FID) in order to determine the distribution of particular fatty acid derivatives as well as chain lengths and degree of saturation of the components of the fatty acid derivative composition. Similarly, other compounds can be analyzed through methods well known in the art.

IV. Methods of Making Recombinant Host Cells and Cultures

Any method known in the art can be used to engineer host cells to produce fatty acid derivatives and/or fatty acid derivative compositions or other compounds. Exemplary methods include e.g., the use of vectors, e.g., expression vectors, which comprise a polynucleotide sequence encoding a mutant or engineered TE variant and/or polynucleotide sequences encoding other fatty acid derivative biosynthetic pathway polypeptides, as disclosed herein. Persons skilled in the art will appreciate that a variety of viral and non-viral vectors can be used in the methods disclosed herein.

In some exemplary embodiments, a polynucleotide (or gene) sequence encoding a mutant or engineered TE variant is provided to the host cell by way of a recombinant vector that comprises a promoter operably linked to the polynucleotide sequence encoding the mutant or engineered TE variant. In some exemplary embodiments, the promoter is a developmentally-regulated, an organelle-specific, a tissue-specific, an inducible, a constitutive, or a cell-specific promoter. In some exemplary embodiments, the promoter is inducible by the addition of lactose or isopropylthiogalactoside (IPTG).

Once a polynucleotide sequence encoding a mutant or engineered TE variant and/or polynucleotide sequences encoding other fatty acid derivative biosynthetic pathway polypeptides have been prepared and isolated, various methods may be used to construct expression cassettes, vectors and other DNA constructs. Expression cassettes comprising a polynucleotide sequence encoding a mutant or engineered TE variant and/or polynucleotide sequences encoding other fatty acid biosynthetic pathway polypeptides can be constructed in a variety of ways. The skilled artisan is well aware of the genetic elements that must be present on an expression construct/vector in order to successfully transform, select and propagate the expression construct in host cells. Techniques for manipulation of polynucleotide sequences, such as those encoding a mutant or engineered TE variant, such as subcloning nucleic acid sequences into expression vectors, labeling probes, DNA hybridization, and the like are described generally in e.g., Sambrook, et al., supra; Current Protocols in Molecular Biology, supra.

DNA constructs comprising a polynucleotide sequence encoding a mutant or engineered TE variant (e.g., SEQ ID NO:3, SEQ ID NO:16 through SEQ NO:46, etc) and/or polynucleotide sequences encoding other fatty acid biosynthetic pathway polypeptides linked to heterologous DNA sequences e.g., promoter sequences, can be inserted into a variety of vectors. In some exemplary embodiments, the vector chosen is an expression vector that is useful in the transformation of bacteria e.g., *Escherichia coli*. The expression vector may be a plasmid, virus, cosmid, artificial chromosome, nucleic acid fragment, or the like. Such vectors are readily constructed by the use of recombinant DNA techniques well known to those of skill in the art (see e.g., Sambrook et al., supra). The expression vector comprising a polynucleotide sequence encoding a mutant or engineered TE variant may then be transfected/transformed into target host cells. Successfully transformed cells are then selected based on the presence of a suitable marker gene by methods well known in the art.

A number of recombinant vectors are available to those of skill in the art for use in the stable transformation/transfection of bacteria and other microorganisms (see e.g., Sambrook, et al., supra). Appropriate vectors are readily chosen by one of skill in the art. In an exemplary embodiment, known vectors are used to create expression constructs comprising a polynucleotide sequence encoding a mutant or engineered TE variant.

Typically, transformation vectors include one or more polynucleotide sequences encoding one or more mutant or engineered TE variants and/or polynucleotide sequences encoding other fatty acid derivative biosynthetic pathway polypeptides operably linked to e.g., a promoter sequence, and a selectable marker. Such transformation vectors also typically include a transcription initiation start site, a ribosome binding site, an RNA processing signal, a transcription termination site, and/or a polyadenylation signal as appropriate.

Thus, in addition to a polynucleotide sequence encoding a mutant or engineered TE variant and/or polynucleotide sequences encoding other fatty acid derivative biosynthetic pathway polypeptides, expression constructs prepared as disclosed herein may comprise additional elements. In exemplary embodiments, expression constructs comprising a polynucleotide sequence encoding a mutant or engineered TE variant and/or polynucleotide sequences encoding other fatty acid derivative biosynthetic pathway polypeptides also comprise an enhancer sequence such that the expression of the heterologous protein may be enhanced. As is known in the art, enhancers are typically found 5' to the start of transcription, they can often be inserted in the forward or reverse orientation, either 5' or 3' to the coding sequence.

As noted above, transformation/expression vectors typically include a selectable and/or screenable marker gene to allow for the ready identification of transformants. Exemplary selectable marker genes include, but are not limited to those encoding antibiotic resistance (e.g. resistance to kanamycin, ampicillin, etc). Exemplary screenable markers include e.g., an introduced six amino acid histidine tag at the C-terminus of the recombinant protein.

In exemplary embodiments, a selectable or screenable marker gene is employed as, or in addition to, a particular gene of interest, to provide or enhance the ability to identify transformants. Numerous selectable marker genes are known to the art (see e.g., Sambrook et al, supra).

In some exemplary embodiments, an expression vector further comprises sequences that are joined to the coding sequence of an expressed heterologous nucleic acid, which are removed post-translationally from the initial translation product. In one exemplary embodiment, post-translationally removed sequences facilitate the transport of the protein into or through intracellular or extracellular membranes, thereby facilitating the transport of the protein into compartments inside and/or outside the cell. In an exemplary embodiment, post-translationally removed sequences protect a nascent protein from intracellular proteolytic degradation. In one exemplary embodiment, a nucleic acid segment encoding a leader peptide sequence upstream and in reading frame with a selected coding sequence is used in recombinant expression of the coding sequence in a host cell.

In another exemplary embodiment, an expression construct comprises a bacterial origin of replication, e.g., a ColE1 origin. In still another exemplary embodiment, an expression construct/vector comprises a bacterial selectable marker e.g., an ampicillin, tetracyclin, hygromycin, neomycin or chloramphenicol resistance gene.

As is well known in the art, expression constructs typically comprise restriction endonuclease sites to facilitate vector construction. Exemplary restriction endonuclease recognition sites include, but are not limited to e.g., recognition site for the restriction endonucleases NotI, AatII, SacII, PmeI HindIII, PstI, EcoRI, and BamHI.

DNA constructs a polynucleotide sequence encoding a mutant or engineered TE variant operably and/or polynucleotide sequences encoding other fatty acid derivative biosynthetic pathway polypeptides linked to a heterologous DNA sequence e.g., a promoter sequence, a marker sequence; a purification moiety; a secretion sequence operatively coupled to the polynucleotide sequence; a targeting sequence, etc. are used to transform cells and produce recombinant host cells having improved activity for the production of medium-chain fatty acid derivatives. Exemplary host cells for transformation with expression constructs comprising a polynucleotide sequence encoding a mutant or engineered TE variant are discussed in detail in Section III above.

The appropriate transformation technique is readily chosen by the skilled practitioner. Exemplary transformation/transfection methods available to those skilled in the art include e.g., electroporation, calcium chloride transformation and etc., such methods being well known to the skilled artisan (see e.g., Sambrook, supra). Accordingly, polynucleotide sequences, comprising open reading frames encoding proteins and operably-linked regulatory sequences can be integrated into a chromosome of the recombinant host cells, incorporated in one or more plasmid expression system resident in the recombinant host cells, or both.

The expression vectors disclosed herein typically include a polynucleotide sequence encoding a mutant or engineered TE variant and/or polynucleotide sequences encoding fatty acid derivative biosynthetic pathway polypeptides in a form suitable for expression of the polynucleotide sequence in a host cell. As will be appreciated by those skilled in the art, the design of the expression vector can depend on such factors as e.g., the choice of the host cell to be transformed, the level of expression of polypeptide desired, etc.

V. Evaluating Recombinant Host Cells

In exemplary embodiments, the activity of an engineered TE variant polypeptide is determined by culturing recombinant host cells and measuring the characteristics of, for example, fatty acid derivative compositions (e.g., medium-chain fatty esters, medium-chain fatty alcohols, medium-chain fatty aldehydes, etc.) or other compounds produced by the recombinant host cells. In exemplary embodiments composition, titer, yield and/or productivity of fatty acid derivatives or other compounds are analyzed.

Engineered TE variant polypeptides and fragments thereof can be assayed for having improved activity for production of medium-chain fatty acid derivatives using routine methods (see e.g., Example 4 herein below).

IV. Products Derived from Recombinant Host Cells

Strategies to increase production of medium-chain fatty acid derivatives by recombinant host cells include increasing flux through a fatty acid biosynthetic pathway by e.g., overexpression of native fatty acid biosynthetic genes and/or expression of heterologous fatty acid biosynthetic genes from the same or different organisms in the production host.

Thus, in exemplary embodiments, recombinant host cells having improved activity for the production of medium-chain fatty acid derivatives are engineered to comprise, in addition to engineered TE variants, one or more polynucleotide sequences encoding one or more "fatty acid derivative biosynthetic polypeptides" or equivalently "fatty acid derivative enzymes". Metabolic engineering of fatty acid derivative biosynthetic pathways to produce fatty acid-derivative compounds (e.g. fatty acid esters, alkanes, olefins, fatty ketones, fatty alcohols, fatty alcohol acetate esters, etc.) using microorganisms to convert biomass-derived sugars to desired products is known in the art see e.g., U.S. Pat. Nos. 9,133,406; 9,340,801; 9,200,299; 9,068,201; 8,999,686; 8,658,404; 8,597,922; 8,535,916; 8,530,221; 8,372,610; 8,323,924; 8,313,934; 8,283,143; 8,268,599; 8,183,028; 8,110,670; 8,110,093; and 8,097,439. Metabolically engineered strains can be cultivated in industrial-scale bioreactors and the resulting products purified using traditional chemical and biochemical engineering techniques.

As is well known in the art, thioesterases catalyze the hydrolysis of alkyl thioesters into free fatty acids (FFAs). Thus, thioesterases play a role in determining the distribution of acyl chain length of fatty acids and fatty acid derivatives (see e.g., Dehesh (1996) supra, PNAS (1995) 92(23): 10639-10643). Therefore, a recombinant host cell having improved activity for the production of medium-chain fatty acid derivatives typically comprises an engineered TE variant having improved activity for the production of medium-chain fatty acid derivatives (e.g., SEQ ID NO:3, and those shown in Table 7). In some exemplary embodiments, such recombinant host cells provide increased amounts of medium-chain fatty acid derivatives e.g., medium-chain fatty alcohols, medium-chain fatty acids, FAEE, FAME, FACE, etc., as compared to an appropriate control host cell which does not comprise the engineered TE variant e.g., an isogenic control host cell having a control thioesterase (e.g., SEQ ID NO:1) instead of the engineered TE variant.

Thus, in some embodiments, a fatty acid derivative composition comprising fatty acids is produced by culturing a recombinant host cell comprising an engineered TE variant in the presence of a carbon source under conditions effective to express the thioesterase.

In some embodiments, substantially all of the fatty acid derivatives produced by culturing a recombinant host cell comprising an engineered TE variant having improved activity for the production of medium-chain fatty acid derivatives under conditions effective to express the TE are produced extracellularly. Thus, in some exemplary embodiments, the fatty acid derivatives produced are recovered from the culture medium. In some exemplary embodiments, the recovered fatty acid derivative composition is analyzed using any suitable method known in the art e.g., GC FID, in order to determine and quantify the distribution of particular fatty acid derivatives as well as chain lengths and degree of saturation of the components of the fatty acid derivative composition.

In other embodiments, the recombinant host cell comprises a polynucleotide sequence encoding a mutant or engineered TE variant having improved activity for production of medium-chain fatty acid derivatives, and one or more additional polynucleotides encoding polypeptides having other fatty acid derivative biosynthetic enzyme activities. Thus, in some embodiments, a first medium-chain fatty acid derivative (e.g., a medium-chain fatty acid, a medium-chain fatty alcohol, etc.) produced by the action of the engineered TE variant is converted by one or more fatty acid derivative biosynthetic enzymes to a second fatty acid derivative, e.g., a medium-chain fatty acid ester, medium-chain fatty aldehyde, medium-chain fatty alcohol acetate ester, hydrocarbon e.g., a straight chain alkane, straight chain alkene, etc.

Table 1 provides a listing of exemplary fatty acid derivative biosynthetic polypeptides that can be expressed in recombinant host cells in addition an engineered TE variant having improved activity for the production of medium-chain fatty acid derivatives to facilitate production of medium-chain fatty acid derivatives.

TABLE 1

Gene Designations of Fatty Acid Derivative Enzymes

| Gene Designation | Source Organism | Enzyme Name | Accession # | EC Number | Exemplary Use |
|---|---|---|---|---|---|
| 1. Fatty Acid Production Increase/Product Production Increase | | | | | |
| accA | Escherichia coli (E. coli), Lactococci | Acetyl-CoA carboxylase, subunit A (carboxyltransferase alpha) | AAC73296, NP_414727 | 6.4.1.2 | Increase Malonyl-CoA production |
| accB | E. coli, Lactococci | Acetyl-CoA carboxylase, subunit B (BCCP: biotin carboxyl carrier protein) | NP_417721 | 6.4.1.2 | increase Malonyl-CoA production |
| accC | E. coli, Lactococci | Acetyl-CoA carboxylase, subunit C (biotin carboxylase) | NP_417722 | 6.4.1.2, 6.3.4.14 | increase Malonyl-CoA production |
| accD | E. coli, Lactococci | Acetyl-CoA carboxylase, subunit D (carboxyltransferase beta) | NP_416819 | 6.4.1.2 | increase Malonyl-CoA production |
| fadD | E. coli W3110 | acyl-CoA synthetase | AP_002424 | 2.3.1.86, 6.2.1.3 | increase Fatty acid production |
| fabA | E. coli K12 | β-hydroxydecanoyl thioester dehydratase/isomerase | NP_415474 | 4.2.1.60 | increase fatty acyl-ACP/CoA production |
| fabB | E. coli | 3-oxoacyl-[acyl-carrier-protein] synthetase I | BAA16180 | 2.3.1.41 | increase fatty acyl-ACP/CoA production |
| fabD | E. coli K12 | [acyl-carrier-protein] S-malonyltransferase | AAC74176 | 2.3.1.39 | increase fatty acyl-ACP/CoA production |
| fabF | E. coli K12 | 3-oxoacyl-[acyl-carrier-protein] synthetase II | AAC74179 | 2.3.1.179 | increase fatty acyl-ACP/CoA production |
| fabG | E. coli K12 | 3-oxoacyl-[acyl-carrier protein] reductase | AAC74177 | 1.1.1.100 | increase fatty acyl-ACP/CoA production |
| fabH | E. coli K12 | 3-oxoacyl-[acyl-carrier-protein] synthetase III | AAC74175 | 2.3.1.180 | increase fatty acyl-ACP/CoA production |
| fabI | E. coli K12 | enoyl-[acyl-carrier-protein] reductase | NP_415804 | 1.3.1.9 | increase fatty acyl-ACP/CoA production |
| fabR | E. coli K12 | Transcriptional Repressor | NP_418398 | none | modulate unsaturated fatty acid production |

TABLE 1-continued

Gene Designations of Fatty Acid Derivative Enzymes

| Gene Designation | Source Organism | Enzyme Name | Accession # | EC Number | Exemplary Use |
|---|---|---|---|---|---|
| fabV | Vibrio cholerae | enoyl-[acyl-carrier-protein] reductase | YP_001217283 | 1.3.1.9 | increase fatty acyl-ACP/CoA production |
| fabZ | E. coli K12 | (3R)-hydroxymyristol acyl carrier protein dehydratase | NP_414722 | 4.2.1.— | increase fatty acyl-ACP/CoA production |
| fadE | E. coli K13 | acyl-CoA dehydrogenase | AAC73325 | 1.3.99.3, 1.3.99.— | reduce fatty acid degradation |
| fadD | E. coli K12 | acyl-CoA synthetase | NP_416319 | 6.2.1.3 | reduce fatty acid degradation |
| fadA | E. coli K12 | 3-ketoacyl-CoA thiolase | YP_02627 | 2.3.1.16 | reduce fatty acid degradation |
| fadB | E. coli K12 | enoyl-CoA hydratase, 3-OH acyl-CoA epimerase/ dehydrogenase | NP_418288 | 4.2.1.17. 5.1.2.3. 1.1.1.35 | reduce fatty acid degradation |
| fadR | E. coli | transcriptional regulatory protein | NP_415705 | none | Block or reverse fatty acid degradation |

2. Chain Length Control

| Gene Designation | Source Organism | Enzyme Name | Accession # | EC Number | Exemplary Use |
|---|---|---|---|---|---|
| fatB1 | Umbellularia californica | thioesterase | Q41635 | 3.1.2.14 | C12:0 Chain Length |
| fatB2 | Cuphea hookeriana | thioesterase | AAC49269 | 3.1.2.14 | C8:0-C10:0 Chain Length |

3. Saturation Level Control

| Gene Designation | Source Organism | Enzyme Name | Accession # | EC Number | Exemplary Use |
|---|---|---|---|---|---|
| Sfa | E. coli | Suppressor of fabA | AAN79592, AAC44390 | none | increase monounsaturated fatty acids |
| fabA | E. coli K12 | β-hydroxydecanoyl thioester dehydratase/isomerase | NP_415474 | 4.2.1.60 | produce unsaturated fatty acids |
| GnsA | E. coli | suppressors of the secG null mutation | ABD18647.1 | none | increase unsaturated fatty acid esters |
| GnsB | E. coli | suppressors of the secG null mutation | AAC74076.1 | none | increase unsaturated fatty acid esters |
| fabB | E. coli | 3-oxoacyl-[acyl-carrier-protein] synthetase I | BAA16180 | 2.3.1.41 | modulate unsaturated fatty acid production |
| des | Bacillus subtilis | D5 fatty acyl desaturase | O34653 | 1.14.19 | modulate unsaturated fatty acid production |

4. Ester Production

| Gene Designation | Source Organism | Enzyme Name | Accession # | EC Number | Exemplary Use |
|---|---|---|---|---|---|
|  | Limnobacter sp. MED 105 | Ester synthase | ZP_01915978 | 2.3.1.75 | ester production |
| AT3G51970 | Arabidopsis thaliana | long-chain-alcohol O-fatty-acyltransferase | NP_190765 | 2.3.1.26 | ester production |
| ELO1 | Pichia angusta | Fatty acid elongase | BAD98251 | 2.3.1.— | produce very long chain length fatty acids |
| plsC | Saccharomyces cerevisiae | acyltransferase | AAA16514 | 2.3.1.51 | ester production |
| DAGAT/ DGAT | Arabidopsis thaliana | diacylglycerol acyltransferase | AAF19262 | 2.3.1.20 | ester production |
| hWS | Homo sapiens | acyl-CoA wax alcohol acyltransferase | AAX48018 | 2.3.1.20 | ester production |
| aft1 | Acinetobacter sp. ADP1 | bifunctional wax ester synthase/acyl-CoA:diacylglycerol acyltransferase | AAO17391 | 2.3.1.20 | ester production |
| ES9 | Marinobacter hydrocarbonoclasticus | wax ester synthase | ABO21021 | 2.3.1.20 | ester production |
| mWS | Simmondsia chinensis | wax ester synthase | AAD38041 | 2.3.1.— | ester production |

5. Fatty Alcohol Output

| Gene Designation | Source Organism | Enzyme Name | Accession # | EC Number | Exemplary Use |
|---|---|---|---|---|---|
| BmFAR | Bombyxmori | FAR (fatty alcohol forming acyl-CoA reductase) | BAC79425 | 1.2.1.50, 1.2.1.84 | convert acyl-CoA to fatty alcohol |

TABLE 1-continued

Gene Designations of Fatty Acid Derivative Enzymes

| Gene Designation | Source Organism | Enzyme Name | Accession # | EC Number | Exemplary Use |
|---|---|---|---|---|---|
| Acr1 | *Acinetobacter* sp. ADP1 | acyl-CoA reductase | YP_047869 | 1.2.1.42, 1.2.1.50 | reduce fatty acyl-CoA to fatty aldehydes |
| AdhE2 | *Clostridium acetobutylicum* | acyl-CoA reductase | AAK09379 | 1.2.1.84 | reduce fatty acyl-CoA to fatty alcohols |
| Ald | *Clostridium beijerinckii* | acyl-CoA reductase | AAT66436 | 1.2.1.80 | reduce fatty acyl-CoA to fatty aldehydes |
| EutE | *Salmonella typhimurium* | acyl-CoA reductase | AAA80209 | 1.2.1.80 | reduce fatty acyl-CoA to fatty aldehydes |
| yqhD | *E. coli* W3110 | alcohol dehydrogenase | AP_003562 | 1.1.1.— | reduce fatty aldehydes to fatty alcohols; increase fatty alcohol production |
| alrA | *Acinetobacter* sp. ADP1 | alcohol dehydrogenase | CAG70252 | 1.1.1.— | reduce fatty aldehydes to fatty alcohols |
| GTNG_1865 | *Geobacillusthermo-denitrificans* NG80-2 | Long-chain aldehyde dehydrogenase | YP_001125970 | 1.2.1.3 | reduce fatty aldehydes to fatty alcohols |
| AAR | *Synechococcus elongatus* | Acyl-ACP reductase | YP_400611 | 1.2.1.42 | reduce fatty acyl-ACP/CoA to fatty aldehydes |
| carB | *Mycobacterium smegmatis* | carboxylic acid reductase protein | YP_889972 | 6.2.1.3, 1.2.1.42 | reduce fatty acids to fatty aldehyde |
| FadD | *E. coli* K12 | acyl-CoA synthetase | NP_416319 | 6.2.1.3 | activates fatty acids to fatty acyl-CoAs |
| atoB | *Erwiniacarotovora* | acetyl-CoA acetyltransferase | YP_049388 | 2.3.1.9 | production of butanol |
| hbd | *Butyrivibrio-fibrisolvens* | Beta-hydroxybutyryl-CoA dehydrogenase | BAD51424 | 1.1.1.157 | production of butanol |
| CPE0095 | *Clostridium perfringens* | crotonasebutyryl-CoA dehydryogenase | BAB79801 | 4.2.1.55 | production of butanol |
| bcd | *Clostridium beijerinckii* | butyryl-CoA dehydryogenase | AAM14583 | 1.3.99.2 | production of butanol |
| ALDH | *Clostridium beijerinckii* | coenzyme A-acylating aldehyde dehydrogenase | AAT66436 | 1.2.1.3 | production of butanol |
| AdhE | *E. coli* CFT073 | aldehyde-alcohol dehydrogenase | AAN80172 | 1.1.1.1, 1.2.1.10 | production of butanol |
| 6. Fatty Alcohol Acetyl Ester Output | | | | | |
| Atf1 | *Saccharomyces cereviceae* | alcohol O-acetyltransferase | P40353 | 2.3.1.84 | Alkyl acetate production |
| acr1 | *Acinetobacter* sp. ADP1 | acyl-CoA reductase | YP_047869 | 1.2.1.42, 1.2.1.50 | Alkyl acetate production |
| yqhD | *E. Coli* K12 | alcohol dehydrogenase | AP_003562 | 1.1.—.— | Alkyl acetate production |
| AAT | *Fragaria x ananassa* | alcohol O-acyltransferase | AAG13130 | 2.3.1.84 | Alkyl acetate production |
| FaAAT2 | *Fragaria x ananassa* | alcohol O-acyltransferase | AEM43830.1 | 2.3.1.84 | Alkyl acetate production |
| SAAT | *F. x ananassa* cv. *Elsanta* | alcohol O-acyltransferase | AAG13130.1 | 2.3.1.84 | Alkyl acetate production |
| PhcFAT | *Petunia* | alcohol O-acyltransferase | ABG75942.1 | 2.3.1.84 | Alkyl acetate production |
| 7. Terminal Olefin Output | | | | | |
| OleT | *Jeotgalicoccus* sp. | Fatty acid decarboxylase | HQ709266 | 1.11.2.4 | decarboxylate fatty acids |
| 8. Product Export | | | | | |
| AtMRP5 | *Arabidopsis thaliana* | *Arabidopsis thaliana* multidrug resistance-associated | NP_171908 | none | modify product export amount |
| AmiS2 | *Rhodococcus* sp. | ABC transporter AmiS2 | JC5491 | none | modify product export amount |
| AtPGP1 | *Arabidopsis thaliana* | *Arabidopsis thaliana* p glycoprotein 1 | NP_181228 | none | modify product export amount |

TABLE 1-continued

Gene Designations of Fatty Acid Derivative Enzymes

| Gene Designation | Source Organism | Enzyme Name | Accession # | EC Number | Exemplary Use |
|---|---|---|---|---|---|
| AcrA | CandidatusProtochlamydiaamoebophila UWE25 | putative multidrug-efflux transport protein acrA | CAF23274 | none | modify product export amount |
| AcrB | CandidatusProtochlamydiaamoebophila UWE25 | probable multidrug-efflux transport protein, acrB | CAF23275 | none | modify product export amount |
| TolC | Francisellatularensis subsp. novicida | Outer membrane protein [Cell envelope biogenesis, | ABD59001 | none | modify product export amount |
| AcrE | Shigellasonnei Ss046 | transmembrane protein affects septum formation and cell membrane permeability | YP_312213 | none | modify product export amount |
| AcrF | E. coli | Acriflavine resistance protein F | P24181 | none | modify product export amount |
| tll1619 | Thermosynechococcus elongatus [BP-1] | multidrug efflux transporter | NP_682409.1 | none | modify product export amount |
| tll0139 | Thermosynechococcus elongatus [BP-1] | multidrug efflux transporter | NP_680930.1 | none | modify product export amount |
| 9. Fermentation | | | | | |
| umuD | Shigellasonnei Ss046 | DNA polymerase V, subunit | YP_310132 | 3.4.21.— | increase output efficiency |
| umuC | E. coli | DNA polymerase V, subunit | ABC42261 | 2.7.7.7 | increase output efficiency |
| pntA, pntB | Shigellaflexneri | NADH:NADPH transhydrogenase (alpha and beta subunits) | P07001, P0AB70 | 1.6.1.2 | increase output efficiency |
| 10. Other | | | | | |
| fabK | Streptococcus pneumoniae | trans-2-enoyl-ACP reductase II | AAF98273 | 1.3.1.9 | Contributes to fatty acid biosynthesis |
| fabL | Bacillus licheniformis DSM 13 | enoyl-(acyl carrier protein) reductase | AAU39821 | 1.3.1.9 | Contributes to fatty acid biosynthesis |
| fabM | Streptococcus mutans | trans-2, cis-3-decenoyl-ACP isomerase | DAA05501 | 4.2.1.17 | Contributes to fatty acid biosynthesis |

Production of Medium-Chain Fatty Acid Derivatives

As discussed above, a recombinant host cell comprising an engineered TE variant having improved activity for the production of medium-chain fatty acid derivatives produces increased amounts of medium-chain fatty acids as compared to an appropriate control host cell which does not comprise the engineered TE variant e.g., an isogenic control host cell having a control TE (such as SEQ ID NO:1).

In other exemplary embodiments, which are discussed in detail below, in addition to an engineered TE variant having improved activity for the production of medium-chain fatty acid derivatives, a recombinant host cell further comprises additional fatty acid derivative biosynthetic polypeptides which facilitate production of particular types of fatty acid derivatives.

Production of Fatty Aldehydes

In some exemplary embodiments in addition to an engineered TE variant having improved activity for the production of medium-chain fatty acid derivatives, a recombinant host cell further comprises carboxylic acid reductase ("CAR") activity, and thus, the recombinant host cell synthesizes fatty aldehydes and fatty alcohols see. e.g., U.S. Pat. No. 9,340,801.

Therefore, in some exemplary embodiments, a fatty aldehyde is produced by expressing or overexpressing in the recombinant host cell a polynucleotide encoding a polypeptide having fatty aldehyde biosynthetic activity such as e.g., carboxylic acid reductase (CAR) activity. Exemplary carboxylic acid reductase (CAR) polypeptides and polynucleotides encoding them include, e.g., FadD9 (EC 6.2.1.-, UniProtKB Q50631, GenBank NP 217106), CarA (GenBank ABK75684), CarB (GenBank YP889972) and related polypeptides disclosed e.g., in U.S. Pat. Nos. 8,097,439 and 9,340,801.

In some exemplary embodiments, the fatty aldehyde produced by the recombinant host cell is then converted into a fatty alcohol or a hydrocarbon. Thus, in some exemplary embodiments in addition to an engineered TE variant having improved activity for the production of medium-chain fatty acid derivatives, a recombinant host cell further comprises acyl-CoA reductase ("FAR" or "ACR") activity, and thus the recombinant host cell synthesizes fatty aldehydes and fatty alcohols (see e.g., U.S. Pat. Nos. 8,658,404, 8,268,599, U.S. Patent Application Publication 2015/0361454).

In some embodiments, the fatty aldehyde produced by the recombinant host cell is converted into a fatty alcohol through the activity of native or heterologous fatty alcohol biosynthetic polypeptides, such as e.g., aldehyde reductases or alcohol dehydrogenases (see e.g., U.S. Patent Application Publication 2011/0250663). Thus, in some exemplary embodiments in addition to an engineered TE variant having improved activity for the production of medium-chain fatty acid derivatives, a recombinant host cell further comprises aldehyde reductase activity or equivalently, alcohol dehydrogenase activity (EC 1.1.1.1), and thus the recombinant host cell synthesizes fatty alcohols. Exemplary fatty alcohol biosynthetic genes include, but are not limited to e.g., alcohol dehydrogenases e.g., AlrA of Acenitobacter sp. M-1 or AlrA homologs; and endogenous E. coli alcohol dehydrogenases such as e.g., DkgA (NP.sub.—417485), DkgB (NP.sub.—414743), YjgB, (AAC77226), YdjL (AAC74846), YdjJ (NP.sub.—416288), AdhP (NP.sub.—415995), YhdH (NP.sub.—417719), YahK (NP.sub.—414859), YphC (AAC75598), and YqhD (Q46856).

Production of Fatty Amines

In some exemplary embodiments, a recombinant host cell which comprises an engineered TE variant having improved activity for the production of medium-chain fatty acid derivatives and which produces fatty aldehydes (e.g., as disclosed herein above) is further modified to comprise a heterologous biosynthetic enzyme that has aminotransferase or amine dehydrogenase activity that converts the fatty aldehydes to fatty amines (see e.g., PCT Publication Number WO 2015/085271).

Production of Fatty Alcohols

In some exemplary embodiments, in addition to an engineered TE variant having improved activity for the production of medium-chain fatty acid derivatives a recombinant host cell further comprises a polynucleotide encoding a polypeptide having fatty alcohol biosynthetic activity, and thus, a fatty alcohol is produced by the recombinant host cell. Thus, in exemplary embodiments, a composition comprising medium-chain fatty alcohols e.g., comprising octanol, is produced by culturing a recombinant host cell in the presence of a carbon source under conditions effective to express an engineered TE variant having improved activity for the production of medium-chain fatty acid derivatives and a fatty alcohol biosynthetic enzyme.

Therefore, in some exemplary embodiments, in addition to an engineered TE variant having improved activity for the production of medium-chain fatty acid derivatives, a recombinant host cell further comprises carboxylic acid reductase (CAR) activity and alcohol dehydrogenase activity and thus, the recombinant host cell synthesizes medium-chain fatty alcohols e.g., octanol (see e.g., U.S. Pat. No. 9,340,801).

In some exemplary embodiments, native fatty aldehyde biosynthetic polypeptides, such as aldehyde reductases/alcohol dehydrogenases present in the host cell, convert medium-chain fatty aldehydes to medium-chain fatty alcohols. In other exemplary embodiments, a native fatty aldehyde reductase/alcohol dehydrogenase is overexpressed to convert medium-chain fatty aldehydes to medium-chain fatty alcohols. In other exemplary embodiments, a heterologous aldehyde reductase/alcohol dehydrogenase is introduced into a recombinant host cell and expressed or overexpressed to convert medium-chain fatty aldehydes to medium-chain fatty alcohols. Exemplary aldehyde reductase/alcohol dehydrogenase polypeptides useful for converting medium-chain fatty aldehydes to medium-chain fatty alcohols are disclosed herein above and in International Patent Application Publication No. WO 2007/136762; WO 2010/062480; U.S. Pat. Nos. 8,110,670; 9,068,201.

In some exemplary embodiments, in addition to an engineered TE variant having improved activity for the production of medium-chain fatty acid derivatives a recombinant host cell further comprises a heterologous polynucleotide encoding a polypeptide having carboxylic acid reductase (EC 6.2.1.3 or EC 1.2.1.42) activity such that the recombinant host cell produces a 1,3 fatty diol when grown in a fermentation broth with a simple carbon source. In other exemplary embodiments, in addition to an engineered TE variant having improved activity for the production of medium-chain fatty acid derivatives, a recombinant host cell further comprises a heterologous polynucleotide encoding a polypeptide having carboxylic acid reductase (EC 6.2.1.3 or EC 1.2.1.42) activity and a heterologous polynucleotide encoding a polypeptide having alcohol dehydrogenase (EC 1.1.1.) activity, wherein the recombinant host cell produces a 1,3 fatty diol, such as a medium-chain 1,3 fatty diol when grown in a fermentation broth with a simple carbon source (see e.g., WO 2016/011430).

Production of Fatty Alcohol Acetate Esters

In some embodiments, fatty alcohols produced in the cell, or in some embodiments fed to a cell, are further processed by a recombinant cell to provide fatty alcohol acetates (FACE). In exemplary embodiments, an alcohol O-acetyltransferase (EC 2.8.1.14) enzyme processes fatty alcohols to fatty alcohol acetate esters (FACE) see e.g., Gabriel M Rodriguez, et al. (2014) Nature Chemical Biology 10, 259-265; Jyun-Liang Lin and Ian Wheeldon (2014) PLoS One. 2014; 9(8): PMCID: PMC4122449.

An exemplary alcohol 0-acetyl transferase is the yeast Aft1 e.g., GenBank accession number AY242062; GenBank accession number AY242063, see e.g., Kevin J. Verstrepen K. J., et al (2003) Appl Environ Microbiol. 2003 September; 69(9): 5228-5237.

In an exemplary embodiment a recombinant host cell comprising an engineered TE variant having an improved ability to produce medium-chain fatty acid derivatives further comprises a carboxylic acid reductase activity (EC 1.2.99.6) sufficient to produce fatty aldehydes and fatty alcohols, and further comprises a fatty alcohol O-acetyl transferase activity which converts the fatty alcohols to fatty alcohol acetate esters.

In a further exemplary embodiment a recombinant host cell comprising an engineered TE variant having an improved ability to produce medium-chain fatty acid derivatives further comprises a carboxylic acid reductase activity (EC 1.2.99.6) which results in the production of a first fatty acid derivative, and further comprises a fatty alcohol O-acetyl transferase activity which converts the first fatty acid derivative to a second fatty acid derivative, where in the second fatty acid derivative has a higher MIC than the first fatty acid derivative.

In a further exemplary embodiment a recombinant host cell comprising an engineered TE variant having an improved ability to produce medium-chain fatty acid derivatives further comprises a carboxylic acid reductase activity (EC 1.2.99.6) which results in the production of a first fatty acid derivative, and further comprises a fatty alcohol O-acetyl transferase activity which converts the first fatty acid derivative to a second fatty acid derivative, where in the second fatty acid derivative has a higher Log P than the first fatty acid derivative.

In a further exemplary embodiment a recombinant host cell comprising an engineered TE variant having an improved ability to produce medium-chain fatty acid derivatives further comprises a carboxylic acid reductase activity (EC 1.2.99.6) which results in the production of a first fatty acid derivative, and further comprises a fatty alcohol O-acetyl transferase activity which converts the first fatty acid derivative to a second fatty acid derivative, where in the presence of the second fatty acid derivative results in an increase in the MIC of the first fatty acid derivative.

In a further exemplary embodiment a recombinant host cell comprising an engineered TE variant having an improved ability to produce medium-chain fatty acid derivatives further comprises a carboxylic acid reductase activity (EC 1.2.99.6) which results in the production of a first fatty acid derivative, and further comprises a fatty alcohol O-acetyl transferase activity which converts the first fatty acid derivative to a second fatty acid derivative, where in the second fatty acid derivative is less toxic than the first fatty acid derivative.

Production of Fatty Esters

In some embodiments, in addition to an engineered TE variant having improved activity for the production of medium-chain fatty acid derivatives a recombinant host cell further comprises a polynucleotide encoding a polypeptide having fatty ester biosynthetic activity, and thus, a medium-chain fatty ester is produced by the recombinant host cell.

As used herein, the term "fatty ester" or equivalently a "fatty acid ester" refers to any ester made from a fatty acid. In exemplary embodiments, a fatty ester contains an "A side" and a "B side". As used herein, an "A side" of an ester refers to the carbon chain attached to the carboxylate oxygen of the ester. As used herein, a "B side" of an ester refers to the carbon chain comprising the parent carboxylate of the ester. In embodiments where the fatty ester is derived from the fatty acid derivative biosynthetic pathway, the A side is contributed by an alcohol, and the B side is contributed by a fatty acid or alkyl thioester.

Any alcohol can be used to form the A side of the fatty esters. In exemplary embodiments, the alcohol is derived from a fatty acid derivative biosynthetic pathway. In other exemplary embodiments, the alcohol is produced through non-fatty acid derivative biosynthetic pathways e.g., the alcohol is provided exogenously e.g., the alcohol is supplied in the fermentation broth.

The carbon chains comprising the A side or B side can be of any length. However, in exemplary embodiments, wherein a fatty acid derivative biosynthetic pathway comprising an engineered TE variant having improved activity for the production of medium-chain fatty acid derivatives provides either the A side and/or B side of the fatty acid ester, the A side and/or B side is a medium-chain fatty acid derivative and thus has a carbon chain length of 6, 7, 8, 9 or 10 carbons in length. Thus, in an exemplary embodiment, a fatty acid derivative biosynthetic pathway comprising an engineered TE variant having improved activity for the production of medium-chain fatty acid derivatives provides the A side of the ester and thus the A side of the fatty ester is 6, 7, 8, 9 or 10 carbons in length. In other exemplary embodiments, a fatty acid biosynthetic pathway comprising an engineered TE variant having improved activity for the production of medium-chain fatty acid derivatives provides the B side of the ester and thus the B side of the fatty ester is 6, 7, 8, 9 or 10 carbons in length.

In one exemplary embodiment, the fatty ester is a fatty acid methyl ester e.g., methyl octanoate, wherein the B side is provided by a fatty acid biosynthetic pathway comprising an engineered TE variant having improved activity for the production of medium-chain fatty acid derivatives and the A side of the ester is 1 carbon in length. Thus, in an exemplary embodiment the fatty acid ester is methyl octanoate. In one exemplary embodiment, the A side is provided through the action of fatty acid O-methyltransferase (FAMT) (EC 2.1.1.15) enzyme (see e.g., Applied and Environmental Microbiology 77(22): 8052-8061).

In another exemplary embodiment, the fatty ester is a fatty acid ethyl ester, wherein the B side is provided by a fatty acid biosynthetic pathway comprising an engineered TE variant having improved activity for the production of medium-chain fatty acid derivatives and the A side of the ester is 2 carbons in length.

In one exemplary embodiment, the A side is straight chained. In another exemplary embodiment, the A side is branch chained. In one exemplary embodiment, the B side is straight chained. In another exemplary embodiment, the B side is branch chained. The branched chains can have one or more points of branching. In one exemplary embodiment, the A side is saturated. In another exemplary embodiment, the A side is unsaturated. In one exemplary embodiment, the B side is saturated. In another exemplary embodiment, the B side is unsaturated.

In exemplary embodiments, in addition to an engineered TE variant having improved activity for the production of medium-chain fatty acid derivatives, a recombinant host cell comprises a polynucleotide encoding a polypeptide having ester synthase activity (EC 3.1.1.67). Ester synthases are known in the art see e.g., International Patent Application Publication WO 2011/038134.

In some exemplary embodiments, a fatty acid ester is produced by a recombinant host cell comprising an engineered TE variant having improved activity for the production of medium-chain fatty acid derivatives, and an acyl-CoA synthetase (fadD) enzyme and an ester synthase enzyme (see e.g., International Patent Application Publication WO/2011/038134; International Patent Application Publication WO 2007/136762; U.S. Pat. No. 8,110,670).

In an exemplary embodiment a recombinant host cell comprising an engineered TE variant having an improved ability to produce medium-chain fatty acid derivatives further comprises ester synthase activity (EC 3.1.1.67) sufficient to produce fatty esters (such as FAME or FAEE).

In a further embodiment a recombinant host cell comprising an engineered TE variant having an improved activity which results in the production of a first fatty acid derivative further comprises ester synthase activity that converts the first fatty acid derivative to a second fatty acid derivative.

In a further embodiment a recombinant host cell comprising an engineered TE variant having an improved activity which results in the production of a first fatty acid derivative further comprises ester synthase activity that converts the first fatty acid derivative to a second fatty acid derivative, wherein the second fatty acid derivative has a higher MIC than the first fatty acid derivative.

In a further embodiment a recombinant host cell comprising an engineered TE variant having an improved activity which results in the production of a first fatty acid derivative further comprises ester synthase activity that converts the first fatty acid derivative to a second fatty acid derivative, wherein the second fatty acid derivative has a higher partition coefficient (Log P) than the first fatty acid derivative.

In a further embodiment a recombinant host cell comprising an engineered TE variant having an improved activity which results in the production of a first fatty acid derivative further comprises ester synthase activity that converts the first fatty acid derivative to a second fatty acid derivative, wherein the presence of the second fatty acid derivative results in an increase in the MIC of the first fatty acid derivative.

In a further embodiment a recombinant host cell comprising an engineered TE variant having an improved activity which results in the production of a first fatty acid derivative further comprises ester synthase activity that converts the first fatty acid derivative to a second fatty acid derivative, wherein the second fatty acid derivative is less toxic than the first fatty acid derivative.

Production of Hydrocarbons

In some embodiments, in addition to an engineered TE variant having improved activity for the production of medium-chain fatty acid derivatives the recombinant host cell further comprises a polynucleotide encoding a polypeptide having fatty aldehyde biosynthetic activity e.g., an acyl-ACP reductase polypeptide (EC 6.4.1.2) and a polynucleotide encoding a polypeptide having hydrocarbon biosynthetic activity, e.g., a decarbonylase (EC 4.1.99.5), oxidative deformylase, or fatty acid decarboxylase, and thus, the recombinant host cell exhibits enhanced production of hydrocarbons (see e.g., U.S. Patent Application Publication 2011/0124071). Thus, in exemplary embodiments, a recombinant host cell comprising an engineered TE variant having improved activity for the production of medium-chain fatty acid derivatives produces a hydrocarbon, e.g., an alkane or an alkene (e.g., a terminal olefin or an internal olefin) or a ketone.

In some exemplary embodiments a fatty aldehyde produced by a recombinant host cell comprising an engineered TE variant having improved activity for the production of medium-chain fatty acid derivatives is converted by decarbonylation, removing a carbon atom, to form a hydrocarbon (see e.g., U.S. Pat. No. 8,110,670 and WO 2009/140695).

In other exemplary embodiments, a fatty acid produced by a recombinant host cell is converted by decarboxylation, removing a carbon atom to form a terminal olefin. Thus, in some exemplary embodiments, in addition to expressing an engineered TE variant having improved activity for the production of medium-chain fatty acid derivatives a recombinant cell further expresses or overexpresses a polynucleotide encoding a hydrocarbon biosynthetic polypeptide, such as a polypeptide having decarboxylase activity as disclosed e.g., in U.S. Pat. No. 8,597,922.

In other exemplary embodiments, alky thioester intermediates are converted by an enzymatic decarboxylative condensation, to form an internal olefin or a ketone. Thus, in some exemplary embodiments, in addition to expressing an engineered TE variant having improved activity for the production of medium-chain fatty acid derivatives, a recombinant cell further expresses or overexpresses a polynucleotide encoding a hydrocarbon biosynthetic polypeptide, such as e.g., a polypeptide having OleA activity thereby producing a ketone (see e.g., in U.S. Pat. No. 9,200,299). In other exemplary embodiments, in addition to expressing an engineered TE variant having improved activity for the production of medium-chain fatty acid derivatives, a recombinant cell further expresses or overexpresses a polynucleotide encoding a hydrocarbon biosynthetic polypeptide, such as e.g., OleCD or OleBCD together with a polypeptide having OleA activity thereby producing an internal olefin is produced (see e.g., U.S. Pat. No. 9,200,299).

Some exemplary hydrocarbon biosynthetic polypeptides are shown in Table 2, below.

TABLE 2

Exemplary Hydrocarbon Biosynthetic Polynucleotides and Polypeptides.

| Protein name | Sequence |
| --- | --- |
| Decarbonylase (ADC) or oxidative deformylase | Synechococcus elongatus PCC7942 YP.sub.--400610 (Synpcc7942.sub.--1593) |

TABLE 2-continued

Exemplary Hydrocarbon Biosynthetic Polynucleotides and Polypeptides.

| Protein name | Sequence |
| --- | --- |
| Acyl-ACP Reductase (AAR) | Synechococcus elongatus PCC7942 YP__400611 (Synpcc7942__1594) |
| Decarbonylase (ADC) or oxidataive deformylase | Prochlorococcus mariunus CCMP1986 PMM0532 |
| Acyl-ACP Reductase (AAR) | Prochlorococcus marinus CCMP1986 PMM0533 (NP__892651) |

Production of Omega ($\omega$)-Hydroxylated Fatty Acid Derivatives

In some embodiments, in addition to an engineered TE variant having improved activity for the production of medium-chain fatty acid derivatives, a recombinant host cell further comprises a polynucleotide encoding a polypeptide having $\omega$-hydroxylase activity (EC 1.14.15.3). In exemplary embodiments, the modified co-hydroxylase has a modified cytochrome P450 monooxygenase (P450) enzymatic activity and efficiently catalyzes the hydroxylastion of the w-position of hydrocarbon chains in vivo. Thus, the recombinant microorganism produces a medium-chain omega-hydroxylated (o-hydroxylated) fatty acid derivative in vivo when grown in a fermentation broth in the presence of a carbon source from a renewable feedstock (see e.g., PCT Application Publication WO 2014/201474).

In other exemplary embodiments, in addition to an sniggered TE variant having improved activity for the production of medium-chain fatty acid derivatives, a recombinant host cell further comprises a polynucleotide encoding a alkane hydroxylase, such as alkA, CYP153A-reductase or a CYP153A-reductase hybrid fusion polypeptide variant (see e.g., WO 2015/195697) such that the recombinant host cell produces omega-hydroxylated-($\omega$-hydroxylated) and bi-functional fatty acid derivatives and compositions thereof including o-hydroxylated fatty acids, o-hydroxylated fatty esters, $\alpha,\omega$-diacids, $\alpha,\omega$-diesters, $\alpha,\omega$-diols and chemicals derived therefrom such as macrolactones and macrocyclic ketones when cultured in medium containing a carbon source under conditions effective to express the alkane hydroxylase, such as AlkA, CYP153 or a CYP153A-reductase hybrid fusion polypeptide variant and engineered TE variant having improved activity for the production of medium-chain fatty acid derivatives.

V. Culture and Fermentation of Recombinant Host Cells

As used herein, fermentation broadly refers to the conversion of organic materials into target substances by recombinant host cells. For example, this includes the conversion of a carbon source by recombinant host cells into fatty acid derivatives such as e.g., medium-chain fatty acids, medium-chain fatty acid esters, medium-chain fatty alcohols, medium-chain fatty alcohol acetates, etc. by propagating a culture of the recombinant host cells in a media comprising a carbon source. Conditions permissive for the production of target substances such as e.g., fatty acids, fatty esters, fatty alcohols, fatty alcohol acetates, etc., are any conditions that allow a host cell to produce a desired product, such as a fatty acid derivative composition. Suitable conditions include, for example, typical fermentation conditions see e.g., *Principles* of *Fermentation Technology*, 3rd Edition (2016) supra; *Fermentation Microbiology and Biotechnology*, 2nd Edition, (2007) supra.

Fermentation conditions can include many parameters, well known in the art, including but not limited to temperature ranges, pH levels, levels of aeration, feed rates and media composition. Each of these conditions, individually and in combination, allows the host cell to grow. Fermentation can be aerobic, anaerobic, or variations thereof (such as micro-aerobic). Exemplary culture media include broths (liquid) or gels (solid). Generally, the medium includes a carbon source (e.g., a simple carbon source derived from a renewable feedstock) that can be metabolized by a host cell directly. In addition, enzymes can be used in the medium to facilitate the mobilization (e.g., the depolymerization of starch or cellulose to fermentable sugars) and subsequent metabolism of the carbon source to produce medium-chain fatty acid derivatives.

For small scale production, the host cells engineered to produce medium-chain fatty acid derivative compositions can be grown in batches of, for example, about 100 µL, 200 µL, 300 µL, 400 µL, 500 µL, 1 mL, 5 mL, 10 mL, 15 mL, 25 mL, 50 mL, 75 mL, 100 mL, 500 mL, 1 L, 2 L, 5 L, or 10 L; fermented; and induced to express desired polynucleotide sequences, such as a polynucleotides encoding polypeptides having specific enzymatic activity (e.g., thioesterase (TE), carboxylic acid reductase (CAR), alcohol dehydrogenase (ADH), fatty acyl CoA/ACP reductase (FAR), acyl-CoA reductase (ACR), acetyl CoA carboxylase (ACC) and/or acyl ACP/CoA reductase (AAR) enzymatic activity). For large scale production, the engineered host cells can be grown in cultures having volume batches of about 10 L, 100 L, 1000 L, 10,000 L, 100,000 L, 1,000,000 L or larger; fermented; and induced to express any desired polynucleotide sequence.

The fatty acid derivative compositions disclosed herein can often be found in the extracellular environment of the recombinant host cell culture and can be readily isolated from the culture medium. A medium-chain fatty acid derivative such as a medium-chain fatty acid, a medium-chain fatty acid ester, medium-chain fatty aldehyde, medium-chain fatty ketone, medium-chain fatty alcohol, a medium-chain fatty alcohol acetate, etc. may be secreted by the recombinant host cell, transported into the extracellular environment or passively transferred into the extracellular environment of the recombinant host cell culture. The medium-chain fatty acid derivative compositions may be isolated from a recombinant host cell culture using routine methods known in the art, including but not limited to centrifugation.

Exemplary microorganisms suitable for use as production host cells include e.g., bacteria, cyanobacteria, yeast, algae, filamentous fungi, etc. To produce fatty acid derivative compositions production host cells (or equivalently, host cells) are engineered to comprise fatty acid biosynthesis pathways that are modified relative to non-engineered or native host cells e.g., engineered as discussed above and as disclosed e.g., in U.S. Patent Application Publication 2015/0064782. Production hosts engineered to comprise modified fatty acid biosynthesis pathways are able to efficiently convert glucose or other renewable feedstocks into fatty acid derivatives. Protocols and procedures for high density fermentations for the production of various compounds have been established (see, e.g., U.S. Pat. Nos. 8,372,610; 8,323,924; 8,313,934; 8,283,143; 8,268,599; 8,183,028; 8,110,670; 8,110,093; and 8,097,439).

In some exemplary embodiments, a production host cell is cultured in a culture medium (e.g., fermentation medium) comprising an initial concentration of a carbon source (e.g., a simple carbon source) of about 20 g/L to about 900 g/L. In other embodiments, the culture medium comprises an initial concentration of a carbon source of about 2 g/L to about 10 g/L; of about 10 g/L to about 20 g/L; of about 20 g/L to about 30 g/L; of about 30 g/L to about 40 g/L; or of about 40 g/L to about 50 g/L. In some embodiments, the level of available carbon source in the culture medium can be monitored during the fermentation proceeding. In some embodiments, the method further includes adding a supplemental carbon source to the culture medium when the level of the initial carbon source in the medium is less than about 0.5 g/L.

In some exemplary embodiments, a supplemental carbon source is added to the culture medium when the level of the carbon source in the medium is less than about 0.4 g/L, less than about 0.3 g/L, less than about 0.2 g/L, or less than about 0.1 g/L. In some embodiments, the supplemental carbon source is added to maintain a carbon source level of about 1 g/L to about 25 g/L. In some embodiments, the supplemental carbon source is added to maintain a carbon source level of about 2 g/L or more (e.g., about 2 g/L or more, about 3 g/L or more, about 4 g/L or more). In certain embodiments, the supplemental carbon source is added to maintain a carbon source level of about 5 g/L or less (e.g., about 5 g/L or less, about 4 g/L or less, about 3 g/L or less). In some embodiments, the supplemental carbon source is added to maintain a carbon source level of about 2 g/L to about 5 g/L, of about 5 g/L to about 10 g/L, or of about 10 g/L to about 25 g/L.

In one exemplary embodiment the carbon source for the fermentation is derived from a renewable feedstock. In some embodiments, the carbon source is glucose. In other embodiments, the carbon source is glycerol. Other possible carbon sources include, but are not limited to, fructose, mannose, galactose, xylose, arabinose, starch, cellulose, hemicellulose, pectin, xylan, sucrose, maltose, cellobiose, turanose, acetic acid, ethane, ethanol, methane, methanol, formic acid, and carbon monoxide; cellulosic material and variants such as hemicelluloses, methyl cellulose and sodium carboxymethyl cellulose; saturated or unsaturated fatty acids, succinate, lactate, and acetate; alcohols, such as ethanol, methanol, and glycerol, or mixtures thereof. In one embodiment, the carbon source is derived from corn, sugar cane, sorghum, beet, switch grass, ensilage, straw, lumber, pulp, sewage, garbage, cellulosic urban waste, flu-gas, syn-gas, or carbon dioxide. The simple carbon source can also be a product of photosynthesis, such as glucose or sucrose. In one embodiment, the carbon source is derived from a waste product such as glycerol, flu-gas, or syn-gas; or from the reformation of organic materials such as biomass; or from natural gas or from methane, or from the reformation of these materials to syn-gas; or from carbon dioxide that is fixed photosynthetically, for example medium-chain fatty acid derivatives may be produced by recombinant cyanobacteria or algae growing photosynthetically and using CO2 as carbon source. In some exemplary embodiments, the carbon source is derived from biomass. An exemplary source of biomass is plant matter or vegetation, such as corn, sugar cane, or switchgrass. Another exemplary source of biomass is metabolic waste products, such as animal matter (e.g., cow manure). Further exemplary sources of biomass include algae and other marine plants. Biomass also includes waste products from industry, agriculture, forestry, and households, including, but not limited to, fermentation waste, ensilage, straw, lumber, sewage, garbage, cellulosic urban waste, municipal solid waste, and food leftovers.

In some exemplary embodiments, a fatty acid derivative e.g., a medium-chain fatty acid, medium-chain fatty ester, medium-chain fatty alcohol, etc., is produced at a concentration of about 0.5 g/L to about 40 g/L. In some embodiments, a fatty acid derivative is produced at a concentration of about 1 g/L or more (e.g., about 1 g/L or more, about 10 g/L or more, about 20 g/L or more, about 50 g/L or more, about 100 g/L or more). In some embodiments, a fatty acid derivative is produced at a concentration of about 1 g/L to about 170 g/L, of about 1 g/L to about 10 g/L, of about 40 g/L to about 170 g/L, of about 100 g/L to about 170 g/L, of about 10 g/L to about 100 g/L, of about 1 g/L to about 40 g/L, of about 40 g/L to about 100 g/L, or of about 1 g/L to about 100 g/L.

In other exemplary embodiments, a fatty acid derivative e.g., a medium-chain fatty acid derivative, is produced at a titer of about 25 mg/L, about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, about 300 mg/L, about 325 mg/L, about 350 mg/L, about 375 mg/L, about 400 mg/L, about 425 mg/L, about 450 mg/L, about 475 mg/L, about 500 mg/L, about 525 mg/L, about 550 mg/L, about 575 mg/L, about 600 mg/L, about 625 mg/L, about 650 mg/L, about 675 mg/L, about 700 mg/L, about 725 mg/L, about 750 mg/L, about 775 mg/L, about 800 mg/L, about 825 mg/L, about 850 mg/L, about 875 mg/L, about 900 mg/L, about 925 mg/L, about 950 mg/L, about 975 mg/L, about 1000 mg/L, about 1050 mg/L, about 1075 mg/L, about 1100 mg/L, about 1125 mg/L, about 1150 mg/L, about 1175 mg/L, about 1200 mg/L, about 1225 mg/L, about 1250 mg/L, about 1275 mg/L, about 1300 mg/L, about 1325 mg/L, about 1350 mg/L, about 1375 mg/L, about 1400 mg/L, about 1425 mg/L, about 1450 mg/L, about 1475 mg/L, about 1500 mg/L, about 1525 mg/L, about 1550 mg/L, about 1575 mg/L, about 1600 mg/L, about 1625 mg/L, about 1650 mg/L, about 1675 mg/L, about 1700 mg/L, about 1725 mg/L, about 1750 mg/L, about 1775 mg/L, about 1800 mg/L, about 1825 mg/L, about 1850 mg/L, about 1875 mg/L, about 1900 mg/L, about 1925 mg/L, about 1950 mg/L, about 1975 mg/L, about 2000 mg/L (2 g/L), 3 g/L, 5 g/L, 10 g/L, 20 g/L, 30 g/L, 40 g/L, 50 g/L, 60 g/L, 70 g/L, 80 g/L, 90 g/L, 100 g/L or a range bounded by any two of the foregoing values. In other embodiments, a fatty acid derivative or other compound is produced at a titer of more than 100 g/L, more than 200 g/L, or more than 300 g/L. In exemplary embodiments, the titer of fatty acid derivative or other compound produced by a recombinant host cell according to the methods disclosed herein is from 5 g/L to 200 g/L, 10 g/L to 150 g/L, 20 g/L to 120 g/L and 30 g/L to 100 g/L. The titer may refer to a particular fatty acid derivative or a combination of fatty acid derivatives or another compound or a combination of other compounds produced by a given recombinant host cell culture. In exemplary embodiments, the expression of an engineered TE variant in a recombinant host cell such as *E. coli* results in the production of a higher titer as compared to a recombinant host cell expressing the corresponding wild type polypeptide. In one embodiment, the higher titer ranges from at least about 5 g/L to about 200 g/L.

In other exemplary embodiments, the host cells engineered to produce a fatty acid derivative e.g., a medium-chain fatty acid derivative, according to the methods of the disclosure have a yield of at least 1%, at least 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, or at least about 30% or a range bounded by any two of the foregoing values. In other embodiments, a fatty acid derivative or derivatives or other compound(s) are produced at a yield of more than about 30%, more than about 35%, more than about 40%, more than about 45%, more than about 50%, more than about 55%, more than about 60%, more than about 65%, more than about 70%, more than about 75%, more than about 80%, more than about 85%, more than about 90%. Alternatively, or in addition, the yield is about 30% or less, about 27% or less, about 25% or less, or about 22% or less. In another embodiment, the yield is about 50% or less, about 45% or less, or about 35% or less. In another embodiment, the yield is about 95% or less, or 90% or less, or 85% or less, or 80% or less, or 75% or less, or 70% or less, or 65% or less, or 60% or less, or 55% or less, or 50% or less. Thus, the yield can be bounded by any two of the above endpoints. For example, the yield of a medium-chain fatty acid derivative e.g., an 8 and/or 10 carbon fatty acid derivative produced by the recombinant host cell according to the methods disclosed herein can be about 5% to about 15%, about 10% to about 25%, about 10% to about 22%, about 15% to about 27%, about 18% to about 22%, about 20% to about 28%, about 20% to about 30%, about 30% to about 40%, about 40% to about 50%, about 50% to about 60%, about 60% to about 70%, about 70% to about 80%, about 80% to about 90%, about 90% to about 100%, about 100% to about 200%, about 200% to about 300%, about 300% to about 400%, about 400% to about 500%, about 500% to about 600%, about 600% to about 700%, or about 700% to about 800%. The yield may refer to a particular medium-chain fatty acid derivative or a combination of fatty acid derivatives. In one embodiment, the higher yield ranges from about 10% to about 800% of theoretical yield. In addition, the yield will also be dependent on the feedstock used.

In some exemplary embodiments, the productivity of the host cells engineered to produce a fatty acid derivative e.g., a medium-chain fatty acid derivative, according to the methods of the disclosure is at least 100 mg/L/hour, at least 200 mg/L/hour, at least 300 mg/L/hour, at least 400 mg/L/hour, at least 500 mg/L/hour, at least 600 mg/L/hour, at least 700 mg/L/hour, at least 800 mg/L/hour, at least 900 mg/L/hour, at least 1000 mg/L/hour, at least 1100 mg/L/hour, at least 1200 mg/L/hour, at least 1300 mg/L/hour, at least 1400 mg/L/hour, at least 1500 mg/L/hour, at least 1600 mg/L/hour, at least 1700 mg/L/hour, at least 1800 mg/L/hour, at least 1900 mg/L/hour, at least 2000 mg/L/hour, at least 2100 mg/L/hour, at least 2200 mg/L/hour, at least 2300 mg/L/hour, at least 2400 mg/L/hour, 2500 mg/L/hour, or as high as 10 g/L/hour (dependent upon cell mass). For example, the productivity of a malonyl-CoA derived compound including a fatty acid derivative or derivatives or other compound(s) produced by a recombinant host cell according to the methods of the disclosure may be from 500 mg/L/hour to 2500 mg/L/hour, or from 700 mg/L/hour to 2000 mg/L/hour. The productivity may refer to a particular 8 and/or 10 carbon fatty acid derivative or a combination of fatty acid derivatives or other compound(s) produced by a given host cell culture. For example, the expression of a an engineered TE variant in a recombinant host cell such as *E. coli* results in increased productivity of an 8 and/or 10 carbon fatty acid derivatives or other compounds as compared to a recombinant host cell expressing the corresponding wild type polypeptide. In exemplary embodiments, higher productivity ranges from about 0.3 g/L/h to about 3 g/L/h to about 10 g/L/h to about 100 g/L/h to about a 1000 g/L/h.

VI. Isolation

Bioproducts e.g., compositions comprising medium-chain fatty acid derivatives as disclosed herein which are produced utilizing recombinant host cells as discussed above are typically isolated from the fermentation broth by methods known in the art. In an exemplary embodiment the compositions comprising medium-chain fatty acid derivatives as disclosed herein which are produced utilizing recombinant host cells are discussed above are isolated from the fermentation broth by gravity settling, centrifugation, or decantation.

VII. Compositions and Formulations of Medium-Chain Fatty Acid Derivatives

Bioproducts e.g., compositions comprising medium-chain fatty acids and medium-chain fatty acid derivatives produced utilizing recombinant host cells as discussed in detail above are produced from renewable sources (e.g., from a simple carbon source derived from renewable feedstocks) and, as such, are new compositions of matter. These new bioproducts can be distinguished from organic compounds derived from petrochemical carbon on the basis of dual carbon-isotopic fingerprinting or $^{14}C$ dating. Additionally, the specific source of biosourced carbon (e.g., glucose vs. glycerol) can be determined by dual carbon-isotopic fingerprinting by methods known in the art (see, e.g., U.S. Pat. No. 7,169,588, WO 2016/011430 A1, etc.).

Further, as shown below, the composition of the bioproducts define unique compositions of natural fatty acid derivatives produced from an organism. These unique compositions that are extraordinarily high in medium-chain fatty acid derivatives provide a novel and unique source of these valuable medium-chain length products.

The following examples are offered to illustrate, but not to limit the invention.

EXAMPLES

The following specific examples are intended to illustrate the disclosure and should not be construed as limiting the scope of the claims.

Example 1

The following Example illustrates that chemical modifications to medium-chain length fatty acid derivative compounds decrease the toxicity experienced by microorganisms to the medium-chain fatty acid derivative compounds relative to the toxicity experienced by the microorganism when grown in the presence of the unmodified medium-chain length fatty acid derivative compound.

As discussed herein above, the production of medium-chain length fatty acid derivative compound(s) using biological systems (e.g., fermentation of microbial cells) is a desirable route for the selective production of medium-chain length fatty acid/aliphatic compounds. Unfortunately, medium-chain fatty acid derivative compound(s) can be highly toxic to microbial cells, and this toxicity is a barrier to the production of medium-chain length fatty acid derivative compounds, at commercial scale, via fermentation.

In this Example, related compounds which differed only in the modification or non-modification were evaluated for toxicity by determining the Minimum Inhibitory Concentration (MIC) (the concentration of a compound that is sufficient to kill 50% of a culture) of each compound. Compounds having less toxicity (i.e. a relatively higher MIC) are easier compounds to produce by fermentation.

*Escherichia coli* (*E. coli*) cell cultures were grown in varying concentrations of these compounds, and their growth was determined by measuring the total protein from a lysed culture after 24 hours of growth as a measure of the total number of cells in the culture.

In particular, *E. coli* cell cultures were grown in the presence of octanol, octanoic acid, methyl octanoate and octylacetate. The results are shown in FIG. 1.

As can be seen in FIG. 1, the medium-chain acid, octanoic acid, and the medium-chain alcohol, octanol, have an MIC of 1-5 g/L. In contrast, the esters of these medium-chain alcohols and acids, octyl acetate and methyl octanoate, ethyl octanoate (not shown) have MICs that are 10-100-fold higher than the corresponding unmodified alcohol and acid. Accordingly, *E. coli* can tolerate 10-100-fold higher concentrations of the chemically modified compounds as compared to the unmodified compounds.

Thus, the above Example demonstrates that esters of medium-chain aliphatic alcohols and acids can be produced and tolerated at high concentrations by an industrial fermentation process. Further, the above Example demonstrates that the toxicity of an aliphatic compound of a given chain length can be significantly decreased by modifying the functional group(s) associated with the toxic molecule or by slightly increasing its molecular weight.

Example 2

The following Example illustrates the correlation of toxicity of medium-chain fatty acid derivative compounds to partition coefficient (Log P).

As shown in Example 1, the esters of medium-chain fatty alcohols and esters of medium-chain fatty acids are less toxic (have a higher MIC) than the corresponding medium-chain fatty alcohols and medium-chain fatty acids.

Many water soluble compounds have a low partition coefficient (Log P). Log P is a measure of the partitioning of a compound between water and octanol (see e.g., Compounds with a low Log P such as acetic acid, lactic acid, pyruvic acid, 1,3 propane diol, amino acids, etc. can be produced and tolerated at high concentrations by microorganisms, e.g., *E. coli*. Accordingly, one might conclude that compounds that are less hydrophobic (or equivalently more hydrophilic) and therefore which have lower Log P would be less toxic. To evaluate if this were true, we measured the log P, of the compounds disclosed in FIG. 1 (i.e., octanol, octanoic acid, octyl acetate and methyl octanoate).

Figure 2:
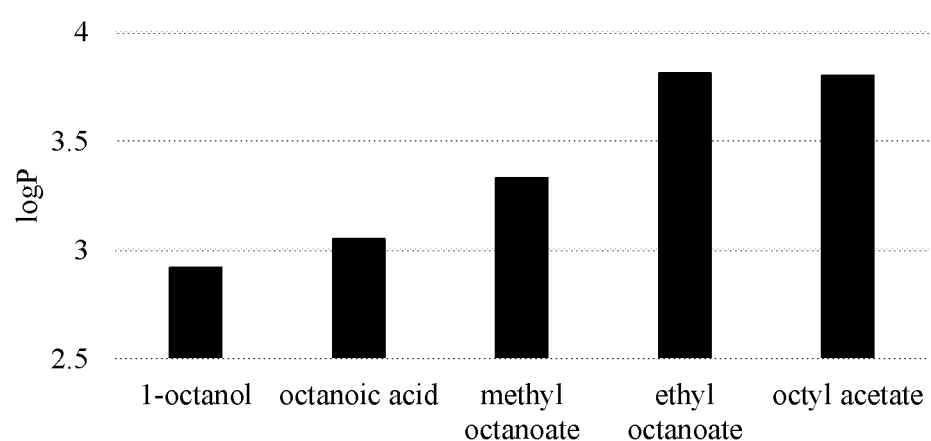
FIG. 2 Illustrates Partition coefficient (log $P_{wo}$) of different medium-chain aliphatic compounds.

Surprisingly, as FIG. 2 shows, for medium-chain aliphatic compounds, toxicity as a function of Log P is opposite of expectation. Namely, the compounds octanol and octanoic acid which have low log P have high toxicity (i.e. low MIC). The compounds octyl acetate, methyl octanoate, and ethyl ocanoate which have high log P have lower toxicity (high MIC).

Thus, this example demonstrates that the modification of toxic medium-chain aliphatic compounds having low Log P to compounds with a higher log $P_{wo}$ is a useful method for decreasing the toxicity of medium-chain aliphatic compounds that are toxic to industrial microorganisms, such as *E. coli*.

Example 3

The following Example illustrates that the expression of novel biochemical pathways that catalyze the conversion of toxic medium-chain aliphatic compounds to their less toxic derivatives enables a microorganism to tolerate the pathway to the toxic compound and to produce high levels of its derivative.

As discussed above in Examples 1 and 2, medium-chain fatty acid derivative compounds, such as fatty alcohols and fatty acids, are toxic to host cells, but their slightly higher molecular weight and high log P derivatives are not. Accordingly, we reasoned that we could produce the more toxic compounds in a microorganism without killing the cell, by biochemically converting the more toxic compounds into the less toxic compounds in vivo. The less toxic compounds could then be produced and tolerated at high levels. These less toxic compounds, once produced, can be isolated and used directly or can be isolated and chemically converted back to the more toxic compounds.

As will be shown below, engineering a cell to modify the functional group of a toxic medium-chain fatty acid derivative, such e.g., as by esterification with short chain acids or alcohols, eliminates the toxic response of the cell to the non-esterified compound and enables an engineered cell to survive the expression of a high producing biochemical pathway to the toxic compound. This enables a novel and selective process to produce these medium-chain length fatty acid derivatives at concentrations well above their inhibitory level.

Furthermore, modification of medium-chain fatty acids and/or medium-chain fatty alcohols by esterification to provide esterified medium-chain fatty acids and/or esterified medium-chain fatty alcohols further decreases toxicity of medium-chain intermediates in the biosynthetic pathway by acting as an extracting agent.

Esterified Medium-Chain Fatty Acid Derivatives as Extracting Agents

Figure 3:
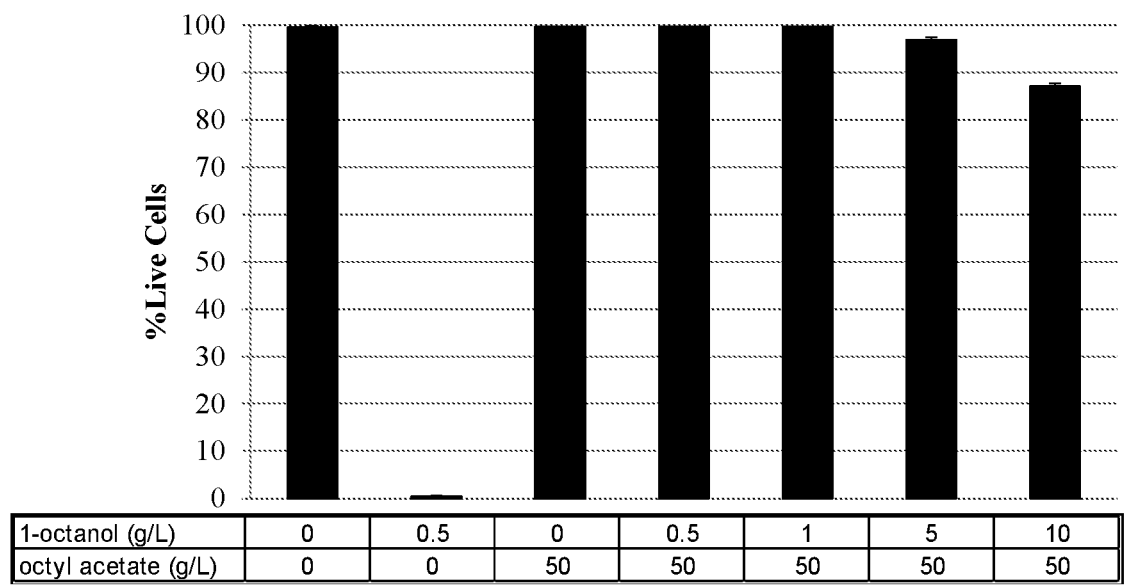
FIG. 3 Illustrates protection from 1-octanol toxicity in the presence of octyl acetate is shown. When exposed to 1-octanol, viability of *E. coli* cells was completely lost after 5 h exposure. However, when octyl acetate was also added at 50 g/L (non-toxic concentration to *E. coli* cells), cell viability was decreased less than 20% in the presence of up to 10 g/L of 1-octanol.

In FIG. 3, the results of experiments designed to test whether the presence of octyl acetate can protect cells from 1-octanol toxicity are shown. As is clear from FIG. 3, after 5 hours exposure to 1-octanol at a concentration of 0.5 gram/liter (g/L), viability of *E. coli* cells was completely lost. However, interestingly, when octyl acetate was also added at 50 g/L (non-toxic concentration to *E. coli* cells), cell viability was maintained at 100% of the control level, when the cells were exposed to 1-octanol at a concentration of 0.5 g/L, and even when exposed to 1-octanol at a concentration of 1 g/L. When cells were exposed to 1-octanol at a concentration of 10 g/L (well beyond the observed MIC for 1-octanol) viability was decreased less than 20%.

Engineering Tolerance to Medium-Chain Fatty Alcohols by Expressing a Fatty Alcohol Acetyl Transferase As discussed and shown above, microbial production of medium-chain (C6 to C10) fatty alcohols is restricted by their toxicity. Significant effort has been made to identify genetic and biochemical mechanisms to increase tolerance to these medium-chain fatty acid derivative compounds (see e.g., Lennen and Pflefer, 2013; Royce et al., 2015; Tan, et al., 2016; Tan, et al., 2017). However, until now, no solutions have been found that would allow the production of commercial titers (e.g., concentrations of between about 10 g/l to 200 g/l or higher).

In Example 1, we demonstrated that medium-chain fatty alcohol acetates, when added to a culture medium, are less toxic than the corresponding medium-chain length fatty alcohols. In the experiment described below we demonstrate that the expression of a pathway to produce medium-chain length fatty alcohols inside a cell is cytotoxic, resulting in poor cell growth and limited production of the medium-chain alcohols by these cells. We further show that when that same strain is further engineered to express a biochemical pathway to convert the medium-chain alcohols to alcohol acetate esters, the cell grows well and produces significant quantities of the fatty alcohol acetate. Thus, the biochemical conversion of medium-chain length fatty alcohols, synthesized in the cell, to their alcohol acetates, eliminates the toxicity of the intermediate medium-chain fatty alcohols and allows high level production of fatty alcohol acetates. This further demonstrates that genes that encode a medium-chain length alcohol-O-acetyl transferase confer resistance to intracellularly produced medium-chain fatty alcohols (FIG. 4).

Figure 4:
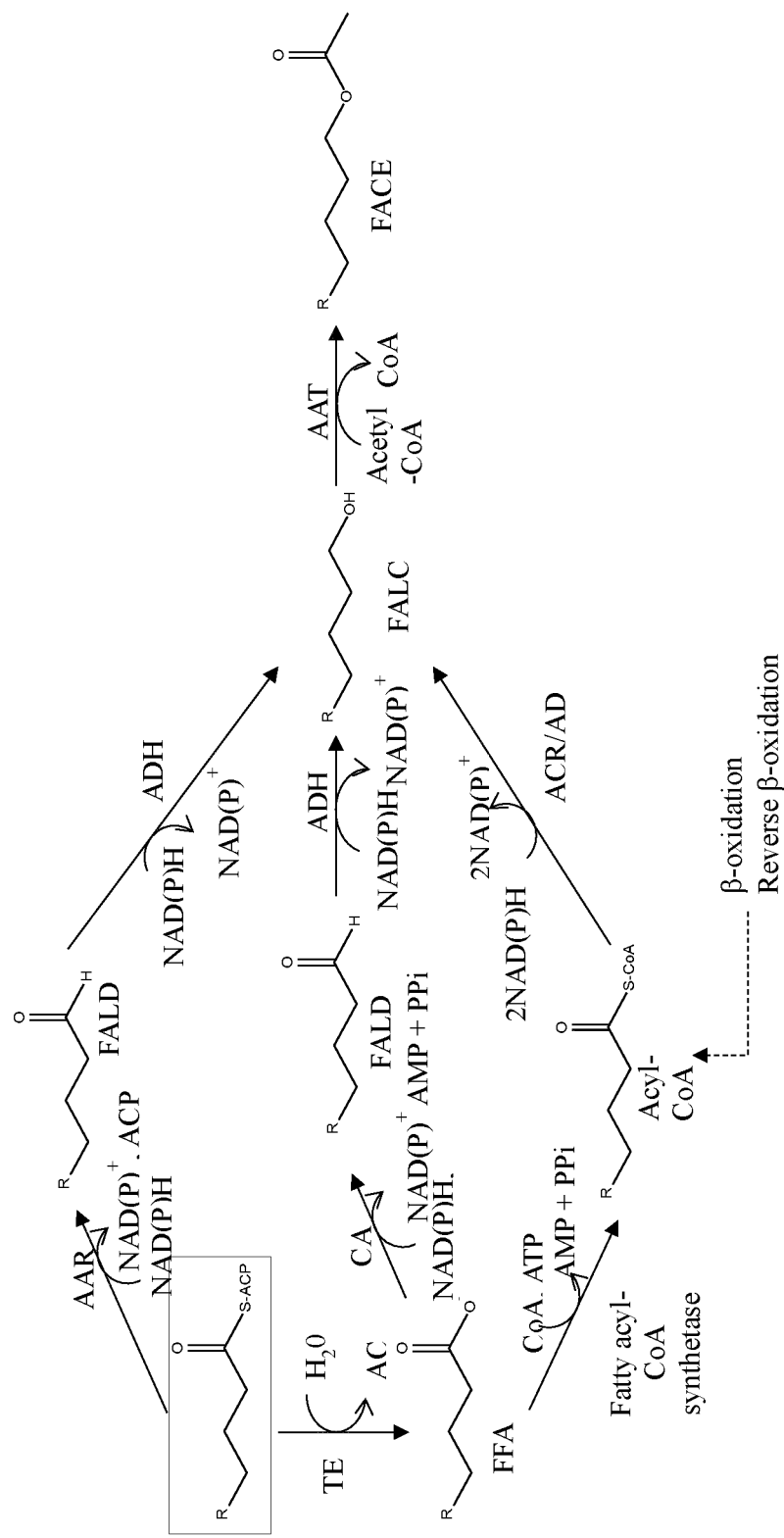
FIG. 4 Illustrates pathways for the production of medium-chain fatty alcohols and their acetylation to fatty acetate esters. R: $CH_3(CH2)_n$ where n=1, 2, 3, 4 or 5; FFA: free fatty acid; FALD: fatty aldehyde; FALC: fatty alcohol; FACE: fatty alcohol acetate esters; ACP: acyl carrier protein; AAR: acyl-ACP reductase; ADH: aldehyde/alcohol dehydrogenase; TE: thioesterase; ACR: acyl-CoA reductase; CAR: carboxyl acid reductase; AAT: o-alcohol acetyl transferase.

A cell can be engineered to produce fatty alcohols through a variety biochemical pathways (see e.g. FIG. 4). These biochemical pathways include, but are not limited to, a pathway comprising a thioesterase (TE) (see e.g., PCT/US1998/011697, U.S. Pat. No. 9,765,368, PCT/US2010/04049) which hydrolyzes fatty acid thioesters in a cell to produce fatty acids, a carboxylic acid reductase, which catalyzes the ATP and NAD(P)H reduction of fatty acids to fatty aldehydes, and an alcohol dehydrogenase, which catalyzes the NAD(P)H dependent reduction of fatty aldehydes to fatty alcohols (note that most cells have sufficient alcohol dehydrogenase activity in the cell to catalyze this reaction, but overexpression of these or similar enzymes can ensure that the fatty aldehyde does not accumulate see e.g., WO 2010/062480). Other pathways that can be engineered to produce fatty alcohols include a fatty acyl reductase, which catalyzes the reduction of fatty acyl thioesters (see e.g. Kim et al, 2015) to fatty aldehydes.

Acetylation of fatty alcohols can be achieved e.g., by the expression of an alcohol-O-acetyl transferase (EC 2.3.1.84), which catalyzes the Acetyl Coenzyme A (CoA) dependent acetylation of alcohols (FIG. 4). The alcohol acetyltransferases (AAT) are diverse and suitable AATs can be selected from the family of plant AATs (such as e.g., strawberry SAAT or FaAAT2, *Petunia* PhcFATB2, etc.), yeast ATF (*Saccharomyces cerevisiae* ATF1) (see e.g., PCT/US2014/053587), etc. As a non-limiting example, here we show the effect of expressing *S. cerevisiae* ATF1 in *E. coli* cells engineered to produce fatty alcohols.

To determine if there was a benefit to expressing the acetylation pathway, the viability of a strain expressing a pathway for the biosynthesis of medium-chain fatty alcohols was compared to the viability of an isogenic strain expressing an ATF that would convert the (toxic) medium-chain fatty alcohols into fatty alcohol acetates (less toxic). In this evaluation strain sRG.674 produces fatty alcohol species, where 85 to 90% of the total fatty species (FAS) produced are of a chain length of 8 or 10 carbons (C8+C10 fatty alcohol (C8+C10 FALC)). Strain sJN.209 is isogenic to sRG.674, except for the addition of the *S. cerevisiae* atf1 gene to the plasmid expressing the fatty alcohol (FALC) pathway.

TABLE 3

Strains producing medium-chain fatty alcohols
(FALC) or fatty alcohol acetate esters (FACE).

| Strain name | Description | Pathway enzymes expressed |
|---|---|---|
| sRG.674 | FALC producer | Engineered thioesterase variant, CarB, AlrA |
| sJN.209 | FACE producer | Engineered thioesterase variant, CarB, AlrA, ATF1 |

Figure 5A:
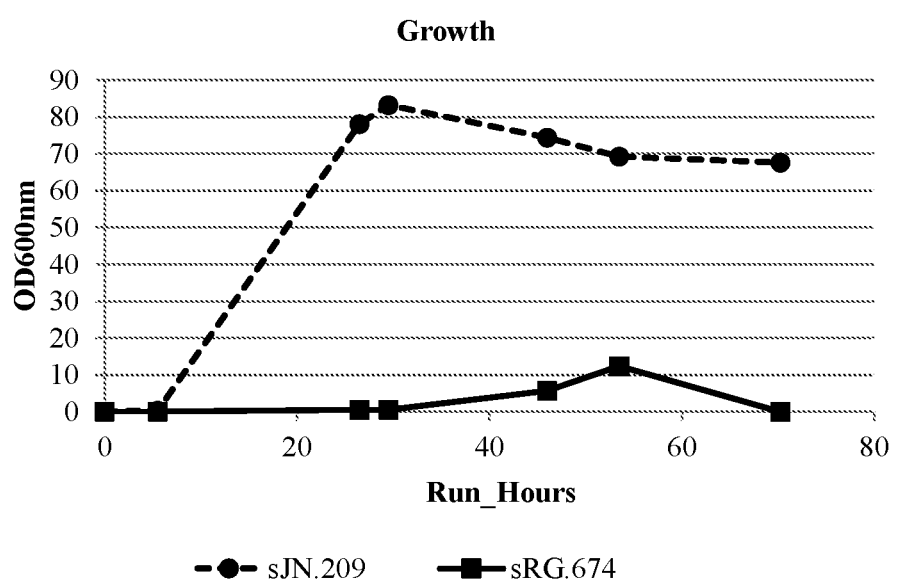
FIG. 5A-5C Illustrates different measures that are indicative of improved tolerance and production of medium-chain fatty alcohol (FALC) compounds by expression of an alcohol acetyltransferase.
Figure 5B:
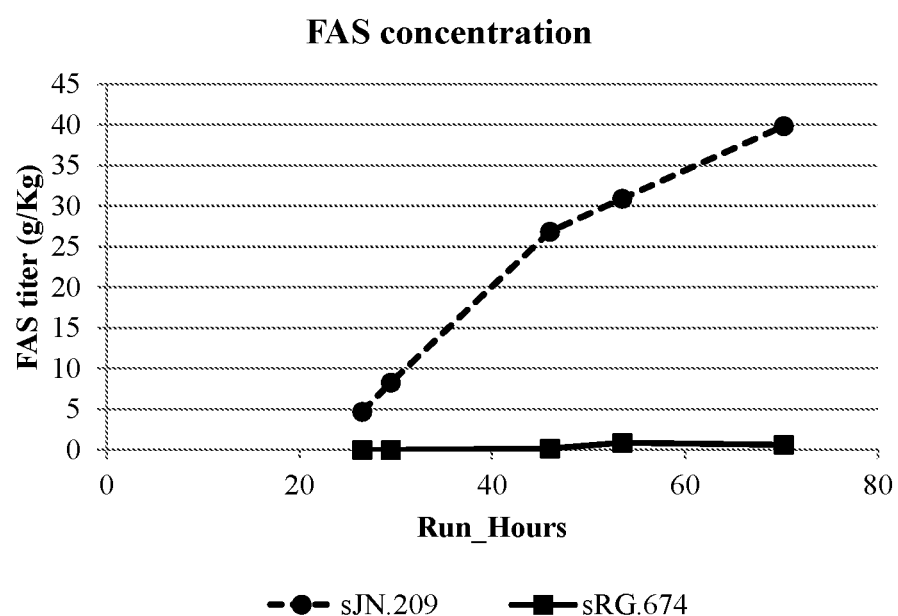
Figure 5C:
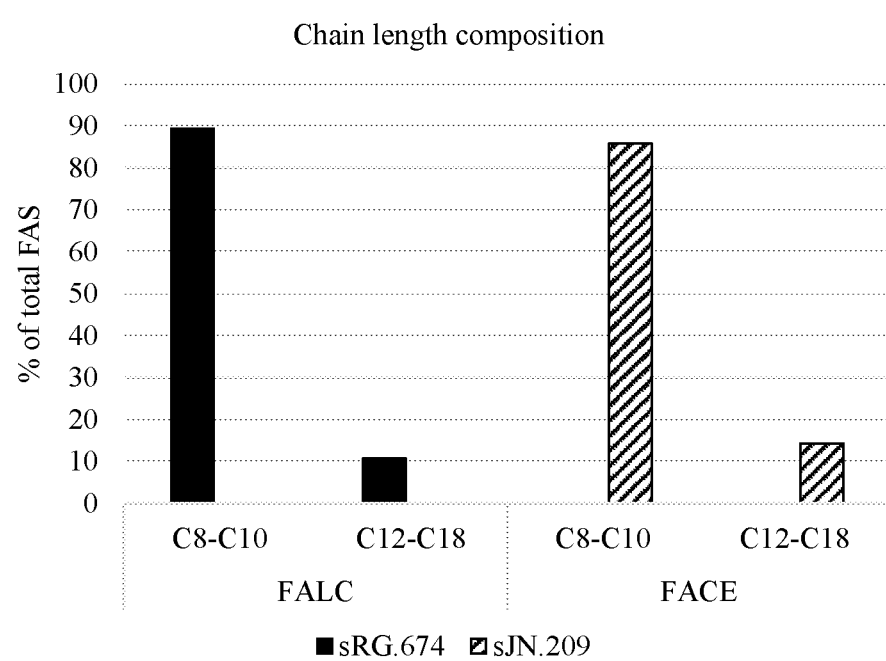

Strains sRG.674 and sJN.209 were grown in 5 L bioreactors, as described in Examples 9 and 10, using minimal salt medium with glucose as the carbon source feed at maximum consumption rate (FIG. 5). Even before addition of IPTG, which induces the expression of the FALC pathway and production of the medium-chain compounds, the FALC-producing strain (sRG.674) was unable to grow (FIG. 5A). Without being bound by theory it is believed that the inability of the FALC producing strain to grow may be due to a constitutive low level expression of the enzymes involved in medium-chain FALC synthesis and early production of inhibitory concentrations of C8 and C10 FALC. In contrast, with the expression of the AAT in strain sJN.209, this growth inhibition was not observed, instead full growth and production of fatty alcohol acetate esters (FACE) for the full 72 h fermentation was observed.

A comparison of the level and composition of the fatty species produced (FIG. 5B and FIG. 5C) further demonstrate the powerful ability of the acetyl transferase gene to enable the transient but high level production of medium-chain length fatty alcohols in the cell by converting them to the less toxic compound fatty alcohol acetate.

Engineering for Tolerance to Medium-Chain Free Fatty Acids

Similar to medium-chain fatty alcohols, medium-chain free fatty acids are toxic to microbial cells (see e.g., FIG. 1). Here we show that production of such compounds can be greatly improved by providing cells with the ability to convert free fatty acids to the less toxic alkyl esters, such as fatty acid methyl (FAME) or ethyl esters (FAEE).

Figure 6:
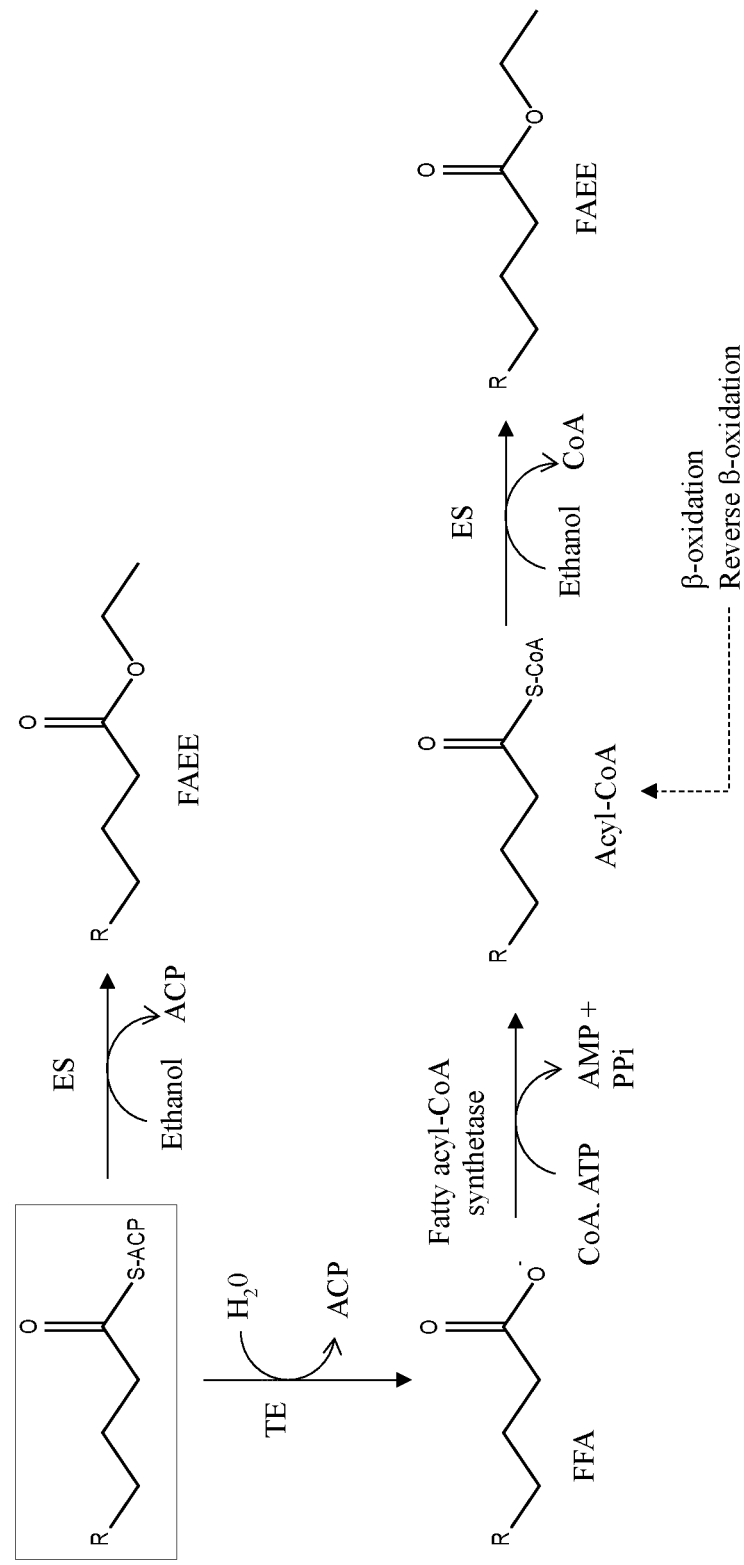
FIG. 6 Illustrates pathways for esterification of free fatty acids. R: $CH_3(CH2)_n$ where, n=1, 2, 3, 4 or 5; FFA: free fatty acids; FAEE: fatty acid ethyl esters; TE: thioesterase; ES: ester synthase.

Esterification of medium-chain FFAs can be achieved through the expression of a fatty acyl-CoA synthetase (such as e.g., FadD from *E. coli*), which catalyzes the Coenzyme A (CoA) and adenosine triphosphate (ATP) dependent synthesis of acyl Coenzyme A (Acyl-CoA), and an ester synthase, which catalyzes the alcoholysis of thioesters, such as acyl-CoA (product of a fatty acyl-CoA synthetase or intermediate in β-oxidation or reverse β-oxidation pathways) (FIG. 6).

Esterification of medium-chain FFAs can also be achieved through the expression of a medium-chain length selective ester synthase that catalyzes the direct alcoholysis of medium-chain length acyl ACPs (which are also alkyl thioesters).

The benefit of expressing an ester synthesis pathway was demonstrated by comparing the viability and the medium-chain fatty acid derivatives produced by a strain engineered to express a thioesterase having improved activity for the production of medium-chain-length fatty acid derivatives with an isogenic strain that also expressed an acyl CoA synthetase and an ester synthase.

Figure 7A:
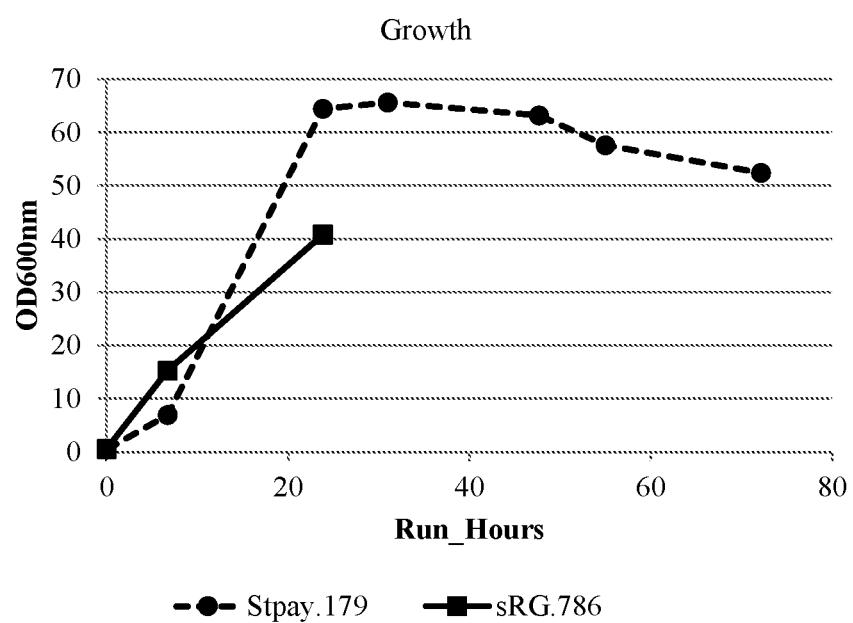
FIG. 7A-7C Illustrates different measures that are indicative of improved viability and production of medium-chain fatty acid derivatives by a strain expressing a medium-chain alkyl ester biosynthesis pathway in comparison to a strain expressing only a medium-chain length fatty acid biosynthesis pathway. Strain sRS.786 is engineered to express a medium-chain length thioesterase (chFatB2) and produces only free fatty acids (FFA). Strain Stpay.179 is isogenic to sRS.786 and also expresses fatty acyl CoA synthetase and an ester synthase and produces medium length fatty alkyl esters when provided short chain alcohols in the medium (such as e.g., methanol, ethanol, etc).
Figure 7B:
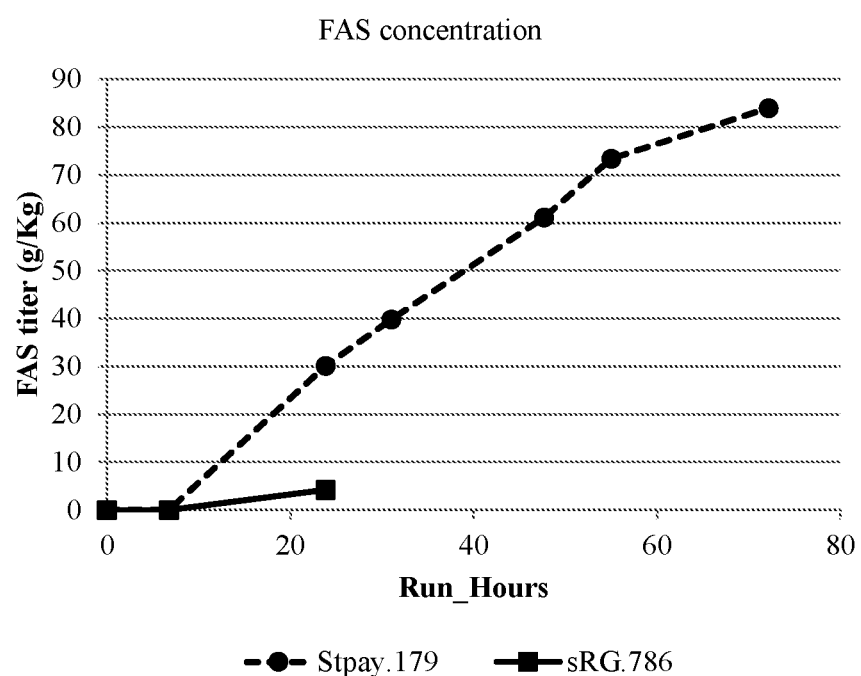
Figure 7C:
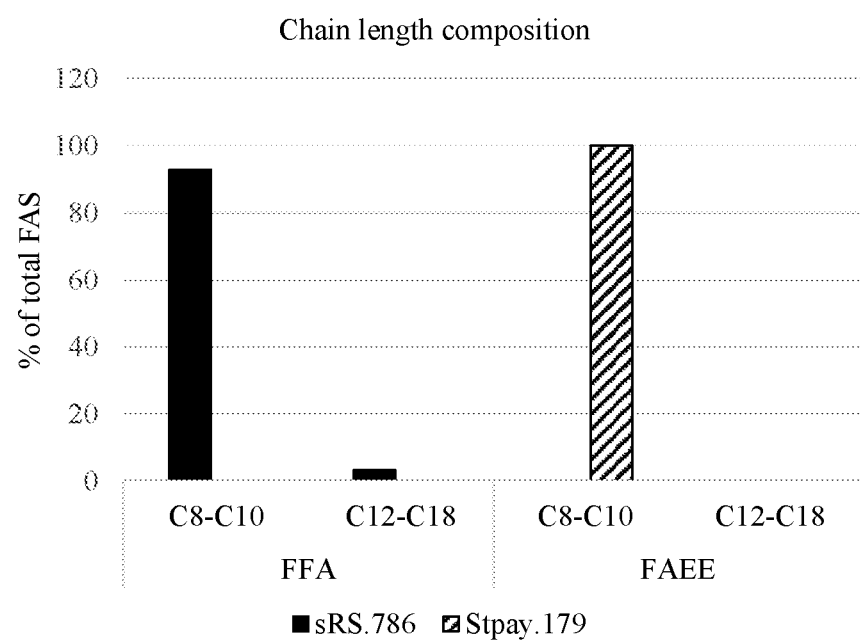

Strain sRS.786 was engineered to express a medium-chain length thioesterase (SEQ ID NO:49) and produces FFAs which are mostly C8 and C10 FFAs (FIG. 7C). Strain Stpay.179 is isogenic to sRS.786, but also expresses fatty acyl CoA synthetase and an ester synthase. Stpay.179 produces medium length fatty alkyl esters when provided short chain alcohols in the medium such as e.g., methanol, ethanol, etc. (FIG. 7C).

TABLE 4

Strains producing medium-chain fatty
acids (FFA) or fatty alkyl esters

| Strain name | Description | Pathway enzymes expressed |
|---|---|---|
| sRS.786 | FFA producer | Engineered thioesterase variant |
| Stpay.179 | Fatty alkyl esters | Engineered thioesterase variant, Acyl CoA Synthetase, Ester synthase |

Strains sRS.786 and Stpay.179 were grown in 5 L bioreactors fed batch, as described below in Example 11 and 12, using minimal salt medium with glucose as the carbon source fed at a rate of 14/g/h. Additionally, either ethanol (FIG. 7) or methanol (not shown) was fed during the course of the fermentation to maintain a concentration around 2 g/L of the alcohol.

The strain producing solely FFAs (sRS.786) stopped growth and glucose consumption approximately 10 h after the addition of IPTG to induce the expression of the medium-chain length acyl-ACP thioesterase (SEQ ID NO:49), and produced about 5 g of C8+C10 FFAs. In contrast, strain Stpay.179, which expressed the esterification pathway, was able to grow and produce a titer of over 84 g/kg of total fatty acid species, 93% of which were C8-C10 FFAs (FIG. 7B and FIG. 7C). Similar results were observed when ethanol or methanol were used as the alcohol supplemented for ester synthesis.

These data demonstrate that the expression of an ester synthesis pathway that catalyzes the conversion of toxic intracellular medium-chain free fatty acids to less toxic alkyl esters (e.g., fatty acid methyl or fatty acid ethyl esters) enables the high level production of medium-chain length fatty acid derivatives. These data further show that the expression of an ester synthesis pathway enables the high level expression of a medium-chain length selective thioesterase by eliminating its toxicity.

Example 4

The following Example illustrates engineered thioesterase variants that contain a single amino acid substitution and have improved activity and/or selectivity for the production of medium-chain length fatty acid derivatives.

The production of medium-chain (C6 to C10) length fatty acid derivatives using biotechnology is currently limited in part by the activity and the selectivity of available thioesterases (TEs). One of the most active and selective TEs available is the Cuphae *hookeriana* thioesterase chFatB2, an enzyme having the amino acid sequence described by SEQ ID NO:1.

Unfortunately, however, this enzyme as found in nature has many limitations. It is poorly expressed as a soluble protein in microorganisms, its specific activity is low, and it is more selective for the hydrolysis of C10 thioesters vs C8 thioesters. To create new TEs having improved activity, selectivity, and solubility, we undertook an extensive engineering effort to identify amino acid substitutions in SEQ ID NO:1 that could result in novel engineered TE variants having improved activity for the production of medium-chain fatty acid derivatives. Such TE variants having improved activity for the production of medium-chain fatty acid derivatives might attain that improved activity for the production of medium-chain fatty acid derivatives through any one or more of; improved catalytic activity, improved selectivity, and/or improved solubility.

SEQ ID NO:1 has 328 amino acids (6560 possible single amino acid variants) and has no reported three dimensional crystal structure that could support a rational enzyme engineering effort. We first undertook an effort to identify and engineer single mutations into SEQ ID NO:1 that would result in engineered TE variants demonstrating a significant increase in enzyme activity and/or medium-chain length selectivity in comparison to that of the parent sequence, SEQ ID NO:1.

To evaluate such mutations, a gene encoding a novel engineered TE having a selected single amino acid substitution was expressed in E. coli and grown under conditions that support the TE dependent production of fatty acid derivatives. The amount and composition of the medium-chain fatty acid derivatives that were produced by that strain were then quantified and compared to the amount and composition of the medium-chain fatty acid derivatives that were produced by a control strain that was identical, except that it expressed an enzyme having SEQ ID NO:1.

E. coli, which does not natively produce free fatty acids, can produce free fatty acids when engineered to express a heterologous TE, and the amount and composition of these fatty acids are directly correlated to the activity and selectivity of the TE being expressed (see e.g., Yuan et al., (1995) supra; International Patent Application Publication WO2007136762; International Patent Application Publication WO2008119082).

As discussed above in Examples 1-3, the production of medium-chain length fatty acids and medium-chain length fatty alcohols are toxic to a microorganism, such as E. coli. To ensure the host E. coli used to evaluate the engineered TEs could tolerate an engineered TE that produced potentially toxic levels of medium-chain length fatty acids, the E. coli used was also engineered to express genes that would increase the cells tolerance to medium-chain length fatty acids by affecting their conversion to fatty alcohol acetates, such that the level and composition of the fatty alcohol acetates produced by the engineered cell were directly correlated to the activity and selectivity of the TE expressed. Generation of the Control Evaluation Strains.

Figure 8:
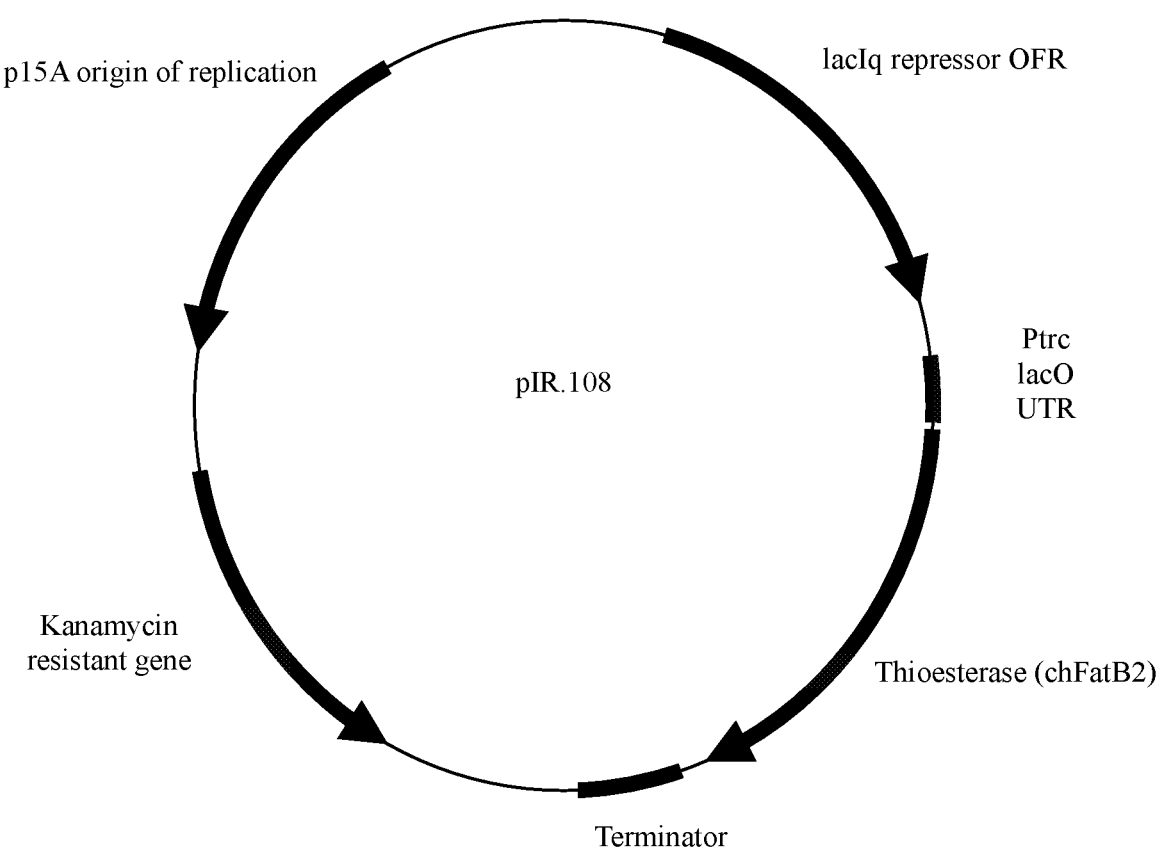
FIG. 8 Illustrates plasmid pIR.108

A gene encoding a polypeptide of SEQ ID NO:1 was synthesized for optimal translation in E. coli, and is shown as SEQ ID NO: 60. This gene was cloned into a pACYC based plasmid (Genbank Accession X06403), which confers resistance to kanamycin, such that the gene was under the transcriptional control of the Ptrc promoter (see e.g., Camsund et al. Journal of Biological Engineering 2014, 8:4), which is induced in the presence of isopropylthiogalactoside (IPTG). The resulting plasmid, pIR.108 (FIG. 8), was transformed into an E. coli derived from MG1655 that was engineered to overexpress the gene EntD from the chromosome (see e.g., International Patent Application Publication WO2010062480) and harbored a Ptrc controlled operon that expressed the genes carB, alrA, and aftA1, which are described above in Example 3 and together affect the biochemical conversion of free fatty acids (FFAs) to fatty alcohol acetates (FACEs).

To ensure that engineered TEs having high activity and specificity could be effectively tested, several Control Evaluation Strains were used that each had different capacity for the production of fatty acid derivatives i.e. they were engineered to support different levels of carbon flux through the fatty acid pathway (Table 5). Further, in some cases novel engineered TE variants having improved activity for the production of medium-chain fatty acid derivatives were used as a control TE in place of SEQ ID NO: 1 to identify highly active improved engineered TE variants. For example, TEs having a single amino acid substitution were compared to SEQ ID NO:1 expressed in a strain engineered to have a modest fatty acid flux. Once novel highly active TE variants had been developed, SEQ ID NO:1 expressed in a strain of modest fatty acid flux was no longer sufficient to act as a control. Instead, a novel highly-active engineered TE variant having multiple amino acid substitutions and expressed in a strain having a high fatty acid capacity was used as a control. All together, we used five different TEs and strains to support the evaluation of the novel engineered TE variants to ensure that the performance improvements of each TE variant could be best quantified and identified. A list of the Control Base Strains with various capacities for the production of fatty acid derivatives are shown in Table 5. Table 6 shows the performance of the control TEs relative to the wild-type sequence (SEQ ID NO:1).

TABLE 5

Description of Control Base Strains with different capacity for the production of fatty acid derivatives

| | Control Base Strain | | | | |
|---|---|---|---|---|---|
| | sAZ303 | sJN.032 | sven.449 | sAZ746 | sCB.243 |
| FAS biosynthetic capacity* (mg/L) | 200-1000 | 200-1200 | 200-1700 | 200-2000 | 200-3000 |

*Range of FAS titer (mg/L) in HTP screening described below in "Quantifying the relative performance of engineered TE variants" depend on the level of flux to alkyl thioesters engineered in each strain.

TABLE 6

Control Engineered thioesterase variants and their performance relative to the wild-type sequence (SEQ ID NO: 1).

| Control TE | Total FAS FOC | % C8 FAS of total FAS FOC | % C8/% C10 FOC |
|---|---|---|---|
| SEQ ID NO: 1 (wild-type) | 1.0 | 1.0 | 1.0 |
| SEQ ID NO: 4 | 1.42 | 1.22 | 1.78 |
| SEQ ID NO: 9 | 1.87 | 1.25 | 2.04 |
| SEQ ID NO: 15 | 1.54 | 1.45 | 3.48 |
| SEQ ID NO: 49 | 2.79 | 1.53 | 2.07 |
| SEQ ID NO: 55 | 2.23 | 2.90 | 25.43 |

Identification of Engineered TEs with Improved Activities in Comparison to SEQ ID NO:1.

Strains expressing the engineered TEs described in Table 7 were each grown under conditions that resulted in the expression of the gene encoding their unique engineered TE, which affects the production of medium-chain fatty acids, and the genes encoding CarB, AlrA, and Aft1, which affect the conversion of those medium-chain fatty acids to medium-chain fatty alcohol acetates. The resulting fatty acid derived products were extracted, quantified, and then compared to the fatty acid derivative products produced by the Control Evaluation Strain 1, expressing SEQ ID NO:1 (Table 6) grown under the same conditions. The detailed method for the growth and analysis of the resulting fatty acid derivatives are described below.

Table 7 describes engineered TEs having improved performance for (1) activity i.e. total fatty acid derived products produced by the culture, (2) C8 selectivity i.e. % C8 FAS of total FAS produced by the culture, and (3) selectivity for C8 as compared to C10 products (% C8 FAS/% C10 FAS) with performance reported as a fold over the control (FOC). Single mutants shown in Table 7 are relative to SEQ ID NO:1. Thus, for example, P3K indicates a substitution mutation (proline to lysine) at amino acid position 3 of SEQ ID NO:1.

TABLE 7

Engineered thioesterase variants with improved ability to produce total FAS, % C8 FAS of total FAS, and/or % C8 FAS/% C10 FAS. FOC: fold over the control.

| SEQ ID NO: | Total FAS FOC | % C8 FAS of total FAS FOC | % C10 FAS of total FAS FOC | % C8/% C10 FOC | Control TE | Screening strain |
|---|---|---|---|---|---|---|
| P3K | 0.77 | 1.07 | 0.90 | 1.19 | SEQ ID NO: 1 | sAZ303 |
| D4M | 1.22 | 1.10 | 0.86 | 1.28 | SEQ ID NO: 1 | sAZ303 |
| S6R | 0.82 | 1.02 | 0.97 | 1.04 | SEQ ID NO: 1 | sAZ303 |
| T14G | 0.81 | 1.02 | 0.97 | 1.05 | SEQ ID NO: 1 | sAZ303 |
| T14R | 1.18 | 1.05 | 0.93 | 1.13 | SEQ ID NO: 1 | sAZ303 |
| V15L | 0.81 | 1.05 | 0.92 | 1.13 | SEQ ID NO: 1 | sAZ303 |
| V15W | 1.20 | 1.06 | 0.92 | 1.14 | SEQ ID NO: 1 | sAZ303 |
| V17A | 0.79 | 1.02 | 0.97 | 1.05 | SEQ ID NO: 1 | sAZ303 |
| V17C | 1.26 | 1.08 | 0.89 | 1.22 | SEQ ID NO: 1 | sAZ303 |
| P22R | 0.79 | 1.02 | 0.96 | 1.06 | SEQ ID NO: 1 | sAZ303 |
| D37P | 0.78 | 1.01 | 0.98 | 1.03 | SEQ ID NO: 1 | sAZ303 |
| T44G | 0.90 | 1.05 | 0.93 | 1.13 | SEQ ID NO: 1 | sAZ303 |
| T44I | 0.83 | 1.09 | 0.87 | 1.26 | SEQ ID NO: 1 | sAZ303 |
| V45S | 0.66 | 1.03 | 0.95 | 1.09 | SEQ ID NO: 1 | sAZ303 |
| V50W | 0.91 | 1.05 | 0.92 | 1.13 | SEQ ID NO: 1 | sAZ303 |
| S54R | 0.84 | 1.10 | 0.83 | 1.33 | SEQ ID NO: 1 | sAZ303 |
| S56C | 1.23 | 0.90 | 1.15 | 0.78 | SEQ ID NO: 1 | sAZ303 |
| S56K | 1.10 | 1.07 | 0.89 | 1.21 | SEQ ID NO: 1 | sAZ303 |
| T64P | 1.14 | 1.05 | 0.94 | 1.11 | SEQ ID NO: 1 | sAZ303 |
| T64R | 0.84 | 0.96 | 1.06 | 0.91 | SEQ ID NO: 1 | sAZ303 |
| T67L | 0.98 | 1.08 | 0.88 | 1.22 | SEQ ID NO: 1 | sAZ303 |
| L73V | 0.79 | 1.06 | 0.90 | 1.18 | SEQ ID NO: 1 | sAZ303 |
| H76F | 0.82 | 1.10 | 0.82 | 1.33 | SEQ ID NO: 1 | sAZ303 |
| H76L | 1.42 | 1.10 | 0.86 | 1.28 | SEQ ID NO: 1 | sAZ303 |
| H76Y | 0.65 | 1.10 | 0.85 | 1.29 | SEQ ID NO: 1 | sAZ303 |
| L91M | 0.90 | 0.96 | 1.06 | 0.91 | SEQ ID NO: 1 | sAZ303 |
| L99K | 0.96 | 1.06 | 0.90 | 1.18 | SEQ ID NO: 1 | sAZ303 |
| L99P | 1.01 | 1.07 | 0.90 | 1.19 | SEQ ID NO: 1 | sAZ303 |
| C102I | 0.80 | 1.03 | 0.95 | 1.09 | SEQ ID NO: 1 | sAZ303 |
| V110L | 0.81 | 1.08 | 0.88 | 1.22 | SEQ ID NO: 1 | sAZ303 |
| I111T | 0.94 | 0.82 | 1.24 | 0.66 | SEQ ID NO: 1 | sAZ303 |
| Q114K | 1.06 | 1.06 | 0.91 | 1.16 | SEQ ID NO: 1 | sAZ303 |
| I129V | 0.79 | 0.98 | 1.03 | 0.95 | SEQ ID NO: 1 | sAZ303 |
| R132W | 1.43 | 1.05 | 0.92 | 1.14 | SEQ ID NO: 1 | sAZ303 |
| G137C | 0.94 | 1.08 | 0.93 | 1.22 | SEQ ID NO: 1 | sAZ303 |
| R158Q | 0.79 | 1.03 | 0.96 | 1.07 | SEQ ID NO: 1 | sAZ303 |
| A162E | 0.90 | 1.07 | 0.89 | 1.21 | SEQ ID NO: 1 | sAZ303 |
| M165T | 1.20 | 1.04 | 0.95 | 1.09 | SEQ ID NO: 1 | sAZ303 |
| L176V | 1.06 | 0.99 | 1.01 | 0.99 | SEQ ID NO: 1 | sAZ303 |
| Y178P | 1.21 | 1.00 | 1.01 | 1.00 | SEQ ID NO: 1 | sAZ303 |
| V185A | 0.88 | 1.10 | 0.86 | 1.28 | SEQ ID NO: 1 | sAZ303 |
| P186G | 0.93 | 1.07 | 0.89 | 1.20 | SEQ ID NO: 1 | sAZ303 |
| D196V | 1.09 | 1.07 | 0.89 | 1.20 | SEQ ID NO: 1 | sAZ303 |
| S197N | 1.10 | 1.03 | 0.95 | 1.08 | SEQ ID NO: 1 | sAZ303 |
| D198W | 0.77 | 1.09 | 0.85 | 1.28 | SEQ ID NO: 1 | sAZ303 |
| K203R | 0.82 | 1.07 | 0.88 | 1.22 | SEQ ID NO: 1 | sAZ303 |
| Q213H | 0.94 | 1.04 | 0.95 | 1.10 | SEQ ID NO: 1 | sAZ303 |
| Q213R | 0.99 | 1.04 | 0.94 | 1.11 | SEQ ID NO: 1 | sAZ303 |
| T217R | 0.80 | 1.04 | 0.93 | 1.12 | SEQ ID NO: 1 | sAZ303 |
| V225L | 0.69 | 1.08 | 0.85 | 1.27 | SEQ ID NO: 1 | sAZ303 |
| Q227G | 0.94 | 0.95 | 1.07 | 0.89 | SEQ ID NO: 1 | sAZ303 |
| G236T | 1.04 | 1.05 | 0.93 | 1.12 | SEQ ID NO: 1 | sAZ303 |
| T244M | 0.67 | 0.94 | 1.06 | 0.88 | SEQ ID NO: 1 | sAZ303 |
| T244R | 0.79 | 1.05 | 0.92 | 1.14 | SEQ ID NO: 1 | sAZ303 |
| S254G | 0.80 | 0.99 | 1.02 | 0.96 | SEQ ID NO: 1 | sAZ303 |
| A256C | 0.83 | 1.01 | 0.98 | 1.03 | SEQ ID NO: 1 | sAZ303 |
| E258T | 0.41 | 1.08 | 0.79 | 1.37 | SEQ ID NO: 1 | sAZ303 |
| E258V | 0.52 | 1.07 | 0.84 | 1.27 | SEQ ID NO: 1 | sAZ303 |
| S278K | 0.83 | 1.03 | 0.94 | 1.10 | SEQ ID NO: 1 | sAZ303 |
| S278T | 1.10 | 1.05 | 0.93 | 1.13 | SEQ ID NO: 1 | sAZ303 |
| V282S | 0.79 | 1.01 | 0.99 | 1.02 | SEQ ID NO: 1 | sAZ303 |
| V282V | 0.97 | 0.99 | 1.01 | 0.98 | SEQ ID NO: 1 | sAZ303 |
| L292F | 0.73 | 1.05 | 0.92 | 1.14 | SEQ ID NO: 1 | sAZ303 |
| A297D | 0.88 | 1.09 | 0.87 | 1.26 | SEQ ID NO: 1 | sAZ303 |
| A297T | 1.01 | 1.05 | 0.93 | 1.13 | SEQ ID NO: 1 | sAZ303 |
| A297V | 1.16 | 0.98 | 1.03 | 0.95 | SEQ ID NO: 1 | sAZ303 |

TABLE 7-continued

Engineered thioesterase variants with improved ability to produce total FAS,
% C8 FAS of total FAS, and/or % C8 FAS/% C10 FAS. FOC: fold over the control.

| SEQ ID NO: | Total FAS FOC | % C8 FAS of total FAS FOC | % C10 FAS of total FAS FOC | % C8/% C10 FOC | Control TE | Screening strain |
|---|---|---|---|---|---|---|
| I298C | 0.49 | 1.02 | 0.90 | 1.14 | SEQ ID NO: 1 | sAZ303 |
| I298V | 0.88 | 1.07 | 0.90 | 1.19 | SEQ ID NO: 1 | sAZ303 |
| V299L | 1.02 | 1.07 | 0.89 | 1.19 | SEQ ID NO: 1 | sAZ303 |
| N300K | 0.73 | 1.29 | 0.60 | 2.15 | SEQ ID NO: 1 | sAZ303 |
| N300L | 1.15 | 1.07 | 0.90 | 1.18 | SEQ ID NO: 1 | sAZ303 |
| N300W | 0.95 | 1.16 | 0.76 | 1.52 | SEQ ID NO: 1 | sAZ303 |
| G301C | 0.45 | 0.86 | 1.19 | 0.72 | SEQ ID NO: 1 | sAZ303 |
| A302T | 0.85 | 0.94 | 1.08 | 0.87 | SEQ ID NO: 1 | sAZ303 |
| I316R | 1.04 | 1.00 | 1.01 | 0.99 | SEQ ID NO: 1 | sAZ303 |
| T321R | 1.00 | 0.99 | 1.01 | 0.97 | SEQ ID NO: 1 | sAZ303 |
| S322K | 0.79 | 1.01 | 0.99 | 1.02 | SEQ ID NO: 1 | sAZ303 |
| SEQ ID NO: 2 | 1.96 | 1.03 | 0.96 | 1.06 | SEQ ID NO: 1 | sAZ303 |
| SEQ ID NO: 3 | 1.85 | 1.03 | 0.96 | 1.08 | SEQ ID NO: 1 | sAZ303 |
| SEQ ID NO: 4 | 1.42 | 1.22 | 0.69 | 1.78 | SEQ ID NO: 1 | sAZ303 |
| SEQ ID NO: 5 | 1.85 | 1.06 | 0.91 | 1.16 | SEQ ID NO: 1 | sAZ303 |
| SEQ ID NO: 6 | 1.82 | 1.04 | 0.94 | 1.11 | SEQ ID NO: 1 | sAZ303 |
| SEQ ID NO: 7 | 1.27 | 1.18 | 0.76 | 1.54 | SEQ ID NO: 1 | sAZ303 |
| SEQ ID NO: 8 | 1.80 | 1.05 | 0.94 | 1.11 | SEQ ID NO: 1 | sAZ303 |
| SEQ ID NO: 9 | 1.87 | 1.25 | 0.61 | 2.04 | SEQ ID NO: 1 | sAZ303 |
| SEQ ID NO: 10 | 0.82 | 1.16 | 0.80 | 1.45 | SEQ ID NO: 4 | sJN.032 |
| SEQ ID NO: 11 | 0.94 | 1.15 | 0.87 | 1.27 | SEQ ID NO: 4 | sJN.032 |
| SEQ ID NO: 12 | 0.77 | 1.18 | 0.91 | 1.17 | SEQ ID NO: 4 | sJN.032 |
| SEQ ID NO: 13 | 0.37 | 1.36 | 0.32 | 4.17 | SEQ ID NO: 9 | sven.449 |
| SEQ ID NO: 14 | 0.42 | 1.31 | 0.41 | 3.18 | SEQ ID NO: 9 | sven.449 |
| SEQ ID NO: 15 | 0.83 | 1.17 | 0.68 | 1.70 | SEQ ID NO: 9 | sven.449 |
| SEQ ID NO: 16 | 0.81 | 1.35 | 0.00 | — | SEQ ID NO: 4 | sJN.032 |
| SEQ ID NO: 17 | 1.15 | 1.25 | 1.22 | 1.03 | SEQ ID NO: 4 | sJN.032 |
| SEQ ID NO: 18 | 1.27 | 1.24 | 0.61 | 2.03 | SEQ ID NO: 4 | sJN.032 |
| SEQ ID NO: 19 | 1.27 | 1.24 | 2.69 | 0.46 | SEQ ID NO: 4 | sJN.032 |
| SEQ ID NO: 20 | 1.15 | 1.24 | 0.51 | 2.45 | SEQ ID NO: 4 | sJN.032 |
| SEQ ID NO: 21 | 1.00 | 1.21 | 0.56 | 2.16 | SEQ ID NO: 4 | sJN.032 |
| SEQ ID NO: 22 | 0.83 | 1.19 | 1.71 | 0.70 | SEQ ID NO: 4 | sJN.032 |
| SEQ ID NO: 23 | 1.28 | 1.19 | 0.62 | 1.93 | SEQ ID NO: 4 | sJN.032 |
| SEQ ID NO: 24 | 1.15 | 1.19 | 0.62 | 1.92 | SEQ ID NO: 4 | sJN.032 |
| SEQ ID NO: 25 | 1.25 | 1.19 | 1.29 | 0.92 | SEQ ID NO: 4 | sJN.032 |
| SEQ ID NO: 26 | 1.03 | 1.19 | 0.00 | — | SEQ ID NO: 4 | sJN.032 |
| SEQ ID NO: 27 | 1.23 | 1.18 | 0.00 | — | SEQ ID NO: 4 | sJN.032 |
| SEQ ID NO: 28 | 1.01 | 1.18 | 1.53 | 0.77 | SEQ ID NO: 4 | sJN.032 |
| SEQ ID NO: 29 | 1.06 | 1.18 | 1.02 | 1.16 | SEQ ID NO: 4 | sJN.032 |
| SEQ ID NO: 30 | 1.09 | 1.17 | 0.78 | 1.50 | SEQ ID NO: 4 | sJN.032 |
| SEQ ID NO: 31 | 1.12 | 1.16 | 1.76 | 0.66 | SEQ ID NO: 4 | sJN.032 |
| SEQ ID NO: 32 | 0.94 | 1.16 | 1.02 | 1.14 | SEQ ID NO: 4 | sJN.032 |
| SEQ ID NO: 33 | 1.20 | 1.16 | 0.98 | 1.18 | SEQ ID NO: 4 | sJN.032 |
| SEQ ID NO: 34 | 1.21 | 1.15 | 1.00 | 1.15 | SEQ ID NO: 4 | sJN.032 |
| SEQ ID NO: 35 | 1.10 | 1.15 | 0.61 | 1.88 | SEQ ID NO: 4 | sJN.032 |
| SEQ ID NO: 36 | 1.23 | 1.14 | 0.62 | 1.83 | SEQ ID NO: 4 | sJN.032 |
| SEQ ID NO: 37 | 0.87 | 1.14 | 0.80 | 1.41 | SEQ ID NO: 4 | sJN.032 |
| SEQ ID NO: 38 | 1.38 | 1.13 | 0.48 | 2.37 | SEQ ID NO: 4 | sJN.032 |
| SEQ ID NO: 39 | 0.95 | 1.12 | 0.98 | 1.15 | SEQ ID NO: 4 | sJN.032 |
| SEQ ID NO: 40 | 1.16 | 1.12 | 0.84 | 1.33 | SEQ ID NO: 4 | sJN.032 |
| SEQ ID NO: 41 | 0.73 | 1.12 | 2.69 | 0.42 | SEQ ID NO: 4 | sJN.032 |
| SEQ ID NO: 42 | 0.97 | 1.11 | 0.82 | 1.35 | SEQ ID NO: 4 | sJN.032 |
| SEQ ID NO: 43 | 0.75 | 1.11 | 1.02 | 1.09 | SEQ ID NO: 4 | sJN.032 |
| SEQ ID NO: 44 | 0.98 | 1.11 | 0.48 | 2.32 | SEQ ID NO: 4 | sJN.032 |
| SEQ ID NO: 45 | 0.97 | 1.11 | 0.97 | 1.14 | SEQ ID NO: 4 | sJN.032 |
| SEQ ID NO: 46 | 1.05 | 1.11 | 2.26 | 0.49 | SEQ ID NO: 4 | sJN.032 |
| SEQ ID NO: 47 | 0.75 | 1.07 | 0.77 | 0.66 | SEQ ID NO: 15 | sAZ746 |
| SEQ ID NO: 48 | 1.74 | 1.09 | 0.71 | 0.72 | SEQ ID NO: 15 | sAZ746 |
| SEQ ID NO: 49 | 1.81 | 1.05 | 0.83 | 0.59 | SEQ ID NO: 15 | sAZ746 |
| SEQ ID NO: 50 | 1.79 | 1.10 | 0.67 | 0.78 | SEQ ID NO: 15 | sAZ746 |
| SEQ ID NO: 51 | 1.60 | 1.05 | 0.85 | 0.58 | SEQ ID NO: 15 | sAZ746 |
| SEQ ID NO: 52 | 1.00 | 1.60 | 0.52 | 3.10 | SEQ ID NO: 49 | sCB.243 |
| SEQ ID NO: 53 | 1.00 | 1.40 | 0.27 | 5.20 | SEQ ID NO: 49 | sCB.243 |
| SEQ ID NO: 54 | 1.10 | 1.70 | 0.53 | 3.20 | SEQ ID NO: 49 | sCB.243 |
| SEQ ID NO: 55 | 0.80 | 1.90 | 0.15 | 12.30 | SEQ ID NO: 49 | sCB.243 |
| SEQ ID NO: 56 | 0.90 | 1.60 | 0.19 | 8.40 | SEQ ID NO: 49 | sCB.243 |
| SEQ ID NO: 57 | 1.10 | 1.80 | 0.60 | 3.00 | SEQ ID NO: 49 | sCB.243 |
| SEQ ID NO: 58 | 1.00 | 1.30 | 0.15 | 8.60 | SEQ ID NO: 49 | sCB.243 |
| SEQ ID NO: 59 | 1.00 | 1.50 | 0.24 | 6.20 | SEQ ID NO: 49 | sCB.243 |

Quantifying the Relative Performance of Engineered TE Variants

To quantify the performance of each engineered TE variant, a culture of cells expressing a variant was grown under conditions supporting expression of the TE, CarB, AlrA, and Atf1, and the resulting fatty acid derivatives were extracted and quantified by Gas Chromatography with Flame Ionization Detection (GC/FID), as described below.

The composition and amount of the resulting fatty acid derivatives (fatty acids, fatty alcohols, and fatty alcohol acetates) were determined and then compared to the fatty acid derivatives produced under identical conditions by the Control Evaluation Strain that expressed the control TE. Briefly, a single colony of each strain was inoculated into the well of a 96-well plate containing 200 uL Luria Bertani broth containing the appropriate antibiotic(s). 40 µL of this culture were used to inoculate 360 µL of the same medium in a 96-deep-well plate, which was shaken for 4 hours at 32° C. 40 µL of this culture were used to inoculate 360 µL of Production Medium (Table 8) in a final 96-deep-well plate. These cultures were overlaid with 60 uL hexadecane, shaken at 32° C. for 2 hours, IPTG was added (to 1 mM) to induce expression of TE, CarB, AlrA, and Atf1, and shaking continued for an additional 20 hours after which the cultures were evaluated as described below.

TABLE 8

Production Medium

| Component | Volume |
| --- | --- |
| Sterile water | 669.05 mL |
| 1M CaCl2 | 0.1 mL |
| 50% Glucose (0.5 g/L) | 70 mL |
| 5X Salt 1/2N (2.5 g/L) | 200 mL |
| NH4Cl (100 g/L, 100X) | 2.5 mL |
| 2M Bis-Tris, pH 7.0 | 50 mL |
| 10% Triton | 1.25 mL |
| TM2 (trace minerals no iron) | 3 mL |
| 10 g/L ferric citrate | 1 mL |
| 1M MgSO4 | 1 mL |
| Thiamine (10 mg/mL) | 0.1 mL |
| Kanamycin (50 mg/mL) | 1 mL |
| Spectinomycin (100 mg/mL) | 1 mL |
| Total | 1000 |

Fatty Acid Derivative (FAS) Sample Prep and Quantification 4004 of butyl acetate (containing 500 mg/L undecanol as an internal analytical standard) was added to each well, the plates were heat-sealed, shaken for 15 minutes at 2000 rpm, centrifuged for 10 minutes at 4500 rpm at room, and 1004 of the top organic layer were transferred to a 96-well plate containing 100 uL of N,O-Bis(trimethylsilyl)trifluoroacetamide (BSTFA) (see e.g., Stalling D L, et al. Biochemical and Biophysical Research Communications. 1968 May 23; 31(4):616-22). The plate was sealed and evaluated by gas chromatography with flame ionization detection (GC-FID).

A Control Evaluation Strain was included in each plate as an "internal plate control" for the strains expressing the engineered TE variants. To determine the relative performance of the engineered TE variants, the total amount of fatty acid derivatives (those products resulting from the action of the expressed TEs and the downstream converting enzymes CarB, AlrA, and Atf1: fatty acids, fatty aldehydes, fatty alcohols, and fatty alcohol acetates) or specific fatty acid derivatives (such as specific chain lengths i.e. C8 or C10) were quantified and then compared to the same parameter for the Control Evaluation Strain from the same plate and reported as Fold Over Control (FOC). For example, the FOC total FAS titer of mutant A was determined by adding up the total titer of all fatty acid species identified in the extract of mutant A and dividing it by the total FAS titer of the internal Control Evaluation Strain. Engineered TE variants that have improved activity over the control would show an FOC of greater than 1.0 for the parameter reported. The FOC total C8 FAS of mutant A was determined by adding up the total concentration of all fatty acid species with chain length of C8 identified in the extract of mutant A and dividing it by the total concentration of all fatty acid species with chain length of C8 identified for the internal Control Evaluation Strain. For engineered thioesterase variants that contain a single amino acid substitution, the primary metrics used to identify hits were the following: a) improved FOC total FAS, b) improved FOC % C8 FAS of total FAS, and or c) improved % C8/% C10.

The mutations shown in Table 7 (above) were surprisingly identified as having the ability to significantly a) improve FOC total FAS; and b) improve FOC % C8 FAS of total FAS. Thus, the engineered thioesterase (TE) variants containing the mutations enumerated in Table 7, represent novel engineered TE variants having improved activity for the production of fatty acid derivatives. In particular, the engineered TE variants shown in Table 7, represent novel TE variants having improved activity for the production of C8 and or C10 fatty acid derivatives.

Example 5

TE variants were engineered to contain multiple amino acid substitutions that created new TEs having improved activity for the production of medium-chain fatty acid derivatives. The variants had improved activity and selectivity over native thioesterase enzyme (SEQ ID NO:1) and over engineered TE variants having single amino acid substitutions (Example 4, Table 7).

Similar to Example 4, genes encoding engineered TE variants having multiple amino acid substitutions were synthesized and cloned into an expression vector that affected their expression when grown in the presence of IPTG. These were transformed into an E. coli strain derived from MG1655 that was engineered to overexpress the gene EntD from the chromosome (see e.g., WO2010062480) and harbored a Ptrc controlled operon that expressed the genes carB, alrA, and aftA1, which are described above in Example 3 and together affect the biochemical conversion of free fatty acids (FFAs) to fatty alcohol acetates (FACEs). The engineered TEs having multiple amino acid substitutions were compared to specific Control Evaluation Strains that were identical except for the TE being expressed.

Table 7 lists novel engineered TEs that have multiple amino acid substitutions and that demonstrate improved activity for the production of medium-chain fatty acid derivatives (FAS) and improved selectivity for producing medium-chain length fatty acid derivatives (SEQ ID NO: 2 to SEQ ID NO: 15) in comparison to the Control Evaluation Strain and TE listed. Accordingly, each of the novel engineered TEs, their individual mutations, and their unique combination of mutations are useful tools for the production of medium-chain length fatty acid derivatives since the novel engineered TEs are thioesterases have improved activity for the production of medium-chain fatty acid derivatives.

Example 6

The following Example illustrates engineered TE variants having an increase in surface charge and improved activity for the production of medium-chain length fatty acid derivatives. Three-dimensional modeling was used to engineer thioestrase variants/mutants having improved activity for production of medium-chain fatty acid derivatives.

In some embodiments SEQ ID NO:1 appears to be toxic when overexpressed in *E. coli*. Without being bound by theory it is believed that the SEQ ID NO:1 could be unstable or easily aggregated in high concentration in the cell. Therefore, in an effort to reduce potential toxicity of the protein a three dimensional model was computationally constructed and used to engineer changes to the surface of SEQ ID NO:1.

In this Example, a three-dimensional molecular model of SEQ ID NO:1 was computationally constructed by templating the x-ray crystal structures of other acyl-ACP thioesterases. Based on the model, specific residues of the SEQ ID NO:1 enzyme that were predicted to change the net surface charge were identified. In particular, negative charged residues (Asp or Glu) were mutated to positive charged residues (Arg or His) on the enzyme surface, thereby modifying the net surface charge from +15 to +25. As is shown in Table 7, the resulting engineered TE variants having an increase surface charge produce a higher percentage of C8 fatty acid derivatives. Thus, the engineered TE variants have improved activity for production of medium-chain fatty acid derivatives.

3-D Modelling of SEQ ID NO:1 Thioesterase. Because the experimental 3D structure of SEQ ID NO:1 was not available, a homology-based 3D model of the enzyme was computationally constructed as disclosed below in steps 1-5.
(1) Identification of Homologous Thioesterases of Known Structure The Protein Data Bank (PDB) is the single worldwide archive of structural data of biological macromolecules (see Berman, H. M. et al, Nucl. Acids Res. (2000) 28 (l): 235-242). The PDB protein databank is available on the World Wide Web at rcsb.org/pdb/home/home.do. The PDB databank was used to identify three solved x-ray crystal structures of thioesterases. In particular, the three solved structures of thioesterases identified were: 1) acyl-ACP thioesterase from *Bacteroides* thetaiotaomicron having Protein Data Bank Identification number (PDB ID):2ESS) oleoyl thioesterase from *Lactobacillus plantarum* (PDB ID:2OWN), and 3) acyl-ACP thioesterase from *Spirosoma linguale* (PDB ID: 4GAK). These structures, which overall show about 25% of sequence identity to SEQ ID NO:1, were used as templates.
(2) Alignment of the Query Sequence to the Template Structures The three solved 3D structures of the thioesterases identified in the PDB (2ESS, 2OWN and 4GAK) and their sequences were aligned with PROMALS3D multiple sequence and structure alignment server (see e.g., J. Pei and N. V. Grishin (2007) Bioinformatics. 23(7): 802-808; J. Pei et al., (2008) Nucl. Acids Res. 36 (7): 2295-2300) available on the World Wide Web at: prodata.swmed.edu/promals3d/promals3d.php. After aligning the sequences and structures of 2ESS, 2OWN and 4GAK, the query sequence of SEQ ID NO:1 was aligned into the existing structure-based sequence alignment using MMFFT version 7 (see e.g., Katoh, K., et al. (2013) Mol. Biol. Evol. April; 30(4): 772-780). The software is available on the World Wide Web at: mafft.cbrc.jp/alignment/software. The alignment of SEQ ID NO:1 and acyl-ACP thioesterases identified in the PDB (2ESS, 2OWN and 4GAK) is shown in FIG. 9
(3) Building the Homology 3D Structure Model of SEQ ID NO:1 Thioesterase A homology model for amino acids 37 to 310 was built by MODELLER software (see e.g., B. Webb, A. Sali. Comparative Protein Structure Modeling Using Modeller. Current Protocols in Bioinformatics, John Wiley & Sons, Inc., 5.6.1-5.6.32, 2014) using all three templates, 2ESS, 2OWN and 4GAK, and the structure-based alignment described in step 2 above. Further structural refinement was performed by the MODELLER built-in refinement mode. The refinement was performed with all default parameters with VTFM optimization and MD refinement modules. Information about MODELLER software and downloads are available on the World Wide Web at: salilab.org/modeller.
(4) Building the Ab Initio Models of N- and C-Terminal Domains As shown in FIG. 9, the SEQ ID NO:1 thioesterase used in these experiments has N- and C-terminal residues that are not included in the template x-ray crystal structures (36 amino acids at N-terminus and 18 amino acids at C-terminus). Thus, there is no proper template for building homology-based models for these parts. Accordingly, ab initio models (see e.g., J. Lee et al., (2009) Ab Initio Protein Structure Prediction pgs. 3-25 In: From Protein Structure to Function with Bioinformatics, D. J. Rigden (ed.) Springer) for both the N- and C-termini were built by the ROBETTA server (see e.g., Kim, D. E., et al. (2004) Nucleic Acids Res. July 1; 32 (Web Server issue): W526-W531; available on the World Wide Web at: robetta.org).
(5) Building Full Length Models for SEQ ID NO:1 Thioesterase and an Engineered Engineered TE Variant The full length model was made using MODELLER software using the three templates: main part homology model, N-terminal ab initio model, and C-terminal ab initio model.

Figure 10:
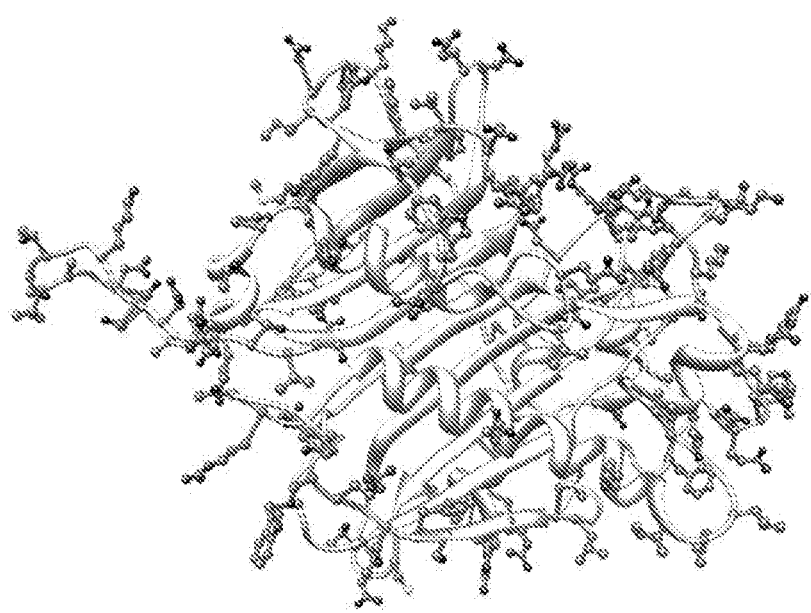
FIG. 10 Illustrates the final full length model for the 3D structure of SEQ ID NO:1. The surface residues are shown as balls & sticks.

The improved engineered TE variant having the amino acid substitutions P3K, L176V, D196V, K203R, V282S (SEQ ID NO:4) over the wild type control, demonstrated an improved ability to produce medium-chain length fatty acid derivatives (Example 5, Table 7). Therefore, the model of SEQ ID NO:1 was remodeled to SEQ ID NO:4 by virtually substituting the 5 variant residues and again performing structural refinement with the MODELLER built-in refinement mode. The surface residues were then defined based on the final model (FIG. 10).

Creating Engineered TE Variants Having an Increase in Modeled Surface Charge.

Based on the 3D structural model for SEQ ID NO:4 described above, twelve Aspartate (D) and Glutamate (E) residues, modeled to contribute negative charges to the surface of SEQ ID NO:4. Genes encoding engineered TE variants having various positive to negative substitutions of these 12 residues were then synthesized and evaluated for improved production of medium-chain length fatty acid derivatives in comparison to the control TE (SEQ ID NO:4), as described in Example 4 and 5.

Table 7 describes a set of engineered TE variants (SEQ ID NO: 16 to SEQ ID NO:46) having amino acid substitutions resulting in increases in modeled surface charge in comparison to SEQ ID NO:4 and having improved activity for the production of medium-chain length fatty acid derivatives. Thus, the TEs listed in Table 7 as SEQ ID NO: 16 to SEQ ID NO:46, are novel engineered TE variants useful for the production of medium-chain length fatty acid derivatives. Further, engineered variant TEs that have amino acid substitutions that increase the modeled surface charge are useful for the improved production of medium-chain length fatty acid derivatives in comparison to TEs that do not have an engineered increase in modeled surface charge.

Creating Novel Thioesterases that Contain Multiple Engineered Mutations Having an Increase in Modeled Surface Charge and Multiple Engineered Mutations that Increase Activity and/or Selectivity for Production of Medium-Chain Length Fatty Acid Derivatives.

Amino acid substitutions predicted to increase the thioesterase surface charge identified by 3-D modeling as described above, and that resulted in improved production of medium-chain length fatty acid derivatives (Table 7) were combined with an engineered TE variant with improved activity for the production of medium-chain fatty acid derivatives over its corresponding control (Example 6, Table 7) and having the SEQ ID NO:15.

Similar to Example 5, genes encoding engineered TE variants having multiple amino acid substitutions were synthesized and cloned into an expression vector that affected their expression when grown in the presence of IPTG. These were transformed into an E. coli strain derived from MG1655 that was engineered to overexpress the gene EntD from the chromosome (see e.g., WO2010062480) and harbored a Ptrc controlled operon that expressed the genes carB, alrA, and aftA1, which are described above in Example 3 and together affect the biochemical conversion of free fatty acids (FFAs) to fatty alcohol acetates (FACEs). The engineered TEs having multiple amino acid substitutions were compared to a Control Evaluation Strain where the only difference was that the TE expressed was the control TE SEQ ID NO:15. Table 7 describes a set of engineered TE variants (SEQ ID NO:47 to SEQ ID NO:51) derived from this example having improved activity for the production fatty acid derivatives over the control (SEQ ID NO:15). TEs listed in Table 7 are novel engineered TE variants useful for the production of medium-chain length fatty acid derivatives since they are thioesterases having improved activity for the production of medium-chain fatty acid derivatives.

Example 7

The following Example illustrates engineered TE variants having N-terminal truncations, an increase in solubility, and improved activity for the production of medium-chain length fatty acid derivatives.

Plant FatB-like thioesterases, have signal peptides that mediate their transfer from the endoplasmic reticulum to the plastid. These enzymes are known to contain an N-terminal hydrophobic region that remains after processing of the signal peptide. This region is thought to be involved in the association of the thioesterase to the thylakoid membrane. When expressed in microorganisms, such as E. coli, wild-type (SEQ ID NO:1) and the novel engineered TE variants described above are insoluble and are associated with the membrane pellet upon cell lysis and centrifugation. Low enzyme solubility suggested that much of the enzyme may be associated with the membrane or is poorly folded and inactive.

To create novel engineered TE variants of improved solubility and activity for the production of medium-chain length fatty acid derivatives, the polypeptide having SEQ ID NO:49 was engineered to have truncations between amino acids 2 and 40, a region modeled to harbor the key hydrophobic residues suspected of being responsible for this enzyme's poor solubility. The solubility and activity of these engineered TE variants were then evaluated in comparison to a control TE of the same amino acid sequence that did not have truncations between amino acids 2 and 40.

Evaluation of the Solubility of Engineered TE Variants Having Truncations Between Amino Acid 2 and 40.

Genes encoding engineered TE variants having deletions between amino acids 2 and 40 of SEQ ID NO:49 were synthesized and cloned under the control of Ptrc promoter in medium copy pACYC based expression plasmid (Gen Bank Accession X06403). These plasmids were then transformed into E. coli and evaluated for their ability to direct the expression of TE variants of increased solubility in comparison to identical strains carrying a plasmid directing the expression of the control TE (SEQ ID NO:49). The only difference between the strains expressing the engineered TE variants having truncations between amino acids 2 and 40 and the strain expressing the control TE (SEQ ID NO:49) were the sequences of the TEs being expressed. The resulting strains expressing control and truncated TEs were each grown in 96-well plates under conditions that resulted in the expression of the gene encoding the TE, as described in Example 4. The cells were harvested by centrifugation and resuspended in 50 µL of a 50 mM Tris-HCl (pH7.8) containing 25 mM NaCl, 5 mM EDTA, and 1 mg/mL of Lysozyme. The samples were incubated at 25° C., 1500 rpm. After 20 min, 10 µl of a 1 mg/mL solution of DNase I and 10 µL of 1 M MgSO4 were added to each sample. The samples were then shaken an additional 20 minutes at 1500 rpm. The resulting whole cell lysates (WCL) were centrifuged at 4500 rpm for 10 min to separate the insoluble fraction (pellet) from the soluble fraction (supernatant).

Figure 11:
FIG. 11 Western-blot to evaluate solubility of diverse FatB2 truncations (1=whole cell fraction, 2=soluble fraction).

A Western blot using an antibody directed to the C-termini of the TE was used to track the presence of the control and engineered TE truncated variants in the soluble fraction of the WCL. As shown in FIG. 11, the control polypeptide (thioesterase having SEQ ID NO:49) is visible in the WCL (indicating that it is expressed in the host cells) but it is not present in the soluble fraction, indicating low solubility. In contrast, the engineered truncated TE variants are found in both WCL and the soluble fractions, with TE variants all showing a significant increase in the presence of the TE in the soluble fraction.

This demonstrates that the solubility of plant FatB like thioesterases, such as SEQ ID NO:1, that are insoluble when expressed in a microorganism can be improved by expressing engineered variants that are truncated in the N-termini of the enzyme. It further shows that engineered truncated variants have an increased solubility when expressed in E. coli as compared to TEs that do not have this truncation, such as the control TE (SEQ ID NO:49).

Growth and Production of Fatty Acid Derivatives.

An increase in the solubility of a poorly soluble medium-chain length TE should result in more active medium-chain length TE present in the cell and thus, result in an increase in the production of medium-chain fatty acids.

To evaluate the relative activity of the engineered TE truncated variants, each enzyme was cloned in a vector such that the gene was under the transcriptional control of the Ptrc promoter (Camsund et al., supra) which is induced in the presence of isopropylthiogalactoside (IPTG), as described in Example 4. These were transformed into an E. coli base strain derived from MG1655 that was engineered to overexpress the gene EntD from the chromosome and harbored a Ptrc controlled operon that expressed the genes carB, alrA, and aftA1 (described in Example 3) for the biochemical conversion of free fatty acids (FFAs) to fatty alcohol acetates (FACEs). The engineered E. coli base was designed for high capacity for the production of fatty acid derivatives to accommodate the expected high activity of these more soluble engineered TE variants.

Performance of each engineered truncated thioesterase was compared with a Control Evaluation Strain expressing the control TE (SEQ ID NO:49). The only difference between the Evaluation Strains expressing engineered truncated TE variants and the Control Evaluation Strain expressing the control TE (SEQ ID NO:49) were the sequences of the genes encoding the TEs being expressed. Each of the strains were grown for the production of medium-chain fatty alcohol acetate esters, and the resulting medium-chain fatty acid derived products were extracted and quantified as described in Example 4.

The activity of each engineered truncated TE variant was assessed by comparing the resulting fatty acid derivative products to those produced by the Control Evaluation Strain (expressing SEQ ID NO:49) as described in Example 4.

Table 7 lists engineered truncated TE variants (SEQ ID NO: 52 to SEQ ID NO:59) having improved performance for (1) solubility (FIG. 11) and (2) activity for the production of medium-chain fatty acid derivatives, with performance reported as a fold over the internal control (FOC). Thus, the truncated mutants are thioesterase variants having improved activity for the production of medium-chain fatty acid derivatives.

To further demonstrate the improved activity of the engineered truncated TE variants having increased solubility, the strains expressing SEQ ID NO:55 and SEQ ID NO:56 were grown in 5 L bioreactors as described in Example 9 and compared to the Control Evaluation Strain expressing TE SEQ ID NO:49, grown under the same conditions. Table 9 describes the performance of these strains reported as a fold over control (FOC) at 72 h time point. Both SEQ ID NO:55 and SEQ ID NO:56 show improved activity (FAS FOC) and selectivity (% C8 FAS and % C8/% C10 FOC) at this larger scale.

$MgSO_4$, 0.1 mM $CaCl_2$, 20 g/L glucose, 1 mL/L of a trace minerals solution (2 g/L of $ZnCl_2 \cdot 4H_2O$, 2 g/L of $CaCl_2 \cdot 6H_2O$, 2 g/L of $Na_2MoO_4 \cdot 2H_2O$, 1.9 g/L of $CuSO_4 \cdot 5H_2O$, 0.5 g/L of $H_3BO_3$, and 10 mL/L of concentrated HCl), 10 mg/L of ferric citrate, 100 mM of Bis-Tris buffer (pH 7.0), and the appropriate antibiotic(s)), in a 500 mL baffled Erlenmeyer shake flask, and incubated on a shaker overnight at 32° C.

Bioreactor Cultivation Protocol.

75 mL (5% v/v) of the overnight seed culture described above was used to inoculate a 5 L Biostat Aplus bioreactor (Sartorius BBI), initially containing 1.5 L of sterilized bioreactor fermentation medium. This medium was composed of 2 g/L of $KH_2PO_4$, 0.5 g/L of $(NH_4)_2SO_4$, 2.2 g/L of $MgSO_4$ heptahydrate, 10 g/L of sterile filtered glucose, 80 mg/L ferric citrate, 1 mL/L of the previously described trace minerals solution, 0.25 mL/L of a vitamin solution (0.42 g/L of riboflavin, 5.4 g/L of pantothenic acid, 6 g/L of niacin, 1.4 g/L of pyridoxine, 0.06 g/L of biotin, and 0.04 g/L of folic acid), 1 g/L NaCl, 1 g/L citric acid, 140 mg/L $CaCl_2$) dihydrate, 10 mg/L $ZnCl_2$, and the appropriate antibiotic(s). The pH of the culture was maintained between 6.9 to 7.2 using 28% w/v ammonia water, the cultivation temperature from 33 to 35° C., depending on the specific product, the aeration rate at 0.75 lpm (0.5 v/v/m), and the dissolved oxygen tension at 30% of saturation, utilizing the agitation loop cascaded to the DO controller and oxygen supplementation. Foaming was controlled by the automated addition of a silicone emulsion based antifoam (Dow Corning 1430).

A nutrient feed composed of about 50% w/w glucose (600 g/L) was initiated when the glucose in the initial medium was completely depleted (approximately 7 hours following inoculation) and fed on demand at a rate of 10 g/l/h using a DOstat controller strategy (each feed shot was of a one hour

TABLE 9

Engineered truncated TE variants showing improved activity in vivo for the production of medium-chain length fatty acid derivatives when grown in 5 L bioreactors.

| SEQ ID NO: | FAS FOC | % C8 FAS FOC | % C8/% C10 FOC | Template | Control TE | Screening strain |
|---|---|---|---|---|---|---|
| SEQ ID NO: 49 | 1.0 | 1.0 | 1.0 | pAZ338 | — | sCB.243 |
| SEQ ID NO: 55 | 1.4 | 1.3 | 2.1 | pAZ338 | SEQ ID NO: 49 | sCB.243 |
| SEQ ID NO: 56 | 1.3 | 1.3 | 2.0 | pAZ338 | SEQ ID NO: 49 | sCB.243 |

Example 8

The following Example illustrates a process that can be used to produce a fatty acid derivatives using genetically modified microorganisms having improved activity for the production of medium-chain fatty acid derivatives. The composition of the fatty acid derivatives produced by this process includes, but is not limited to medium-chain fatty acids, medium-chain fatty alcohols, medium-chain fatty alcohol acetate esters (FACE), medium-chain fatty acid methyl esters (FAME), medium-chain fatty acid ethyl esters (FAEE), as well as other medium-chain fatty acid esters.

Generation of Seed Culture Expansion.

A frozen cell bank vial of the selected engineered *E. coli* strain was used to inoculate 20 mL of LB broth in a 125 mL baffled shake flask containing the appropriate antibiotic(s). This shake flask was incubated in an orbital shaker at 32° C. for approximately six hours, then 1.25 mL of the broth (1% v/v) was transferred into 125 mL of minimal overnight seed media (2 g/L $NH_4Cl$, 0.5 g/L NaCl, 0.3 g/L $KH_2PO_4$, 1 mM duration). The genes involved in the production of medium-chain fatty acid derivatives were induced by the addition of isopropylthiogalactoside (IPTG) to a final concentration of 1 mM. The bioreactor run was ended at about 72 hours elapsed fermentation time. Samples of the fermentation broth were tanked throughout the fermentation process.

Analysis of Broth Composition.

Fatty acid derivatives present in samples of the fermentation broth were extracted and separated using conventional GC-FID in a single run. For this purpose, 0.5 mL of each homogenous fermentation broth sample was aliquoted into a 15 mL falcon tube. The mass of the sample was recorded and 5.0 mL of butyl acetate with 500 ppm of an internal standard (C11 FAME or C9/C11/C15 FALC) were added to the broth to achieve 10 fold extractions. The sample was mechanically shaken for 30 minutes @ 2500 rpm and centrifuged for 10 minutes @4500 rpm @ 25° C. 50 µl of extract (top layer) was transferred into a GC vial and derivatized with 50 uL of BSTFA w/10% TCMS followed by vortexing for ~15 seconds. The sample was then run in a conventional GC-FID system using an Agilent DB1 column, 10 m×180 µm×0.2 µm to separate all fatty acid derivatives present in the extracted sample. The concentration of each fatty acid derivative are reported in g/Kg.

Example 9

The following Example illustrates a process that can be used to produce medium-chain fatty alcohol acetate esters using genetically modified microorganisms having improved activity for the production of medium-chain fatty acid derivatives. The composition of the fatty acid derivatives produced by this process may include medium-chain fatty acids, medium-chain fatty alcohols and medium-chain fatty alcohol acetate esters (FACE) with acyl chains of 6 to 12 carbons. Production of medium-chain fatty alcohol acetate esters in 5 L bioreactors was performed as described in Example 8.

Figure 12:
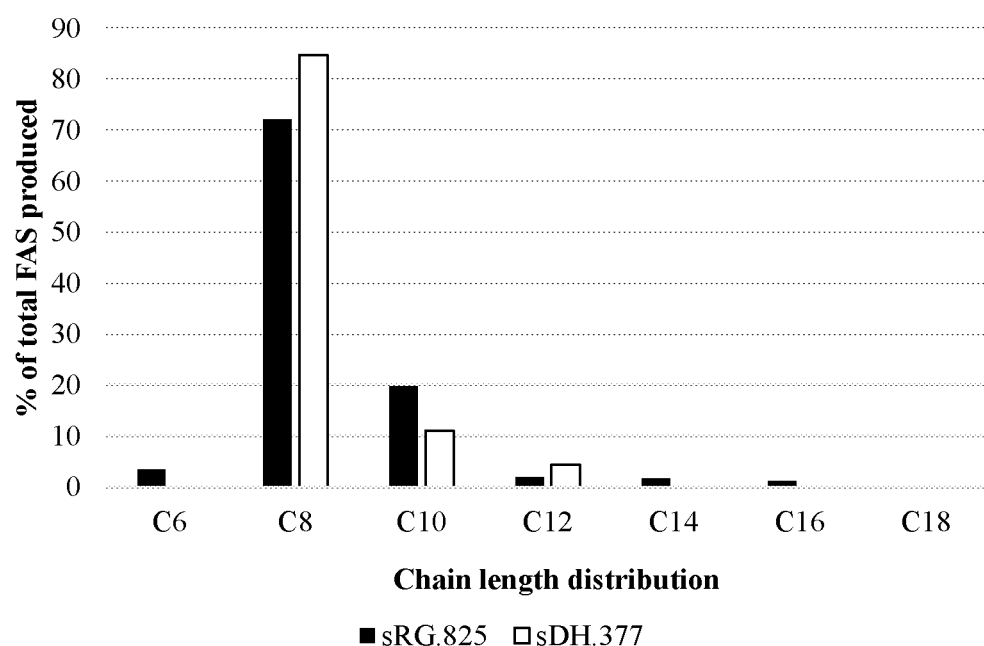
FIG. 12 Illustrates the characteristic final product composition of medium-chain length fatty alcohol acetate production with strain sRG.825 and sDH.377 when cultivated under Example 8 conditions FIG. 13 Illustrates Characteristic final product composition of medium-chain length fatty acid ethyl ester production with strain sAZ918 when cultivated under Example 11 conditions.

In this example, E. coli strains derived from MG1655 that were engineered to overexpress the gene EntD from the chromosome and harbored high capacity for the production of medium-chain fatty acid derivatives were used. These strains contained an engineered thioesterase with improved activity for the production of medium-chain fatty acids as well as an operon that expressed the genes carB, alr A, and aftA1 (described in Example 3) for the biochemical conversion of free fatty acids (FFAs) to fatty alcohol acetates (FACEs). The engineered thioesterase with SEQ ID NO:9 was expressed in strain sRG.825, while the engineered thioesterase with SEQ ID NO:49 was expressed in strain sDH.377. The genes encoding the engineered thioesterase, carB, alr A, and aftA1 were all under the transcriptional control of an inducible (Ptrc) promoter, activated by the addition of isopropylthiogalactoside (IPTG) to the bioreactor at about 24 hours elapsed fermentation time. The bioreactor run was ended at about 72 hours elapsed fermentation time, the fermentation broth was collected and analyzed as described above in Example 8. Results are shown in Table 10 and FIG. 12.

TABLE 10

Total fatty acid species (FAS) concentration produced by representative strains engineered for the production of medium-chain fatty alcohol acetate or fatty acid alkyl esters.

| Strain | Total FAS (g/Kg) | Fatty acid derivatives in the broth |
| --- | --- | --- |
| sRG.825 | 65 | Medium-chain fatty alcohol acetate esters |
| sDH.377 | 60 | Medium-chain fatty alcohol acetate esters |
| sAZ918 | 60 | Medium-chain fatty acid ethyl esters |

Example 10

The following Example illustrates a process that can be used to produce medium-chain fatty alcohols using genetically modified microorganisms with improved ability to produce fatty acid derivatives. The composition of the fatty acid derivatives produced by this process may include fatty acids, fatty aldehydes and fatty alcohols with acyl chains of 6 to 12 carbons. Production of medium-chain fatty alcohol in 5 L bioreactors was performed as described in example 8, using an E. coli strain engineered to overexpress the gene EntD from the chromosome and containing a medium-chain thioesterase as well as an operon expressing the genes carB and alr A for the biochemical conversion of free fatty acids (FFAs) to fatty alcohols (FALC). The genes encoding for the thioesterase, carB and alr A were all under the transcriptional control of an inducible (Ptrc) promoter activated by the addition of isopropylthiogalactoside (IPTG) to the bioreactor at about 7 hours elapsed fermentation time. Medium-chain fatty alcohols are highly toxic to E. coli, therefore accumulation of these compounds during production in 5 L bioreactors stopped growth and production soon after inhibitory concentrations were reached (below 1 g/L, see Example 3).

Example 11

The following Example illustrates a process for producing medium-chain fatty acid alkyl esters using genetically modified microorganisms comprising a thioesterase variant having improved activity for the production of medium-chain fatty acid derivatives. The composition of the fatty acid derivatives produced by this process may include medium-chain fatty acids, medium-chain fatty acid methyl esters (FAME) and/or medium-chain fatty acid ethyl esters (FAEE) with acyl chains of 6 to 12 carbons.

This example illustrates production of fatty acid ethyl esters (FAEE) using an E. coli strain (sAZ918) derived from MG1655 that was engineered to harbored high capacity for the production of medium-chain fatty acid derivatives. This strain contained an engineered thioesterase with improved activity for the production of medium-chain fatty acids (SEQ ID NO:49) as well as an operon expressing an acyl CoA synthetase and an ester synthase (described in Example 3) for the biochemical conversion of free fatty acids (FFAs) to fatty acid alkyl esters (FAME or FAEE). The engineered thioesterase, the acyl CoA synthetase and the ester synthase were all under the transcriptional control of an inducible (Ptrc) promoter, activated by the addition of isopropylthiogalactoside (IPTG).

Production of medium-chain fatty acid ethyl esters in 5 L bioreactors was performed as described in Example 8, but with the addition of ethanol to the nutrient feed. After inoculation of the 5 L bioreactor with the seed culture, a nutrient feed composed of 47.5% w/w glucose and 50 mL/L ethanol was initiated when the glucose in the initial medium was completely depleted (approximately 7 hours following inoculation) and fed on demand at a rate of 10 g/1 L/h using a pHstat controller strategy (each feed shot was of a one hour duration). The minimum agitation rate was fixed at 1200 rpm once this parameter value was achieved to prevent a biofilm from coating the dissolved oxygen probe and result in an erroneously low signal reading. Additional ethanol was added to the culture if the residual concentration dropped below 10 g/L. The strain's ethyl octanoate production pathway was induced at about 24 hours elapsed fermentation time by the addition of IPTG to a final concentration of 1 mM. The bioreactor run was ended at about 72 hours elapsed fermentation time. The fermentation broth was collected and analyzed as described above in Example 8.

Figure 13:
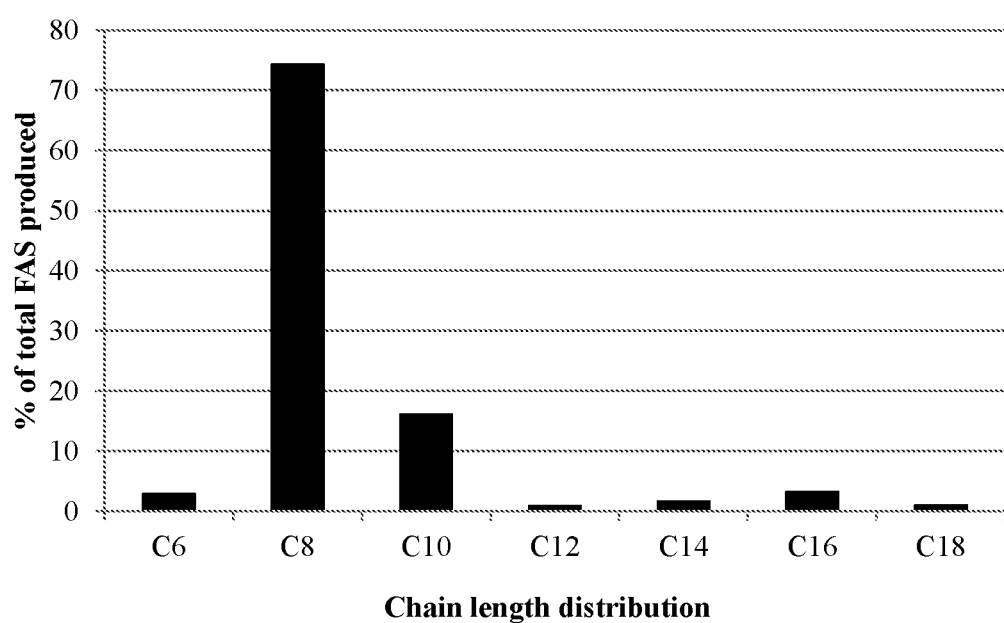

Results are shown in FIG. 13.

Example 12

The following Example illustrates a process for the production of medium-chain fatty acids using genetically modified microorganisms comprising a thioesterase having improved activity for the production of medium-chain fatty acid derivatives. The composition of the fatty acids produced by this process include medium-chain fatty acids with acyl chains of 6 to 12 carbons. In this example, the production of medium-chain fatty acids in 5 L bioreactors was performed as described in Example 8, using an *E. coli* strain engineered to overexpress a medium-chain thioesterase under the transcriptional control of an inducible (Ptrc) promoter activated by the addition of isopropylthiogalactoside (IPTG) to the bioreactor at about 13 hours elapsed fermentation time. Medium-chain fatty acids are highly toxic to *E. coli*, therefore accumulation of these compounds during production in 5 L bioreactors stopped growth and production soon after inhibitory concentrations were reached (below 5 g/L, see Example 3).

APPENDIX A

Sequences

```
SEQ ID NO: 1
    1   MLPDWSRLLT AITTVFVKSK RPDMHDRKSK RPDMLVDSFG LESTVQDGLV FRQSFSIRSY
        EIGTDRTASI
   71   ETLMNHLQET SLNHCKSTGI LLDGFGRTLE MCKRDLIWVV IKMQIKVNRY PAWGDTVEIN
        TRFSRLGKIG
  141   MGRDWLISDC NTGEILVRAT SAYAMMNQKT RRLSKLPYEV HQEIVPLFVD SPVIEDSDLK
        VHKFKVKTGD
  211   SIQKGLTPGW NDLDVNQHVS NVKYIGWILE SMPTEVLETQ ELCSLALEYR RECGRDSVLE
        SVTAMDPSKV
  281   GVRSQYQHLL RLEDGTAIVN GATEWRPKNA GANGAISTGK TSNGNSVS

SEQ ID NO: 2
    1   MLPDWSRLLT AITTVFAKSK RPDMHDRKSK RPDMLVDSFG LESTVQDGLV FRQSFSIRSY
        EIGRDRTASI
   71   ETLMNHLQET SLNHCKSTGI LLDGFGRTLE MCKRDLIWVV IKMQIKVNRY PAWGDTVEIN
        TRFSRLGKIG
  141   MGRDWLISDC NTGEILVRAT SAYAMMNQKT RRLSKVPYEV HQEIVPLFVD SPVIEDSDLK
        VHRFKVKTGD
  211   SIQKGLTPGW NDLDVNQHVS NVKYIGWILE SMPTEVLETQ ELCSLCLEYR RECGRDSVLE
        SVTAMDPSKV
  281   GSRSQYQHLL RLEDGTAIVN GATEWRPKNA GANGAISTGK TSNGNSVS

SEQ ID NO: 3
    1   MLKDWSRLLT AITTVFVKSK RPDMHDRKSK RPDMLVPSFG LESTVQDGLV FRQSFSIRSY
        EIGTDRTASI
   71   ETLMNHLQET SLNHCKSTGI LLDGFGRTLE MCKRDLIWVV IKMQIKVNRY PAWGDTVEVN
        TRFSRLGKIG
  141   MGRDWLISDC NTGEILVRAT SAYAMMNQKT RRLSKVPYEV HQEIVPLFVD SPVIEDSDLK
        VHKFKVKTGD
  211   SIQKGLTPGW NDLDVNQHVS NVKYIGWILE SMPTEVLETQ ELCSLALEYR RECGRDSVLE
        SVTAMDPSKV
  281   GVRSQYQHLL RLEDGTAIVN GATEWRPKNA GANGAISTGK TSNGNSVS

SEQ ID NO: 4
    1   MLKDWSRLLT AITTVFVKSK RPDMHDRKSK RPDMLVDSFG LESTVQDGLV FRQSFSIRSY
        EIGTDRTASI
   71   ETLMNHLQET SLNHCKSTGI LLDGFGRTLE MCKRDLIWVV IKMQIKVNRY PAWGDTVEIN
        TRFSRLGKIG
  141   MGRDWLISDC NTGEILVRAT SAYAMMNQKT RRLSKVPYEV HQEIVPLFVD SPVIEVSDLK
        VHRFKVKTGD
  211   SIQKGLTPGW NDLDVNQHVS NVKYIGWILE SMPTEVLETQ ELCSLALEYR RECGRDSVLE
        SVTAMDPSKV
  281   GSRSQYQHLL RLEDGTAIVN GATEWRPKNA GANGAISTGK TSNGNSVS

SEQ ID NO: 5
    1   MLPDWSRLLT AITTVFVKSK RPDMHDRKSK RPDMLVDSFG LESTVQDGLV FRQSFSIRSY
        EIGTDRTASI
   71   ETLMNHLQET SLNHCKSTGI LLDGFGRTLE MCKRDLIWVL IKMQIKVNRY PAWGDTVEVN
        TRFSRLGKIG
  141   MGRDWLISDC NTGEILVRAT SAYAMMNQKT RRLSKVDYEV HQEIVTLFVD SPVIEDSDLK
        VHRFKVKTGD
  211   SIQKGLTDGW NDLDVNQHVS NVKYIGWILE SMPTEVLETQ ELCSLALEYR RECGRDSVLE
        SVTAMDPSKV
  281   GVRSQYQHLL RLEDGTAIVN GATEWRDKNA GANGAISTGK TSNGNSVK

SEQ ID NO: 6
    1   MLKDWSRLLT AITTVFVKSK RPDMHDRKSK RPDMLVDSFG LESTVQDGLV FRQSFSIRSY
        EIGTDRTASI
   71   ETLMNHLQET SLNHCKSTGI LLDGFGRTLE MCKRDLIWVV IKMQIKVNRY PAWGDTVEVN
        TRFSRLGKIG
  141   MGRDWLISDC NTGEILVRAT SAYAMMNQKT RRLSKVDYEV HQEIVTLFVD SPVIEDSDLK
        VHKFKVKTGD
  211   SIQKGLTDGW NDLDVNQHVS NVKYIGWILE SMPTEVLETQ ELCSLALEYR RECGRDSVLE
        SVTAMDPSKV
  281   GVRSQYQHLL RLEDGTAIVN GATEWRDKNA GANGAISTGK TSNGNSVK

SEQ ID NO: 7
    1   MLPDWRRLLT AITTLFVKSK RPDMHDRKSK RPDMLVDSFG LESTVQDGLV FRQSFSIRSY
        EIGTDRTASI
   71   ETLMNHLQET SLNHCKSTGI LLDGFGRTLE MCKRDLIWVV IKMQIKVNRY PAWGDTVEIN
        TRFSRLGKIG
```

APPENDIX A-continued

Sequences

```
    141 MGRDWLISDC NTGEILVRAT SAYAMMNQKT RRLSKLDYEV HQEIVTLFVD SPVIEVSDLK
        VHKFKVKTGD
    211 SIQKGLTDGW NDLDVNQHVS NVKYIGWILE SMPTEVLETQ ELCSLALEYR RECGRDSVLE
        SVTAMDPSKV
    281 GVRSQYQHLL RLEDGTAIVN GATEWRDKNA GANGATSTGK TKNGNSVK

SEQ ID NO: 8
      1 MLKDWSRLLT AITTVFVKSK RPDMHDRKSK RPDMLVDSFG LESTVQDGLV FRQSFSIRSY
        EIGTDRTASI
     71 ETLMNHLQET SLNHCKSTGI LLDGFGRTLE MCKRDLIWVV IKMQIKVNRY PAWGDTVEIN
        TRFSRLGKIG
    141 MGRDWLISDC NTGEILVRAT SAYAMMNQKT RRLSKVDYEV HQEIVTLFVD SPVIEVSDLK
        VHKFKVKTGD
    211 SIQKGLTDGW NDLDVNGHVS NVKYIGWILE SMPTEVLETQ ELCSLALEYR RECGRDSVLE
        SVTAMDPSKV
    281 GVRSQYQHLL RLEDGTAIVN GATEWRDKNA GANGAISTGK TSNGNSVS

SEQ ID NO: 9
      1 MLPDWSRLLT AITTVFVKSK RPDMHDRKSK RPDMLVDSFG LESGVQDGLV FRQSFSIRSY
        EIGPDRTASI
     71 ETLMNHLQET SLNHCKSTGI LLDGFGRTKE MCKRDLIWVV IKMQIKVNRY PAWGDTVEIN
        TRFSRLGKIG
    141 MGRDWLISDC NTGEILVRAT SAYAMMNQKT RRLSKLDYEV HQEIVTLFVD SPVIEVSDLK
        VHRFKVKTGD
    211 SIQKGLTDGW NDLDVNQHVS NVKYIGWILE SMPTEVLETQ ELCSLALEYR RECGRDSVLE
        SVTAMDPSKV
    281 GSRSQYQHLL RLEDGTAIVN GATEWRDKNA GANGARSTGK TSNGNSVS

SEQ ID NO: 10
      1 MLKDWSRLLT AITTVFVKSK RPDMHDRKSK RPDMLVDSFG LESGVQDGLV FRQSFSIRSY
        EIGPDRTASI
     71 ETLMNHLQET SLNHCKSTGI LLDGFGRTKE MCKRDLIWVV IKMQIKVNRY PAWGDTVEIN
        TRFSRLGKIG
    141 MGRDWLISDC NTGEILVRAT SAYAMMNQKT RRLSKLDYEV HQEIVTLFVD SPVIEVSDLK
        VHRFKVKTGD
    211 SIQKGLTDGW NDLDVNQHVS NVKYIGWILE SMPTEVLETQ ELCSLALEYR RECGRDSVLE
        SVTAMDPSKV
    281 GSRSQYQHLL RLEDGTAIVN GATEWRDKNA GANGARSTGK TSNGNSVS

SEQ ID NO: 11
      1 MLKDWSRLLT AITTVFVKSK RPDMHDRKSK RPDMLVDSFG LESTVQDGLV FRQSFCIRSY
        EIGTDRTASI
     71 ETLMNHLQET SLNHCKSTGI LLDGFGRTLE MCKRDLIWVL IKMQIKVNRY PAWGDTVEIN
        TRFSRLGKIG
    141 MGRDWLISDC NTGEILVRAT SAYAMMNQKT RRLSKVDYEV HQEIVTLFVD SPVIEVSDLK
        VHRFKVKTGD
    211 SIQKGLTDGW NDLDVNQHVS NVKYIGWILE SMPTEVLETQ ELCSLALEYR RECGRDSVLE
        SVTAMDPSKV
    281 GVRSQYQHLL RLEDGTAIVN GATEWRDKNA GANGAISTGK TSNGNSVS

SEQ ID NO: 12
      1 MLPDWSRLLT AITTVFCKSK RPDMHDRKSK RPDMLVDSFG LESTVQDGLV FRQSFSIRSY
        EIGPDRTASI
     71 ETLMNHLQET SLNHCKSTGI LLDGFGRTKE MCKRDLIWVL IKMQIKVNRY PAWGDTVEIN
        TRFSRLGKIG
    141 MGRDWLISDC NTGEILVRAT SAYAMMNQKT RRLSKVDYEV HQEIVGLFVD SPVIEVSDLK
        VHRFKVKTGD
    211 SIQKGLTDGW NDLDVNQHVS NVKYIGWILE SMPTEVLETQ ELCSLALEYR RECGRDSVLE
        SVTAMDPSKV
    281 GSRSQYQHLL RLEDGTAIVN GATEWRDKNA GANGAISTGK TSNGNSVS

SEQ ID NO: 13
      1 MLPDWSRLLT AITRVFVKSK RPDMHDRKSK RPDMLVDSFG LESGVQDGLV FRQSFSIRSY
        EIGPDRTASI
     71 ETLMNLLQET SLNHCKSTGI LLDGFGRTKE MCKRDLIWVV IKMQIKVNRY PAWGDTVEIN
        TRFSRLGKIG
    141 MGRDWLISDC NTGEILVRAT SAYAMMNQKT RRLSKLDYEV HQEIAPLFVD SPVIEVSDLK
        VHRFKVKTGD
    211 SIHKGLTDGW NDLDVNQHVS NVKYIGWILE SMPTEVLETQ ELCSLALEYR RECGRDSVLE
        SVTAMDPSKV
    281 GSRSQYQHLL RLEDGTAIVW GATEWRDKNA GANGARSTGK TSNGKSVS

SEQ ID NO: 14
      1 MLPMWSRLLT AITTVFCKSK RPDMHDRKSK RPDMLVDSFG LESGVQDGLV FRQSFSIRSY
        EIGPDRTASI
     71 ETLMNHLQET SLNHCKSTGI LLDGFGRTKE MCKRDLIWVV IKMQIKVNRY PAWGDTVEIN
        TRFSRLGKIG
```

APPENDIX A-continued

Sequences

```
    141 MGRDWLISDC NTGEILVRAT SAYAMMNQKT RRLSKLDYEV HQEIAPLFVD SPVIEDSDLK
        VHRFKVKTGD
    211 SIQKGLTDGW NDLDVNQHVS NVKYIGWILE SMPTEVLETQ ELCSLALEYR RECGRDSVLE
        SVTAMDPSKV
    281 GSRSQYQHLL RLEDGTAIVW GATEWRDKNA GANGARSTGK TSNGKSVS

SEQ ID NO: 15
      1 MLPDWSRLLT AITTVFAKSK RPDMHDRKSK RPDMLVDSFG LESGVQDGLV FRQSFSIRSY
        EIGPDRLASI
     71 ETLMNHLQET SLNHCKSTGI LLDGFGRTKE MCKRDLIWVV IKMQIKVNRY PAWGDTVEIN
        TRFSRLGKIG
    141 MGRDWLISDC NTGEILVRAT SAYAMMNQKT RRLSKLDYEV HQEIAPLFVD SPVIEVSDLK
        VHRFKVKTGD
    211 SIHKGLTDGW NDLDVNQHVS NVKYIGWILE SMPTEVLETQ ELCSLALEYR RECGRDSVLE
        SVTAMDPSKV
    281 GSRSQYQHLL RLEDGTAIVN GATEWRDKNA GANGARSTGK TSNGKSVS

SEQ ID NO: 16
      1 MLKDWSRLLT AITTVFVKSK RPHMHDRKSK RPDMLVHSFG LESTVQDGLV FRQSFSIRSY
        EIGTDRTAI
     71 ETLMNHLQET SLNHCKSTGI LLHGFGRTLE MCKRDLIWVV IKMQIKVNRY PAWGDTVEIN
        TRFSRLGKIG
    141 MGRDWLISDC NTGEILVRAT SAYAMMNQKT RRLSKVDYEV HQEIVTLFVD SPVIEVSDLK
        VHRFKVKTGD
    211 SIQKGLTDGW NDLDVNQHVS NVKYIGWILR SMPTEVLETQ ELCSLALEYR RECGRDSVLE
        SVTAMDPSKV
    281 GSRSQYQHLL RLEDGTAIVN GATEWRDKNA GANGAISTGK TSNGNSVS

SEQ ID NO: 17
      1 MLKDWSRLLT AITTVFVKSK RPDMHDRKSK RPDMLVRSFG LESTVQDGLV FRQSFSIRSY
        EIGTDRTASI
     71 ETLMNHLQET SLNHCKSTGI LLHGFGRTLE MCKRDLIWVV IKMQIKVNRY PAWGDTVEIN
        TRFSRLGKIG
    141 MGRDWLISDC NTGEILVRAT SAYAMMNQKT RRLSKVDYEV HQEIVTLFVD SPVIEVSDLK
        VHRFKVKTGD
    211 SIQKGLTDGW NDLDVNQHVS NVKYIGWILE SMPTEVLETQ ELCSLALEYR RECGRDSVLE
        SVTAMDPSKV
    281 GSRSQYQHLL RLEDGTAIVN GATEWRDKNA GANGAISTGK TSNGNSVS

SEQ ID NO: 18
      1 MLKDWSRLLT AITTVFVKSK RPDMHDRKSK RPDMLVDSFG LESTVQDGLV FRQSFSIRSY
        EIGTDRTASI
     71 ETLMNHLQET SLNHCKSTGI LLHGFGRTLE MCKRDLIWVV IKMQIKVNRY PAWGDTVEIN
        TRFSRLGKIG
    141 MGRDWLISDC NTGEILVRAT SAYAMMNQKT RRLSKVDYRV HQEIVTLFVD SPVIEVSDLK
        VHRFKVKTGD
    211 SIQKGLTDGW NDLDVNQHVS NVKYIGWILV SMPTEVLETQ ELCSLALEYR RECGRDSVLE
        SVTAMDPSKV
    281 GSRSQYQHLL RLHDGTAIVN GATEWRDKNA GANGAISTGK TSNGNSVS

SEQ ID NO: 19
      1 MLKHWSRLLT AITTVFVKSK RPDMHDRKSK RPDMLVRSFG LESTVQDGLV FRQSFSIRSY
        EIGTDRTASI
     71 ETLMNHLQET SLNHCKSTGI LLHGFGRTLE MCKRDLIWVV IKMQIKVNRY PAWGDTVEIN
        TRFSRLGKIG
    141 MGRDWLISDC NTGEILVRAT SAYAMMNQKT RRLSKVPYHV HQEIVPLFVD SPVIEVSDLK
        VHRFKVKTGD
    211 SIQKGLTPGW NDLDVNQHVS NVKYIGWILR SMPTEVLETQ ELCSLALEYR RECGRDSVLE
        SVTAMDPSKV
    281 GSRSQYQHLL RLEDGTAIVN GATEWRPKNA GANGAISTGK TSNGNSVS

SEQ ID NO: 20
      1 MLKDWSRLLT AITTVFVKSK RPDMHDRKSK RPDMLVHSFG LESTVQDGLV FRQSFSIRSY
        EIGTDRTASI
     71 ETLMNHLQET SLNHCKSTGI LLHGFGRTLE MCKRDLIWVV IKMQIKVNRY PAWGDTVEIN
        TRFSRLGKIG
    141 MGRDWLISDC NTGEILVRAT SAYAMMNQKT RRLSKVPYEV HQEIVPLFVD SPVIEVSDLK
        VHRFKVKTGD
    211 SIQKGLTPGW NDLDVNQHVS NVKYIGWILE SMPTEVLETQ ELCSLALEYR RECGRDSVLE
        SVTAMDPSKV
    281 GSRSQYQHLL RLEDGTAIVN GATEWRPKNA GANGAISTGK TSNGNSVS

SEQ ID NO: 21
      1 MLKDWSRLLT AITTVFVKSK RPDMHDRKSK RPDMLVHSFG LESTVQDGLV FRQSFSIRSY
        EIGTDRTASI
     71 ETLMNHLQET SLNHCKSTGI LLHGFGRTLE MCKRDLIWVV IKMQIKVNRY PAWGDTVEIN
        TRFSRLGKIG
```

APPENDIX A-continued

Sequences

```
    141 MGRDWLISDC NTGEILVRAT SAYAMMNQKT RRLSKVPYEV HQEIVPLFVD SPVIEVSDLK
        VHRFKVKTGD
    211 SIQKGLTPGW NDLDVNQHVS NVKYIGWILE SMPTEVLETQ ELCSLALEYR RECGRRSVLE
        SVTAMDPSKV
    281 GSRSQYQHLL RLEDGTAIVN GATEWRPKNA GANGAISTGK TSNGNSVS

SEQ ID NO: 22
      1 MLKRWSRLLT AITTVFVKSK RPDMHDRKSK RPDMLVDSFG LESTVQDGLV FRQSFSIRSY
        EIGTDRTASI
     71 ETLMNHLQET SLNHCKSTGI LLDGFGRTLE MCKRDLIWVV IKMQIKVNRY PAWGDTVEIN
        TRFSRLGKIG
    141 MGRDWLISDC NTGEILVRAT SAYAMMNQKT RRLSKVPYEV HQEIVPLFVD SPVIEVSDLK
        VHRFKVKTGD
    211 SIQKGLTPGW NDLDVNQHVS NVKYIGWILE SMPTEVLETQ ELCSLALEYR RECGRDSVLE
        SVTAMDPSKV
    281 GVRSQYQHLL RLEDGTAIVN GATEWRPKNA GANGAISTGK TSNGNSVS

SEQ ID NO: 23
      1 MLKDWSRLLT AITTVFVKSK RPDMHDRKSK RPDMLVRSFG LESTVQDGLV FRQSFSIRSY
        EIGTDRTASI
     71 ETLMNHLQET SLNHCKSTGI LLHGFGRTLE MCKRDLIWVV IKMQIKVNRY PAWGDTVEIN
        TRFSRLGKIG
    141 MGRDWLISDC NTGEILVRAT SAYAMMNQKT RRLSKVPYHV HQEIVPLFVD SPVIEVSDLK
        VHRFKVKTGD
    211 SIQKGLTPGW NDLDVNQHVS NVKYIGWILE SMPTEVLETQ ELCSLALEYR RECGRHSVLE
        SVTAMDPSKV
    281 GSRSQYQHLL RLEDGTAIVN GATEWRPKNA GANGAISTGK TSNGNSVS

SEQ ID NO: 24
      1 MLKRWSRLLT AITTVFVKSK RPDMHDRKSK RPDMLVDSFG LESTVQDGLV FRQSFSIRSY
        EIGTDRTASI
     71 ETLMNHLQET SLNHCKSTGI LLRGFGRTLE MCKRDLIWVV IKMQIKVNRY PAWGDTVEIN
        TRFSRLGKIG
    141 MGRDWLISDC NTGEILVRAT SAYAMMNQKT RRLSKVPYRV HQEIVPLFVD SPVIEVSDLK
        VHRFKVKTGD
    211 SIQKGLTPGW NDLDVNQHVS NVKYIGWILR SMPTEVLETQ ELCSLALEYR RECGRDSVLE
        SVTAMDPSKV
    281 GSRSQYQHLL RLEDGTAIVN GATEWRPKNA GANGAISTGK TSNGNSVS

SEQ ID NO: 25
      1 MLKDWSRLLT AITTVFVKSK RPDMHDRKSK RPDMLVRSFG LESTVQDGLV FRQSFSIRSY
        EIGTDRTASI
     71 ETLMNHLQET SLNHCKSTGI LLHGFGRTLE MCKRDLIWVV IKMQIKVNRY PAWGDTVEIN
        TRFSRLGKIG
    141 MGRDWLISDC NTGEILVRAT SAYAMMNQKT RRLSKVPYEV HQEIVPLFVD SPVIEVSDLK
        VHRFKVKTGH
    211 SIQKGLTPGW NDLDVNQHVS NVKYIGWILE SMPTEVLETQ ELCSLALEYR RECGRDSVLE
        SVTAMDPSKV
    281 GSRSQYQHLL RLEDGTAIVN GATEWRPKNA GANGAISTGK TSNGNSVS

SEQ ID NO: 26
      1 MLKDWSRLLT AITTVFVKSK RPDMHDRKSK RPDMLVHSFG LESTVQDGLV FRQSFSIRSY
        EIGTDRTASI
     71 ETLMNHLQET SLNHCKSTGI LLHGFGRTLE MCKRDLIWVV IKMQIKVNRY PAWGDTVEIN
        TRFSRLGKIG
    141 MGRDWLISDC NTGEILVRAT SAYAMMNQKT RRLSKVPYEV HQEIVPLFVD SPVIEVSDLK
        VHRFKVKTGD
    211 SIQKGLTPGW NDLDVNQHVS NVKYIGWILE SMPTHVLETQ ELCSLALEYR RECGRRSVLE
        SVTAMDPSKV
    281 GSRSQYQHLL RLEDGTAIVN GATEWRPKNA GANGAISTGK TSNGNSVS

SEQ ID NO: 27
      1 MLKDWSRLLT AITTVFVKSK RPHMHDRKSK RPDMLVHSFG LESTVQDGLV FRQSFSIRSY
        EIGTDRTASI
     71 ETLMNHLQET SLNHCKSTGI LLHGFGRTLE MCKRDLIWVV IKMQIKVNRY PAWGDTVEIN
        TRFSRLGKIG
    141 MGRDWLISDC NTGEILVRAT SAYAMMNQKT RRLSKVPYHV HQEIVPLFVD SPVIEVSDLK
        VHRFKVKTGD
    211 SIQKGLTPGW NDLDVNQHVS NVKYIGWILE SMPTEVLETQ ELCSLALEYR RECGRDSVLE
        SVTAMDPSKV
    281 GSRSQYQHLL RLEDGTAIVN GATEWRPKNA GANGAISTGK TSNGNSVS

SEQ ID NO: 28
      1 MLKRWSRLLT AITTVFVKSK RPDMHDRKSK RPDMLVDSFG LESTVQDGLV FRQSFSIRSY
        EIGTDRTASI
```

APPENDIX A-continued

Sequences

```
     71 ETLMNHLQET SLNHCKSTGI LLHGFGRTLE MCKRDLIWVV IKMQIKVNRY PAWGDTVEIN
        TRFSRLGKIG
    141 MGRDWLISDC NTGEILVRAT SAYAMMNQKT RRLSKVPYHV HQEIVPLFVD SPVIEVSDLK
        VHRFKVKTGD
    211 SIQKGLTPGW NDLDVNQHVS NVKYIGWILE SMPTEVLETQ ELCSLALEYR RECGRRSVLE
        SVTAMDPSKV
    281 GSRSQYQHLL RLEDGTAIVN GATEWRPKNA GANGAISTGK TSNGNSVS

SEQ ID NO: 29
      1 MLKDWSRLLT AITTVFVKSK RPDMHDRKSK RPDMLVHSFG LESTVQDGLV FRQSFSIRSY
        EIGTDRTASI
     71 ETLMNHLQET SLNHCKSTGI LLHGFGRTLE MCKRDLIWVV IKMQIKVNRY PAWGDTVEIN
        TRFSRLGKIG
    141 MGRDWLISDC NTGEILVRAT SAYAMMNQKT RRLSKVPYEV HQEIVPLFVD SPVIEVSDLK
        VHRFKVKTGD
    211 SIQKGLTPGW NDLDVNQHVS NVKYIGWILE SMPTEVLHTQ ELCSLALEYR RECGRDSVLE
        SVTAMDPSKV
    281 GSRSQYQHLL RLEDGTAIVN GATEWRPKNA GANGAISTGK TSNGNSVS

SEQ ID NO: 30
      1 MLKDWSRLLT AITTVFVKSK RPDMHDRKSK RPDMLVRSFG LESTVQDGLV FRQSFSIRSY
        EIGTDRTASI
     71 ETLMNHLQET SLNHCKSTGI LLHGFGRTLE MCKRDLIWVV IKMQIKVNRY PAWGDTVEIN
        TRFSRLGKIG
    141 MGRDWLISDC NTGEILVRAT SAYAMMNQKT RRLSKVPYEV HQEIVPLFVD SPVIEVSDLK
        VHRFKVKTGD
    211 SIQKGLTPGW NDLDVNQHVS NVKYIGWILE SMPTEVLETQ ELCSLALEYR RECGRRSVLE
        SVTAMDPSKV
    281 GSRSQYQHLL RLHDGTAIVN GATEWRPKNA GANGAISTGK TSNGNSVS

SEQ ID NO: 31
      1 MLKDWSRLLT AITTVFVKSK RPDMHDRKSK RPDMLVRSFG LESTVQDGLV FRQSFSIRSY
        EIGTDRTASI
     71 ETLMNHLQET SLNHCKSTGI LLDGFGRTLE MCKRDLIWVV IKMQIKVNRY PAWGDTVEIN
        TRFSRLGKIG
    141 MGRDWLISDC NTGEILVRAT SAYAMMNQKT RRLSKVPYEV HQEIVPLFVD SPVIEVSDLK
        VHRFKVKTGH
    211 SIQKGLTPGW NDLDVNQHVS NVKYIGWILE SMPTEVLETQ ELCSLALEYR RECGRRSVLE
        SVTAMDPSKV
    281 GSRSQYQHLL RLEDGTAIVN GATEWRPKNA GANGAISTGK TSNGNSVS

SEQ ID NO: 32
      1 MLKRWSRLLT AITTVFVKSK RPDMHDRKSK RPDMLVDSFG LESTVQDGLV FRQSFSIRSY
        EIGTDRTASI
     71 ETLMNHLQET SLNHCKSTGI LLRGFGRTLE MCKRDLIWVV IKMQIKVNRY PAWGDTVEIN
        TRFSRLGKIG
    141 MGRDWLISDC NTGEILVRAT SAYAMMNQKT RRLSKVPYEV HQEIVPLFVD SPVIEVSDLK
        VHRFKVKTGR
    211 SIQKGLTPGW NDLDVNQHVS NVKYIGWILE SMPTEVLETQ ELCSLALEYR RECGRRSVLE
        SVTAMDPSKV
    281 GSRSQYQHLL RLEDGTAIVN GATEWRPKNA GANGAISTGK TSNGNSVS

SEQ ID NO: 33
      1 MLKDWSRLLT AITTVFVKSK RPDMHDRKSK RPDMLVDSFG LESTVQDGLV FRQSFSIRSY
        EIGTDRTASI
     71 ETLMNHLQET SLNHCKSTGI LLHGFGRTLE MCKRDLIWVV IKMQIKVNRY PAWGDTVEIN
        TRFSRLGKIG
    141 MGRDWLISDC NTGEILVRAT SAYAMMNQKT RRLSKVPYHV HQEIVPLFVD SPVIEVSDLK
        VHRFKVKTGD
    211 SIQKGLTPGW NDLDVNQHVS NVKYIGWILE SMPTEVLETQ ELCSLALEYR RECGRHSVLE
        SVTAMDPSKV
    281 GSRSQYQHLL RLEDGTAIVN GATEWRPKNA GANGAISTGK TSNGNSVS

SEQ ID NO: 34
      1 MLKDWSRLLT AITTVFVKSK RPDMHDRKSK RPDMLVDSFG LESTVQDGLV FRQSFSIRSY
        EIGTDRTASI
     71 ETLMNHLQET SLNHCKSTGI LLHGFGRTLE MCKRDLIWVV IKMQIKVNRY PAWGDTVEIN
        TRFSRLGKIG
    141 MGRDWLISDC NTGEILVRAT SAYAMMNQKT RRLSKVPYEV HQEIVPLFVD SPVIEVSDLK
        VHRFKVKTGR
    211 SIQKGLTPGW NDLDVNQHVS NVKYIGWILE SMPTHVLETQ ELCSLALEYR RECGRHSVLE
        SVTAMDPSKV
    281 GSRSQYQHLL RLEDGTAIVN GATEWRPKNA GANGAISTGK TSNGNSVS

SEQ ID NO: 35
      1 MLKHWSRLLT AITTVFVKSK RPDMHDRKSK RPDMLVRSFG LESTVQDGLV FRQSFSIRSY
        EIGTDRTASI
```

APPENDIX A-continued

Sequences

```
     71 ETLMNHLQET SLNHCKSTGI LLRGFGRTLE MCKRDLIWVV IKMQIKVNRY PAWGDTVEIN
        TRFSRLGKIG
    141 MGRDWLISDC NTGEILVRAT SAYAMMNQKT RRLSKVPYEV HQEIVPLFVD SPVIEVSDLK
        VHRFKVKTGD
    211 SIQKGLTPGW NDLDVNQHVS NVKYIGWILR SMPTEVLETQ ELCSLALEYR RECGRDSVLE
        SVTAMDPSKV
    281 GSRSQYQHLL RLEDGTAIVN GATEWRPKNA GANGAISTGK TSNGNSVS

SEQ ID NO: 36
      1 MLKDWSRLLT AITTVFVKSK RPDMHDRKSK RPDMLVDSFG LESTVQDGLV FRQSFSIRSY
        EIGTDRTASI
     71 ETLMNHLQET SLNHCKSTGI LLRGFGRTLE MCKRDLIWVV IKMQIKVNRY PAWGDTVEIN
        TRFSRLGKIG
    141 MGRDWLISDC NTGEILVRAT SAYAMMNQKT RRLSKVPYEV HQEIVPLFVD SPVIEVSDLK
        VHRFKVKTGD
    211 SIQKGLTPGW NDLDVNQHVS NVKYIGWILE SMPTEVLETQ ELCSLALEYR RECGRDSVLE
        SVTAMDPSKV
    281 GSRSQYQHLL RLEDGTAIVN GATEWRPKNA GANGAISTGK TSNGNSVS

SEQ ID NO: 37
      1 MLKDWSRLLT AITTVFVKSK RPDMHDRKSK RPDMLVHSFG LESTVQDGLV FRQSFSIRSY
        EIGTDRTASI
     71 ETLMNHLQET SLNHCKSTGI LLHGFGRTLE MCKRDLIWVV IKMQIKVNRY PAWGDTVEIN
        TRFSRLGKIG
    141 MGRDWLISDC NTGEILVRAT SAYAMMNQKT RRLSKVPYEV HQEIVPLFVD SPVIEVSDLK
        VHRFKVKTGD
    211 SIQKGLTPGW NDLDVNQHVS NVKYIGWILE SMPTEVLETQ ELCSLALEYR RECGRRSVLE
        SVTAMDPSKV
    281 GSRSQYQHLL RLRDGTAIVN GATEWRPKNA GANGAISTGK TSNGNSVS

SEQ ID NO: 38
      1 MLKHWSRLLT AITTVFVKSK RPDMHDRKSK RPDMLVDSFG LESTVQDGLV FRQSFSIRSY
        EIGTDRTASI
     71 ETLMNHLQET SLNHCKSTGI LLHGFGRTLE MCKRDLIWVV IKMQIKVNRY PAWGDTVEIN
        TRFSRLGKIG
    141 MGRDWLISDC NTGEILVRAT SAYAMMNQKT RRLSKVPYEV HQEIVPLFVD SPVIEVSDLK
        VHRFKVKTGD
    211 SIQKGLTPGW NDLDVNQHVS NVKYIGWILE SMPTEVLETQ ELCSLALEYR RECGRDSVLE
        SVTAMDPSKV
    281 GSRSQYQHLL RLEDGTAIVN GATEWRPKNA GANGAISTGK TSNGNSVS

SEQ ID NO: 39
      1 MLKDWSRLLT AITTVFVKSK RPDMHDRKSK RPDMLVDSFG LESTVQDGLV FRQSFSIRSY
        EIGTDRTASI
     71 ETLMNHLQET SLNHCKSTGI LLHGFGRTLE MCKRDLIWVV IKMQIKVNRY PAWGDTVEIN
        TRFSRLGKIG
    141 MGRDWLISDC NTGEILVRAT SAYAMMNQKT RRLSKVPYEV HQEIVPLFVD SPVIEVSDLK
        VHRFKVKTGD
    211 SIQKGLTPGW NDLDVNQHVS NVKYIGWILE SMPTRVLETQ ELCSLALEYR RECGRHSVLE
        SVTAMDPSKV
    281 GSRSQYQHLL RLHDGTAIVN GATEWRPKNA GANGAISTGK TSNGNSVS

SEQ ID NO: 40
      1 MLKHWSRLLT AITTVFVKSK RPDMHDRKSK RPDMLVDSFG LESTVQDGLV FRQSFSIRSY
        EIGTDRTASI
     71 ETLMNHLQET SLNHCKSTGI LLRGFGRTLE MCKRDLIWVV IKMQIKVNRY PAWGDTVEIN
        TRFSRLGKIG
    141 MGRDWLISDC NTGEILVRAT SAYAMMNQKT RRLSKVPYEV HQEIVPLFVD SPVIEVSDLK
        VHRFKVKTGD
    211 SIQKGLTPGW NDLDVNQHVS NVKYIGWILH SMPTEVLETQ ELCSLALEYR RECGRDSVLE
        SVTAMDPSKV
    281 GSRSQYQHLL RLEDGTAIVN GATEWRPKNA GANGAISTGK TSNGNSVS

SEQ ID NO: 41
      1 MLKDWSRLLT AITTVFVKSK RPDMHDRKSK RPDMLVDSFG LESTVQDGLV FRQSFSIRSY
        EIGTDRTAI
     71 ETLMNHLQET SLNHCKSTGI LLRGFGRTLE MCKRDLIWVV IKMQIKVNRY PAWGDTVEIN
        TRFSRLGKIG
    141 MGRDWLISDC NTGEILVRAT SAYAMMNQKT RRLSKVPYHV HQEIVPLFVD SPVIEVSDLK
        VHRFKVKTGD
    211 SIQKGLTPGW NDLDVNQHVS NVKYIGWILE SMPTEVLHTQ ELCSLALEYR RECGRRSVLE
        SVTAMDPSKV
    281 GSRSQYQHLL RLEDGTAIVN GATEWRPKNA GANGAISTGK TSNGNSVS

SEQ ID NO: 42
      1 MLKDWSRLLT AITTVFVKSK RPDMHDRKSK RPDMLVDSFG LESTVQDGLV FRQSFSIRSY
        EIGTDRTAcI
```

APPENDIX A-continued

Sequences

```
     71 ETLMNHLQET SLNHCKSTGI LLDGFGRTLE MCKRDLIWVV IKMQIKVNRY PAWGDTVEIN
        TRFSRLGKIG
    141 MGRDWLISDC NTGEILVRAT SAYAMMNQKT RRLSKVPYEV HQEIVPLFVD SPVIEVSDLK
        VHRFKVKTGD
    211 SIQKGLTPGW NDLDVNQHVS NVKYIGWILH SMPTEVLETQ ELCSLALEYR RECGRDSVLE
        SVTAMDPSKV
    281 GSRSQYQHLL RLEHGTAIVN GATEWRPKNA GANGAISTGK TSNGNSVS

SEQ ID NO: 43
      1 MLKDWSRLLT AITTVFVKSK RPRMHDRKSK RPDMLVRSFG LESTVQDGLV FRQSFSIRSY
        EIGTDRTASI
     71 ETLMNHLQET SLNHCKSTGI LLDGFGRTLE MCKRDLIWVV IKMQIKVNRY PAWGDTVEIN
        TRFSRLGKIG
    141 MGRDWLISDC NTGEILVRAT SAYAMMNQKT RRLSKVDYEV HQEIVTLFVD SPVIEVSDLK
        VHRFKVKTGD
    211 SIQKGLTDGW NDLDVNQHVS NVKYIGWILR SMPTEVLETQ ELCSLALEYR RECGRDSVLE
        SVTAMDPSKV
    281 GSRSQYQHLL RLHDGTAIVN GATEWRDKNA GANGAISTGK TSNGNSVS

SEQ ID NO: 44
      1 MLKDWSRLLT AITTVFVKSK RPDMHDRKSK RPDMLVDSFG LESTVQDGLV FRQSFSIRSY
        EIGTDRTASI
     71 ETLMNHLQET SLNHCKSTGI LLHGFGRTLE MCKRDLIWVV IKMQIKVNRY PAWGDTVEIN
        TRFSRLGKIG
    141 MGRDWLISDC NTGEILVRAT SAYAMMNQKT RRLSKVDYRV HQEIVTLFVD SPVIEVSDLK
        VHRFKVKTGD
    211 SIQKGLTDGW NDLDVNQHVS NVKYIGWILH SMPTEVLETQ ELCSLALEYR RECGRDSVLE
        SVTAMDPSKV
    281 GSRSQYQHLL RLRDGTAIVN GATEWRDKNA GANGAISTGK TSNGNSVS

SEQ ID NO: 45
      1 MLKDWSRLLT AITTVFVKSK RPDMHDRKSK RPDMLVDSFG LESTVQDGLV FRQSFSIRSY
        EIGTDRTASI
     71 ETLMNHLQET SLNHCKSTGI LLHGFGRTLE MCKRDLIWVV IKMQIKVNRY PAWGDTVEIN
        TRFSRLGKIG
    141 MGRDWLISDC NTGEILVRAT SAYAMMNQKT RRLSKVDYHV HQEIVTLFVD SPVIEVSDLK
        VHRFKVKTGD
    211 SIQKGLTDGW NDLDVNQHVS NVKYIGWILE SMPTHVLETQ ELCSLALEYR RECGRRSVLE
        SVTAMDPSKV
    281 GSRSQYQHLL RLEDGTAIVN GATEWRDKNA GANGAISTGK TSNGNSVS

SEQ ID NO: 46
      1 MLKDWSRLLT AITTVFVKSK RPRMHDRKSK RPDMLVDSFG LESTVQDGLV FRQSFSIRSY
        EIGTDRTASI
     71 ETLMNHLQET SLNHCKSTGI LLRGFGRTLE MCKRDLIWVV IKMQIKVNRY PAWGDTVEIN
        TRFSRLGKIG
    141 MGRDWLISDC NTGEILVRAT SAYAMMNQKT RRLSKVDYEV HQEIVTLFVD SPVIEVSDLK
        VHRFKVKTGD
    211 SIQKGLTDGW NDLDVNQHVS NVKYIGWILE SMPTEVLETQ ELCSLALEYR RECGRRSVLE
        SVTAMDPSKV
    281 GSRSQYQHLL RLEDGTAIVN GATEWRDKNA GANGAISTGK TSNGNSVS

SEQ ID NO: 47
      1 MLPDWSRLLT AITTVFAKSK RPHMHDRKSK RPDMLVHSFG LESGVQDGLV FRQSFSIRSY
        EIGPDRLASI
     71 ETLMNHLQET SLNHCKSTGI LLHGFGRTKE MCKRDLIWVV IKMQIKVNRY PAWGDTVEIN
        TRFSRLGKIG
    141 MGRDWLISDC NTGEILVRAT SAYAMMNQKT RRLSKLDYEV HQEIAPLFVD SPVIEVSDLK
        VHRFKVKTGD
    211 SIHKGLTDGW NDLDVNQHVS NVKYIGWILR SMPTEVLETQ ELCSLALEYR RECGRDSVLE
        SVTAMDPSKV
    281 GSRSQYQHLL RLEDGTAIVN GATEWRDKNA GANGARSTGK TSNGNSVS

SEQ ID NO: 48
      1 MLPDWSRLLT AITTVFAKSK RPHMHDRKSK RPDMLVDSFG LESGVQDGLV FRQSFSIRSY
        EIGPDRLASI
     71 ETLMNHLQET SLNHCKSTGI LLHGFGRTKE MCKRDLIWVV IKMQIKVNRY PAWGDTVEIN
        TRFSRLGKIG
    141 MGRDWLISDC NTGEILVRAT SAYAMMNQKT RRLSKLDYEV HQEIAPLFVD SPVIEVSDLK
        VHRFKVKTGD
    211 SIHKGLTDGW NDLDVNQHVS NVKYIGWILR SMPTEVLETQ ELCSLALEYR RECGRDSVLE
        SVTAMDPSI
    281 GSRSQYQHLL RLEDGTAIVN GATEWRDKNA GANGARSTGK TSNGNSVS

SEQ ID NO: 49
      1 MLPDWSRLLT AITTVFAKSK RPHMHDRKSK RPDMLVDSFG LESGVQDGLV FRQSFSIRSY
        EIGPDRLASI
```

APPENDIX A-continued

Sequences

```
     71 ETLMNHLQET SLNHCKSTGI LLDGFGRTKE MCKRDLIWVV IKMQIKVNRY PAWGDTVEIN
        TRFSRLGKIG
    141 MGRDWLISDC NTGEILVRAT SAYAMMNQKT RRLSKLDYEV HQEIAPLFVD SPVIEVSDLK
        VHRFKVKTGD
    211 SIHKGLTDGW NDLDVNQHVS NVKYIGWILR SMPTEVLETQ ELCSLALEYR RECGRDSVLE
        SVTAMDPSKV
    281 GSRSQYQHLL RLEDGTAIVN GATEWRDKNA GANGARSTGK TSNGNSVS

SEQ ID NO: 50
      1 MLPDWSRLLT AITTVFAKSK RPHMHDRKSK RPDMLVDSFG LESGVQDGLV FRQSFSIRSY
        EIGPDRLASI
     71 ETLMNHLQET SLNHCKSTGI LLHGFGRTKE MCKRDLIWVV IKMQIKVNRY PAWGDTVEIN
        TRFSRLGKIG
    141 MGRDWLISDC NTGEILVRAT SAYAMMNQKT RRLSKLDYEV HQEIAPLFVD SPVIEVSDLK
        VHRFKVKTGD
    211 SIKGLTDGW NDLDVNQHVS NVKYIGWILE SMPTEVLETQ ELCSLALEYR RECGRDSVLE
        SVTAMDPSKV
    281 GSRSQYQHLL RLEDGTAIVN GATEWRDKNA GANGARSTGK TSNGNSVS

SEQ ID NO: 51
      1 MLPDWSRLLT AITTVFAKSK RPDMHDRKSK RPDMLVDSFG LESGVQDGLV FRQSFSIRSY
        EIGPDRLASI
     71 ETLMNHLQET SLNHCKSTGI LLDGFGRTKE MCKRDLIWVV IKMQIKVNRY PAWGDTVEIN
        TRFSRLGKIG
    141 MGRDWLISDC NTGEILVRAT SAYAMMNQKT RRLSKLDYEV HQEIAPLFVD SPVIEVSDLK
        VHRFKVKTGD
    211 SIHKGLTDGW NDLDVNQHVS NVKYIGWILR SMPTEVLETQ ELCSLALEYR RECGRDSVLE
        SVTAMDPSKV
    281 GSRSQYQHLL RLEDGTAIVN GATEWRDKNA GANGARSTGK TSNGNSVS

SEQ ID NO: 52
      1 MTTVFAKSKR PHMHDRKSKR DDMLVDSFGL ESGVQDGLVF RQSFSIRSYE IGPDRLASIE
        TLMNHLQETS
     71 LNHCKSTGIL LDGFGRTKEM CKRDLIWVVI KMQIKVNRYD AWGDTVEINT RFSRLGKIGM
        GRDWLISDCN
    141 TGEILVRATS AYAMMNQKTR RLSKLDYEVH QEIAPLFVDS PVIEVSDLKV HRFKVKTGDS
        IHKGLTDGWN
    211 DLDVNQHVSN VKYIGWILRS MDTEVLETQE LCSLALEYRR ECGRDSVLES VTAMDPSKVG
        SRSQYQHLLR
    281 LEDGTAIVNG ATEWRDKNAG ANGARSTGKT SNGNSVS

SEQ ID NO: 53
      1 MFAKSKRPHM HDRKSKRPDM LVDSFGLESG VQDGLVFRQS FSIRSYEIGP DRLASIETLM
        NHLQETSLNH
     71 CKSTGILLDG FGRTKEMCKR DLIWVVIKMQ IKVNRYPAWG DTVEINTRFS RLGKIGMGRD
        WLISDCNTGE
    141 ILVRATSAYA MMNQKTRRLS KLDYEVHQEI APLFVDSDVI EVSDLKVHRF KVKTGDSIHK
        GLTDGWNDLD
    211 VNQHVSNVKY IGWILRSMPT EVLETQELCS LALEYRRECG RDSVLESVTA MDDSKVGSRS
        QYQHLLRLED
    281 GTAIVNGATE WRDKNAGANG ARSTGKTSNG NSVS

SEQ ID NO: 54
      1 MAKSKRDHMH DRKSKRPDML VDSFGLESGV QDGLVFRQSF SIRSYEIGPD RLASIETLMN
        HLQETSLNHC
     71 KSTGILLDGF GRTKEMCKRD LIWVVIKMQI KVNRYPAWGD TVEINTRFSR LGKIGMGRDW
        LISDCNTGEI
    141 LVRATSAYAM MNQKTRRLSK LDYEVHQEIA PLFVDSPVIE VSDLKVHRFK VKTGDSIHKG
        LTDGWNDLDV
    211 NQHVSNVKYI GWILRSMPTE VLETQELCSL ALEYRRECGR DSVLESVTAM DDSKVGSRSQ
        YQHLLRLEDG
    281 TAIVNGATEW RDKNAGANGA RSTGKTSNGN SVS

SEQ ID NO: 55
      1 MHDRKSKRDD MLVDSFGLES GVQDGLVFRQ SFSIRSYEIG PDRLASIETL MNHLQETSLN
        HCKSTGILLD
     71 GFGRTKEMCK RDLIWVVIKM QIKVNRYDAW GDTVEINTRF SRLGKIGMGR DWLISDCNTG
        EILVRATSAY
    141 AMMNQKTRRL SKLDYEVHQE IAPLFVDSDV IEVSDLKVHR FKVKTGDSIH KGLTDGWNDL
        DVNQHVSNVK
    211 YIGWILRSMP TEVLETQELC SLALEYRREC GRDSVLESVT AMDDSKVGSR SQYQHLLRLE
        DGTAIVNGAT
    281 EWRDKNAGAN GARSTGKTSN GNSVS

SEQ ID NO: 56
      1 MRPDMLVDSF GLESGVQDGL VFRQSFSIRS YEIGPDRLAS IETLMNHLQE TSLNHCKSTG
        ILLDGFGRTK
```

APPENDIX A-continued

Sequences

```
     71 EMCKRDLIWV VIKMQIKVNR YPAWGDTVEI NTRFSRLGKI GMGRDWLISD CNTGEILVRA
        TSAYAMMNQK
    141 TRRLSKLDYE VHQEIADLEV DSPVIEVSDL KVHRFKVTG DSIHKGLTDG WNDLDVNQHV
        SNVKYIGWIL
    211 RSMPTEVLET QELCSLALEY RRECGRDSVL ESVTAMDPSK VGSRSQYQHL LRLEDGTAIV
        NGATEWRDKN
    281 AGANGARSTG KTSNGNSVS

SEQ ID NO: 57
      1 MDMLVDSFGL ESGVQDGLVF RQSFSIRSYE IGPDRLASIE TLMNHLQETS LNHCKSTGIL
        LDGFGRTKEM
     71 CKRDLIWVVI KMQIKVNRYD AWGDTVEINT RFSRLGKIGM GRDWLISDCN TGEILVRATS
        AYAMMNQKTR
    141 RLSKLPYEVH QEIAPLFVDS PVIEVSDLKV HRFKVKTGDS IHKGLTDGWN DLDVNQHVSN
        VKYIGWILRS
    211 MPTEVLETQE LCSLALEYRR ECGRDSVLES VTAMDPSKVG SRSQYQHLLR LEDGTAIVNG
        ATEWRDKNAG
    281 ANGARSTGKT SNGNSVS

SEQ ID NO: 58
      1 MLVDSFGLES GVQDGLVFRQ SFSIRSYEIG PDRLASIETL MNHLQETSLN HCKSTGILLD
        GFGRTKEMCK
     71 RDLIWVVIKM QIKVNRYDAW GDTVEINTRF SRLGKIGMGR DWLISDCNTG EILVRATSAY
        AMMNQKTRRL
    141 SKLDYEVHQE IAPLFVDSPV IEVSDLKVHR FKVKTGDSIH KGLTDGWNDL DVNQHVSNVK
        YIGWILRSMP
    211 TEVLETQELC SLALEYRREC GRDSVLESVT AMDPSKVGSR SQYQHLLRLE DGTAIVNGAT
        EWRDKNAGAN
    281 GARSTGKTSN GNSVS

SEQ ID NO: 59
      1 MVDSFGLESG VQDGLVFRQS FSIRSYEIGP DRLASIETLM NHLQETSLNH CKSTGILLDG
        FGRTKEMCKR
     71 DLIWVVIKMQ IKVNRYPAWG DTVEINTRFS RLGKIGMGRD WLISDCNTGEI LVRATSAYA
        MMNQKTRRLS
    141 KLPYEVHQEI APLEVDSPVI EVSDLKVHRF KVKTGDSIHK GLTDGWNDLD VNQHVSNVKY
        IGWILRSMPT
    211 EVLETQELCS LALEYRRECG RDSVLESVTA MDPSKVGSRS QYQHLLRLED GTAIVNGATE
        WRDKNAGANG
    281 ARSTGKTSNG NSVS

SEQ ID NO: 60
      1 ATGCTCCCCG ATTGGTCCCG CCTGCTGACA GCTATCACCA CGGTGTTTGT TAAGTCGAAA CGGCCGGACA TGCATGATAG
     81 AAAAAGCAAG CGACCAGACA TGTTAGTCGA TTCTTTCGGA TTGGAGAGTA CTGTACAAGA TGGCCTTGTG TTTCGTCAGT
    161 CATTCTCCAT ACGCAGCTAT GAAATTGGTA CAGACCGTAC CGCGTCGATC GAGACGCTGA TGAACCACCT CCAGGAAACC
    241 TCTCTGAATC ATTGCAAAAG TACTGGCATT TTACTGGATG GTTTTGGGCG CACATTGAA ATGTGTAAAC GGGACCTTAT
    321 CTGGGTTGTC ATAAAGATGC AAATTAAAGT GAACCGTTAC CCTGCCTGGG GAGATACGGT AGAGATCAAT ACCCGCTTTT
    401 CAAGACTGGG CAAAATTGGT ATGGGCCGAG ACTGGCTCAT AAGCGATTGC AACACTGGTG AAATCTTAGT TCGTGCAACA
    481 TCCGCTTATG CGATGATGAA TCAGAAGACC CGCCGGCTGT CGAAATTGCC GTACGAGGTG CACCAAGAAA TTGTCCCACT
    561 TTTCGTTGAT TCTCCGGTAA TCGAAGCAG TGATCTGAAA GTGCATAAGT TTAAAGTCAA AACGGGGGAC AGCATTCAGA
    641 AGGGATTAAC CCCCGGCTGG AACGATCTGG ATGTTAATCA GCACGTGTCA AACGTAAAAT ATATAGGTTG GATTCTGGAG
    721 TCCATGCCTA CTGAAGTCCT GGAGACACAA GAATTGTGTT CGCTTGCCCT GGAATACCGT CGCGAGTGCG GGCGTGACTC
    801 TGTTTTAGAA AGCGTGACGG CAATGGACCC GAGTAAAGTA GGCGTTCGCT CACAGTATCA ACATCTGCTC AGATTGGAGG
    881 ACGGTACCGC GATTGTGAAT GGAGCTACTG AATGGCGACC AAAGAACGCC GGCGCAAATG GTGCGATATC CACAGGGAAA
    961 ACGAGCAACG GCAATTCGGT CTCTTAA
```

As is apparent to one of skill in the art, various modifications and variations of the above aspects and embodiments can be made without departing from the spirit and scope of this disclosure.

We claim:

1. An engineered thioesterase variant having an amino acid sequence that has at least 90% sequence identity to SEQ ID NO:1 and at least one substitution mutation at an amino acid position selected from the group consisting of: 3, 4, 6, 14, 15, 17, 22, 23, 37, 44, 45, 50, 54, 56, 64, 67, 91, 93, 110, 111, 114, 129, 132, 137, 158, 162, 165, 176, 178, 179, 185, 186, 196, 197, 198, 203, 210, 213, 217, 225, 227, 236, 240, 244, 245, 248, 254, 256, 258, 266, 278, 282, 292, 293, 294, 297, 298, 299, 300, 301, 302, 316, 321, 322, 325, and 328; wherein the engineered thioesterase variant has improved activity for production of medium-chain fatty acid derivatives as compared to an enzyme having SEQ ID NO: 1.

2. The engineered thioesterase of claim 1, wherein the engineered thioesterase variant has improved activity for production of C8 fatty acid derivatives, C10 fatty acid derivatives, or both.

3. The engineered thioesterase variant of claim 1, wherein the engineered thioesterase variant comprises a mutation corresponding to P3K, D4H, D4M, D4R, S6R, T14G, T14R, V15L, V15W, V17A, V17C, P22R, D23H, D23R, D37H, D37R, D37P, T44G, T44I, V45S, V50W, S54R, S56C, S56K, T64P, T64R, T67L, L73V, H76F, H76L, H76Y, L91M, D93H, D93R, L99K, L99P, C102I, V110L, I111T, Q114K, I129V, R132W, G137C, R158Q, A162B, M165T, I176V, Y178P, B179H, B179R, V185A, P186G, D196V, S197N, D198W, K203R, D210H, D210R, Q213H, Q213R, T217R, V225L, Q227G, G236T, E240H, E240R, E240V, T244M, T244R, E245H, E245R, E248H, S254G, A256C, A256R, E258T, E258V, D266H, D266R, S278K, S278V, S278T, V282S, L292F, E293H, B293R, D294H, A297D, A297T, A297V, I298C, I298V, V299L, N300K, N300L, N300W, G301C, A302T, I316R, I316T, T321R, S322K, N325K, or S328K.

4. The engineered thioesterase variant of claim 1, wherein the engineered thioesterase variant has an amino acid sequence corresponding to SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, or SEQ ID NO:59.

5. The engineered thioesterase variant of claim 1, wherein:
(a) the engineered thioesterase variant has an overall increased net positive charge as compared to a thioesterase of SEQ ID NO: 1 or SEQ ID NO:4; or
(b) the engineered thioesterase variant has an increased positive surface charge by comparison to SEQ ID NO:1, SEQ ID NO:4, or SEQ ID NO: 15.

6. The engineered thioesterase variant of claim 1, wherein:
(a) the engineered thioesterase variant has improved solubility by comparison to SEQ ID NO:1;
(b) the engineered thioesterase variant has improved solubility by comparison to SEQ ID NO:49;
(c) the engineered thioesterase variant further comprises a truncation mutation between amino acids 2 and 40 of SEQ ID NO:1;
(d) the engineered thioesterase variant further comprises a truncation mutation between amino acids 2 and 40 of SEQ ID NO:49; or
(e) the engineered thioesterase variant has an amino acid sequence corresponding to SEQ ID NO:52, SEQ ID NO:53, SEQ ID NO:54, SEQ ID NO:55, SEQ ID NO:56, SEQ ID NO:57, SEQ ID NO:58, or SEQ ID NO:59.

7. The engineered thioesterase variant of claim 3, wherein the engineered thioesterase variant further comprises a truncation mutation between amino acids 2 and 40 of SEQ ID NO:1.

8. A recombinant host cell, comprising the engineered thioesterase variant of claim 1.

9. The recombinant host cell of claim 8, wherein the engineered thioesterase variant comprises a mutation corresponding to P3K, D4H, D4M, D4R, S6R, T14G, T14R, V15L, V15W, V17A, V17C, P22R, D23H, D23R, D37H, D37R, D37P, T44G, T44I, V45S, V50W, S54R, S56C, S56K, T64P, T64R, T67L, L73V, H76F, H76L, H76Y, L91M, D93H, D93R, L99K, L99P, C102I, V110L, I111T, Q114K, I129V, R132W, G137C, R158Q, A162E, M165T, L176V, Y178P, E179H, E179R, V185A, P186G, D196V, S197N, D198W, K203R, D210H, D210R, Q213H, Q213R, T217R, V225L, Q227G, G236T, E240H, E240R, E240V, T244M, T244R, E245H, E245R, E248H, S254G, A256C, A256R, E258T, E258V, D266H, D266R, S278K, S278V, S278T, V282S, L292F, E293H, E293R, D294H, A297D, A297T, A297V, I298C, I298V, V299L, N300K, N300L, N300W, G301C, A302T, I316R, I316T, T321R, S322K, N325K, or S328K.

10. The recombinant host cell of claim 9, wherein the engineered thioesterase variant further comprises a truncation mutation between amino acids 2 and 40 of SEQ ID NO:1.

11. The recombinant host cell of claim 8, wherein:
(a) the engineered thioesterase variant has an overall increased net positive charge as compared to a thioesterase of SEQ ID NO: 1 or SEQ ID NO:4;
(b) the engineered thioesterase variant has an increased positive surface charge by comparison to SEQ ID NO:1, SEQ ID NO:4, or SEQ ID NO: 15;
(c) the engineered thioesterase variant has an amino acid sequence corresponding to SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO:11, SEQ ID NO: 12, SEQ ID NO:13, SEQ ID NO:14, SEQ ID NO:15, SEQ ID NO: 16, SEQ ID NO: 17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, or SEQ ID NO:59;

(d) the engineered thioesterase variant has improved solubility by comparison to SEQ ID NO:1;
(e) the engineered thioesterase variant has improved solubility by comparison to SEQ ID NO:49; or
(f) the engineered thioesterase variant has a truncation mutation between amino acids 2 and 40 of SEQ ID NO:1; or
(g) the engineered thioesterase variant has a truncation mutation between amino acids 2 and 40 of SEQ ID NO:49.

12. The recombinant host cell of claim 8, wherein:
the recombinant host cell further expresses one or more of an ester synthase, an acyl-ACP reductase, an alcohol dehydrogenase, an aldehyde reductase, an acyl-CoA reductase, an acyl-CoA synthetase, a fatty alcohol forming acyl-CoA reductase, a carboxylic acid reductase, an alcohol O-acetyltransferase, an O-methyl transferase, a decarbonylase, an oxidative deformylase, a decarboxylase, OleA, OleCD, or OleBCD; and
the recombinant host cell produces a fatty acid derivative that is a fatty acid, fatty ester, fatty alcohol, fatty alcohol acetate ester (FACE), fatty acid methyl ester (FAME), fatty acid ethyl ester (FAEE), fatty amine, fatty aldehyde, bifunctional fatty acid derivative, diacid, diol, hydrocarbon, alkane, alkene, olefin, or ketone.

13. The recombinant host cell of claim 8, wherein:
the recombinant host cell further comprises a biochemical pathway that converts a first fatty acid derivative to a second fatty acid derivative, wherein the first fatty acid derivative and the second fatty acid derivative are medium-chain fatty acid derivatives; and
(i) the second fatty acid derivative has a higher minimum inhibitory concentration (MIC) than the first fatty acid derivative, and wherein the presence of the second fatty acid derivative increases the MIC of the first fatty acid derivative; or
(ii) the second fatty acid derivative has a higher Log P than the first fatty acid derivative; or
(iii) the second fatty acid derivative is less toxic than the first fatty acid derivative.

14. The recombinant host cell of claim 13, wherein:
(i) the biochemical pathway comprises:
a) a carboxylic acid reductase;
b) a carboxylic acid reductase and an alcohol dehydrogenase;
c) a carboxylic acid reductase and an alcohol O-acetyltransferase;
d) a carboxylic acid reductase, an alcohol dehydrogenase, and an alcohol O-acetyltransferase;
e) an ester synthase;
f) an ester synthase and an acyl-CoA synthetase;
g) an acyl-CoA reductase;
h) an acyl-CoA reductase and an acyl-CoA synthetase;
i) an acyl-CoA reductase and an alcohol O-acetyltransferase;
j) an acyl-CoA reductase, an alcohol O-acetyltransferase, and an acyl-CoA synthetase;
k) an O-methyltransferase;
l) an acyl-ACP reductase;
m) an acyl-ACP reductase and aldehyde decarbonylase;
n) an acyl-ACP reductase and aldehyde oxidative deformylase;
o) an acyl-ACP reductase and an alcohol O-acetyltransferase;
p) an acyl-ACP reductase, an alcohol O-acetyltransferase, and an alcohol dehydrogenase;
q) OleA;
r) OleA, OleC, and OleD;
s) OleA and an acyl-CoA synthetase; or
t) OleA, OleC, OleD, and an acyl-CoA synthetase; or
(ii) the first fatty acid derivative is a fatty acid and the second fatty acid derivative is a fatty acid alkyl ester, a fatty acid methyl ester, or a fatty acid ethyl ester, and the biochemical pathway comprises an ester synthase or comprises an ester synthase and an acyl-CoA synthetase; or
(iii) the first fatty acid derivative is a fatty alcohol and the second fatty acid derivative is a fatty alcohol acetate, and the biochemical pathway comprises a carboxylic acid reductase and an alcohol O-acetyltransferase or comprises a carboxylic acid reductase, an alcohol dehydrogenase, and an alcohol O-acetyltransferase.

\* \* \* \* \*

SEQUENCE LISTING

<160> NUMBER OF SEQ IDS: 60

<210> SEQ ID NO 1
<211> LENGTH: 328
<212> TYPE: PRT
<213> ORGANISM: Cuphea hookeriana

<400> SEQUENCE: 1

Met Leu Pro Asp Trp Ser Arg Leu Leu Thr Ala Ile Thr Thr Val Phe

```
                1               5                    10                   15
            Val Lys Ser Lys Arg Pro Asp Met His Asp Arg Lys Ser Lys Arg Pro
                            20                  25                  30
            Asp Met Leu Val Asp Ser Phe Gly Leu Glu Ser Thr Val Gln Asp Gly
                            35                  40                  45
            Leu Val Phe Arg Gln Ser Phe Ser Ile Arg Ser Tyr Glu Ile Gly Thr
                        50                  55                  60
            Asp Arg Thr Ala Ser Ile Glu Thr Leu Met Asn His Leu Gln Glu Thr
            65                  70                  75                  80
            Ser Leu Asn His Cys Lys Ser Thr Gly Ile Leu Leu Asp Gly Phe Gly
                                85                  90                  95
            Arg Thr Leu Glu Met Cys Lys Arg Asp Leu Ile Trp Val Val Ile Lys
                            100                 105                 110
            Met Gln Ile Lys Val Asn Arg Tyr Pro Ala Trp Gly Asp Thr Val Glu
                            115                 120                 125
            Ile Asn Thr Arg Phe Ser Arg Leu Gly Lys Ile Gly Met Gly Arg Asp
                        130                 135                 140
            Trp Leu Ile Ser Asp Cys Asn Thr Gly Glu Ile Leu Val Arg Ala Thr
            145                 150                 155                 160
            Ser Ala Tyr Ala Met Met Asn Gln Lys Thr Arg Arg Leu Ser Lys Leu
                                165                 170                 175
            Pro Tyr Glu Val His Gln Glu Ile Val Pro Leu Phe Val Asp Ser Pro
                            180                 185                 190
            Val Ile Glu Asp Ser Asp Leu Lys Val His Lys Phe Lys Val Lys Thr
                            195                 200                 205
            Gly Asp Ser Ile Gln Lys Gly Leu Thr Pro Gly Trp Asn Asp Leu Asp
                        210                 215                 220
            Val Asn Gln His Val Ser Asn Val Lys Tyr Ile Gly Trp Ile Leu Glu
            225                 230                 235                 240
            Ser Met Pro Thr Glu Val Leu Glu Thr Gln Glu Leu Cys Ser Leu Ala
                                245                 250                 255
            Leu Glu Tyr Arg Arg Glu Cys Gly Arg Asp Ser Val Leu Glu Ser Val
                            260                 265                 270
            Thr Ala Met Asp Pro Ser Lys Val Gly Val Arg Ser Gln Tyr Gln His
                            275                 280                 285
            Leu Leu Arg Leu Glu Asp Gly Thr Ala Ile Val Asn Gly Ala Thr Glu
                        290                 295                 300
            Trp Arg Pro Lys Asn Ala Gly Ala Asn Gly Ala Ile Ser Thr Gly Lys
            305                 310                 315                 320
            Thr Ser Asn Gly Asn Ser Val Ser
                                325

<210> SEQ ID NO 2
<211> LENGTH: 328
<212> TYPE: PRT
<213> ORGANISM: Cuphea hookeriana

<400> SEQUENCE: 2

Met Leu Pro Asp Trp Ser Arg Leu Leu Thr Ala Ile Thr Thr Val Phe
            1               5                   10                  15

Ala Lys Ser Lys Arg Pro Asp Met His Asp Arg Lys Ser Lys Arg Pro
                            20                  25                  30

Asp Met Leu Val Asp Ser Phe Gly Leu Glu Ser Thr Val Gln Asp Gly
                        35                  40                  45
```

```
Leu Val Phe Arg Gln Ser Phe Ser Ile Arg Ser Tyr Glu Ile Gly Arg
 50                  55                  60

Asp Arg Thr Ala Ser Ile Glu Thr Leu Met Asn His Leu Gln Glu Thr
 65                  70                  75                  80

Ser Leu Asn His Cys Lys Ser Thr Gly Ile Leu Leu Asp Gly Phe Gly
                 85                  90                  95

Arg Thr Leu Glu Met Cys Lys Arg Asp Leu Ile Trp Val Val Ile Lys
                100                 105                 110

Met Gln Ile Lys Val Asn Arg Tyr Pro Ala Trp Gly Asp Thr Val Glu
            115                 120                 125

Ile Asn Thr Arg Phe Ser Arg Leu Gly Lys Ile Gly Met Gly Arg Asp
130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Glu Val His Gln Glu Ile Val Pro Leu Phe Val Asp Ser Pro
            180                 185                 190

Val Ile Glu Asp Ser Asp Leu Lys Val His Arg Phe Lys Val Lys Thr
            195                 200                 205

Gly Asp Ser Ile Gln Lys Gly Leu Thr Pro Gly Trp Asn Asp Leu Asp
210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Cys
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
            275                 280                 285

Leu Leu Arg Leu Glu Asp Gly Thr Ala Ile Val Asn Gly Ala Thr Glu
290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 3
<211> LENGTH: 328
<212> TYPE: PRT
<213> ORGANISM: Cuphea hookeriana

<400> SEQUENCE: 3

Met Leu Lys Asp Trp Ser Arg Leu Leu Thr Ala Ile Thr Thr Val Phe
 1               5                  10                  15

Val Lys Ser Lys Arg Pro Asp Met His Asp Arg Lys Ser Lys Arg Pro
                 20                  25                  30

Asp Met Leu Val Pro Ser Phe Gly Leu Glu Ser Thr Val Gln Asp Gly
             35                  40                  45

Leu Val Phe Arg Gln Ser Phe Ser Ile Arg Ser Tyr Glu Ile Gly Thr
 50                  55                  60

Asp Arg Thr Ala Ser Ile Glu Thr Leu Met Asn His Leu Gln Glu Thr
 65                  70                  75                  80

Ser Leu Asn His Cys Lys Ser Thr Gly Ile Leu Leu Asp Gly Phe Gly
                 85                  90                  95
```

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
            115                 120                 125

Val Asn Thr Arg Phe Ser Arg Leu Gly Lys Ile Gly Met Gly Arg Asp
130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Glu Val His Gln Glu Ile Val Pro Leu Phe Val Asp Ser Pro
            180                 185                 190

Val Ile Glu Asp Ser Asp Leu Lys Val His Lys Phe Lys Val Lys Thr
            195                 200                 205

Gly Asp Ser Ile Gln Lys Gly Leu Thr Pro Gly Trp Asn Asp Leu Asp
            210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Val Arg Ser Gln Tyr Gln His
            275                 280                 285

Leu Leu Arg Leu Glu Asp Gly Thr Ala Ile Val Asn Gly Ala Thr Glu
            290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 4
<211> LENGTH: 328
<212> TYPE: PRT
<213> ORGANISM: Cuphea hookeriana

<400> SEQUENCE: 4

Met Leu Lys Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

Asp Met Leu Val Asp Ser Phe Gly Leu Glu Ser Thr Val Gln Asp Gly
            35                  40                  45

Leu Val Phe Arg Gln Ser Phe Ser Ile Arg Ser Tyr Glu Ile Gly Thr
50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu Asp Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
            115                 120                 125

Ile Asn Thr Arg Phe Ser Arg Leu Gly Lys Ile Gly Met Gly Arg Asp

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Glu Val His Gln Glu Ile Val Pro Leu Phe Val Asp Ser Pro
                180                 185                 190

Val Ile Glu Val Ser Asp Leu Lys Val His Arg Phe Lys Val Lys Thr
            195                 200                 205

Gly Asp Ser Ile Gln Lys Gly Leu Thr Pro Gly Trp Asn Asp Leu Asp
        210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 5
<211> LENGTH: 328
<212> TYPE: PRT
<213> ORGANISM: Cuphea hookeriana

<400> SEQUENCE: 5

Met Leu Pro Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

Asp Met Leu Val Asp Ser Phe Gly Leu Glu Ser Thr Val Gln Asp Gly
        35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu Asp Gly Phe Gly
                85                  90                  95

Arg Thr Leu Glu Met Cys Lys Arg Asp Leu Ile Trp Val Leu Ile Lys
            100                 105                 110

Met Gln Ile Lys Val Asn Arg Tyr Pro Ala Trp Gly Asp Thr Val Glu
        115                 120                 125

Val Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

```
Pro Tyr Glu Val His Gln Glu Ile Val Pro Leu Phe Val Asp Ser Pro
            180                 185                 190

Val Ile Glu Asp Ser Asp Leu Lys Val His Arg Phe Lys Val Lys Thr
195                 200                 205

Gly Asp Ser Ile Gln Lys Gly Leu Thr Pro Gly Trp Asn Asp Leu Asp
            210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
            245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Val Arg Ser Gln Tyr Gln His
            275                 280                 285

Leu Leu Arg Leu Glu Asp Gly Thr Ala Ile Val Asn Gly Ala Thr Glu
            290                 295                 300

Trp Arg Pro Lys Asn Ala Gly Ala Asn Gly Ala Ile Ser Thr Gly Lys
305                 310                 315                 320

Thr Ser Asn Gly Asn Ser Val Lys
            325

<210> SEQ ID NO 6
<211> LENGTH: 328
<212> TYPE: PRT
<213> ORGANISM: Cuphea hookeriana

<400> SEQUENCE: 6

Met Leu Lys Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

Asp Met Leu Val Asp Ser Phe Gly Leu Glu Ser Thr Val Gln Asp Gly
            35                  40                  45

Leu Val Phe Arg Gln Ser Phe Ser Ile Arg Ser Tyr Glu Ile Gly Thr
50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu Asp Gly Phe Gly
            85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
            115                 120                 125

Val Asn Thr Arg Phe Ser Arg Leu Gly Lys Ile Gly Met Gly Arg Asp
130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
            165                 170                 175

Pro Tyr Glu Val His Gln Glu Ile Val Pro Leu Phe Val Asp Ser Pro
            180                 185                 190

Val Ile Glu Asp Ser Asp Leu Lys Val His Lys Phe Lys Val Lys Thr
            195                 200                 205

Gly Asp Ser Ile Gln Lys Gly Leu Thr Pro Gly Trp Asn Asp Leu Asp
            210                 215                 220
```

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Val Arg Ser Gln Tyr Gln His
        275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Lys
                325

<210> SEQ ID NO 7
<211> LENGTH: 328
<212> TYPE: PRT
<213> ORGANISM: Cuphea hookeriana

<400> SEQUENCE: 7

Met Leu Pro Asp Trp Arg Arg Leu Leu Thr Ala Ile Thr Thr Leu Phe
1               5                   10                  15

Val Lys Ser Lys Arg Pro Asp Met His Asp Arg Lys Ser Lys Arg Pro
                20                  25                  30

Asp Met Leu Val Asp Ser Phe Gly Leu Glu Ser Thr Val Gln Asp Gly
            35                  40                  45

Leu Val Phe Arg Gln Ser Phe Ser Ile Arg Ser Tyr Glu Ile Gly Thr
        50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu Asp Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Leu
                165                 170                 175

Pro Tyr Glu Val His Gln Glu Ile Val Pro Leu Phe Val Asp Ser Pro
            180                 185                 190

Val Ile Glu Val Ser Asp Leu Lys Val His Lys Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val

```
                260                 265                 270
Thr Ala Met Asp Pro Ser Lys Val Gly Val Arg Ser Gln Tyr Gln His
            275                 280                 285

Leu Leu Arg Leu Glu Asp Gly Thr Ala Ile Val Asn Gly Ala Thr Glu
        290                 295                 300

Trp Arg Pro Lys Asn Ala Gly Ala Asn Gly Ala Thr Ser Thr Gly Lys
305                 310                 315                 320

Thr Lys Asn Gly Asn Ser Val Lys
                325

<210> SEQ ID NO 8
<211> LENGTH: 328
<212> TYPE: PRT
<213> ORGANISM: Cuphea hookeriana

<400> SEQUENCE: 8

Met Leu Lys Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

Asp Met Leu Val Asp Ser Phe Gly Leu Glu Ser Thr Val Gln Asp Gly
        35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu Asp Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Glu Val His Gln Glu Ile Val Pro Leu Phe Val Asp Ser Pro
            180                 185                 190

Val Ile Glu Val Ser Asp Leu Lys Val His Lys Phe Lys Val Lys Thr
        195                 200                 205

Gly Asp Ser Ile Gln Lys Gly Leu Thr Pro Gly Trp Asn Asp Leu Asp
    210                 215                 220

Val Asn Gly His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Val Arg Ser Gln Tyr Gln His
        275                 280                 285

Leu Leu Arg Leu Glu Asp Gly Thr Ala Ile Val Asn Gly Ala Thr Glu
    290                 295                 300
```

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 9
<211> LENGTH: 328
<212> TYPE: PRT
<213> ORGANISM: Cuphea hookeriana

<400> SEQUENCE: 9

Met Leu Pro Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
                20                  25                  30

Asp Met Leu Val Asp Ser Phe Gly Leu Glu Ser Gly Val Gln Asp Gly
            35                  40                  45

Leu Val Phe Arg Gln Ser Phe Ser Ile Arg Ser Tyr Glu Ile Gly Pro
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu Asp Gly Phe Gly
                85                  90                  95

Arg Thr Lys Glu Met Cys Lys Arg Asp Leu Ile Trp Val Val Ile Lys
                100                 105                 110

Met Gln Ile Lys Val Asn Arg Tyr Pro Ala Trp Gly Asp Thr Val Glu
            115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Leu
                165                 170                 175

Pro Tyr Glu Val His Gln Glu Ile Val Pro Leu Phe Val Asp Ser Pro
            180                 185                 190

Val Ile Glu Val Ser Asp Leu Lys Val His Arg Phe Lys Val Lys Thr
    195                 200                 205

Gly Asp Ser Ile Gln Lys Gly Leu Thr Pro Gly Trp Asn Asp Leu Asp
210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
    275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Arg Ser Thr Gly Lys
305                 310                 315                 320

Thr Ser Asn Gly Asn Ser Val Ser
                325

<210> SEQ ID NO 10

```
<211> LENGTH: 328
<212> TYPE: PRT
<213> ORGANISM: Cuphea hookeriana

<400> SEQUENCE: 10
```

| | | | | | | | | | | | | | | | |
|---|---|---|---|---|---|---|---|---|---|---|---|---|---|---|---|
|Met|Leu|Lys|Asp|Trp|Ser|Arg|Leu|Leu|Thr|Ala|Ile|Thr|Thr|Val|Phe|
|1| | | |5| | | | |10| | | | |15| |
|Val|Lys|Ser|Lys|Arg|Pro|Asp|Met|His|Asp|Arg|Lys|Ser|Lys|Arg|Pro|
| | | |20| | | | |25| | | | |30| | |
|Asp|Met|Leu|Val|Asp|Ser|Phe|Gly|Leu|Glu|Ser|Gly|Val|Gln|Asp|Gly|
| | |35| | | | |40| | | | |45| | | |
|Leu|Val|Phe|Arg|Gln|Ser|Phe|Ser|Ile|Arg|Ser|Tyr|Glu|Ile|Gly|Pro|
| |50| | | | |55| | | | |60| | | | |
|Asp|Arg|Thr|Ala|Ser|Ile|Glu|Thr|Leu|Met|Asn|His|Leu|Gln|Glu|Thr|
|65| | | | |70| | | | |75| | | | |80|
|Ser|Leu|Asn|His|Cys|Lys|Ser|Thr|Gly|Ile|Leu|Leu|Asp|Gly|Phe|Gly|
| | | | |85| | | | |90| | | | |95| |
|Arg|Thr|Lys|Glu|Met|Cys|Lys|Arg|Asp|Leu|Ile|Trp|Val|Val|Ile|Lys|
| | | |100| | | | |105| | | | |110| | |
|Met|Gln|Ile|Lys|Val|Asn|Arg|Tyr|Pro|Ala|Trp|Gly|Asp|Thr|Val|Glu|
| | |115| | | | |120| | | | |125| | | |
|Ile|Asn|Thr|Arg|Phe|Ser|Arg|Leu|Gly|Lys|Ile|Gly|Met|Gly|Arg|Asp|
| |130| | | | |135| | | | |140| | | | |
|Trp|Leu|Ile|Ser|Asp|Cys|Asn|Thr|Gly|Glu|Ile|Leu|Val|Arg|Ala|Thr|
|145| | | | |150| | | | |155| | | | |160|
|Ser|Ala|Tyr|Ala|Met|Met|Asn|Gln|Lys|Thr|Arg|Arg|Leu|Ser|Lys|Leu|
| | | | |165| | | | |170| | | | |175| |
|Pro|Tyr|Glu|Val|His|Gln|Glu|Ile|Val|Pro|Leu|Phe|Val|Asp|Ser|Pro|
| | | |180| | | | |185| | | | |190| | |
|Val|Ile|Glu|Val|Ser|Asp|Leu|Lys|Val|His|Arg|Phe|Lys|Val|Lys|Thr|
| | |195| | | | |200| | | | |205| | | |
|Gly|Asp|Ser|Ile|Gln|Lys|Gly|Leu|Thr|Pro|Gly|Trp|Asn|Asp|Leu|Asp|
| |210| | | | |215| | | | |220| | | | |
|Val|Asn|Gln|His|Val|Ser|Asn|Val|Lys|Tyr|Ile|Gly|Trp|Ile|Leu|Glu|
|225| | | | |230| | | | |235| | | | |240|
|Ser|Met|Pro|Thr|Glu|Val|Leu|Glu|Thr|Gln|Glu|Leu|Cys|Ser|Leu|Ala|
| | | | |245| | | | |250| | | | |255| |
|Leu|Glu|Tyr|Arg|Arg|Glu|Cys|Gly|Arg|Asp|Ser|Val|Leu|Glu|Ser|Val|
| | | |260| | | | |265| | | | |270| | |
|Thr|Ala|Met|Asp|Pro|Ser|Lys|Val|Gly|Ser|Arg|Ser|Gln|Tyr|Gln|His|
| | |275| | | | |280| | | | |285| | | |
|Leu|Leu|Arg|Leu|Glu|Asp|Gly|Thr|Ala|Ile|Val|Asn|Gly|Ala|Thr|Glu|
| |290| | | | |295| | | | |300| | | | |
|Trp|Arg|Pro|Lys|Asn|Ala|Gly|Ala|Asn|Gly|Ala|Arg|Ser|Thr|Gly|Lys|
|305| | | | |310| | | | |315| | | | |320|
|Thr|Ser|Asn|Gly|Asn|Ser|Val|Ser| | | | | | | | |
| | | | |325| | | | | | | | | | | |

```
<210> SEQ ID NO 11
<211> LENGTH: 328
<212> TYPE: PRT
<213> ORGANISM: Cuphea hookeriana

<400> SEQUENCE: 11
```

| | | | | | | | | | | | | | | | |
|---|---|---|---|---|---|---|---|---|---|---|---|---|---|---|---|
|Met|Leu|Lys|Asp|Trp|Ser|Arg|Leu|Leu|Thr|Ala|Ile|Thr|Thr|Val|Phe|
|1| | | |5| | | | |10| | | | |15| |

Val Lys Ser Lys Arg Pro Asp Met His Asp Arg Lys Ser Lys Arg Pro
            20                  25                  30

Asp Met Leu Val Asp Ser Phe Gly Leu Glu Ser Thr Val Gln Asp Gly
            35                  40                  45

Leu Val Phe Arg Gln Ser Phe Cys Ile Arg Ser Tyr Glu Ile Gly Thr
 50                  55                  60

Asp Arg Thr Ala Ser Ile Glu Thr Leu Met Asn His Leu Gln Glu Thr
 65                  70                  75                  80

Ser Leu Asn His Cys Lys Ser Thr Gly Ile Leu Leu Asp Gly Phe Gly
                 85                  90                  95

Arg Thr Leu Glu Met Cys Lys Arg Asp Leu Ile Trp Val Leu Ile Lys
            100                 105                 110

Met Gln Ile Lys Val Asn Arg Tyr Pro Ala Trp Gly Asp Thr Val Glu
            115                 120                 125

Ile Asn Thr Arg Phe Ser Arg Leu Gly Lys Ile Gly Met Gly Arg Asp
130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Glu Val His Gln Glu Ile Val Pro Leu Phe Val Asp Ser Pro
            180                 185                 190

Val Ile Glu Val Ser Asp Leu Lys Val His Arg Phe Lys Val Lys Thr
            195                 200                 205

Gly Asp Ser Ile Gln Lys Gly Leu Thr Pro Gly Trp Asn Asp Leu Asp
            210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Val Arg Ser Gln Tyr Gln His
            275                 280                 285

Leu Leu Arg Leu Glu Asp Gly Thr Ala Ile Val Asn Gly Ala Thr Glu
            290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 12
<211> LENGTH: 328
<212> TYPE: PRT
<213> ORGANISM: Cuphea hookeriana

<400> SEQUENCE: 12

Met Leu Pro Asp Trp Ser Arg Leu Leu Thr Ala Ile Thr Thr Val Phe
1               5                   10                  15

Cys Lys Ser Lys Arg Pro Asp Met His Asp Arg Lys Ser Lys Arg Pro
            20                  25                  30

Asp Met Leu Val Asp Ser Phe Gly Leu Glu Ser Thr Val Gln Asp Gly
            35                  40                  45

Leu Val Phe Arg Gln Ser Phe Ser Ile Arg Ser Tyr Glu Ile Gly Pro

```
                    50                  55                  60
Asp Arg Thr Ala Ser Ile Glu Thr Leu Met Asn His Leu Gln Glu Thr
 65                  70                  75                  80

Ser Leu Asn His Cys Lys Ser Thr Gly Ile Leu Leu Asp Gly Phe Gly
                 85                  90                  95

Arg Thr Lys Glu Met Cys Lys Arg Asp Leu Ile Trp Val Leu Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Glu Val His Gln Glu Ile Val Gly Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 13
<211> LENGTH: 328
<212> TYPE: PRT
<213> ORGANISM: Cuphea hookeriana

<400> SEQUENCE: 13

Met Leu Pro Asp Trp Ser Arg Leu Leu Thr Ala Ile Thr Arg Val Phe
 1               5                  10                  15

Val Lys Ser Lys Arg Pro Asp Met His Asp Arg Lys Ser Lys Arg Pro
                20                  25                  30

Asp Met Leu Val Asp Ser Phe Gly Leu Glu Ser Gly Val Gln Asp Gly
            35                  40                  45

Leu Val Phe Arg Gln Ser Phe Ser Ile Arg Ser Tyr Glu Ile Gly Pro
        50                  55                  60

Asp Arg Thr Ala Ser Ile Glu Thr Leu Met Asn Leu Leu Gln Glu Thr
 65                  70                  75                  80

Ser Leu Asn His Cys Lys Ser Thr Gly Ile Leu Leu Asp Gly Phe Gly
                 85                  90                  95
```

```
Arg Thr Lys Glu Met Cys Lys Arg Asp Leu Ile Trp Val Val Ile Lys
                100                 105                 110

Met Gln Ile Lys Val Asn Arg Tyr Pro Ala Trp Gly Asp Thr Val Glu
            115                 120                 125

Ile Asn Thr Arg Phe Ser Arg Leu Gly Lys Ile Gly Met Gly Arg Asp
130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Leu
                165                 170                 175

Pro Tyr Glu Val His Gln Glu Ile Ala Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile His Lys Gly Leu Thr Pro Gly Trp Asn Asp Leu Asp
    210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Glu Asp Gly Thr Ala Ile Val Trp Gly Ala Thr Glu
    290                 295                 300

Trp Arg Pro Lys Asn Ala Gly Ala Asn Gly Ala Arg Ser Thr Gly Lys
305                 310                 315                 320

Thr Ser Asn Gly Lys Ser Val Ser
                325

<210> SEQ ID NO 14
<211> LENGTH: 328
<212> TYPE: PRT
<213> ORGANISM: Cuphea hookeriana

<400> SEQUENCE: 14

Met Leu Pro Met Trp Ser Arg Leu Leu Thr Ala Ile Thr Thr Val Phe
1               5                   10                  15

Cys Lys Ser Lys Arg Pro Asp Met His Asp Arg Lys Ser Lys Arg Pro
            20                  25                  30

Asp Met Leu Val Asp Ser Phe Gly Leu Glu Ser Gly Val Gln Asp Gly
        35                  40                  45

Leu Val Phe Arg Gln Ser Phe Ser Ile Arg Ser Tyr Glu Ile Gly Pro
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu Asp Gly Phe Gly
                85                  90                  95

Arg Thr Lys Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
130                 135                 140
```

```
Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Leu
                165                 170                 175

Pro Tyr Glu Val His Gln Glu Ile Ala Pro Leu Phe Val Asp Ser Pro
            180                 185                 190

Val Ile Glu Asp Ser Asp Leu Lys Val His Arg Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
                260                 265                 270

Thr Ala Met Asp Pro Ser Lys Val Gly Ser Arg Ser Gln Tyr Gln His
            275                 280                 285

Leu Leu Arg Leu Glu Asp Gly Thr Ala Ile Val Trp Gly Ala Thr Glu
        290                 295                 300

Trp Arg Pro Lys Asn Ala Gly Ala Asn Gly Ala Arg Ser Thr Gly Lys
305                 310                 315                 320

Thr Ser Asn Gly Lys Ser Val Ser
                325

<210> SEQ ID NO 15
<211> LENGTH: 328
<212> TYPE: PRT
<213> ORGANISM: Cuphea hookeriana

<400> SEQUENCE: 15

Met Leu Pro Asp Trp Ser Arg Leu Leu Thr Ala Ile Thr Thr Val Phe
1               5                   10                  15

Ala Lys Ser Lys Arg Pro Asp Met His Asp Arg Lys Ser Lys Arg Pro
                20                  25                  30

Asp Met Leu Val Asp Ser Phe Gly Leu Glu Ser Gly Val Gln Asp Gly
            35                  40                  45

Leu Val Phe Arg Gln Ser Phe Ser Ile Arg Ser Tyr Glu Ile Gly Pro
        50                  55                  60

Asp Arg Leu Ala Ser Ile Glu Thr Leu Met Asn His Leu Gln Glu Thr
65                  70                  75                  80

Ser Leu Asn His Cys Lys Ser Thr Gly Ile Leu Leu Asp Gly Phe Gly
                85                  90                  95

Arg Thr Lys Glu Met Cys Lys Arg Asp Leu Ile Trp Val Val Ile Lys
                100                 105                 110

Met Gln Ile Lys Val Asn Arg Tyr Pro Ala Trp Gly Asp Thr Val Glu
            115                 120                 125

Ile Asn Thr Arg Phe Ser Arg Leu Gly Lys Ile Gly Met Gly Arg Asp
        130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Leu
                165                 170                 175

Pro Tyr Glu Val His Gln Glu Ile Ala Pro Leu Phe Val Asp Ser Pro
```

```
            180                 185                 190
Val Ile Glu Val Ser Asp Leu Lys Val His Arg Phe Lys Val Lys Thr
            195                 200                 205
Gly Asp Ser Ile His Lys Gly Leu Thr Pro Gly Trp Asn Asp Leu Asp
            210                 215                 220
Val Asn Gln His Val Ser Asn Val Lys Tyr Ile Gly Trp Ile Leu Glu
225                 230                 235                 240
Ser Met Pro Thr Glu Val Leu Glu Thr Gln Glu Leu Cys Ser Leu Ala
                    245                 250                 255
Leu Glu Tyr Arg Arg Glu Cys Gly Arg Asp Ser Val Leu Glu Ser Val
                    260                 265                 270
Thr Ala Met Asp Pro Ser Lys Val Gly Ser Arg Ser Gln Tyr Gln His
                275                 280                 285
Leu Leu Arg Leu Glu Asp Gly Thr Ala Ile Val Asn Gly Ala Thr Glu
                290                 295                 300
Trp Arg Pro Lys Asn Ala Gly Ala Asn Gly Ala Arg Ser Thr Gly Lys
305                 310                 315                 320
Thr Ser Asn Gly Lys Ser Val Ser
                325

<210> SEQ ID NO 16
<211> LENGTH: 328
<212> TYPE: PRT
<213> ORGANISM: Cuphea hookeriana

<400> SEQUENCE: 16

Met Leu Lys Asp Trp Ser Arg Leu Leu Thr Ala Ile Thr Thr Val Phe
1               5                   10                  15
Val Lys Ser Lys Arg Pro His Met His Asp Arg Lys Ser Lys Arg Pro
                20                  25                  30
Asp Met Leu Val His Ser Phe Gly Leu Glu Ser Thr Val Gln Asp Gly
            35                  40                  45
Leu Val Phe Arg Gln Ser Phe Ser Ile Arg Ser Tyr Glu Ile Gly Thr
    50                  55                  60
Asp Arg Thr Ala Ser Ile Glu Thr Leu Met Asn His Leu Gln Glu Thr
65                  70                  75                  80
Ser Leu Asn His Cys Lys Ser Thr Gly Ile Leu Leu His Gly Phe Gly
                85                  90                  95
Arg Thr Leu Glu Met Cys Lys Arg Asp Leu Ile Trp Val Val Ile Lys
                100                 105                 110
Met Gln Ile Lys Val Asn Arg Tyr Pro Ala Trp Gly Asp Thr Val Glu
            115                 120                 125
Ile Asn Thr Arg Phe Ser Arg Leu Gly Lys Ile Gly Met Gly Arg Asp
    130                 135                 140
Trp Leu Ile Ser Asp Cys Asn Thr Gly Glu Ile Leu Val Arg Ala Thr
145                 150                 155                 160
Ser Ala Tyr Ala Met Met Asn Gln Lys Thr Arg Arg Leu Ser Lys Val
                165                 170                 175
Pro Tyr Glu Val His Gln Glu Ile Val Pro Leu Phe Val Asp Ser Pro
                180                 185                 190
Val Ile Glu Val Ser Asp Leu Lys Val His Arg Phe Lys Val Lys Thr
            195                 200                 205
Gly Asp Ser Ile Gln Lys Gly Leu Thr Pro Gly Trp Asn Asp Leu Asp
            210                 215                 220
```

```
Val Asn Gln His Val Ser Asn Val Lys Tyr Ile Gly Trp Ile Leu Arg
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Glu Asp Gly Thr Ala Ile Val Asn Gly Ala Thr Glu
        290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 17
<211> LENGTH: 328
<212> TYPE: PRT
<213> ORGANISM: Cuphea hookeriana

<400> SEQUENCE: 17

Met Leu Lys Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
                20                  25                  30

Asp Met Leu Val Arg Ser Phe Gly Leu Glu Ser Thr Val Gln Asp Gly
            35                  40                  45

Leu Val Phe Arg Gln Ser Phe Ser Ile Arg Ser Tyr Glu Ile Gly Thr
50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Glu Val His Gln Glu Ile Val Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile Gln Lys Gly Leu Thr Pro Gly Trp Asn Asp Leu Asp
210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270
```

-continued

Thr Ala Met Asp Pro Ser Lys Val Gly Ser Arg Ser Gln Tyr Gln His
            275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 18
<211> LENGTH: 328
<212> TYPE: PRT
<213> ORGANISM: Cuphea hookeriana

<400> SEQUENCE: 18

Met Leu Lys Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

Asp Met Leu Val Asp Ser Phe Gly Leu Glu Ser Thr Val Gln Asp Gly
        35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Arg Val His Gln Glu Ile Val Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu Val
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu His Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys

```
305                 310                 315                 320

Thr Ser Asn Gly Asn Ser Val Ser
                325

<210> SEQ ID NO 19
<211> LENGTH: 328
<212> TYPE: PRT
<213> ORGANISM: Cuphea hookeriana

<400> SEQUENCE: 19

Met Leu Lys His Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
                20                  25                  30

Asp Met Leu Val Arg Ser Phe Gly Leu Glu Ser Thr Val Gln Asp Gly
            35                  40                  45

Leu Val Phe Arg Gln Ser Phe Ser Ile Arg Ser Tyr Glu Ile Gly Thr
        50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
                85                  90                  95

Arg Thr Leu Glu Met Cys Lys Arg Asp Leu Ile Trp Val Val Ile Lys
                100                 105                 110

Met Gln Ile Lys Val Asn Arg Tyr Pro Ala Trp Gly Asp Thr Val Glu
            115                 120                 125

Ile Asn Thr Arg Phe Ser Arg Leu Gly Lys Ile Gly Met Gly Arg Asp
        130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr His Val His Gln Glu Ile Val Pro Leu Phe Val Asp Ser Pro
                180                 185                 190

Val Ile Glu Val Ser Asp Leu Lys Val His Arg Phe Lys Val Lys Thr
            195                 200                 205

Gly Asp Ser Ile Gln Lys Gly Leu Thr Pro Gly Trp Asn Asp Leu Asp
        210                 215                 220

Val Asn Gln His Val Ser Asn Val Lys Tyr Ile Gly Trp Ile Leu Arg
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
                260                 265                 270

Thr Ala Met Asp Pro Ser Lys Val Gly Ser Arg Ser Gln Tyr Gln His
            275                 280                 285

Leu Leu Arg Leu Glu Asp Gly Thr Ala Ile Val Asn Gly Ala Thr Glu
        290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 20
<211> LENGTH: 328
```

<212> TYPE: PRT
<213> ORGANISM: Cuphea hookeriana

<400> SEQUENCE: 20

Met Leu Lys Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

Asp Met Leu Val His Ser Phe Gly Leu Glu Ser Thr Val Gln Asp Gly
        35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Glu Val His Gln Glu Ile Val Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 21
<211> LENGTH: 328
<212> TYPE: PRT
<213> ORGANISM: Cuphea hookeriana

<400> SEQUENCE: 21

Met Leu Lys Asp Trp Ser Arg Leu Leu Thr Ala Ile Thr Thr Val Phe
1               5                   10                  15

-continued

Val Lys Ser Lys Arg Pro Asp Met His Asp Arg Lys Ser Lys Arg Pro
            20                  25                  30

Asp Met Leu Val His Ser Phe Gly Leu Glu Ser Thr Val Gln Asp Gly
            35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
            115                 120                 125

Ile Asn Thr Arg Phe Ser Arg Leu Gly Lys Ile Gly Met Gly Arg Asp
        130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Glu Val His Gln Glu Ile Val Pro Leu Phe Val Asp Ser Pro
            180                 185                 190

Val Ile Glu Val Ser Asp Leu Lys Val His Arg Phe Lys Val Lys Thr
            195                 200                 205

Gly Asp Ser Ile Gln Lys Gly Leu Thr Pro Gly Trp Asn Asp Leu Asp
        210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Arg Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Glu Asp Gly Thr Ala Ile Val Asn Gly Ala Thr Glu
290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 22
<211> LENGTH: 328
<212> TYPE: PRT
<213> ORGANISM: Cuphea hookeriana

<400> SEQUENCE: 22

Met Leu Lys Arg Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

Asp Met Leu Val Asp Ser Phe Gly Leu Glu Ser Thr Val Gln Asp Gly
            35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu Asp Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
            115                 120                 125

Ile Asn Thr Arg Phe Ser Arg Leu Gly Lys Ile Gly Met Gly Arg Asp
130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Glu Val His Gln Glu Ile Val Pro Leu Phe Val Asp Ser Pro
            180                 185                 190

Val Ile Glu Val Ser Asp Leu Lys Val His Arg Phe Lys Val Lys Thr
            195                 200                 205

Gly Asp Ser Ile Gln Lys Gly Leu Thr Pro Gly Trp Asn Asp Leu Asp
210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Val Arg Ser Gln Tyr Gln His
            275                 280                 285

Leu Leu Arg Leu Glu Asp Gly Thr Ala Ile Val Asn Gly Ala Thr Glu
290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 23
<211> LENGTH: 328
<212> TYPE: PRT
<213> ORGANISM: Cuphea hookeriana

<400> SEQUENCE: 23

Met Leu Lys Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

Asp Met Leu Val Arg Ser Phe Gly Leu Glu Ser Thr Val Gln Asp Gly
            35                  40                  45

Leu Val Phe Arg Gln Ser Phe Ser Ile Arg Ser Tyr Glu Ile Gly Thr
50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
                85                  90                  95

Arg Thr Leu Glu Met Cys Lys Arg Asp Leu Ile Trp Val Val Ile Lys

```
            100                 105                 110
Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr His Val His Gln Glu Ile Val Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg His Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 24
<211> LENGTH: 328
<212> TYPE: PRT
<213> ORGANISM: Cuphea hookeriana

<400> SEQUENCE: 24

Met Leu Lys Arg Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

Asp Met Leu Val Asp Ser Phe Gly Leu Glu Ser Thr Val Gln Asp Gly
        35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu Arg Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140
```

```
Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Arg Val His Gln Glu Ile Val Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu Arg
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 25
<211> LENGTH: 328
<212> TYPE: PRT
<213> ORGANISM: Cuphea hookeriana

<400> SEQUENCE: 25

Met Leu Lys Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
                20                  25                  30

Asp Met Leu Val Arg Ser Phe Gly Leu Glu Ser Thr Val Gln Asp Gly
            35                  40                  45

Leu Val Phe Arg Gln Ser Phe Ser Ile Arg Ser Tyr Glu Ile Gly Thr
        50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Glu Val His Gln Glu Ile Val Pro Leu Phe Val Asp Ser Pro
            180                 185                 190
```

```
Val Ile Glu Val Ser Asp Leu Lys Val His Arg Phe Lys Val Lys Thr
            195                 200                 205
Gly His Ser Ile Gln Lys Gly Leu Thr Pro Gly Trp Asn Asp Leu Asp
        210                 215                 220
Val Asn Gln His Val Ser Asn Val Lys Tyr Ile Gly Trp Ile Leu Glu
225                 230                 235                 240
Ser Met Pro Thr Glu Val Leu Glu Thr Gln Glu Leu Cys Ser Leu Ala
            245                 250                 255
Leu Glu Tyr Arg Arg Glu Cys Gly Arg Asp Ser Val Leu Glu Ser Val
            260                 265                 270
Thr Ala Met Asp Pro Ser Lys Val Gly Ser Arg Ser Gln Tyr Gln His
            275                 280                 285
Leu Leu Arg Leu Glu Asp Gly Thr Ala Ile Val Asn Gly Ala Thr Glu
        290                 295                 300
Trp Arg Pro Lys Asn Ala Gly Ala Asn Gly Ala Ile Ser Thr Gly Lys
305                 310                 315                 320
Thr Ser Asn Gly Asn Ser Val Ser
            325

<210> SEQ ID NO 26
<211> LENGTH: 328
<212> TYPE: PRT
<213> ORGANISM: Cuphea hookeriana

<400> SEQUENCE: 26

Met Leu Lys Asp Trp Ser Arg Leu Leu Thr Ala Ile Thr Thr Val Phe
1               5                   10                  15
Val Lys Ser Lys Arg Pro Asp Met His Asp Arg Lys Ser Lys Arg Pro
            20                  25                  30
Asp Met Leu Val His Ser Phe Gly Leu Glu Ser Thr Val Gln Asp Gly
        35                  40                  45
Leu Val Phe Arg Gln Ser Phe Ser Ile Arg Ser Tyr Glu Ile Gly Thr
    50                  55                  60
Asp Arg Thr Ala Ser Ile Glu Thr Leu Met Asn His Leu Gln Glu Thr
65                  70                  75                  80
Ser Leu Asn His Cys Lys Ser Thr Gly Ile Leu Leu His Gly Phe Gly
            85                  90                  95
Arg Thr Leu Glu Met Cys Lys Arg Asp Leu Ile Trp Val Val Ile Lys
            100                 105                 110
Met Gln Ile Lys Val Asn Arg Tyr Pro Ala Trp Gly Asp Thr Val Glu
        115                 120                 125
Ile Asn Thr Arg Phe Ser Arg Leu Gly Lys Ile Gly Met Gly Arg Asp
    130                 135                 140
Trp Leu Ile Ser Asp Cys Asn Thr Gly Glu Ile Leu Val Arg Ala Thr
145                 150                 155                 160
Ser Ala Tyr Ala Met Met Asn Gln Lys Thr Arg Arg Leu Ser Lys Val
            165                 170                 175
Pro Tyr Glu Val His Gln Glu Ile Val Pro Leu Phe Val Asp Ser Pro
            180                 185                 190
Val Ile Glu Val Ser Asp Leu Lys Val His Arg Phe Lys Val Lys Thr
            195                 200                 205
Gly Asp Ser Ile Gln Lys Gly Leu Thr Pro Gly Trp Asn Asp Leu Asp
        210                 215                 220
Val Asn Gln His Val Ser Asn Val Lys Tyr Ile Gly Trp Ile Leu Glu
```

Ser Met Pro Thr His Val Leu Glu Thr Gln Glu Leu Cys Ser Leu Ala
            245                 250                 255

Leu Glu Tyr Arg Arg Glu Cys Gly Arg Arg Ser Val Leu Glu Ser Val
        260                 265                 270

Thr Ala Met Asp Pro Ser Lys Val Gly Ser Arg Ser Gln Tyr Gln His
            275                 280                 285

Leu Leu Arg Leu Glu Asp Gly Thr Ala Ile Val Asn Gly Ala Thr Glu
        290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
            325

<210> SEQ ID NO 27
<211> LENGTH: 328
<212> TYPE: PRT
<213> ORGANISM: Cuphea hookeriana

<400> SEQUENCE: 27

Met Leu Lys Asp Trp Ser Arg Leu Leu Thr Ala Ile Thr Thr Val Phe
1               5                   10                  15

Val Lys Ser Lys Arg Pro His Met His Asp Arg Lys Ser Lys Arg Pro
            20                  25                  30

Asp Met Leu Val His Ser Phe Gly Leu Glu Ser Thr Val Gln Asp Gly
        35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr His Val His Gln Glu Ile Val Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

```
Thr Ala Met Asp Pro Ser Lys Val Gly Ser Arg Ser Gln Tyr Gln His
            275                 280                 285

Leu Leu Arg Leu Glu Asp Gly Thr Ala Ile Val Asn Gly Ala Thr Glu
        290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 28
<211> LENGTH: 328
<212> TYPE: PRT
<213> ORGANISM: Cuphea hookeriana

<400> SEQUENCE: 28

Met Leu Lys Arg Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

Asp Met Leu Val Asp Ser Phe Gly Leu Glu Ser Thr Val Gln Asp Gly
        35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr His Val His Gln Glu Ile Val Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Arg Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320
```

Thr Ser Asn Gly Asn Ser Val Ser
            325

<210> SEQ ID NO 29
<211> LENGTH: 328
<212> TYPE: PRT
<213> ORGANISM: Cuphea hookeriana

<400> SEQUENCE: 29

Met Leu Lys Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

Asp Met Leu Val His Ser Phe Gly Leu Glu Ser Thr Val Gln Asp Gly
        35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Glu Val His Gln Glu Ile Val Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
            325

<210> SEQ ID NO 30
<211> LENGTH: 328
<212> TYPE: PRT

<213> ORGANISM: Cuphea hookeriana

<400> SEQUENCE: 30

Met Leu Lys Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

Asp Met Leu Val Arg Ser Phe Gly Leu Glu Ser Thr Val Gln Asp Gly
        35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Glu Val His Gln Glu Ile Val Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Arg Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu His Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 31
<211> LENGTH: 328
<212> TYPE: PRT
<213> ORGANISM: Cuphea hookeriana

<400> SEQUENCE: 31

Met Leu Lys Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro

```
                    20                  25                  30
Asp Met Leu Val Arg Ser Phe Gly Leu Glu Ser Thr Val Gln Asp Gly
                35                  40                  45
Leu Val Phe Arg Gln Ser Phe Ser Ile Arg Ser Tyr Glu Ile Gly Thr
            50                  55                  60
Asp Arg Thr Ala Ser Ile Glu Thr Leu Met Asn His Leu Gln Glu Thr
65                  70                  75                  80
Ser Leu Asn His Cys Lys Ser Thr Gly Ile Leu Leu Asp Gly Phe Gly
                85                  90                  95
Arg Thr Leu Glu Met Cys Lys Arg Asp Leu Ile Trp Val Val Ile Lys
            100                 105                 110
Met Gln Ile Lys Val Asn Arg Tyr Pro Ala Trp Gly Asp Thr Val Glu
        115                 120                 125
Ile Asn Thr Arg Phe Ser Arg Leu Gly Lys Ile Gly Met Gly Arg Asp
            130                 135                 140
Trp Leu Ile Ser Asp Cys Asn Thr Gly Glu Ile Leu Val Arg Ala Thr
145                 150                 155                 160
Ser Ala Tyr Ala Met Met Asn Gln Lys Thr Arg Arg Leu Ser Lys Val
                165                 170                 175
Pro Tyr Glu Val His Gln Glu Ile Val Pro Leu Phe Val Asp Ser Pro
            180                 185                 190
Val Ile Glu Val Ser Asp Leu Lys Val His Arg Phe Lys Val Lys Thr
        195                 200                 205
Gly His Ser Ile Gln Lys Gly Leu Thr Pro Gly Trp Asn Asp Leu Asp
            210                 215                 220
Val Asn Gln His Val Ser Asn Val Lys Tyr Ile Gly Trp Ile Leu Glu
225                 230                 235                 240
Ser Met Pro Thr Glu Val Leu Glu Thr Gln Glu Leu Cys Ser Leu Ala
                245                 250                 255
Leu Glu Tyr Arg Arg Glu Cys Gly Arg Arg Ser Val Leu Glu Ser Val
            260                 265                 270
Thr Ala Met Asp Pro Ser Lys Val Gly Ser Arg Ser Gln Tyr Gln His
        275                 280                 285
Leu Leu Arg Leu Glu Asp Gly Thr Ala Ile Val Asn Gly Ala Thr Glu
    290                 295                 300
Trp Arg Pro Lys Asn Ala Gly Ala Asn Gly Ala Ile Ser Thr Gly Lys
305                 310                 315                 320
Thr Ser Asn Gly Asn Ser Val Ser
                325

<210> SEQ ID NO 32
<211> LENGTH: 328
<212> TYPE: PRT
<213> ORGANISM: Cuphea hookeriana

<400> SEQUENCE: 32

Met Leu Lys Arg Trp Ser Arg Leu Leu Thr Ala Ile Thr Thr Val Phe
1               5                   10                  15
Val Lys Ser Lys Arg Pro Asp Met His Asp Arg Lys Ser Lys Arg Pro
                20                  25                  30
Asp Met Leu Val Asp Ser Phe Gly Leu Glu Ser Thr Val Gln Asp Gly
                35                  40                  45
Leu Val Phe Arg Gln Ser Phe Ser Ile Arg Ser Tyr Glu Ile Gly Thr
            50                  55                  60
```

```
Asp Arg Thr Ala Ser Ile Glu Thr Leu Met Asn His Leu Gln Glu Thr
 65                  70                  75                  80

Ser Leu Asn His Cys Lys Ser Thr Gly Ile Leu Leu Arg Gly Phe Gly
                 85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Glu Val His Gln Glu Ile Val Pro Leu Phe Val Asp Ser Pro
            180                 185                 190

Val Ile Glu Val Ser Asp Leu Lys Val His Arg Phe Lys Val Lys Thr
        195                 200                 205

Gly Arg Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Arg Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 33
<211> LENGTH: 328
<212> TYPE: PRT
<213> ORGANISM: Cuphea hookeriana

<400> SEQUENCE: 33

Met Leu Lys Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

Asp Met Leu Val Asp Ser Phe Gly Leu Glu Ser Thr Val Gln Asp Gly
        35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
                85                  90                  95

Arg Thr Leu Glu Met Cys Lys Arg Asp Leu Ile Trp Val Val Ile Lys
            100                 105                 110
```

```
Met Gln Ile Lys Val Asn Arg Tyr Pro Ala Trp Gly Asp Thr Val Glu
            115                 120                 125

Ile Asn Thr Arg Phe Ser Arg Leu Gly Lys Ile Gly Met Gly Arg Asp
        130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr His Val His Gln Glu Ile Val Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg His Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 34
<211> LENGTH: 328
<212> TYPE: PRT
<213> ORGANISM: Cuphea hookeriana

<400> SEQUENCE: 34

Met Leu Lys Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
                20                  25                  30

Asp Met Leu Val Asp Ser Phe Gly Leu Glu Ser Thr Val Gln Asp Gly
            35                  40                  45

Leu Val Phe Arg Gln Ser Phe Ser Ile Arg Ser Tyr Glu Ile Gly Thr
        50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
            115                 120                 125

Ile Asn Thr Arg Phe Ser Arg Leu Gly Lys Ile Gly Met Gly Arg Asp
        130                 135                 140

Trp Leu Ile Ser Asp Cys Asn Thr Gly Glu Ile Leu Val Arg Ala Thr
```

```
            145                 150                 155                 160
        Ser Ala Tyr Ala Met Met Asn Gln Lys Thr Arg Arg Leu Ser Lys Val
                            165                 170                 175

Pro Tyr Glu Val His Gln Glu Ile Val Pro Leu Phe Val Asp Ser Pro
                        180                 185                 190

Val Ile Glu Val Ser Asp Leu Lys Val His Arg Phe Lys Val Lys Thr
                    195                 200                 205

Gly Arg Ser Ile Gln Lys Gly Leu Thr Pro Gly Trp Asn Asp Leu Asp
                210                 215                 220

Val Asn Gln His Val Ser Asn Val Lys Tyr Ile Gly Trp Ile Leu Glu
        225                 230                 235                 240

Ser Met Pro Thr His Val Leu Glu Thr Gln Glu Leu Cys Ser Leu Ala
                            245                 250                 255

Leu Glu Tyr Arg Arg Glu Cys Gly Arg His Ser Val Leu Glu Ser Val
                        260                 265                 270

Thr Ala Met Asp Pro Ser Lys Val Gly Ser Arg Ser Gln Tyr Gln His
                    275                 280                 285

Leu Leu Arg Leu Glu Asp Gly Thr Ala Ile Val Asn Gly Ala Thr Glu
                290                 295                 300

Trp Arg Pro Lys Asn Ala Gly Ala Asn Gly Ala Ile Ser Thr Gly Lys
        305                 310                 315                 320

Thr Ser Asn Gly Asn Ser Val Ser
                            325

<210> SEQ ID NO 35
<211> LENGTH: 328
<212> TYPE: PRT
<213> ORGANISM: Cuphea hookeriana

<400> SEQUENCE: 35

Met Leu Lys His Trp Ser Arg Leu Leu Thr Ala Ile Thr Thr Val Phe
        1               5                   10                  15

Val Lys Ser Lys Arg Pro Asp Met His Asp Arg Lys Ser Lys Arg Pro
                        20                  25                  30

Asp Met Leu Val Arg Ser Phe Gly Leu Glu Ser Thr Val Gln Asp Gly
                    35                  40                  45

Leu Val Phe Arg Gln Ser Phe Ser Ile Arg Ser Tyr Glu Ile Gly Thr
                50                  55                  60

Asp Arg Thr Ala Ser Ile Glu Thr Leu Met Asn His Leu Gln Glu Thr
        65                  70                  75                  80

Ser Leu Asn His Cys Lys Ser Thr Gly Ile Leu Leu Arg Gly Phe Gly
                            85                  90                  95

Arg Thr Leu Glu Met Cys Lys Arg Asp Leu Ile Trp Val Val Ile Lys
                        100                 105                 110

Met Gln Ile Lys Val Asn Arg Tyr Pro Ala Trp Gly Asp Thr Val Glu
                    115                 120                 125

Ile Asn Thr Arg Phe Ser Arg Leu Gly Lys Ile Gly Met Gly Arg Asp
                130                 135                 140

Trp Leu Ile Ser Asp Cys Asn Thr Gly Glu Ile Leu Val Arg Ala Thr
        145                 150                 155                 160

Ser Ala Tyr Ala Met Met Asn Gln Lys Thr Arg Arg Leu Ser Lys Val
                            165                 170                 175

Pro Tyr Glu Val His Gln Glu Ile Val Pro Leu Phe Val Asp Ser Pro
                        180                 185                 190
```

```
Val Ile Glu Val Ser Asp Leu Lys Val His Arg Phe Lys Val Lys Thr
            195                 200                 205

Gly Asp Ser Ile Gln Lys Gly Leu Thr Pro Gly Trp Asn Asp Leu Asp
210                 215                 220

Val Asn Gln His Val Ser Asn Val Lys Tyr Ile Gly Trp Ile Leu Arg
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Glu Asp Gly Thr Ala Ile Val Asn Gly Ala Thr Glu
290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 36
<211> LENGTH: 328
<212> TYPE: PRT
<213> ORGANISM: Cuphea hookeriana

<400> SEQUENCE: 36

Met Leu Lys Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
                20                  25                  30

Asp Met Leu Val Asp Ser Phe Gly Leu Glu Ser Thr Val Gln Asp Gly
            35                  40                  45

Leu Val Phe Arg Gln Ser Phe Ser Ile Arg Ser Tyr Glu Ile Gly Thr
        50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu Arg Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Glu Val His Gln Glu Ile Val Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile Gln Lys Gly Leu Thr Pro Gly Trp Asn Asp Leu Asp
210                 215                 220

Val Asn Gln His Val Ser Asn Val Lys Tyr Ile Gly Trp Ile Leu Glu
225                 230                 235                 240
```

```
Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 37
<211> LENGTH: 328
<212> TYPE: PRT
<213> ORGANISM: Cuphea hookeriana

<400> SEQUENCE: 37

Met Leu Lys Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

Asp Met Leu Val His Ser Phe Gly Leu Glu Ser Thr Val Gln Asp Gly
        35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Glu Val His Gln Glu Ile Val Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Arg Ser Val Leu Glu Ser Val
            260                 265                 270

Thr Ala Met Asp Pro Ser Lys Val Gly Ser Arg Ser Gln Tyr Gln His
```

```
            275                 280                 285
Leu Leu Arg Leu Arg Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 38
<211> LENGTH: 328
<212> TYPE: PRT
<213> ORGANISM: Cuphea hookeriana

<400> SEQUENCE: 38

Met Leu Lys His Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
                20                  25                  30

Asp Met Leu Val Asp Ser Phe Gly Leu Glu Ser Thr Val Gln Asp Gly
            35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
    115                 120                 125

Ile Asn Thr Arg Phe Ser Arg Leu Gly Lys Ile Gly Met Gly Arg Asp
130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Glu Val His Gln Glu Ile Val Pro Leu Phe Val Asp Ser Pro
            180                 185                 190

Val Ile Glu Val Ser Asp Leu Lys Val His Arg Phe Lys Val Lys Thr
    195                 200                 205

Gly Asp Ser Ile Gln Lys Gly Leu Thr Pro Gly Trp Asn Asp Leu Asp
210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
    275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320
```

-continued

Thr Ser Asn Gly Asn Ser Val Ser
            325

<210> SEQ ID NO 39
<211> LENGTH: 328
<212> TYPE: PRT
<213> ORGANISM: Cuphea hookeriana

<400> SEQUENCE: 39

Met Leu Lys Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

Asp Met Leu Val Asp Ser Phe Gly Leu Glu Ser Thr Val Gln Asp Gly
        35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
            85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
            165                 170                 175

Pro Tyr Glu Val His Gln Glu Ile Val Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu Glu
225                 230                 235                 240

Ser Met Pro Thr Arg Val Leu Glu Thr Gln Glu Leu Cys Ser Leu Ala
            245                 250                 255

Leu Glu Tyr Arg Arg Glu Cys Gly Arg His Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu His Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
            325

<210> SEQ ID NO 40
<211> LENGTH: 328
<212> TYPE: PRT
<213> ORGANISM: Cuphea hookeriana

<400> SEQUENCE: 40

Met Leu Lys His Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

Asp Met Leu Val Asp Ser Phe Gly Leu Glu Ser Thr Val Gln Asp Gly
        35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu Arg Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Glu Val His Gln Glu Ile Val Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu His
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 41
<211> LENGTH: 328
<212> TYPE: PRT
<213> ORGANISM: Cuphea hookeriana

<400> SEQUENCE: 41

Met Leu Lys Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

```
Asp Met Leu Val Asp Ser Phe Gly Leu Glu Ser Thr Val Gln Asp Gly
            35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu Arg Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr His Val His Gln Glu Ile Val Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu Glu
225                 230                 235                 240

Ser Met Pro Thr Glu Val Leu His Thr Gln Glu Leu Cys Ser Leu Ala
                245                 250                 255

Leu Glu Tyr Arg Arg Glu Cys Gly Arg Arg Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 42
<211> LENGTH: 328
<212> TYPE: PRT
<213> ORGANISM: Cuphea hookeriana

<400> SEQUENCE: 42

Met Leu Lys Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

Asp Met Leu Val Asp Ser Phe Gly Leu Glu Ser Thr Val Gln Asp Gly
        35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
```

```
                65                  70                  75                  80
Ser Leu Asn His Cys Lys Ser Thr Gly Ile Leu Leu Asp Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Glu Val His Gln Glu Ile Val Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu His
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Glu His Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 43
<211> LENGTH: 328
<212> TYPE: PRT
<213> ORGANISM: Cuphea hookeriana

<400> SEQUENCE: 43

Met Leu Lys Asp Trp Ser Arg Leu Leu Thr Ala Ile Thr Thr Val Phe
1               5                   10                  15

Val Lys Ser Lys Arg Pro Arg Met His Asp Arg Lys Ser Lys Arg Pro
            20                  25                  30

Asp Met Leu Val Arg Ser Phe Gly Leu Glu Ser Thr Val Gln Asp Gly
        35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu Asp Gly Phe Gly
                85                  90                  95

Arg Thr Leu Glu Met Cys Lys Arg Asp Leu Ile Trp Val Val Ile Lys
            100                 105                 110
```

```
Met Gln Ile Lys Val Asn Arg Tyr Pro Ala Trp Gly Asp Thr Val Glu
            115                 120                 125

Ile Asn Thr Arg Phe Ser Arg Leu Gly Lys Ile Gly Met Gly Arg Asp
        130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr Glu Val His Gln Glu Ile Val Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu Arg
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu His Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 44
<211> LENGTH: 328
<212> TYPE: PRT
<213> ORGANISM: Cuphea hookeriana

<400> SEQUENCE: 44

Met Leu Lys Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

Asp Met Leu Val Asp Ser Phe Gly Leu Glu Ser Thr Val Gln Asp Gly
        35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
            115                 120                 125

Ile Asn Thr Arg Phe Ser Arg Leu Gly Lys Ile Gly Met Gly Arg Asp
        130                 135                 140

Trp Leu Ile Ser Asp Cys Asn Thr Gly Glu Ile Leu Val Arg Ala Thr
145                 150                 155                 160
```

Ser Ala Tyr Ala Met Met Asn Gln Lys Thr Arg Arg Leu Ser Lys Val
                165                 170                 175

Pro Tyr Arg Val His Gln Glu Ile Val Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu His
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Arg Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 45
<211> LENGTH: 328
<212> TYPE: PRT
<213> ORGANISM: Cuphea hookeriana

<400> SEQUENCE: 45

Met Leu Lys Asp Trp Ser Arg Leu Leu Thr Ala Ile Thr Thr Val Phe
1               5                   10                  15

Val Lys Ser Lys Arg Pro Asp Met His Asp Arg Lys Ser Lys Arg Pro
            20                  25                  30

Asp Met Leu Val Asp Ser Phe Gly Leu Glu Ser Thr Val Gln Asp Gly
        35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Val
                165                 170                 175

Pro Tyr His Val His Gln Glu Ile Val Pro Leu Phe Val Asp Ser Pro
            180                 185                 190

Val Ile Glu Val Ser Asp Leu Lys Val His Arg Phe Lys Val Lys Thr

```
                195                 200                 205
    Gly Asp Ser Ile Gln Lys Gly Leu Thr Pro Gly Trp Asn Asp Leu Asp
        210                 215                 220
    Val Asn Gln His Val Ser Asn Val Lys Tyr Ile Gly Trp Ile Leu Glu
225                 230                 235                 240
    Ser Met Pro Thr His Val Leu Glu Thr Gln Glu Leu Cys Ser Leu Ala
                    245                 250                 255
    Leu Glu Tyr Arg Arg Glu Cys Gly Arg Arg Ser Val Leu Glu Ser Val
                260                 265                 270
    Thr Ala Met Asp Pro Ser Lys Val Gly Ser Arg Ser Gln Tyr Gln His
                    275                 280                 285
    Leu Leu Arg Leu Glu Asp Gly Thr Ala Ile Val Asn Gly Ala Thr Glu
                290                 295                 300
    Trp Arg Pro Lys Asn Ala Gly Ala Asn Gly Ala Ile Ser Thr Gly Lys
305                 310                 315                 320
    Thr Ser Asn Gly Asn Ser Val Ser
                    325

<210> SEQ ID NO 46
<211> LENGTH: 328
<212> TYPE: PRT
<213> ORGANISM: Cuphea hookeriana

<400> SEQUENCE: 46

Met Leu Lys Asp Trp Ser Arg Leu Leu Thr Ala Ile Thr Thr Val Phe
1               5                   10                  15
Val Lys Ser Lys Arg Pro Arg Met His Asp Arg Lys Ser Lys Arg Pro
                20                  25                  30
Asp Met Leu Val Asp Ser Phe Gly Leu Glu Ser Thr Val Gln Asp Gly
            35                  40                  45
Leu Val Phe Arg Gln Ser Phe Ser Ile Arg Ser Tyr Glu Ile Gly Thr
    50                  55                  60
Asp Arg Thr Ala Ser Ile Glu Thr Leu Met Asn His Leu Gln Glu Thr
65                  70                  75                  80
Ser Leu Asn His Cys Lys Ser Thr Gly Ile Leu Leu Arg Gly Phe Gly
                85                  90                  95
Arg Thr Leu Glu Met Cys Lys Arg Asp Leu Ile Trp Val Val Ile Lys
            100                 105                 110
Met Gln Ile Lys Val Asn Arg Tyr Pro Ala Trp Gly Asp Thr Val Glu
        115                 120                 125
Ile Asn Thr Arg Phe Ser Arg Leu Gly Lys Ile Gly Met Gly Arg Asp
    130                 135                 140
Trp Leu Ile Ser Asp Cys Asn Thr Gly Glu Ile Leu Val Arg Ala Thr
145                 150                 155                 160
Ser Ala Tyr Ala Met Met Asn Gln Lys Thr Arg Arg Leu Ser Lys Val
                165                 170                 175
Pro Tyr Glu Val His Gln Glu Ile Val Pro Leu Phe Val Asp Ser Pro
            180                 185                 190
Val Ile Glu Val Ser Asp Leu Lys Val His Arg Phe Lys Val Lys Thr
        195                 200                 205
Gly Asp Ser Ile Gln Lys Gly Leu Thr Pro Gly Trp Asn Asp Leu Asp
    210                 215                 220
Val Asn Gln His Val Ser Asn Val Lys Tyr Ile Gly Trp Ile Leu Glu
225                 230                 235                 240
```

```
Ser Met Pro Thr Glu Val Leu Glu Thr Gln Glu Leu Cys Ser Leu Ala
                245                 250                 255

Leu Glu Tyr Arg Arg Glu Cys Gly Arg Arg Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325

<210> SEQ ID NO 47
<211> LENGTH: 328
<212> TYPE: PRT
<213> ORGANISM: Cuphea hookeriana

<400> SEQUENCE: 47

Met Leu Pro Asp Trp Ser Arg Leu Leu Thr Ala Ile Thr Thr Val Phe
1               5                   10                  15

Ala Lys Ser Lys Arg Pro His Met His Asp Arg Lys Ser Lys Arg Pro
            20                  25                  30

Asp Met Leu Val His Ser Phe Gly Leu Glu Ser Gly Val Gln Asp Gly
        35                  40                  45

Leu Val Phe Arg Gln Ser Phe Ser Ile Arg Ser Tyr Glu Ile Gly Pro
    50                  55                  60

Asp Arg Leu Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
                85                  90                  95

Arg Thr Lys Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Leu
                165                 170                 175

Pro Tyr Glu Val His Gln Glu Ile Ala Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile His Lys Gly Leu Thr Pro Gly Trp Asn Asp Leu Asp
    210                 215                 220

Val Asn Gln His Val Ser Asn Val Lys Tyr Ile Gly Trp Ile Leu Arg
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
        275                 280                 285
```

```
Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Arg Ser Thr Gly Lys
305                 310                 315                 320

Thr Ser Asn Gly Asn Ser Val Ser
                325
```

<210> SEQ ID NO 48
<211> LENGTH: 328
<212> TYPE: PRT
<213> ORGANISM: Cuphea hookeriana

<400> SEQUENCE: 48

```
Met Leu Pro Asp Trp Ser Arg Leu Leu Thr Ala Ile Thr Thr Val Phe
1               5                   10                  15

Ala Lys Ser Lys Arg Pro His Met His Asp Arg Lys Ser Lys Arg Pro
                20                  25                  30

Asp Met Leu Val Asp Ser Phe Gly Leu Glu Ser Gly Val Gln Asp Gly
            35                  40                  45

Leu Val Phe Arg Gln Ser Phe Ser Ile Arg Ser Tyr Glu Ile Gly Pro
    50                  55                  60

Asp Arg Leu Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
                85                  90                  95

Arg Thr Lys Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
    115                 120                 125

Ile Asn Thr Arg Phe Ser Arg Leu Gly Lys Ile Gly Met Gly Arg Asp
130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Leu
                165                 170                 175

Pro Tyr Glu Val His Gln Glu Ile Ala Pro Leu Phe Val Asp Ser Pro
            180                 185                 190

Val Ile Glu Val Ser Asp Leu Lys Val His Arg Phe Lys Val Lys Thr
    195                 200                 205

Gly Asp Ser Ile His Lys Gly Leu Thr Pro Gly Trp Asn Asp Leu Asp
210                 215                 220

Val Asn Gln His Val Ser Asn Val Lys Tyr Ile Gly Trp Ile Leu Arg
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
    275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Arg Ser Thr Gly Lys
305                 310                 315                 320

Thr Ser Asn Gly Asn Ser Val Ser
```

<210> SEQ ID NO 49
<211> LENGTH: 328
<212> TYPE: PRT
<213> ORGANISM: Cuphea hookeriana

<400> SEQUENCE: 49

```
Met Leu Pro Asp Trp Ser Arg Leu Leu Thr Ala Ile Thr Thr Val Phe
1               5                   10                  15
Ala Lys Ser Lys Arg Pro His Met His Asp Arg Lys Ser Lys Arg Pro
            20                  25                  30
Asp Met Leu Val Asp Ser Phe Gly Leu Glu Ser Gly Val Gln Asp Gly
        35                  40                  45
Leu Val Phe Arg Gln Ser Phe Ser Ile Arg Ser Tyr Glu Ile Gly Pro
    50                  55                  60
Asp Arg Leu Ala Ser Ile Glu Thr Leu Met Asn His Leu Gln Glu Thr
65                  70                  75                  80
Ser Leu Asn His Cys Lys Ser Thr Gly Ile Leu Leu Asp Gly Phe Gly
                85                  90                  95
Arg Thr Lys Glu Met Cys Lys Arg Asp Leu Ile Trp Val Val Ile Lys
            100                 105                 110
Met Gln Ile Lys Val Asn Arg Tyr Pro Ala Trp Gly Asp Thr Val Glu
        115                 120                 125
Ile Asn Thr Arg Phe Ser Arg Leu Gly Lys Ile Gly Met Gly Arg Asp
    130                 135                 140
Trp Leu Ile Ser Asp Cys Asn Thr Gly Glu Ile Leu Val Arg Ala Thr
145                 150                 155                 160
Ser Ala Tyr Ala Met Met Asn Gln Lys Thr Arg Arg Leu Ser Lys Leu
                165                 170                 175
Pro Tyr Glu Val His Gln Glu Ile Ala Pro Leu Phe Val Asp Ser Pro
            180                 185                 190
Val Ile Glu Val Ser Asp Leu Lys Val His Arg Phe Lys Val Lys Thr
        195                 200                 205
Gly Asp Ser Ile His Lys Gly Leu Thr Pro Gly Trp Asn Asp Leu Asp
    210                 215                 220
Val Asn Gln His Val Ser Asn Val Lys Tyr Ile Gly Trp Ile Leu Arg
225                 230                 235                 240
Ser Met Pro Thr Glu Val Leu Glu Thr Gln Glu Leu Cys Ser Leu Ala
                245                 250                 255
Leu Glu Tyr Arg Arg Glu Cys Gly Arg Asp Ser Val Leu Glu Ser Val
            260                 265                 270
Thr Ala Met Asp Pro Ser Lys Val Gly Ser Arg Ser Gln Tyr Gln His
        275                 280                 285
Leu Leu Arg Leu Glu Asp Gly Thr Ala Ile Val Asn Gly Ala Thr Glu
    290                 295                 300
Trp Arg Pro Lys Asn Ala Gly Ala Asn Gly Ala Arg Ser Thr Gly Lys
305                 310                 315                 320
Thr Ser Asn Gly Asn Ser Val Ser
                325
```

<210> SEQ ID NO 50
<211> LENGTH: 328
<212> TYPE: PRT
<213> ORGANISM: Cuphea hookeriana -continued

<400> SEQUENCE: 50

Met Leu Pro Asp Trp Ser Arg Leu Leu Thr Ala Ile Thr Thr Val Phe
1               5                   10                  15

Ala Lys Ser Lys Arg Pro His Met His Asp Arg Lys Ser Lys Arg Pro
            20                  25                  30

Asp Met Leu Val Asp Ser Phe Gly Leu Glu Ser Gly Val Gln Asp Gly
        35                  40                  45

Leu Val Phe Arg Gln Ser Phe Ser Ile Arg Ser Tyr Glu Ile Gly Pro
    50                  55                  60

Asp Arg Leu Ala Ser Ile Glu Thr Leu Met Asn His Leu Gln Glu Thr
65                  70                  75                  80

Ser Leu Asn His Cys Lys Ser Thr Gly Ile Leu Leu His Gly Phe Gly
                85                  90                  95

Arg Thr Lys Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Leu
                165                 170                 175

Pro Tyr Glu Val His Gln Glu Ile Ala Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile His Lys Gly Leu Thr Pro Gly Trp Asn Asp Leu Asp
    210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Arg Ser Thr Gly Lys
305                 310                 315                 320

Thr Ser Asn Gly Asn Ser Val Ser
                325

<210> SEQ ID NO 51
<211> LENGTH: 328
<212> TYPE: PRT
<213> ORGANISM: Cuphea hookeriana

<400> SEQUENCE: 51

Met Leu Pro Asp Trp Ser Arg Leu Leu Thr Ala Ile Thr Thr Val Phe
1               5                   10                  15

Ala Lys Ser Lys Arg Pro Asp Met His Asp Arg Lys Ser Lys Arg Pro
            20                  25                  30

-continued

```
Asp Met Leu Val Asp Ser Phe Gly Leu Glu Ser Gly Val Gln Asp Gly
             35                  40                  45

Leu Val Phe Arg Gln Ser Phe Ser Ile Arg Ser Tyr Glu Ile Gly Pro
 50                  55                  60

Asp Arg Leu Ala Ser Ile Glu Thr Leu Met Asn His Leu Gln Glu Thr
 65                  70                  75                  80

Ser Leu Asn His Cys Lys Ser Thr Gly Ile Leu Leu Asp Gly Phe Gly
                 85                  90                  95

Arg Thr Lys Glu Met Cys Lys Arg Asp Leu Ile Trp Val Val Ile Lys
                100                 105                 110

Met Gln Ile Lys Val Asn Arg Tyr Pro Ala Trp Gly Asp Thr Val Glu
            115                 120                 125

Ile Asn Thr Arg Phe Ser Arg Leu Gly Lys Ile Gly Met Gly Arg Asp
        130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Leu
                165                 170                 175

Pro Tyr Glu Val His Gln Glu Ile Ala Pro Leu Phe Val Asp Ser Pro
            180                 185                 190

Val Ile Glu Val Ser Asp Leu Lys Val His Arg Phe Lys Val Lys Thr
        195                 200                 205

Gly Asp Ser Ile His Lys Gly Leu Thr Pro Gly Trp Asn Asp Leu Asp
    210                 215                 220

Val Asn Gln His Val Ser Asn Val Lys Tyr Ile Gly Trp Ile Leu Arg
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Ser Arg Ser Gln Tyr Gln His
        275                 280                 285

Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Arg Ser Thr Gly Lys
305                 310                 315                 320

Thr Ser Asn Gly Asn Ser Val Ser
                325

<210> SEQ ID NO 52
<211> LENGTH: 317
<212> TYPE: PRT
<213> ORGANISM: Cuphea hookeriana

<400> SEQUENCE: 52

Met Thr Thr Val Phe Ala Lys Ser Lys Arg Pro His Met His Asp Arg
 1               5                  10                  15

Lys Ser Lys Arg Pro Asp Met Leu Val Asp Ser Phe Gly Leu Glu Ser
             20                  25                  30

Gly Val Gln Asp Gly Leu Val Phe Arg Gln Ser Phe Ser Ile Arg Ser
         35                  40                  45

Tyr Glu Ile Gly Pro Asp Arg Leu Ala Ser Ile Glu Thr Leu Met Asn
     50                  55                  60

His Leu Gln Glu Thr Ser Leu Asn His Cys Lys Ser Thr Gly Ile Leu
 65                  70                  75                  80
```

```
Leu Asp Gly Phe Gly Arg Thr Lys Glu Met Cys Lys Arg Asp Leu Ile
                85                  90                  95

Trp Val Val Ile Lys Met Gln Ile Lys Val Asn Arg Tyr Pro Ala Trp
            100                 105                 110

Gly Asp Thr Val Glu Ile Asn Thr Arg Phe Ser Arg Leu Gly Lys Ile
            115                 120                 125

Gly Met Gly Arg Asp Trp Leu Ile Ser Asp Cys Asn Thr Gly Glu Ile
130                 135                 140

Leu Val Arg Ala Thr Ser Ala Tyr Ala Met Met Asn Gln Lys Thr Arg
145                 150                 155                 160

Arg Leu Ser Lys Leu Pro Tyr Glu Val His Gln Glu Ile Ala Pro Leu
                165                 170                 175

Phe Val Asp Ser Pro Val Ile Glu Val Ser Asp Leu Lys Val His Arg
            180                 185                 190

Phe Lys Val Lys Thr Gly Asp Ser Ile His Lys Gly Leu Thr Pro Gly
            195                 200                 205

Trp Asn Asp Leu Asp Val Asn Gln His Val Ser Asn Val Lys Tyr Ile
        210                 215                 220

Gly Trp Ile Leu Arg Ser Met Pro Thr Glu Val Leu Glu Thr Gln Glu
225                 230                 235                 240

Leu Cys Ser Leu Ala Leu Glu Tyr Arg Arg Glu Cys Gly Arg Asp Ser
                245                 250                 255

Val Leu Glu Ser Val Thr Ala Met Asp Pro Ser Lys Val Gly Ser Arg
            260                 265                 270

Ser Gln Tyr Gln His Leu Leu Arg Leu Glu Asp Gly Thr Ala Ile Val
            275                 280                 285

Asn Gly Ala Thr Glu Trp Arg Pro Lys Asn Ala Gly Ala Asn Gly Ala
        290                 295                 300

Arg Ser Thr Gly Lys Thr Ser Asn Gly Asn Ser Val Ser
305                 310                 315

<210> SEQ ID NO 53
<211> LENGTH: 314
<212> TYPE: PRT
<213> ORGANISM: Cuphea hookeriana

<400> SEQUENCE: 53

Met Phe Ala Lys Ser Lys Arg Pro His Met His Asp Arg Lys Ser Lys
1               5                   10                  15

Arg Pro Asp Met Leu Val Asp Ser Phe Gly Leu Glu Ser Gly Val Gln
            20                  25                  30

Asp Gly Leu Val Phe Arg Gln Ser Phe Ser Ile Arg Ser Tyr Glu Ile
            35                  40                  45

Gly Pro Asp Arg Leu Ala Ser Ile Glu Thr Leu Met Asn His Leu Gln
        50                  55                  60

Glu Thr Ser Leu Asn His Cys Lys Ser Thr Gly Ile Leu Leu Asp Gly
65                  70                  75                  80

Phe Gly Arg Thr Lys Glu Met Cys Lys Arg Asp Leu Ile Trp Val Val
                85                  90                  95

Ile Lys Met Gln Ile Lys Val Asn Arg Tyr Pro Ala Trp Gly Asp Thr
            100                 105                 110

Val Glu Ile Asn Thr Arg Phe Ser Arg Leu Gly Lys Ile Gly Met Gly
            115                 120                 125

Arg Asp Trp Leu Ile Ser Asp Cys Asn Thr Gly Glu Ile Leu Val Arg
```

-continued

```
            130                 135                 140
Ala Thr Ser Ala Tyr Ala Met Met Asn Gln Lys Thr Arg Arg Leu Ser
145                 150                 155                 160

Lys Leu Pro Tyr Glu Val His Gln Glu Ile Ala Pro Leu Phe Val Asp
                165                 170                 175

Ser Pro Val Ile Glu Val Ser Asp Leu Lys Val His Arg Phe Lys Val
            180                 185                 190

Lys Thr Gly Asp Ser Ile His Lys Gly Leu Thr Pro Gly Trp Asn Asp
                195                 200                 205

Leu Asp Val Asn Gln His Val Ser Asn Val Lys Tyr Ile Gly Trp Ile
210                 215                 220

Leu Arg Ser Met Pro Thr Glu Val Leu Glu Thr Gln Glu Leu Cys Ser
225                 230                 235                 240

Leu Ala Leu Glu Tyr Arg Arg Glu Cys Gly Arg Asp Ser Val Leu Glu
                245                 250                 255

Ser Val Thr Ala Met Asp Pro Ser Lys Val Gly Ser Arg Ser Gln Tyr
            260                 265                 270

Gln His Leu Leu Arg Leu Glu Asp Gly Thr Ala Ile Val Asn Gly Ala
        275                 280                 285

Thr Glu Trp Arg Pro Lys Asn Ala Gly Ala Asn Gly Ala Arg Ser Thr
290                 295                 300

Gly Lys Thr Ser Asn Gly Asn Ser Val Ser
305                 310

<210> SEQ ID NO 54
<211> LENGTH: 313
<212> TYPE: PRT
<213> ORGANISM: Cuphea hookeriana

<400> SEQUENCE: 54

Met Ala Lys Ser Lys Arg Pro His Met His Asp Arg Lys Ser Lys Arg
1               5                   10                  15

Pro Asp Met Leu Val Asp Ser Phe Gly Leu Glu Ser Gly Val Gln Asp
            20                  25                  30

Gly Leu Val Phe Arg Gln Ser Phe Ser Ile Arg Ser Tyr Glu Ile Gly
        35                  40                  45

Pro Asp Arg Leu Ala Ser Ile Glu Thr Leu Met Asn His Leu Gln Glu
    50                  55                  60

Thr Ser Leu Asn His Cys Lys Ser Thr Gly Ile Leu Leu Asp Gly Phe
65                  70                  75                  80

Gly Arg Thr Lys Glu Met Cys Lys Arg Asp Leu Ile Trp Val Val Ile
                85                  90                  95

Lys Met Gln Ile Lys Val Asn Arg Tyr Pro Ala Trp Gly Asp Thr Val
            100                 105                 110

Glu Ile Asn Thr Arg Phe Ser Arg Leu Gly Lys Ile Gly Met Gly Arg
        115                 120                 125

Asp Trp Leu Ile Ser Asp Cys Asn Thr Gly Glu Ile Leu Val Arg Ala
    130                 135                 140

Thr Ser Ala Tyr Ala Met Met Asn Gln Lys Thr Arg Arg Leu Ser Lys
145                 150                 155                 160

Leu Pro Tyr Glu Val His Gln Glu Ile Ala Pro Leu Phe Val Asp Ser
                165                 170                 175

Pro Val Ile Glu Val Ser Asp Leu Lys Val His Arg Phe Lys Val Lys
            180                 185                 190
```

Thr Gly Asp Ser Ile His Lys Gly Leu Thr Pro Gly Trp Asn Asp Leu
        195                 200                 205

Asp Val Asn Gln His Val Ser Asn Val Lys Tyr Ile Gly Trp Ile Leu
210                 215                 220

Arg Ser Met Pro Thr Glu Val Leu Glu Thr Gln Glu Leu Cys Ser Leu
225                 230                 235                 240

Ala Leu Glu Tyr Arg Arg Glu Cys Gly Arg Asp Ser Val Leu Glu Ser
            245                 250                 255

Val Thr Ala Met Asp Pro Ser Lys Val Gly Ser Arg Ser Gln Tyr Gln
                260                 265                 270

His Leu Leu Arg Leu Glu Asp Gly Thr Ala Ile Val Asn Gly Ala Thr
        275                 280                 285

Glu Trp Arg Pro Lys Asn Ala Gly Ala Asn Gly Ala Arg Ser Thr Gly
290                 295                 300

Lys Thr Ser Asn Gly Asn Ser Val Ser
305                 310

<210> SEQ ID NO 55
<211> LENGTH: 305
<212> TYPE: PRT
<213> ORGANISM: Cuphea hookeriana

<400> SEQUENCE: 55

Met His Asp Arg Lys Ser Lys Arg Pro Asp Met Leu Val Asp Ser Phe
1               5                   10                  15

Gly Leu Glu Ser Gly Val Gln Asp Gly Leu Val Phe Arg Gln Ser Phe
            20                  25                  30

Ser Ile Arg Ser Tyr Glu Ile Gly Pro Asp Arg Leu Ala Ser Ile Glu
        35                  40                  45

Thr Leu Met Asn His Leu Gln Glu Thr Ser Leu Asn His Cys Lys Ser
    50                  55                  60

Thr Gly Ile Leu Leu Asp Gly Phe Gly Arg Thr Lys Glu Met Cys Lys
65                  70                  75                  80

Arg Asp Leu Ile Trp Val Val Ile Lys Met Gln Ile Lys Val Asn Arg
                85                  90                  95

Tyr Pro Ala Trp Gly Asp Thr Val Glu Ile Asn Thr Arg Phe Ser Arg
            100                 105                 110

Leu Gly Lys Ile Gly Met Gly Arg Asp Trp Leu Ile Ser Asp Cys Asn
        115                 120                 125

Thr Gly Glu Ile Leu Val Arg Ala Thr Ser Ala Tyr Ala Met Met Asn
    130                 135                 140

Gln Lys Thr Arg Arg Leu Ser Lys Leu Pro Tyr Glu Val His Gln Glu
145                 150                 155                 160

Ile Ala Pro Leu Phe Val Asp Ser Pro Val Ile Glu Val Ser Asp Leu
                165                 170                 175

Lys Val His Arg Phe Lys Val Lys Thr Gly Asp Ser Ile His Lys Gly
            180                 185                 190

Leu Thr Pro Gly Trp Asn Asp Leu Asp Val Asn Gln His Val Ser Asn
        195                 200                 205

Val Lys Tyr Ile Gly Trp Ile Leu Arg Ser Met Pro Thr Glu Val Leu
    210                 215                 220

Glu Thr Gln Glu Leu Cys Ser Leu Ala Leu Glu Tyr Arg Arg Glu Cys
225                 230                 235                 240

Gly Arg Asp Ser Val Leu Glu Ser Val Thr Ala Met Asp Pro Ser Lys
                245                 250                 255

```
Val Gly Ser Arg Ser Gln Tyr Gln His Leu Leu Arg Leu Glu Asp Gly
            260                 265                 270

Thr Ala Ile Val Asn Gly Ala Thr Glu Trp Arg Pro Lys Asn Ala Gly
        275                 280                 285

Ala Asn Gly Ala Arg Ser Thr Gly Lys Thr Ser Asn Gly Asn Ser Val
    290                 295                 300

Ser
305

<210> SEQ ID NO 56
<211> LENGTH: 299
<212> TYPE: PRT
<213> ORGANISM: Cuphea hookeriana

<400> SEQUENCE: 56

Met Arg Pro Asp Met Leu Val Asp Ser Phe Gly Leu Glu Ser Gly Val
1               5                   10                  15

Gln Asp Gly Leu Val Phe Arg Gln Ser Phe Ser Ile Arg Ser Tyr Glu
            20                  25                  30

Ile Gly Pro Asp Arg Leu Ala Ser Ile Glu Thr Leu Met Asn His Leu
        35                  40                  45

Gln Glu Thr Ser Leu Asn His Cys Lys Ser Thr Gly Ile Leu Leu Asp
    50                  55                  60

Gly Phe Gly Arg Thr Lys Glu Met Cys Lys Arg Asp Leu Ile Trp Val
65                  70                  75                  80

Val Ile Lys Met Gln Ile Lys Val Asn Arg Tyr Pro Ala Trp Gly Asp
                85                  90                  95

Thr Val Glu Ile Asn Thr Arg Phe Ser Arg Leu Gly Lys Ile Gly Met
            100                 105                 110

Gly Arg Asp Trp Leu Ile Ser Asp Cys Asn Thr Gly Glu Ile Leu Val
        115                 120                 125

Arg Ala Thr Ser Ala Tyr Ala Met Met Asn Gln Lys Thr Arg Arg Leu
    130                 135                 140

Ser Lys Leu Pro Tyr Glu Val His Gln Glu Ile Ala Pro Leu Phe Val
145                 150                 155                 160

Asp Ser Pro Val Ile Glu Val Ser Asp Leu Lys Val His Arg Phe Lys
                165                 170                 175

Val Lys Thr Gly Asp Ser Ile His Lys Gly Leu Thr Pro Gly Trp Asn
            180                 185                 190

Asp Leu Asp Val Asn Gln His Val Ser Asn Val Lys Tyr Ile Gly Trp
        195                 200                 205

Ile Leu Arg Ser Met Pro Thr Glu Val Leu Glu Thr Gln Glu Leu Cys
    210                 215                 220

Ser Leu Ala Leu Glu Tyr Arg Arg Glu Cys Gly Arg Asp Ser Val Leu
225                 230                 235                 240

Glu Ser Val Thr Ala Met Asp Pro Ser Lys Val Gly Ser Arg Ser Gln
                245                 250                 255

Tyr Gln His Leu Leu Arg Leu Glu Asp Gly Thr Ala Ile Val Asn Gly
            260                 265                 270

Ala Thr Glu Trp Arg Pro Lys Asn Ala Gly Ala Asn Gly Ala Arg Ser
        275                 280                 285

Thr Gly Lys Thr Ser Asn Gly Asn Ser Val Ser
    290                 295
```

<210> SEQ ID NO 57
<211> LENGTH: 297
<212> TYPE: PRT
<213> ORGANISM: Cuphea hookeriana

<400> SEQUENCE: 57

| | | | | | | | | | | | | | | | |
|---|---|---|---|---|---|---|---|---|---|---|---|---|---|---|---|
| Met | Asp | Met | Leu | Val | Asp | Ser | Phe | Gly | Leu | Glu | Ser | Gly | Val | Gln | Asp |
| 1 | | | | 5 | | | | | 10 | | | | | 15 | |
| Gly | Leu | Val | Phe | Arg | Gln | Ser | Phe | Ser | Ile | Arg | Ser | Tyr | Glu | Ile | Gly |
| | | | 20 | | | | | 25 | | | | | 30 | | |
| Pro | Asp | Arg | Leu | Ala | Ser | Ile | Glu | Thr | Leu | Met | Asn | His | Leu | Gln | Glu |
| | | 35 | | | | | 40 | | | | | 45 | | | |
| Thr | Ser | Leu | Asn | His | Cys | Lys | Ser | Thr | Gly | Ile | Leu | Leu | Asp | Gly | Phe |
| | 50 | | | | | 55 | | | | | 60 | | | | |
| Gly | Arg | Thr | Lys | Glu | Met | Cys | Lys | Arg | Asp | Leu | Ile | Trp | Val | Val | Ile |
| 65 | | | | | 70 | | | | | 75 | | | | | 80 |
| Lys | Met | Gln | Ile | Lys | Val | Asn | Arg | Tyr | Pro | Ala | Trp | Gly | Asp | Thr | Val |
| | | | | 85 | | | | | 90 | | | | | 95 | |
| Glu | Ile | Asn | Thr | Arg | Phe | Ser | Arg | Leu | Gly | Lys | Ile | Gly | Met | Gly | Arg |
| | | | 100 | | | | | 105 | | | | | 110 | | |
| Asp | Trp | Leu | Ile | Ser | Asp | Cys | Asn | Thr | Gly | Glu | Ile | Leu | Val | Arg | Ala |
| | | | 115 | | | | | 120 | | | | | 125 | | |
| Thr | Ser | Ala | Tyr | Ala | Met | Met | Asn | Gln | Lys | Thr | Arg | Arg | Leu | Ser | Lys |
| | 130 | | | | | 135 | | | | | 140 | | | | |
| Leu | Pro | Tyr | Glu | Val | His | Gln | Glu | Ile | Ala | Pro | Leu | Phe | Val | Asp | Ser |
| 145 | | | | | 150 | | | | | 155 | | | | | 160 |
| Pro | Val | Ile | Glu | Val | Ser | Asp | Leu | Lys | Val | His | Arg | Phe | Lys | Val | Lys |
| | | | | 165 | | | | | 170 | | | | | 175 | |
| Thr | Gly | Asp | Ser | Ile | His | Lys | Gly | Leu | Thr | Pro | Gly | Trp | Asn | Asp | Leu |
| | | | 180 | | | | | 185 | | | | | 190 | | |
| Asp | Val | Asn | Gln | His | Val | Ser | Asn | Val | Lys | Tyr | Ile | Gly | Trp | Ile | Leu |
| | | | 195 | | | | | 200 | | | | | 205 | | |
| Arg | Ser | Met | Pro | Thr | Glu | Val | Leu | Glu | Thr | Gln | Glu | Leu | Cys | Ser | Leu |
| | 210 | | | | | 215 | | | | | 220 | | | | |
| Ala | Leu | Glu | Tyr | Arg | Arg | Glu | Cys | Gly | Arg | Asp | Ser | Val | Leu | Glu | Ser |
| 225 | | | | | 230 | | | | | 235 | | | | | 240 |
| Val | Thr | Ala | Met | Asp | Pro | Ser | Lys | Val | Gly | Ser | Arg | Ser | Gln | Tyr | Gln |
| | | | | 245 | | | | | 250 | | | | | 255 | |
| His | Leu | Leu | Arg | Leu | Glu | Asp | Gly | Thr | Ala | Ile | Val | Asn | Gly | Ala | Thr |
| | | | 260 | | | | | 265 | | | | | 270 | | |
| Glu | Trp | Arg | Pro | Lys | Asn | Ala | Gly | Ala | Asn | Gly | Ala | Arg | Ser | Thr | Gly |
| | | | 275 | | | | | 280 | | | | | 285 | | |
| Lys | Thr | Ser | Asn | Gly | Asn | Ser | Val | Ser | | | | | | | |
| | | | 290 | | | | | 295 | | | | | | | |

<210> SEQ ID NO 58
<211> LENGTH: 295
<212> TYPE: PRT
<213> ORGANISM: Cuphea hookeriana

<400> SEQUENCE: 58

| | | | | | | | | | | | | | | | |
|---|---|---|---|---|---|---|---|---|---|---|---|---|---|---|---|
| Met | Leu | Val | Asp | Ser | Phe | Gly | Leu | Glu | Ser | Gly | Val | Gln | Asp | Gly | Leu |
| 1 | | | | 5 | | | | | 10 | | | | | 15 | |
| Val | Phe | Arg | Gln | Ser | Phe | Ser | Ile | Arg | Ser | Tyr | Glu | Ile | Gly | Pro | Asp |
| | | | 20 | | | | | 25 | | | | | 30 | | |
| Arg | Leu | Ala | Ser | Ile | Glu | Thr | Leu | Met | Asn | His | Leu | Gln | Glu | Thr | Ser |

```
                35                  40                  45
Leu Asn His Cys Lys Ser Thr Gly Ile Leu Leu Asp Gly Phe Gly Arg
    50                  55                  60
Thr Lys Glu Met Cys Lys Arg Asp Leu Ile Trp Val Val Ile Lys Met
65                  70                  75                  80
Gln Ile Lys Val Asn Arg Tyr Pro Ala Trp Gly Asp Thr Val Glu Ile
                85                  90                  95
Asn Thr Arg Phe Ser Arg Leu Gly Lys Ile Gly Met Gly Arg Asp Trp
            100                 105                 110
Leu Ile Ser Asp Cys Asn Thr Gly Glu Ile Leu Val Arg Ala Thr Ser
        115                 120                 125
Ala Tyr Ala Met Met Asn Gln Lys Thr Arg Arg Leu Ser Lys Leu Pro
    130                 135                 140
Tyr Glu Val His Gln Glu Ile Ala Pro Leu Phe Val Asp Ser Pro Val
145                 150                 155                 160
Ile Glu Val Ser Asp Leu Lys Val His Arg Phe Lys Val Lys Thr Gly
                165                 170                 175
Asp Ser Ile His Lys Gly Leu Thr Pro Gly Trp Asn Asp Leu Asp Val
            180                 185                 190
Asn Gln His Val Ser Asn Val Lys Tyr Ile Gly Trp Ile Leu Arg Ser
        195                 200                 205
Met Pro Thr Glu Val Leu Glu Thr Gln Glu Leu Cys Ser Leu Ala Leu
    210                 215                 220
Glu Tyr Arg Arg Glu Cys Gly Arg Asp Ser Val Leu Glu Ser Val Thr
225                 230                 235                 240
Ala Met Asp Pro Ser Lys Val Gly Ser Arg Ser Gln Tyr Gln His Leu
                245                 250                 255
Leu Arg Leu Glu Asp Gly Thr Ala Ile Val Asn Gly Ala Thr Glu Trp
            260                 265                 270
Arg Pro Lys Asn Ala Gly Ala Asn Gly Ala Arg Ser Thr Gly Lys Thr
        275                 280                 285
Ser Asn Gly Asn Ser Val Ser
    290                 295

<210> SEQ ID NO 59
<211> LENGTH: 294
<212> TYPE: PRT
<213> ORGANISM: Cuphea hookeriana

<400> SEQUENCE: 59

Met Val Asp Ser Phe Gly Leu Glu Ser Gly Val Gln Asp Gly Leu Val
1               5                   10                  15
Phe Arg Gln Ser Phe Ser Ile Arg Ser Tyr Glu Ile Gly Pro Asp Arg
            20                  25                  30
Leu Ala Ser Ile Glu Thr Leu Met Asn His Leu Gln Glu Thr Ser Leu
        35                  40                  45
Asn His Cys Lys Ser Thr Gly Ile Leu Leu Asp Gly Phe Gly Arg Thr
    50                  55                  60
Lys Glu Met Cys Lys Arg Asp Leu Ile Trp Val Val Ile Lys Met Gln
65                  70                  75                  80
Ile Lys Val Asn Arg Tyr Pro Ala Trp Gly Asp Thr Val Glu Ile Asn
                85                  90                  95
Thr Arg Phe Ser Arg Leu Gly Lys Ile Gly Met Gly Arg Asp Trp Leu
            100                 105                 110
```

```
Ile Ser Asp Cys Asn Thr Gly Glu Ile Leu Val Arg Ala Thr Ser Ala
            115                 120                 125

Tyr Ala Met Met Asn Gln Lys Thr Arg Arg Leu Ser Lys Leu Pro Tyr
        130                 135                 140

Glu Val His Gln Glu Ile Ala Pro Leu Phe Val Asp Ser Pro Val Ile
145                 150                 155                 160

Glu Val Ser Asp Leu Lys Val His Arg Phe Lys Val Lys Thr Gly Asp
                165                 170                 175

Ser Ile His Lys Gly Leu Thr Pro Gly Trp Asn Asp Leu Asp Val Asn
            180                 185                 190

Gln His Val Ser Asn Val Lys Tyr Ile Gly Trp Ile Leu Arg Ser Met
        195                 200                 205

Pro Thr Glu Val Leu Glu Thr Gln Glu Leu Cys Ser Leu Ala Leu Glu
    210                 215                 220

Tyr Arg Arg Glu Cys Gly Arg Asp Ser Val Leu Glu Ser Val Thr Ala
225                 230                 235                 240

Met Asp Pro Ser Lys Val Gly Ser Arg Ser Gln Tyr Gln His Leu Leu
                245                 250                 255

Arg Leu Glu Asp Gly Thr Ala Ile Val Asn Gly Ala Thr Glu Trp Arg
            260                 265                 270

Pro Lys Asn Ala Gly Ala Asn Gly Ala Arg Ser Thr Gly Lys Thr Ser
        275                 280                 285

Asn Gly Asn Ser Val Ser
    290

<210> SEQ ID NO 60
<211> LENGTH: 987
<212> TYPE: DNA
<213> ORGANISM: Cuphea hookeriana

<400> SEQUENCE: 60
atgctccccg attggtcccg cctgctgaca gctatcacca cggtgtttgt taagtcgaaa      60
cggccggaca tgcatgatag aaaaagcaag cgaccagaca tgttagtcga ttctttcgga     120
ttggagagta ctgtacaaga tggccttgtg tttcgtcagt cattctccat acgcagctat     180
gaaattggta cagaccgtac cgcgtcgatc gagacgctga tgaaccacct ccaggaaacc     240
tctctgaatc attgcaaaag tactggcatt ttactggatg gttttgggcg cacattggaa     300
atgtgtaaac gggaccttat ctgggttgtc ataaagatgc aaattaaagt gaaccgttac     360
cctgcctggg gagatacggt agagatcaat acccgctttt caagactggg caaaattggt     420
atgggccgag actggctcat aagcgattgc aacactggtg aaatcttagt cgtgcaaca     480
tccgcttatg cgatgatgaa tcagaagacc cgccggctgt cgaaattgcc gtacgaggtg     540
caccaagaaa ttgtcccact tttcgttgat tctccggtaa tcgaagacag tgatctgaaa     600
gtgcataagt ttaaagtcaa acgggggac agcattcaga agggattaac ccccggctgg     660
aacgatctgg atgttaatca gcacgtgtca aacgtaaaat atataggttg gattctggag     720
tccatgccta ctgaagtcct ggagacacaa gaattgtgtt cgcttgccct ggaataccgt     780
cgcgagtgcg gcgtgactc tgttttagaa agcgtgacgg caatggaccc gagtaaagta     840
ggcgttcgct cacagtatca acatctgctc agattggagg acggtaccgc gattgtgaat     900
ggagctactg aatggcgacc aaagaacgcc ggcgcaaatg gtgcgatatc cacagggaaa     960
acgagcaacg gcaattcggt ctcttaa                                         987
```